US010633383B2

(12) United States Patent
Nampally

(10) Patent No.: US 10,633,383 B2
(45) Date of Patent: Apr. 28, 2020

(54) COMPOUNDS FOR THE TREATMENT, ALLEVIATION OR PREVENTION OF DISORDERS ASSOCIATED WITH TAU AGGREGATES

(71) Applicant: AC Immune SA, Lausanne (CH)

(72) Inventor: Sreenivasachary Nampally, Ecublens (CH)

(73) Assignee: AC Immune SA, Lausanne (CH)

( * ) Notice: Subject to any disclaimer, the term of this patent is extended or adjusted under 35 U.S.C. 154(b) by 0 days.

(21) Appl. No.: 16/351,848

(22) Filed: Mar. 13, 2019

(65) Prior Publication Data

US 2019/0211012 A1 Jul. 11, 2019

Related U.S. Application Data

(63) Continuation of application No. PCT/EP2019/050180, filed on Jan. 4, 2019.

(30) Foreign Application Priority Data

Jan. 5, 2018 (EP) .................................... 18150422
Jun. 4, 2018 (EP) .................................... 18175852

(51) Int. Cl.
| | |
|---|---|
| C07D 471/04 | (2006.01) |
| A61P 25/28 | (2006.01) |
| C07D 471/14 | (2006.01) |
| A61K 31/4375 | (2006.01) |
| A61K 31/5386 | (2006.01) |
| A61K 31/473 | (2006.01) |
| A61K 31/27 | (2006.01) |
| A61K 31/445 | (2006.01) |
| A61K 31/55 | (2006.01) |

(Continued)

(52) U.S. Cl.
CPC ............ *C07D 471/04* (2013.01); *A61K 31/13* (2013.01); *A61K 31/27* (2013.01); *A61K 31/437* (2013.01); *A61K 31/4375* (2013.01); *A61K 31/444* (2013.01); *A61K 31/445* (2013.01); *A61K 31/455* (2013.01); *A61K 31/473* (2013.01); *A61K 31/4709* (2013.01); *A61K 31/5377* (2013.01); *A61K 31/5386* (2013.01); *A61K 31/55* (2013.01); *A61P 25/28* (2018.01); *C07D 471/14* (2013.01); *C07D 491/147* (2013.01); *C07D 519/00* (2013.01)

(58) Field of Classification Search
CPC ......................... C07D 491/147; C07D 471/14; C07D 471/04; A61K 31/4375; A61P 25/28

See application file for complete search history.

(56) References Cited

FOREIGN PATENT DOCUMENTS

| EP | 3118202 A1 | 1/2017 |
|---|---|---|
| WO | 2010/080253 A1 | 7/2010 |

(Continued)

OTHER PUBLICATIONS

Written Opinion for PCT/EP2019/050180 dated Feb. 21, 2019.
International Search Report for PCT/EP2019/050180 dated Feb. 21, 2019.

*Primary Examiner* — Marcos L Sznaidman
*Assistant Examiner* — Rayna Rodriguez
(74) *Attorney, Agent, or Firm* — Kyle W Grimshaw

(57) ABSTRACT

The present invention relates to novel compounds that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

24 Claims, 5 Drawing Sheets

(51) Int. Cl.
*A61K 31/455* (2006.01)
*A61K 31/13* (2006.01)
*A61K 31/5377* (2006.01)
*A61K 31/437* (2006.01)
*C07D 519/00* (2006.01)
*A61K 31/4709* (2006.01)
*A61K 31/444* (2006.01)
*C07D 491/147* (2006.01)

(56) References Cited

FOREIGN PATENT DOCUMENTS

| WO | 2011/084439 A1 | 7/2011 |
| WO | 2011/128455 A1 | 10/2011 |
| WO | 2012/170867 A1 | 12/2012 |
| WO | 2014/117919 A1 | 8/2014 |
| WO | 2017/009454 A1 | 1/2017 |

A       B

COMPOUNDS FOR THE TREATMENT, ALLEVIATION OR PREVENTION OF DISORDERS ASSOCIATED WITH TAU AGGREGATES

The present application is a continuation of International Application Number PCT/EP2019/050180 (filed on 4 Jan. 2019), which claims the benefit of Application No. EP18150422.6 (filed 5 Jan. 2018) and Application No. EP18175852.5 (filed 4 Jun. 2018).

FIELD OF THE INVENTION

The present invention relates to novel compounds that can be employed in the treatment, alleviation or prevention of a group of disorders and abnormalities associated with Tau (Tubulin associated unit) protein aggregates including, but not limited to, Neurofibrillary Tangles (NFTs), such as Alzheimer's disease (AD).

BACKGROUND OF THE INVENTION

Many aging diseases are based on or associated with extracellular or intracellular deposits of amyloid or amyloid-like proteins that contribute to the pathogenesis as well as to the progression of the disease. The best characterized amyloid protein that forms extracellular aggregates is amyloid beta (Aβ). Other examples of amyloid proteins that form extracellular aggregates are prion, ATTR (transthyretin) or ADan (ADanPP). Amyloid-like proteins, that form mainly intracellular aggregates, include, but are not limited to Tau, alpha-synuclein, TAR DNA-binding protein 43 (TDP-43), and huntingtin (htt). Diseases involving Tau aggregates are generally listed as tauopathies such as AD.

Amyloid or amyloid-like deposits result from misfolding of proteins followed by aggregation to give β-sheet assemblies in which multiple peptides or proteins are held together by inter-molecular hydrogen-bonds. While amyloid or amyloid-like proteins have different primary amino acid sequences, their deposits often contain many shared molecular constituents, in particular the presence of β-sheet quaternary structures. The association between amyloid deposits and diseases remains largely unclear. A diverse range of protein aggregates, including both those associated and not associated with disease pathologies, have been found to be toxic suggesting that the common molecular features of amyloid are implicated or responsible for disease on-set (Bucciantini et al., Nature, 2002, 416, 507-11). Various multimers of β-sheet aggregated peptides or proteins have also been associated with toxicity for different peptides or proteins ranging from dimers, through to soluble low molecular weight oligomers, protofibrils or insoluble fibrillar deposits.

Alzheimer's disease (AD) is a neurological disorder primarily thought to be caused by amyloid plaques, an extracellular accumulation of abnormal deposit of (amyloid-beta) Aβ aggregates in the brain. The other major neuropathological hallmarks in AD are the intracellular neurofibrillary tangles (NFT) that originate by the aggregation of the hyperphosphorylated Tau protein, misfolded Tau or pathological Tau and its conformers. AD shares its etiopathology with many neurodegenerative tauopathies, in particular with specified types of frontotemporal dementia (FTD). The Tau protein is a freely soluble, "naturally unfolded" protein that binds avidly to microtubuli (MT) to promote their assembly and stability. MT are of major importance for the cytoskeletal integrity of neurons—and thereby for the proper formation and functioning of neuronal circuits, hence for learning and memory. The binding of Tau to MT is controlled by dynamic phosphorylation and de-phosphorylation, as demonstrated mainly in vitro and in non-neuronal cells. In AD brain, Tau pathology (tauopathy) develops later than amyloid pathology, but it is still discussed controversially if AI protein is the causative agent in AD which constitutes the essence of the so-called amyloid cascade hypothesis (Hardy et al., Science 1992, 256, 184-185; Musiek et al., Nature Neurosciences 2015, 18(6), 800-806). The exact mechanisms that link amyloid to Tau pathology remain largely unknown, but are proposed to involve activation of neuronal signaling pathways that act on or by GSK3 and cdk5 as the major "Tau-kinases" (Muyllaert et al., Rev. Neurol. (Paris), 2006, 162, 903-7; Muyllaert et al., Genes Brain and Behav. 2008, Suppl 1, 57-66). Even if the tauopathy develops later than amyloid, it is not just an innocent side-effect but a major pathological executer in AD. In experimental mouse models the cognitive defects caused by amyloid pathology are nearly completely alleviated by the absence of Tau protein (Roberson et al., Science, 2007, 316(5825), 750-4) and the severity of cognitive dysfunction and dementia correlates with the tauopathy, not with amyloid pathology.

Diseases involving Tau aggregates are generally listed as tauopathies and they include, but are not limited to, Alzheimer's disease (AD), familial AD, PART (primary age-related Tauopathy), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease. (Williams et al., Intern. Med. J., 2006, 36, 652-60; Kovacs et al., J Neuropathol Exp Neurol. 2008; 67(10): 963-975; Higuchi et al., Neuropsychopharmacology—5th Generation of Progress, 2002, Section 9, Chapter 94: 1339-1354; Hilton et al., Acta Neuropathol. 1995; 90(1):101-6; Iqbal et al., Biochimica et Biophysica Acta 1739 (2005) 198-210; McQuaid et al., Neuropathol Appl Neurobiol. 1994 April; 20(2):103-10; Vossel et al., Lancet Neurol 2017; 16: 311-22; Stephan et al., Molecular Psychiatry (2012) 17, 1056-1076; Anderson et al., Brain (2008), 131, 1736-1748; Savica et al., JAMA Neurol. 2013; 70(7):859-866; Brown et al. Molecular Neurodegeneration 2014, 9:40; El Khoury et al., Front. Cell. Neurosci., 2014, Volume 8, Article22: 1-18; Tanskanen et al., Ann. Med.

2008; 40(3):232-9; Gupta et al., CAN J OPHTHALMOL—VOL. 43, NO. 1, 2008: 53-60; Dickson et al., Int J Clin Exp Pathol 2010; 3(1):1-23; Fernández-Nogales et al., Nature Medicine, 20, 881-885 (2014); Bi et al., Nature Communications volume 8, Article number: 473 (2017); Murray et al., Biol Psychiatry. 2014 April 1; 75(7): 542-552).

Of all the agents in clinical trials for the treatment of Alzheimer's disease in 2017, the ones targeting Tau are very scarce and represent only 8% of the Phase II clinical trials (Cummings et al., Alzheimer's & Dementia: Translational Research & Clinical Interventions 3 (2017) 367-384). Current therapeutic approaches that target Tau protein comprise mainly antibody-based approaches with the main limitation of targeting only extracellular Tau. Among the approaches using small molecules, several Tau kinase inhibitors have been developed, despite being very challenging with respect to toxicity and specificity. Nevertheless, currently only one kinase inhibitor, Nilotinib, is tested in clinical trials. Lastly, among the Tau aggregation inhibitors only one, LMTX, is currently in clinical trials (Cummings et al., 2017). Although in recent years, Tau-based treatments have become a point of increasing focus, there is still a big need for additional therapeutic agents that target the pathological Tau conformers that are known or presumed to cause tauopathies.

WO2011/128455 refers to specific compounds which are suitable for treating disorders associated with amyloid proteins or amyloid-like proteins.

WO2010/080253 refers to dipyridyl-pyrrole derivative compounds which are useful in the treatment of diseases amenable to protein kinase signal transduction inhibition, regulation and/or modulation.

SUMMARY OF THE INVENTION

It was an object of the present invention to provide compounds that can be employed in the treatment, alleviation or prevention of a group of disorders and abnormalities associated with Tau protein aggregates including, but not limited to, NFTs, such as Alzheimer's disease (AD). Furthermore, there exists a need in the art for compounds which can be used as therapeutic agents for (a) decreasing Tau aggregates/NFTs by recognizing aggregated Tau and disaggregating Tau, for example by changing the Tau aggregate molecular conformation, and/or (b) preventing the formation of Tau aggregates, and/or (c) interfering intracellularly with Tau aggregates, and/or (d) reducing Tau misfolding and hyperphosphorylation in vivo and/or (f) reducing neuroinflammatory markers. The present inventors have surprisingly found that these objects can be achieved by the compounds of formula (I) as described hereinafter.

The compounds of formula (I) (a) display high capability in decreasing Tau aggregates by recognizing aggregated Tau and disaggregating Tau, for example by changing the Tau aggregate molecular conformation, and/or (b) prevent the formation of Tau aggregates, and/or (c) interfere intracellularly with Tau aggregates, and/or (d) reduce Tau misfolding and hyperphosphorylation in vivo and/or (f) reduce neuroinflammatory markers. While not wishing to be bound by theory, it is assumed that the compounds of formula (I) inhibit the Tau aggregation or disaggregate preformed Tau aggregates including when present intracellularly. Due to their unique design features, these compounds display properties such as appropriate lipophilicity and molecular weight, brain uptake and pharmacokinetics, cell permeability, solubility and metabolic stability, in order to be a successful medicament for the treatment, alleviation or prevention of tauopathies.

The accumulation of Tau NFT lesions has been shown to correlate well with cognitive deficits in AD, both through histopathological analyses as well as through in vivo Tau PET imaging. The compounds of this invention can either prevent the formation of Tau aggregates, or disaggregate pre-existing Tau aggregates and can therefore be expected to prevent or reduce the associated cognitive deficits in AD.

Ultrastructural analyses have shown that Tau inclusions are composed of paired helical filaments (PHF) or straight filaments (SF). High resolution structural analyses have shown that these filaments are composed of a core region comprising amino acids 306-378 of Tau which adopt a cross beta/beta-helix structure. The compounds of this invention can recognize aggregated Tau and disaggregate Tau, for example, by changing the Tau aggregate molecular conformation, and can therefore be expected to facilitate Tau clearance.

In addition, it has been shown that Tau is able to both propagate from cell-to-cell and that certain forms of Tau (acting as seeds) are able to induce the structural change of native Tau protein within the healthy cell to undergo misfolding and aggregation. It is considered that aggregated Tau is responsible for the seeding and thus of the Tau pathology spreading. The compounds of this invention can interfere intracellularly with aggregated Tau and can therefore be expected to reduce Tau pathology spreading and finally prevent or reduce the associated cognitive deficits in AD.

The Tau aggregation cascade initiates with Tau misfolding and hyperphosphorylation. These events are believed to precede the formation of the intracellular Tau neuronal inclusions and therefore the establishment and spreading of the Tau pathology. The compounds of this invention can reduce Tau misfolding and hyperphosphorylation in vivo and can therefore be expected to be beneficial in treating, alleviating, or preventing the diseases associated with Tau pathology.

Lastly, the link between Tau pathology and neuroinflammation is now well established. Neuroinflammation is a key event already in early AD stages and is believed to be one of the causes that trigger aggregation of Tau in PHF. Moreover, several tauopathy mouse models showed significant neuroinflammation once the Tau pathology is well established in the brain indicating that Tau pathology can also induce a neuroinflammatory process. These two findings indicate that Tau pathology and neuroinflammation are linked in a positive feedback loop. The compounds of this invention reduce neuroinflammatory markers in the contest of Tau pathology.

The present invention discloses novel compounds of formula (I) having capabilities to (a) decrease Tau aggregates, recognize aggregated Tau and disaggregate Tau, for example, by changing the Tau aggregate molecular conformation, and/or (b) prevent the formation of Tau aggregates, and/or (c) interfere intracellularly with Tau aggregates, and/or (d) reduce Tau misfolding and hyperphosphorylation in vivo and/or (f) reduce neuroinflammatory markers. The present invention provides methods for the treatment of disorders and abnormalities associated with Tau protein aggregates including, but not limited to, NFTs, using a compound of formula (I) or a pharmaceutical composition thereof. The present invention further provides a pharmaceutical composition comprising a compound of formula (I) and a pharmaceutically acceptable carrier or excipient.

The present invention is summarized in the following items:
1. A compound of formula (I):

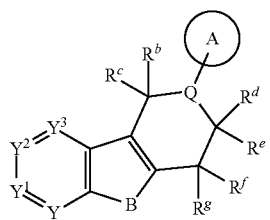

and all stereoisomers, racemic mixtures, tautomers, pharmaceutically acceptable salts, prodrugs, hydrates, solvates and polymorphs thereof;
wherein
A is selected from the group consisting of

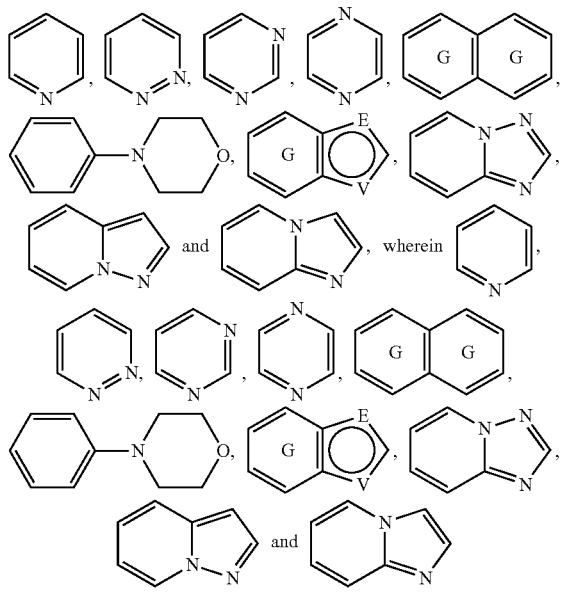

and N can be attached to Q at any available position, wherein and

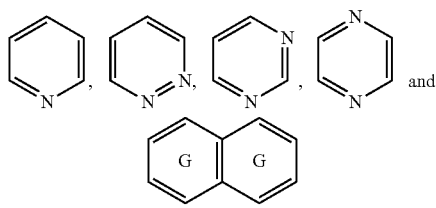

is substituted by one or more substituents $R^j$, and wherein

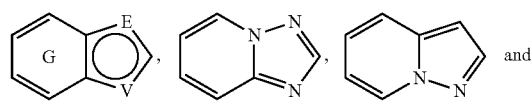

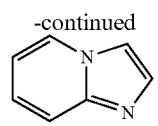

can be optionally substituted by one or more substituents R;
B is selected from the group consisting of O and $NR^a$;
E and V are independently selected from the group consisting of N, $NR^5$, O and S;
G is selected from the group consisting of a benzene ring, a pyrimidine ring and a pyridine ring;
J is selected from the group consisting of O and N—$R^1$;
Q is selected from the group consisting of N and C—$R^1$;
Y is selected from the group consisting of CZ and N, provided that when Y is N and $Y^1$, $Y^2$ and $Y^3$ are CZ, B is N-alkyl or O;
$Y^1$ is selected from the group consisting of CZ and N;
$Y^2$ is selected from the group consisting of CZ and N;
$Y^3$ is selected from the group consisting of CZ and N;
Z is independently selected from the group consisting of H, halogen, O-alkyl, alkyl and CN;
R is independently selected from the group consisting of

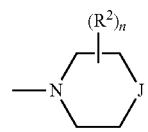

and —$NR^3R^4$;
$R^a$ is selected from the group consisting of H and alkyl;
$R^b$, $R^c$, $R^d$, $R^e$, $R^f$, and $R^g$ are independently selected from the group consisting of H and alkyl, or any two of $R^b$, $R^c$, $R^d$, $R^e$, $R^f$, and $R^g$ may be joined to form a 3 to 8-membered ring;
$R^1$ is independently selected from the group consisting of -halogen, —O-alkyl, —$CF_3$, —CN, —$NR^3R^4$,

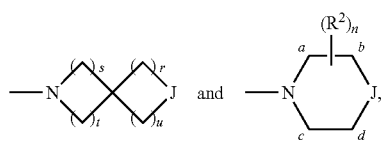

wherein a $C_{1-2}$ carbon atom-containing bridge can be present between the a carbon atom and the c or d carbon atom or wherein a $C_{1-2}$ carbon atom-containing bridge can be present between the b carbon atom and the c or d carbon atom;
$R^1$ is selected from the group consisting of H and alkyl;
$R^2$ is independently selected from the group consisting of alkyl, F and =O, wherein the alkyl can be optionally substituted by halogen, —OH or —O-alkyl and wherein if two $R^2$ are geminal they can be joined to form a 3 to 6-membered ring;
$R^3$ and $R^4$ are independently selected from the group consisting of H and alkyl, wherein the alkyl can be optionally substituted by halogen, —OH or —O-alkyl;
$R^5$ is selected from the group consisting of H and alkyl;
n is 0, 1, 2, 3 or 4.
r and s are independently 0, 1, 2 or 3; and
t and u are independently 1, 2 or 3.
2. The compound according to item 1, which is a compound of formula (Ia):

(Ia)

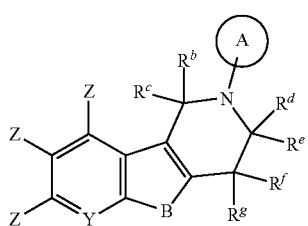

wherein A, B, $R^b$, $R^c$, $R^d$, $R^e$, $R^f$, $R^g$, Y and Z are as defined in item 1.

3. The compound according to item 1, which is a compound of formula (Ib):

(Ib)

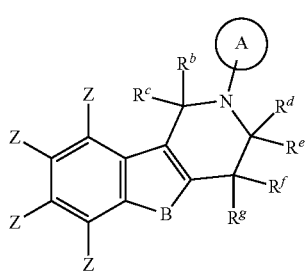

wherein A, B, $R^b$, $R^c$, $R^d$, $R^e$, $R^f$, $R^g$ and Z are as defined in item 1.

4. The compound according to any one of items 1 to 3, wherein A is

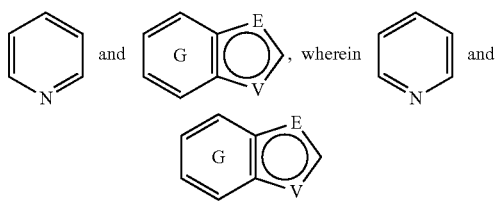, wherein

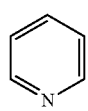

is substituted by one or more substituents $R^j$, and wherein

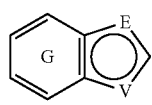

can be optionally substituted by one or more substituents R.

5. The compound according to any one of items 1 to 3, wherein A is

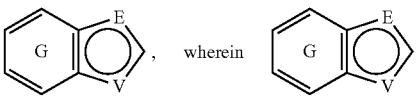, wherein 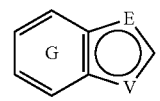

can be attached to Q or to N at any available position, and wherein

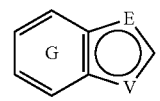

can be optionally substituted by one or more substituents R.

6. The compound according to any one of items 1 to 5, which is a compound of the formula (Ic):

(Ic)

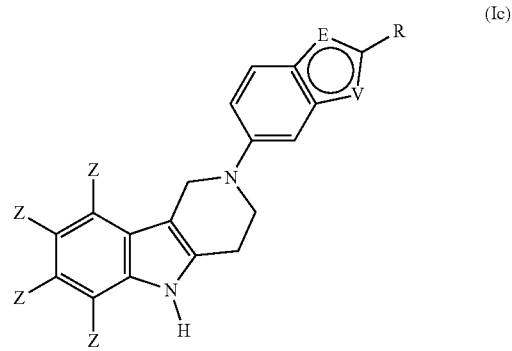

wherein E, R, V and Z are as defined in item 1.

7. The compound according to any one of items 1 to 4, which is a compound of the formula (Id):

(Id)

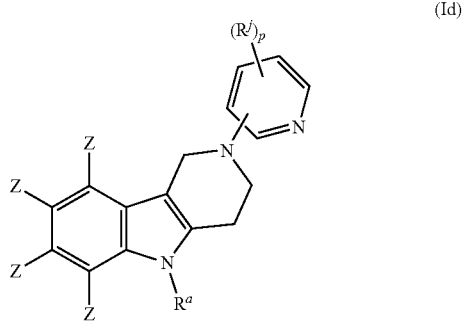

wherein $R^a$, $R^j$ and Z are as defined in item 1 and p is 1 or 2.

8. The compound according to item 1, wherein the compound is selected from the group consisting of

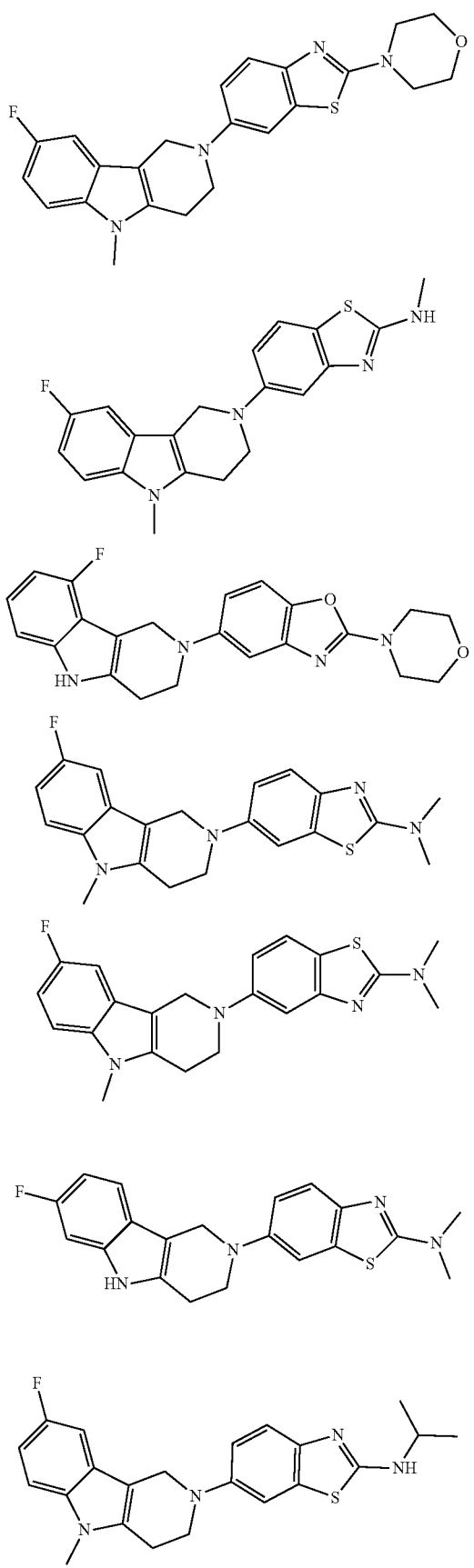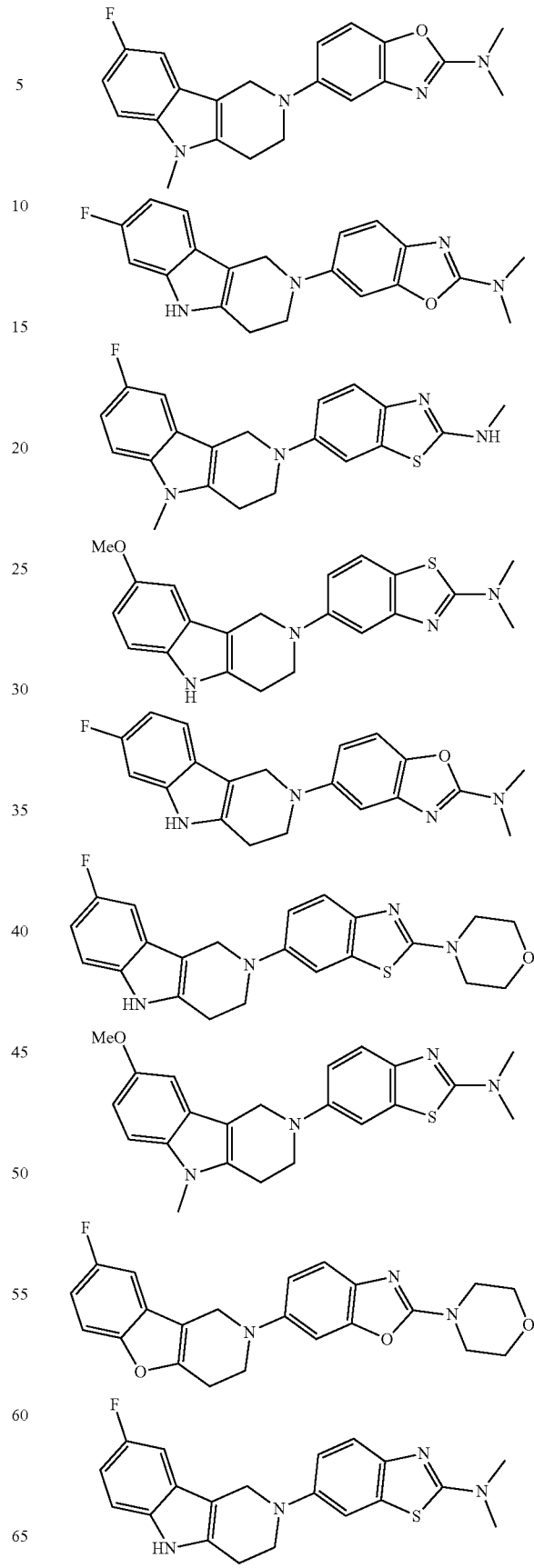

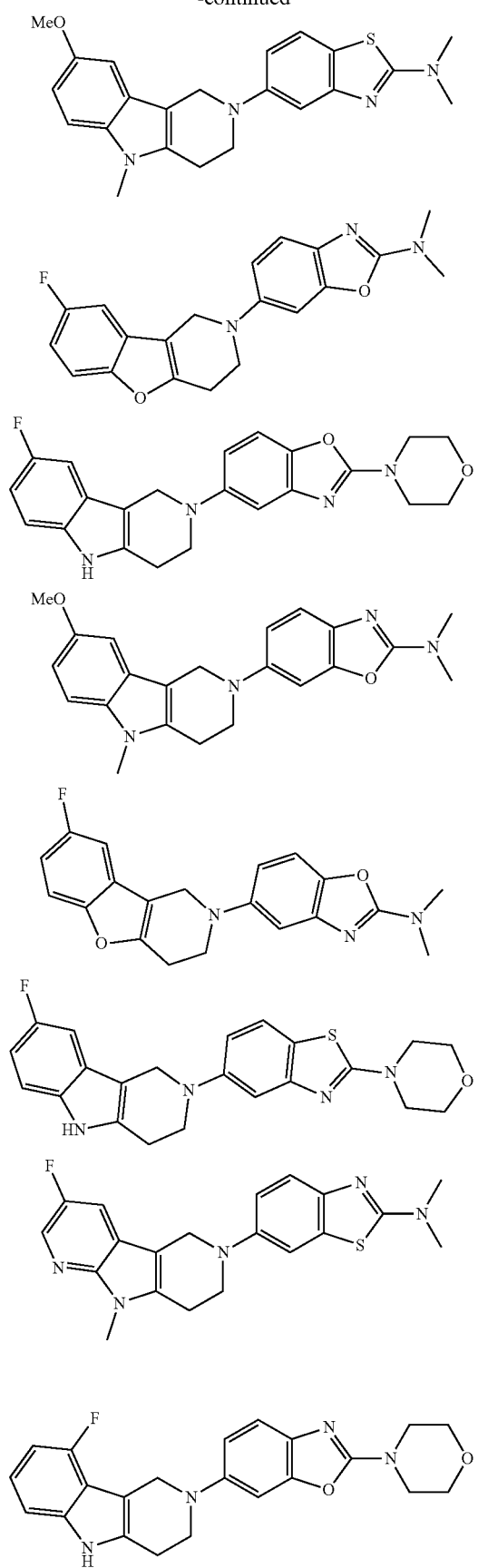
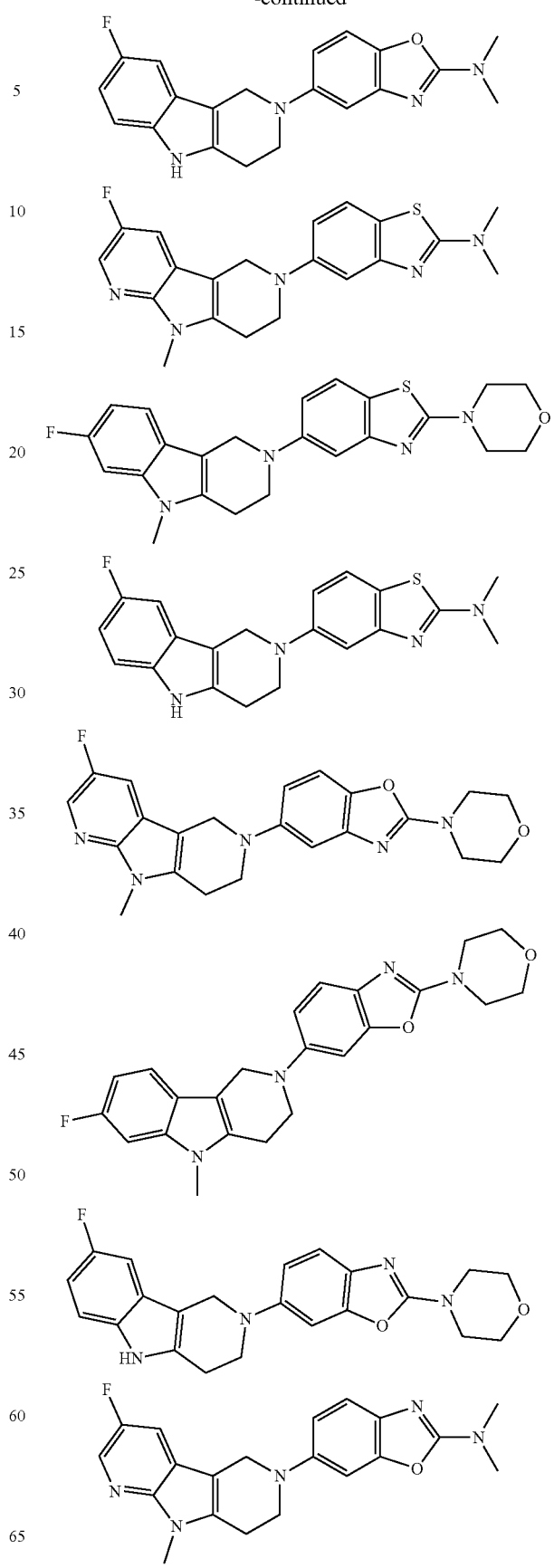

-continued
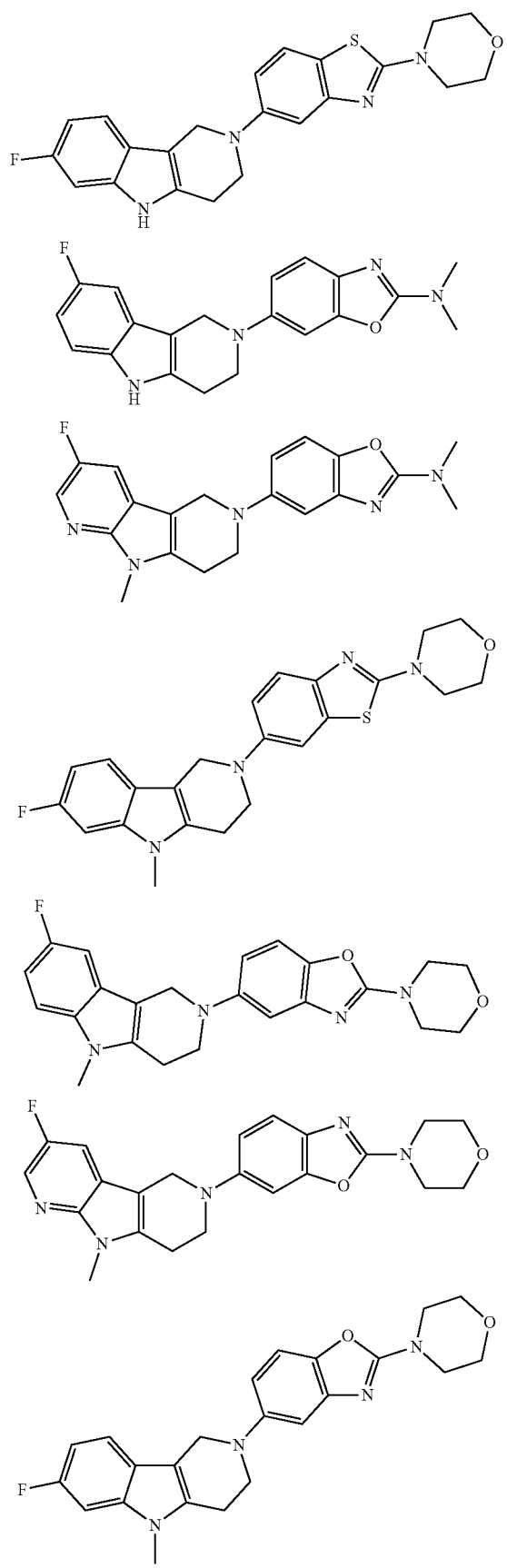
-continued
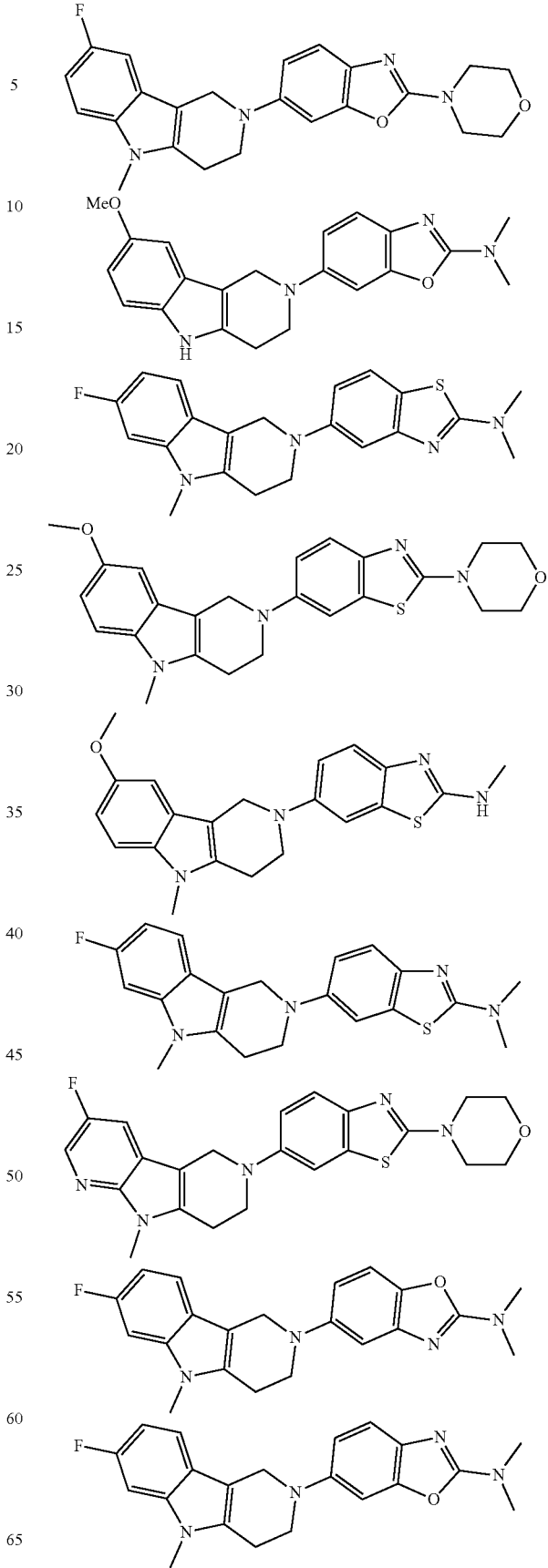

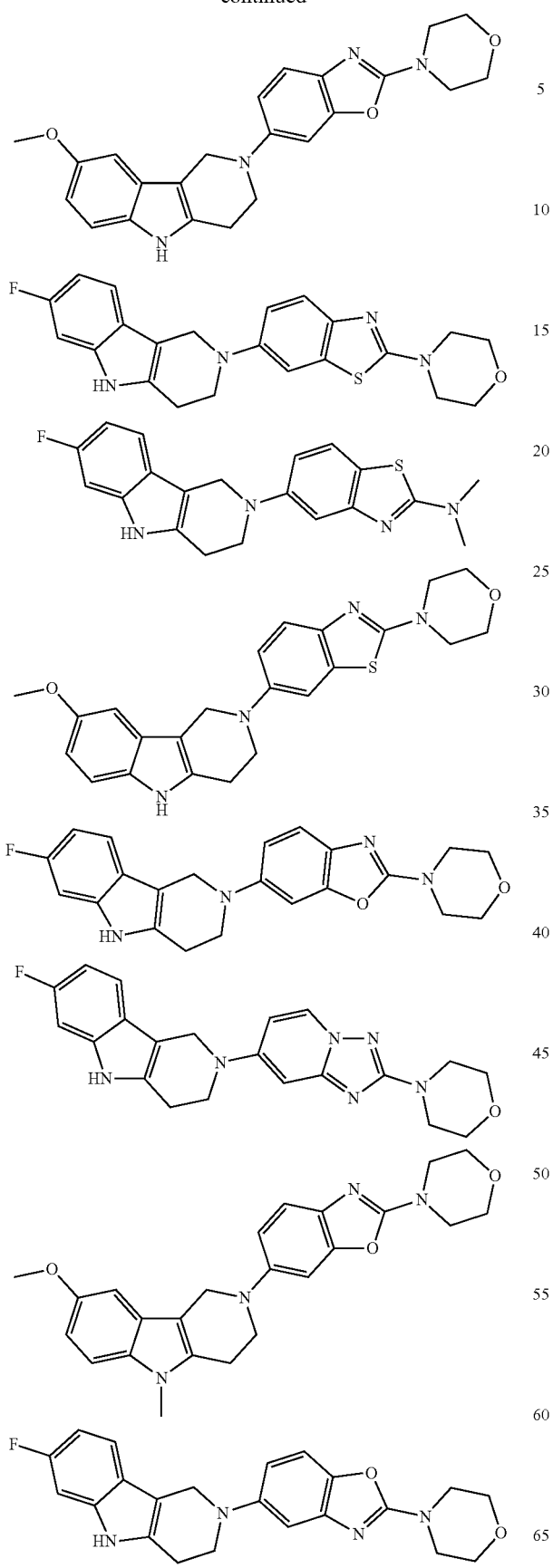
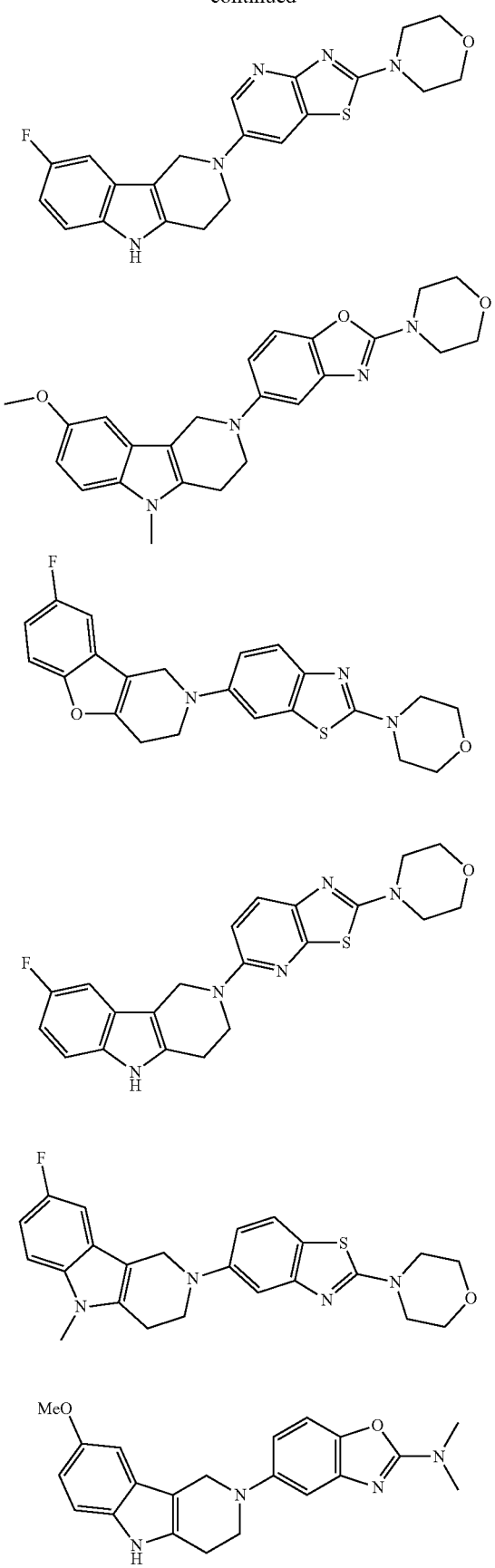

-continued
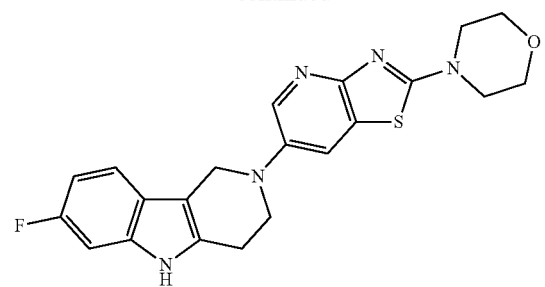
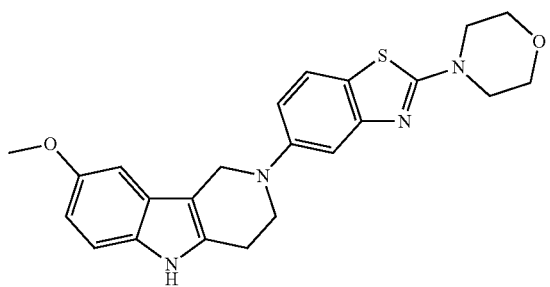 [SMILES: COc1ccc2[nH]c3c(c2c1)CN(c1ccc2sc(N4CCOCC4)nc2c1)CC3]
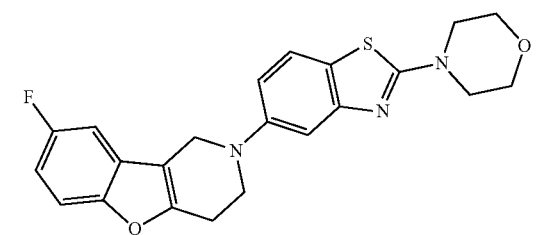
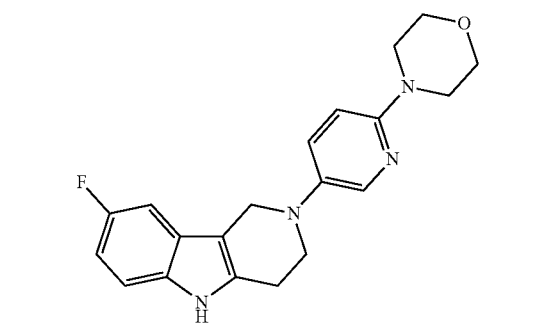
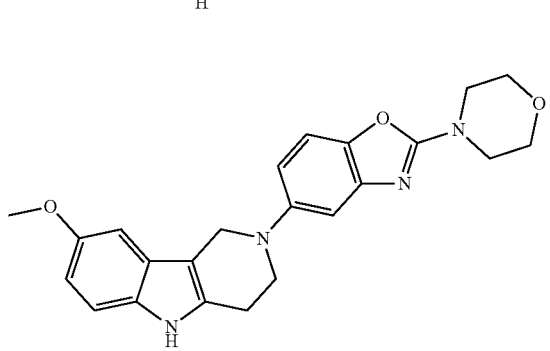
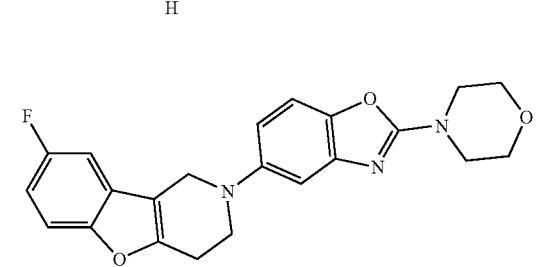
-continued
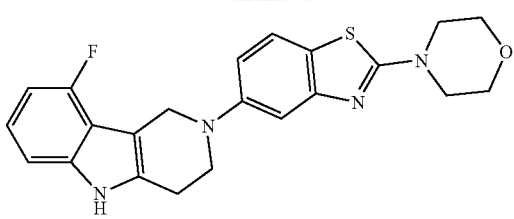 [SMILES: Fc1cccc2[nH]c3c(c12)CN(c1ccc2sc(N4CCOCC4)nc2c1)CC3]
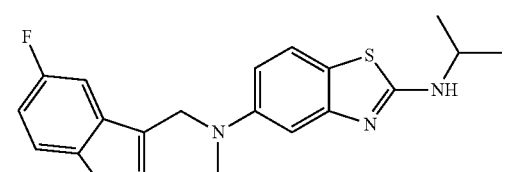
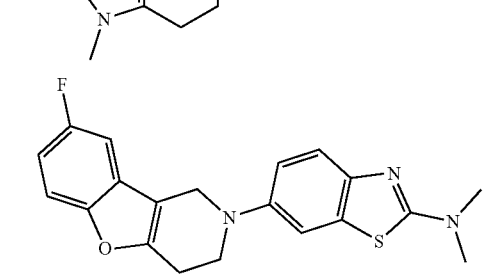
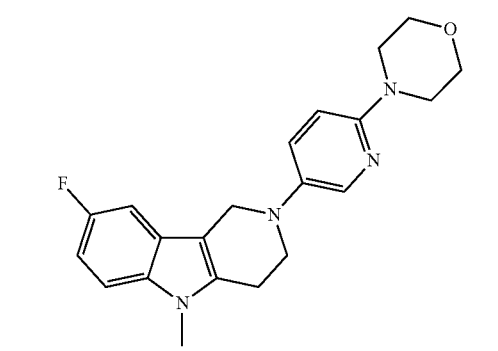 [SMILES: Cn1c2c(c3cc(F)ccc31)CN(c1ccc(N3CCOCC3)nc1)CC2]
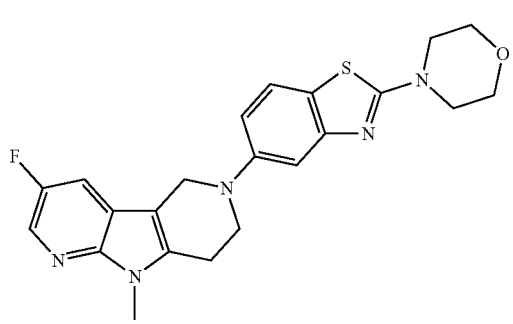
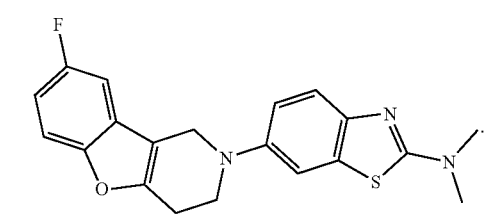

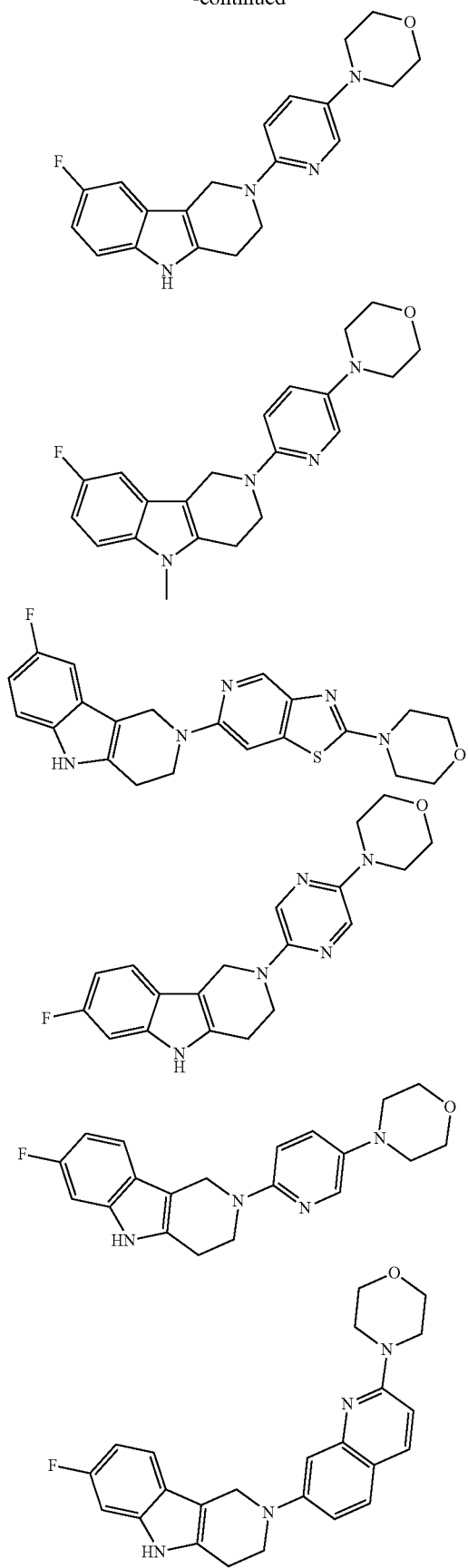
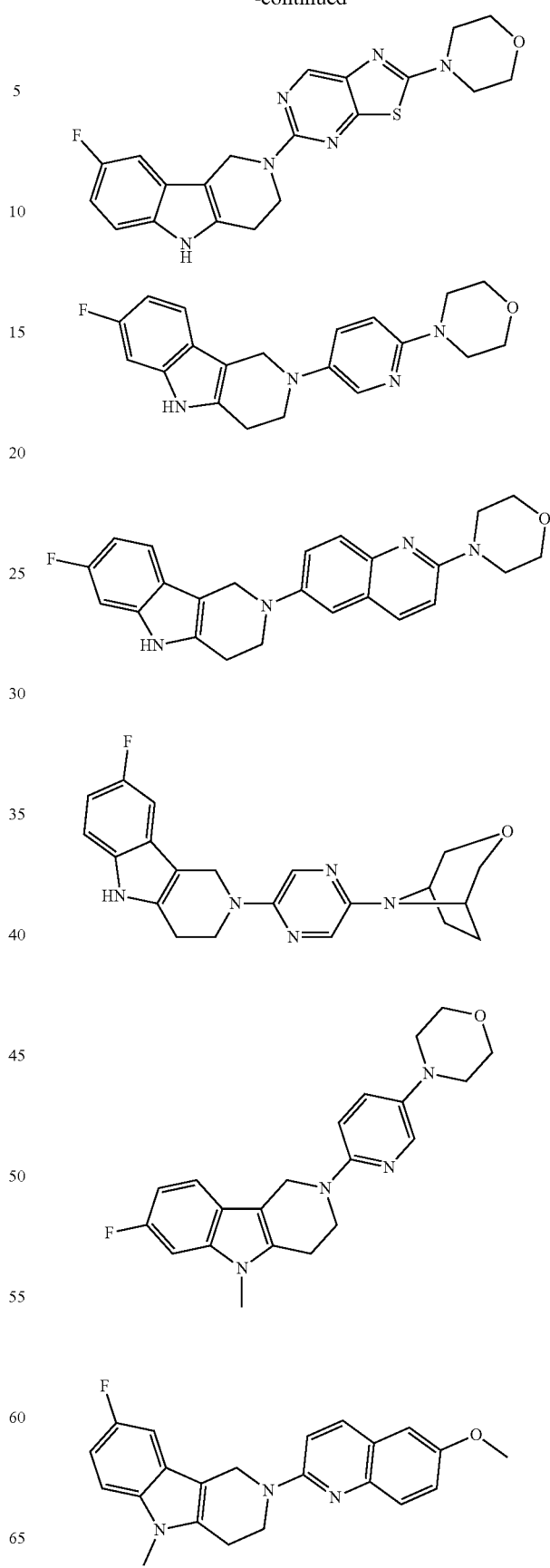

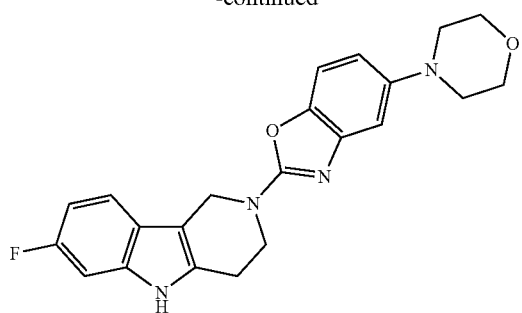
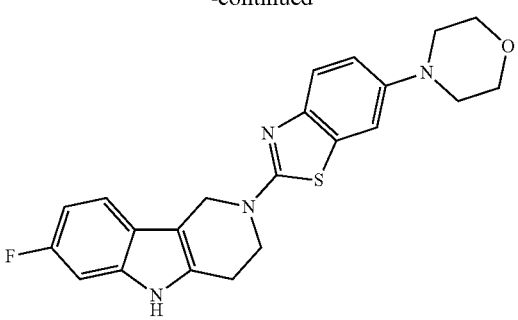
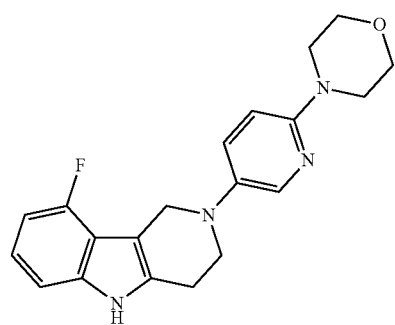 [SMILES: Fc1cccc2[nH]c3c(c12)CN(c1ccc(N2CCOCC2)nc1)CC3]
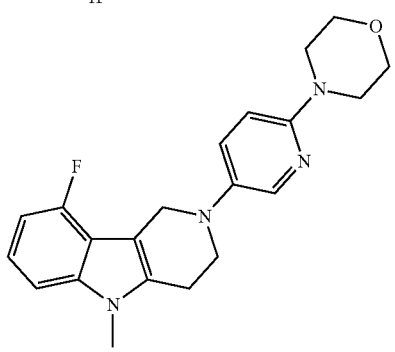
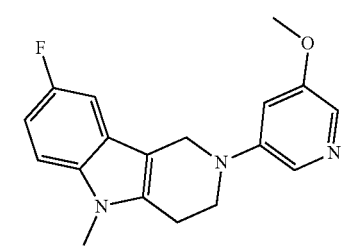
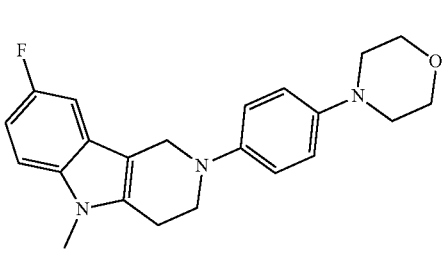
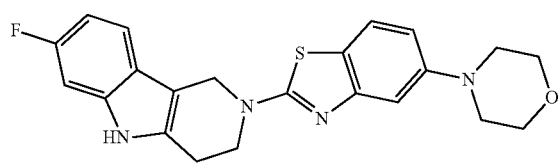
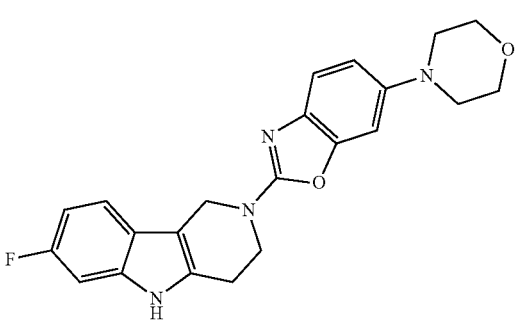
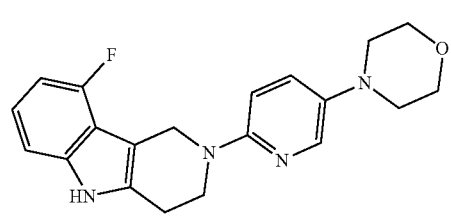
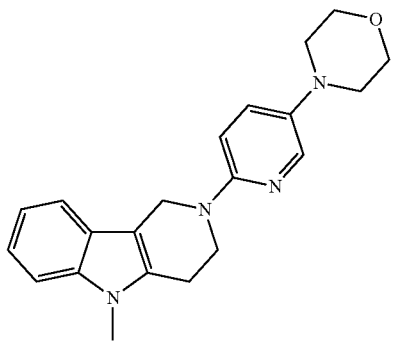 [SMILES: Cn1c2c(c3ccccc31)CN(c1ccc(N3CCOCC3)cn1)CC2]
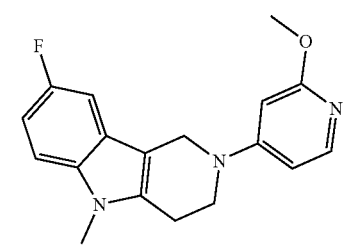 [SMILES: COc1cc(N2CCc3c(c4cc(F)ccc4n3C)C2)ccn1]

-continued
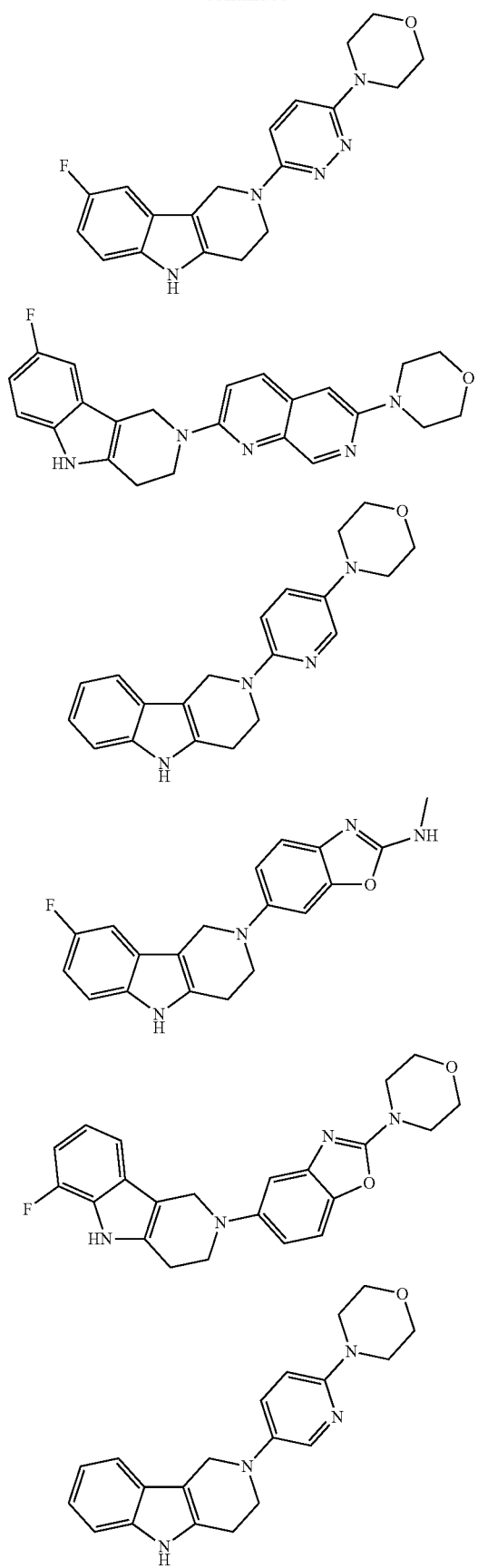
-continued
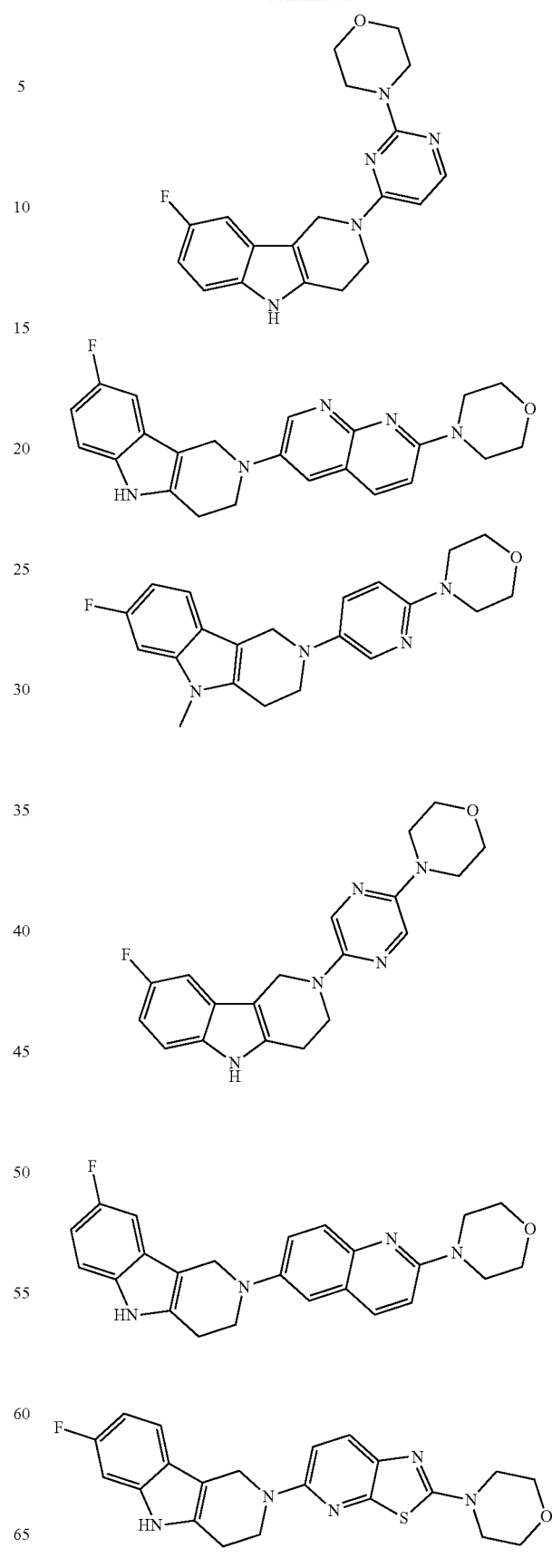

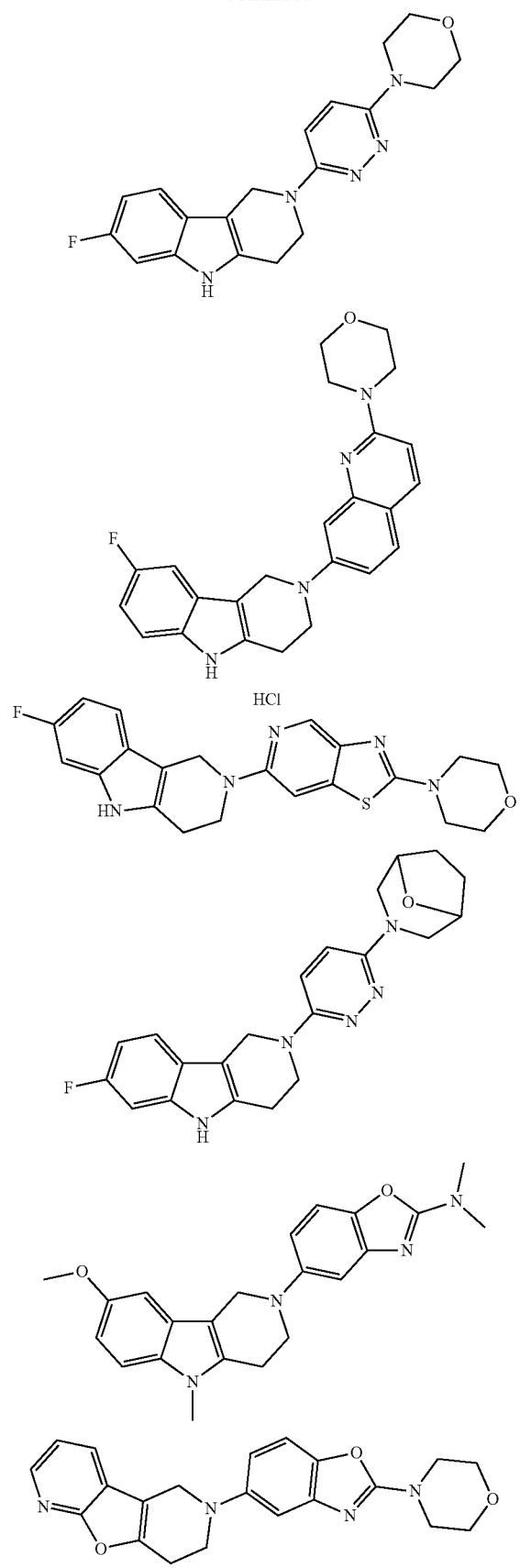
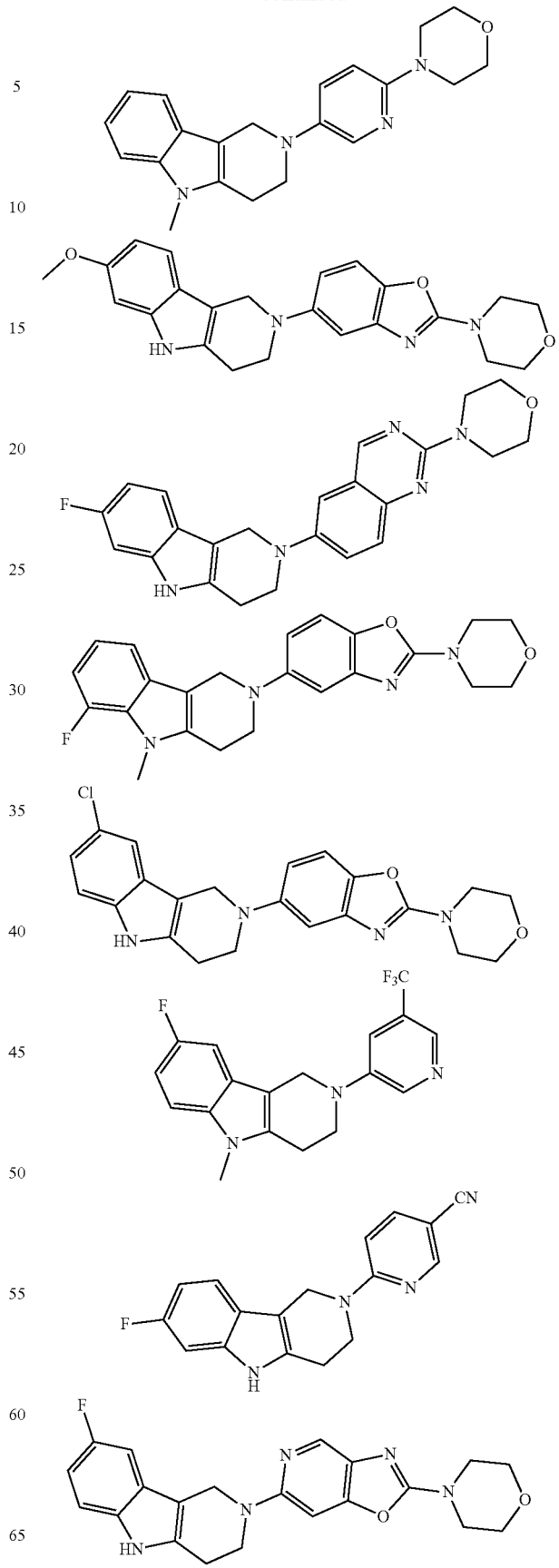

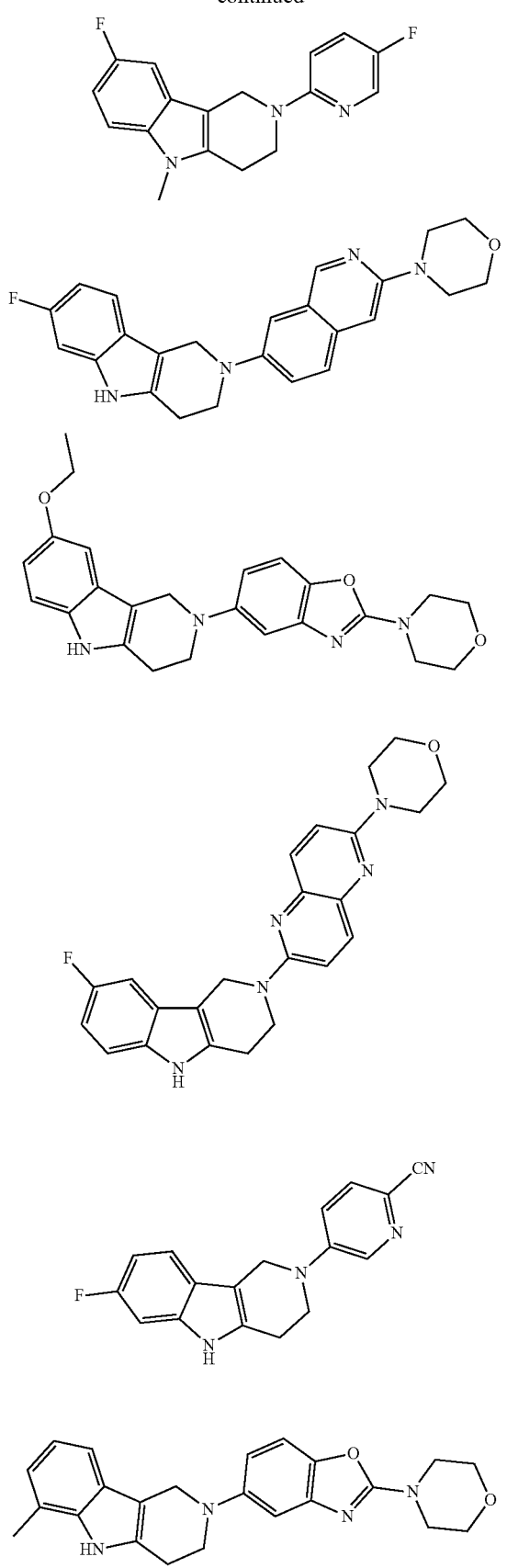
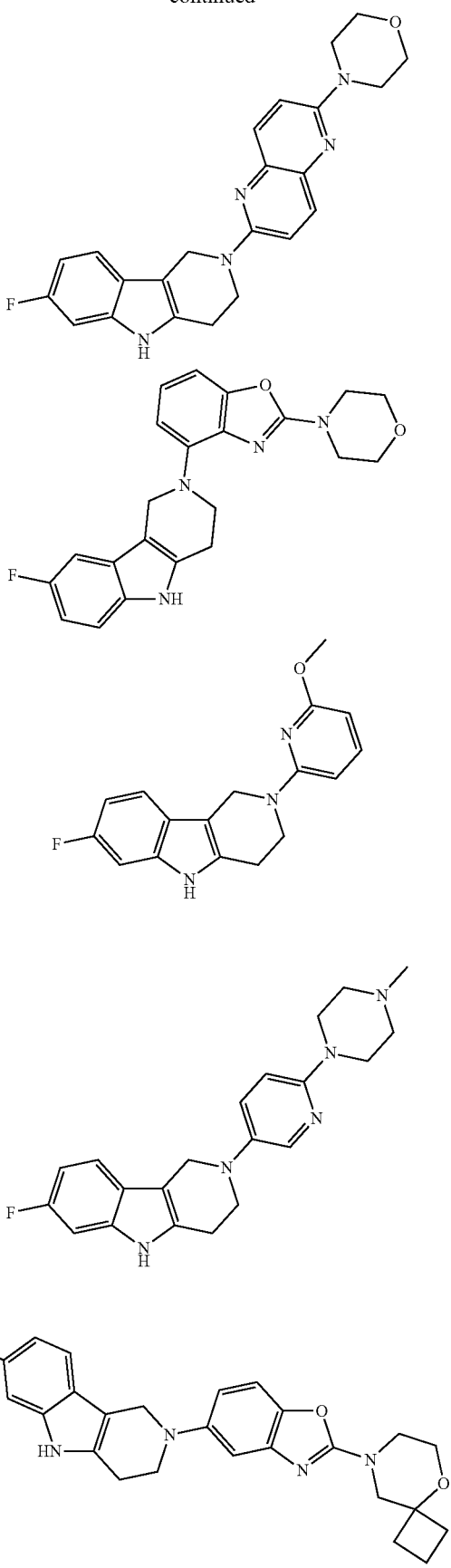

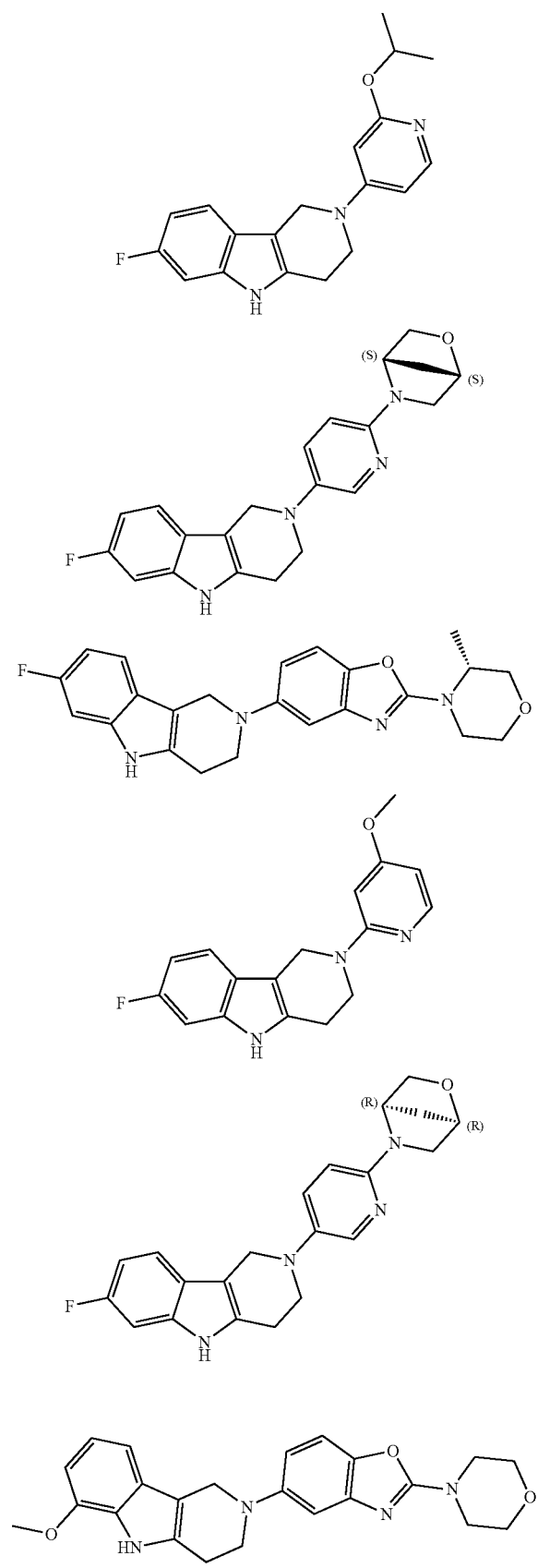
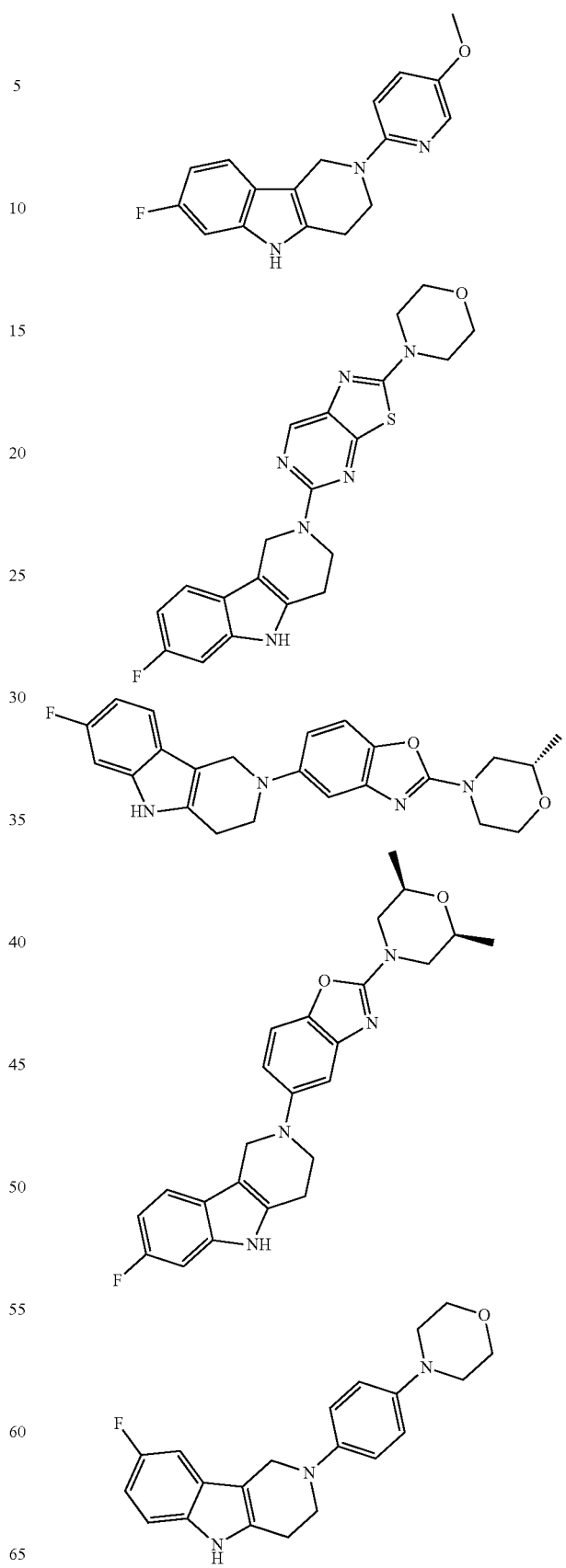

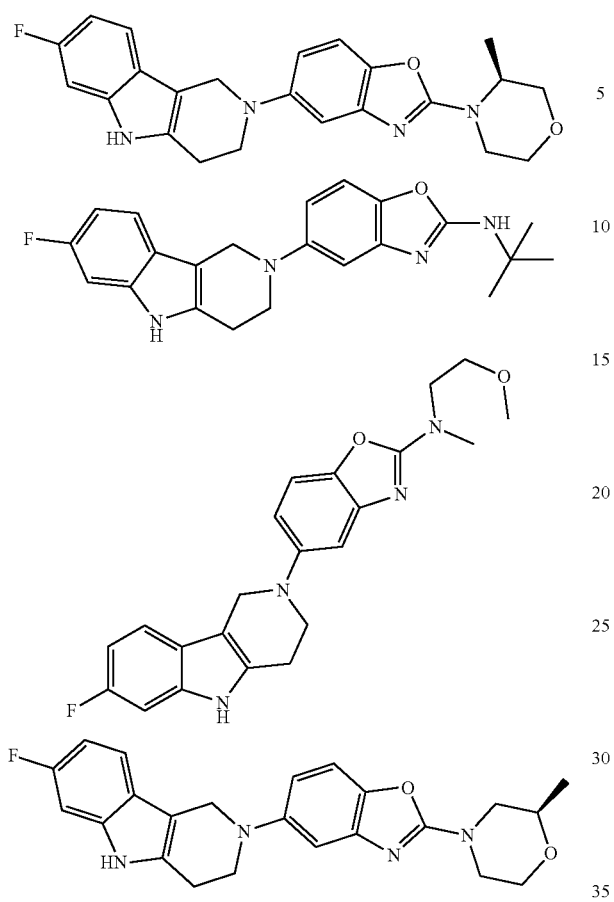
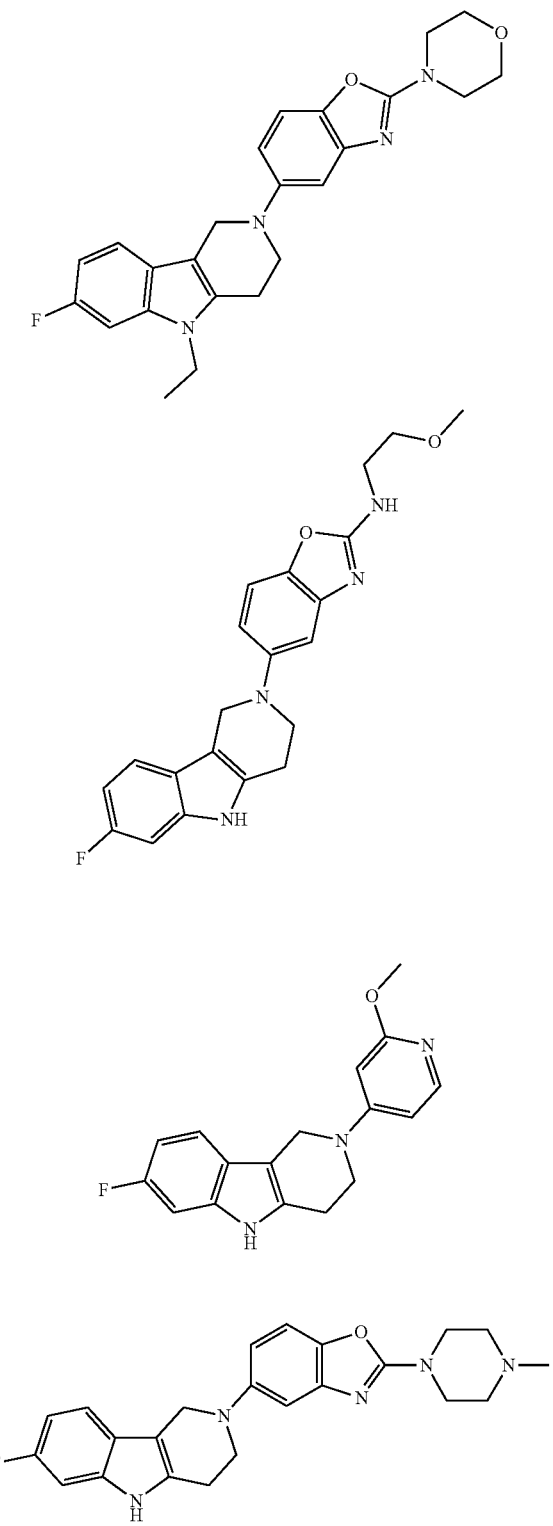
9. A pharmaceutical composition comprising a compound as defined in any one of items 1 to 8 and optionally a pharmaceutically acceptable carrier or excipient.
10. The compound as defined in any one of items 1 to 8 for use as a medicament.

11. A compound of formula (I):

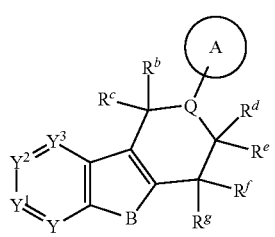

and all stereoisomers, racemic mixtures, tautomers, pharmaceutically acceptable salts, prodrugs, hydrates, solvates and polymorphs thereof;
for use in the treatment, alleviation or prevention of a disorder or abnormality associated with Tau protein aggregates,
wherein
A is selected from the group consisting of

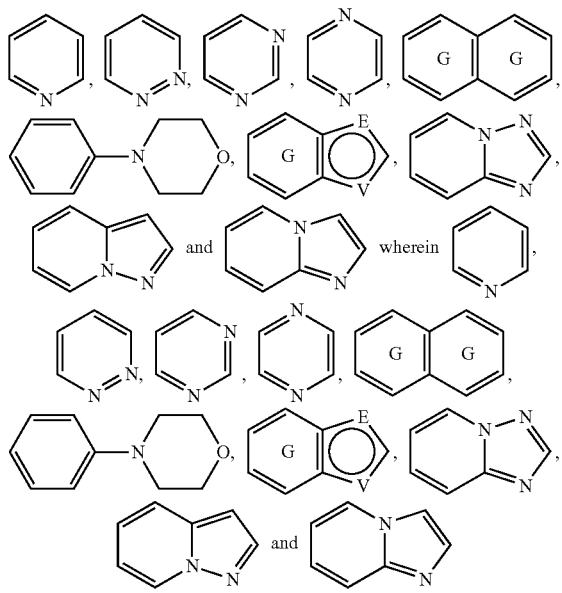

can be attached to Q at any available position, wherein

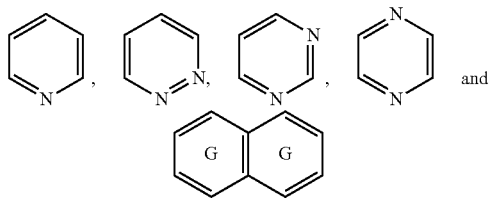

is substituted by one or more substituents $R^j$, and wherein

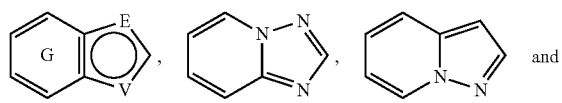

can be optionally substituted by one or more substituents R;
B is selected from the group consisting of O and $NR^a$;
E and V are independently selected from the group consisting of N, $NR^5$, O and S;
G is selected from the group consisting of a benzene ring, a pyrimidine ring and a pyridine ring;
J is selected from the group consisting of O and N—$R^1$;
Q is selected from the group consisting of N and C—$R^1$;
Y is selected from the group consisting of CZ and N;
$Y^1$ is selected from the group consisting of CZ and N;
$Y^2$ is selected from the group consisting of CZ and N;
$Y^3$ is selected from the group consisting of CZ and N;
Z is independently selected from the group consisting of H, halogen, O-alkyl, alkyl and CN;
R is independently selected from the group consisting of

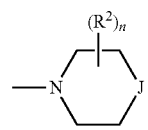

and —$NR^3R^4$;
$R^a$ is selected from the group consisting of H and alkyl;
$R^b$, $R^c$, $R^d$, $R^e$, $R^f$, and $R^g$ are independently selected from the group consisting of H and alkyl, or any two of $R^b$, $R^c$, $R^d$, $R^e$, $R^f$, and $R^g$ may be joined to form a 3 to 8-membered ring;
$R^j$ is independently selected from the group consisting of -halogen, —O-alkyl, —$CF_3$, —CN, —$NR^3R^4$,

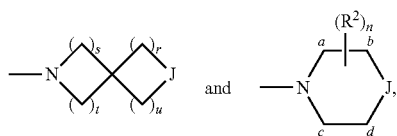

wherein a $C_{1-2}$ carbon atom-containing bridge can be present between the a carbon atom and the c or d carbon atom or wherein a $C_{1-2}$ carbon atom-containing bridge can be present between the b carbon atom and the c or d carbon atom;
$R^1$ is selected from the group consisting of H and alkyl;
$R^2$ is independently selected from the group consisting of alkyl, F and =O, wherein the alkyl can be optionally substituted by halogen, —OH or —O-alkyl and wherein if two $R^2$ are geminal they can be joined to form a 3 to 6-membered ring;
$R^3$ and $R^4$ are independently selected from the group consisting of H and alkyl, wherein the alkyl can be optionally substituted by halogen, —OH or —O-alkyl;
$R^5$ is selected from the group consisting of H and alkyl;
n is 0, 1, 2, 3 or 4;
r and s are independently 0, 1, 2 or 3; and
t and u are independently 1, 2 or 3.

12. The compound for use according to item 11, wherein the compound of formula (I) is as defined in any one of items 1 to 8.

13. The compound as defined in any one of items 1 to 8 or 11 for use in decreasing Tau aggregation.
14. The compound as defined in any one of items 1 to 8 or 11 for use in preventing the formation of Tau aggregates and/or for use in inhibiting Tau aggregation.
15. The compound as defined in any one of items 1 to 8 or 11 for use in interfering intracellularly with Tau aggregates.
16. The compound as defined in any one of items 1 to 8 or 11 for use in reducing Tau misfolding and hyperphosphorylation in vivo.
17. The compound as defined in any one of items 1 to 8 or 11 for use in reducing neuroinflammatory markers.
18. A method of treating, preventing or alleviating a disorder or abnormality associated with Tau protein aggregates, the method comprising administering an effective amount of a compound as defined in any one of items 1 to 8 or 11 to a subject in need thereof.
19. A method of decreasing Tau aggregation, the method comprising administering an effective amount of a compound as defined in any one of items 1 to 8 or 11 to a subject in need thereof.
20. A method of preventing the formation of Tau aggregates and/or of inhibiting Tau aggregation, the method comprising administering an effective amount of a compound as defined in any one of items 1 to 8 or 11 to a subject in need thereof.
21. A method of interfering intracellularly with Tau aggregates, the method comprising administering an effective amount of a compound as defined in any one of items 1 to 8 or 11 to a subject in need thereof.
22. A method of reducing Tau misfolding and hyperphosphorylation in vivo, the method comprising administering an effective amount of a compound as defined in any one of items 1 to 8 or 11 to a subject in need thereof.
23. A method of reducing neuroinflammatory markers, the method comprising administering an effective amount of a compound as defined in any one of items 1 to 8 or 11 to a subject in need thereof.
24. The use of a compound as defined in any of items 1 to 8 or 11 in the manufacture of a medicament for treating, preventing or alleviating a disorder or abnormality associated with Tau protein aggregates.
25. The use of a compound as defined in any of items 1 to 8 or 11 in the manufacture of a medicament for decreasing Tau aggregation.
26. The use of a compound as defined in any of items 1 to 8 or 11 in the manufacture of a medicament for preventing the formation of Tau aggregates and/or for use in inhibiting Tau aggregation.
27. The use of a compound as defined in any of items 1 to 8 or 11 in the manufacture of a medicament for interfering intracellularly with Tau aggregates.
28. The use of a compound as defined in any of items 1 to 8 or 11 in the manufacture of a medicament for reducing Tau misfolding and hyperphosphorylation in vivo.
29. The use of a compound as defined in any of items 1 to 8 or 11 in the manufacture of a medicament for reducing neuroinflammatory markers.
29. A mixture comprising a compound as defined in any one of items 1 to 8 and at least one further biologically active compound selected from a therapeutic agent different from the compound as defined in any one of items 1 to 8, wherein the mixture further comprises at least one of a pharmaceutically acceptable carrier, a diluent and an excipient.
30. The mixture according to item 29, wherein the further biologically active compound is a compound used in the treatment of amyloidosis.
31. The mixture according to item 29 or 30, wherein the compound and/or the further biologically active compound is/are present in a therapeutically effective amount.
32. The mixture according to any of items 29 to 31, wherein the further biologically active compound is selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, glycogen synthase kinase 3 inhibitors, O-glcnacase (OGA) inhibitors, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof or a vaccine.
33. The mixture according to item 32, wherein the further biologically active compound is a cholinesterase inhibitor (ChEI).
34. The mixture according to item 32, wherein the further biologically active compound is selected from the group consisting of tacrine, rivastigmine, donepezil, galantamine, niacin and memantine.
35. The mixture according to item 32, wherein the further biologically active compound is an antibody, particularly a monoclonal antibody, including any functionally equivalent antibody or functional parts thereof.
36. The mixture according to any one of items 29 to 35, wherein the compound and/or the further biologically active compound is/are present in a therapeutically effective amount.
37. The compound for use according to item 11, the method according to item 18, or the use according to item 24, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallidoponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease, preferably Alzheimer's disease (AD), corticobasal degeneration (CBD), Pick's disease (PiD), and progressive supranuclear palsy (PSP).

38. Use of the compound as defined in any of items 1 to 8 or 11 as an analytical reference or an in vitro screening tool.

DEFINITIONS

Within the meaning of the present application the following definitions apply:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl and isobutyl. Alkyl can be optionally substituted by a halogen (preferably F), —OH or —Oalkyl (preferably —OMe).

"Hal" or "halogen" refers to F, Cl, Br, and I.

"3- to 8-membered ring" refers to a three-, four-, five-, six-, seven- or eight-membered ring wherein none, one or more of the carbon atoms in the ring have been replaced by 1 or 2 (for the three-membered ring), 1, 2 or 3 (for the four-membered ring), 1, 2, 3, or 4 (for the five-membered ring) or 1, 2, 3, 4, or 5 (for the six-membered ring) 1, 2, 3, 4, 5 or 6 (for the seven-membered ring), or 1, 2, 3, 4, 5, 6 or 7 (for the eight-membered ring) of the same or different heteroatoms, whereby the heteroatoms are selected from O, N and S.

Compounds of the present invention having one or more optically active carbons can exist as racemates and racemic mixtures (including mixtures in all ratios), stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all pharmaceutically acceptable salts, prodrugs, polymorphs, hydrates and solvates.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph.

Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric acid and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, $18^{th}$ ed., Mack Publishing Company, Easton, Pa., 1990, p. 1445, the disclosure of which is hereby incorporated by reference.

The compounds of the present invention can also be provided in the form of a prodrug, namely a compound which is metabolized in vivo to the active metabolite. As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

"Tau" as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitination, sumoylation and oxidation.

"Aggregated Tau" refers to aggregated monomers of Tau peptides or proteins which are folded into the oligomeric or polymeric structures.

"Neurofibrillary Tangles" (NFTs) as used herein refer to insoluble aggregates of the hyperphosphorylated Tau protein containing paired helical filaments (PHF) and straight filaments. Their presence is a hallmark of AD and other diseases known as tauopathies.

The terms "antibody" or "antibodies" as used herein is an art recognized term and is understood to refer to molecules or active fragments of molecules that bind to known antigens, or refer particularly to immunoglobulin molecules and to antigen binding portions of immunoglobulin molecules. In particular the mixture of the present invention includes the compounds of the present invention and anti Tau or anti Abeta antibodies.

The term "functional equivalent antibody or functional part thereof" as used herein is understood to refer to an equivalent molecule or active fragments of a molecule that binds to a known antigen, or refer particularly to an immunoglobulin molecule and to antigen binding portions of an immunoglobulin molecule and has essentially the same (biological) activity as the antibody from which it is derived.

The "vaccine" or "vaccines" reported in the mixtures of the present invention, are in particular Tau or Abeta vaccines.

The definitions and preferred definitions given in the "Definition"-section apply to all of the embodiments described below unless stated otherwise.

DETAILED DESCRIPTION OF THE INVENTION

Figure 1:
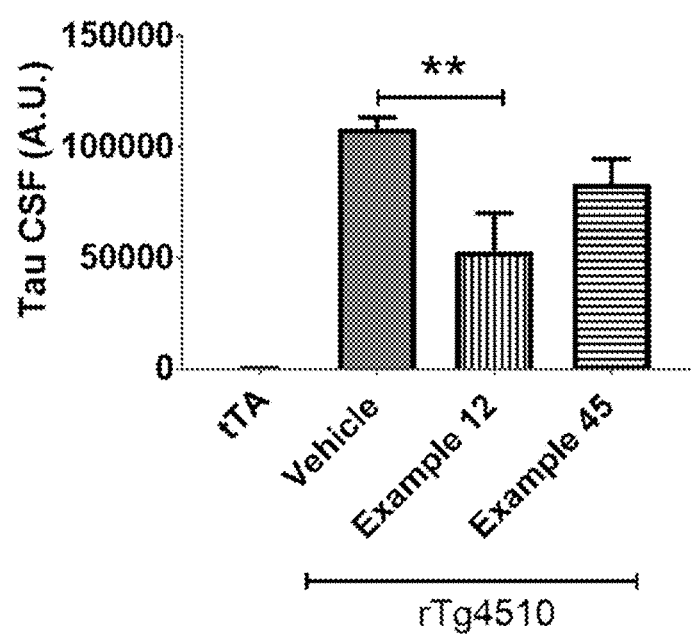
FIG. 1: Tau in CSF quantified in rTg4510 mice treated with Example 12 and Example 45.

The compounds of the present invention will be described in the following. It is to be understood that all possible combinations of the following definitions are also envisaged.

In one embodiment, the present invention relates to a compound of formula (I):

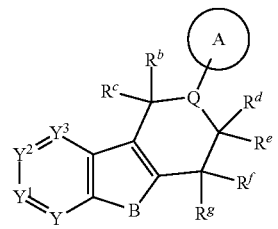

(I)

and all stereoisomers, racemic mixtures, tautomers, pharmaceutically acceptable salts, prodrugs, hydrates, solvates and polymorphs thereof.

A preferred embodiment of the compound of formula (I) is

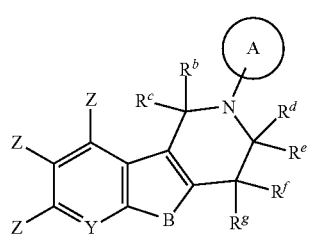

(Ia)

A further preferred embodiment of the compound of formula (I) is

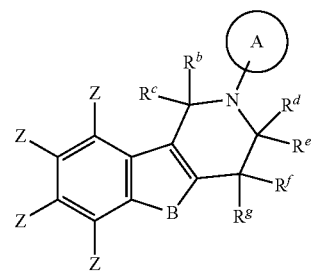

(Ib)

A further preferred embodiment of the compound of formula (I) is

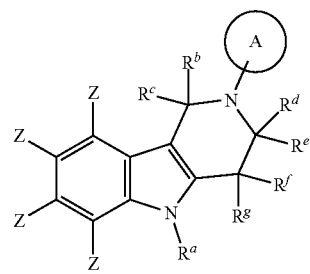

In a further preferred embodiment the compound of formula (I) is

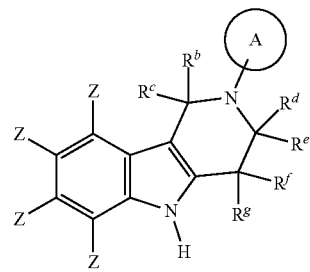

Even more preferably the compound of formula (I) is

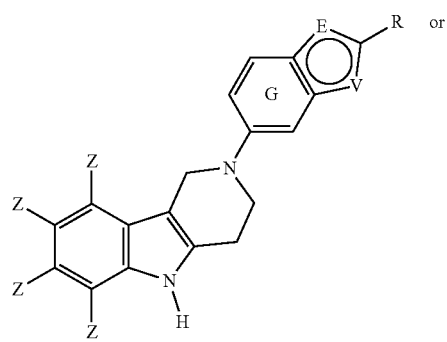

-continued

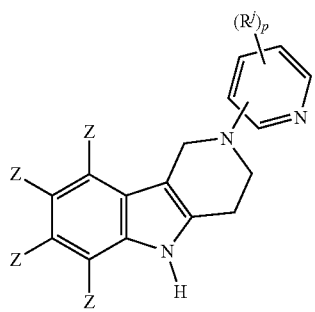
(Id)

Even more preferably

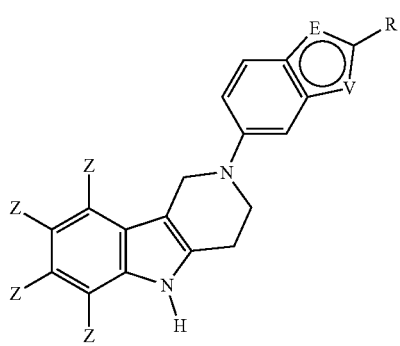
(Ic)

The following definitions of A apply to the compounds of formula (I) and its preferred embodiments.
A is selected from the group consisting of

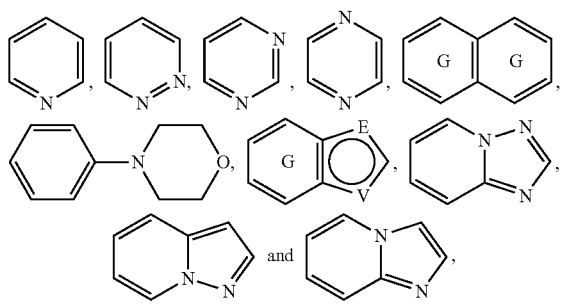

wherein G is selected from a benzene ring, a pyrimidine ring and a pyridine ring. Therefore

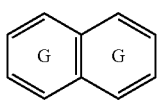

covers the following preferred embodiments

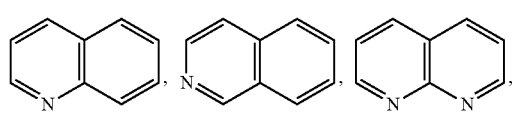

-continued

And therefore,

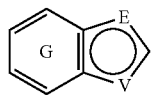

covers the following embodiments

In a preferred embodiment,

is selected from and

The following rings can be envisaged:

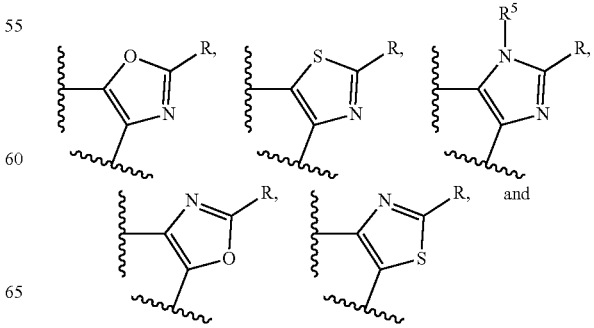

-continued

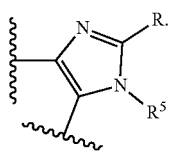

Preferred embodiments include

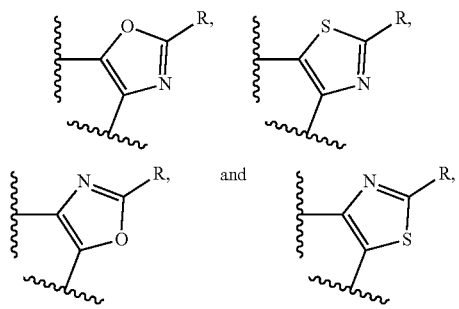

In these structural formulae the ring G is not completely shown but is only indicated by the partial bonds

In one preferred embodiment, A is selected from

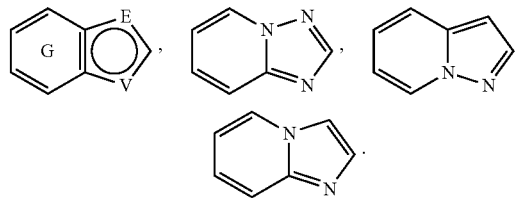

In another preferred embodiment, A is

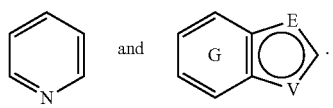

In one preferred embodiment, A is

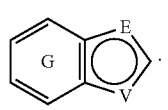

In a more preferred embodiment, A is selected from

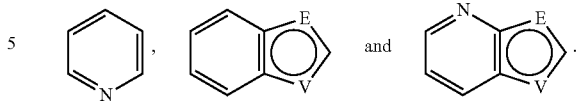

In a more preferred embodiment, A is selected from

In a further preferred embodiment, A is selected from

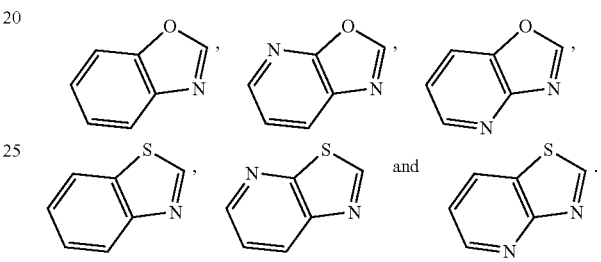

In an even more preferred embodiment, A is

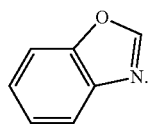

In the above definitions of A and the preferred embodiments thereof,

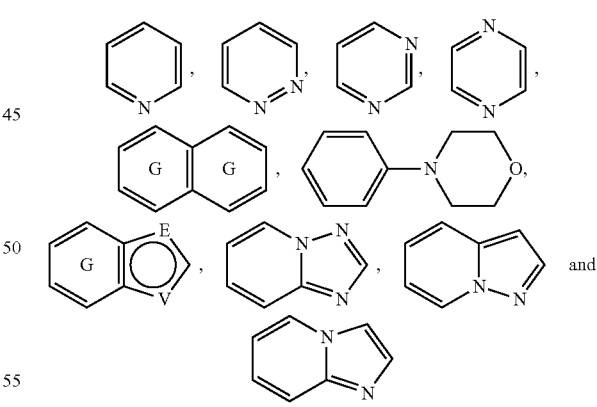

can be attached to Q at any available position.

In the above definitions of A and the preferred embodiments thereof,

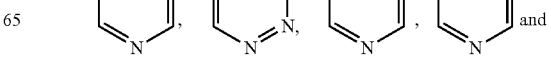

-continued

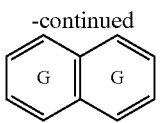

is substituted by one or more substituents R$^j$.

In the above definitions of A and the preferred embodiments thereof,

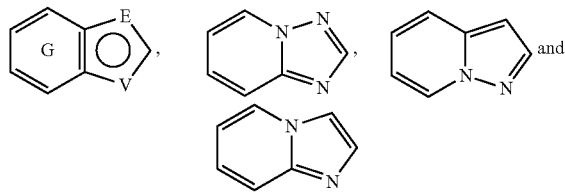

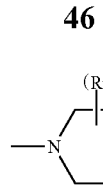

can be optionally substituted by one or more substituents R.

The following definitions apply to the formula (I) and their preferred embodiments, as appropriate.

B is selected from the group consisting of O and NR$^a$. More preferably B is NR$^a$, most preferably NH.

E and V are independently selected from the group consisting of N, NR$^5$, O and S. Since the ring containing E and V is unsaturated, at least one of E and V is N.

J is selected from the group consisting of O and N—R$^1$, more preferably O.

Q is selected from the group consisting of N and C—R$^1$. Preferably Q is selected from the group consisting of N and CH, more preferably Q is N.

Y is selected from the group consisting of CZ and N. More preferably Y is selected from the group consisting of CH and N. Even more preferably Y is CH. In one embodiment, if Y is N and Y$^1$, Y$^2$ and Y$^3$ are CZ, B is N-alkyl or O, preferably B is N-alkyl.

Y$^1$ is selected from the group consisting of CZ and N. Preferably Y$^1$ is CZ.

Y$^2$ is selected from the group consisting of CZ and N. Preferably Y$^2$ is CZ.

Y$^3$ is selected from the group consisting of CZ and N. Preferably Y$^3$ is CZ.

Z is independently selected from the group consisting of H, halogen (preferably F), O-alkyl, alkyl and CN, preferably H, halogen (preferably F), and O-alkyl. In one preferred embodiment, one Z is independently halogen (preferably F), or O-alkyl and the other Z are H. In a more preferred embodiment, one Z is halogen (preferably F) and the other Z are H.

R is independently selected from the group consisting of

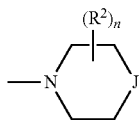

and —NR$^3$R$^4$, preferably R is selected from the group consisting of

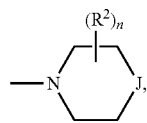

and —NR$^3$R$^4$, more preferably R is

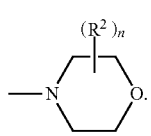

such as

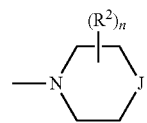

In these embodiments,

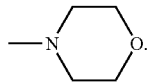

is preferably

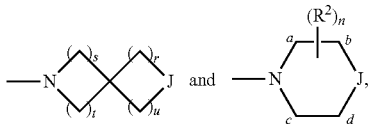

R$^a$ is selected from the group consisting of H and alkyl, more preferably H and Me, even more preferably H.

R$^b$, R$^c$, R$^d$, R$^e$, R$^f$, R$^g$ are independently selected from the group consisting of H and alkyl, or any two of R$^b$, R$^c$, R$^d$, R$^e$, R$^f$, R$^g$ (e.g., which are attached to the same or adjacent ring atoms) may be joined to form a 3 to 8 membered ring. More preferably R$^b$, R$^c$, R$^d$, R$^e$, R$^f$, R$^g$ are independently H or alkyl, even more preferably H.

R$^j$ is independently selected from the group consisting of -halogen, —O-alkyl, —CF$_3$, —CN, —NR$^3$R$^4$, wherein a C$_{1-2}$ carbon atom-containing bridge can be present between the a carbon atom and the c or d carbon atom or wherein a C$_{1-2}$ carbon atom-containing bridge can be present between the b carbon atom and the c or d carbon atom. More preferably R$^j$ is selected from the group consisting of -halogen, —O-alkyl, —NR$^3$R$^4$, and

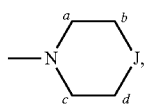

even more preferably R$^j$ is

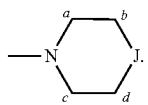

R$^1$ is selected from the group consisting of H and alkyl, preferably alkyl, more preferably CH$_3$.

R$^2$ is independently selected from the group consisting of alkyl, F and =O, wherein the alkyl can be optionally substituted by halogen, —OH or —O-alkyl and wherein if two R$^2$ are geminal they can be joined to form a 3 to 6-membered ring. In one embodiment R$^2$ is optionally substituted alkyl, in another embodiment R$^2$ is F, in a further embodiment R$^2$ is =O.

R$^3$ and R$^4$ are independently selected from the group consisting of H and alkyl, wherein the alkyl can be optionally substituted by halogen, —OH or —O-alkyl. In one embodiment R$^3$ or R$^4$ is optionally substituted alkyl and the other is H. In another embodiment R$^3$ is alkyl and R$^4$ is optionally substituted alkyl. In a further embodiment R$^3$ and R$^4$ are H.

R$^5$ is selected from the group consisting of H and alkyl, in one embodiment R$^5$ is H, in another embodiment R$^5$ is alkyl.

n is 0, 1, 2, 3 or 4, preferably n is 0 or 1, more preferably n is 0.

p is 1 or 2, more preferably 1.

r and s are independently 0, 1, 2 or 3.

t and u are independently 1, 2 or 3.

Preferred compounds of formula (I) are

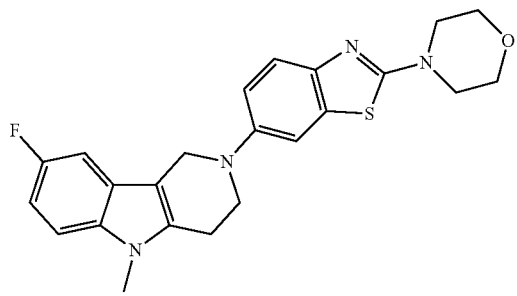

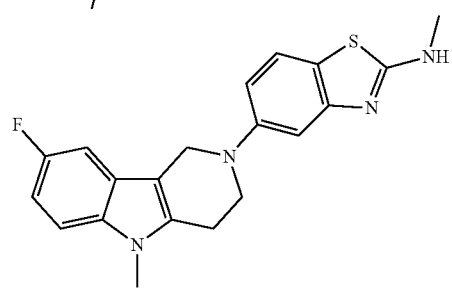

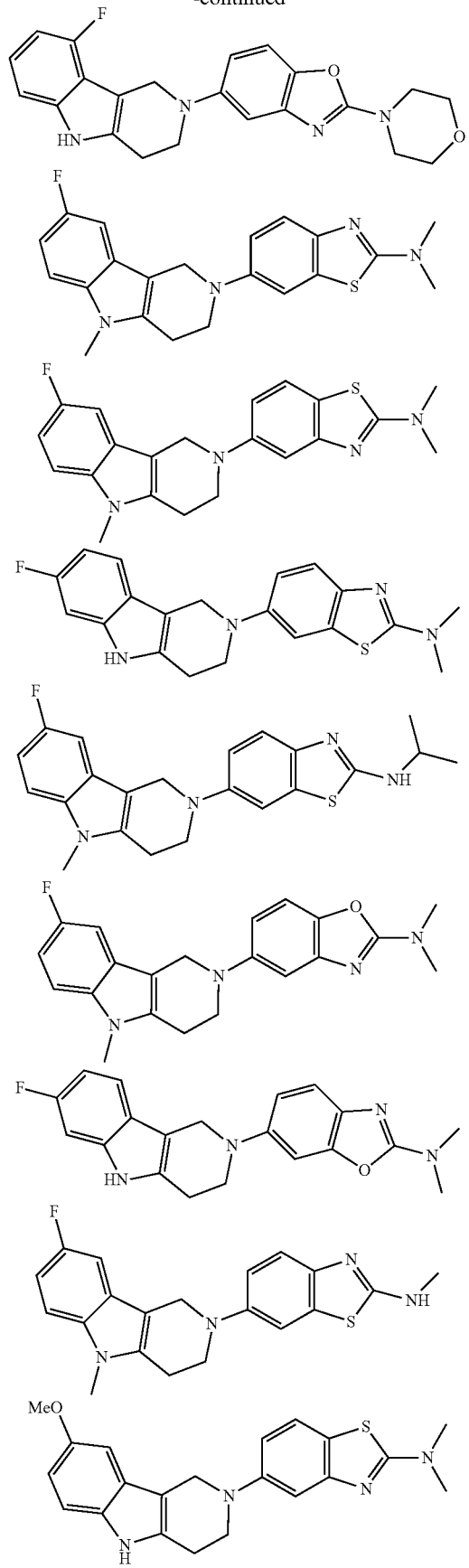

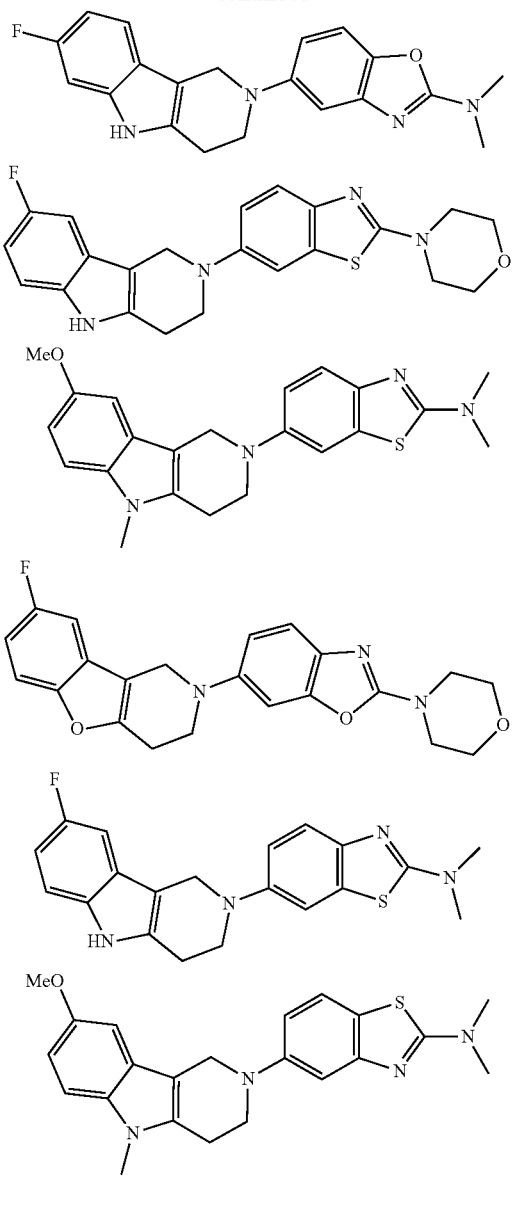
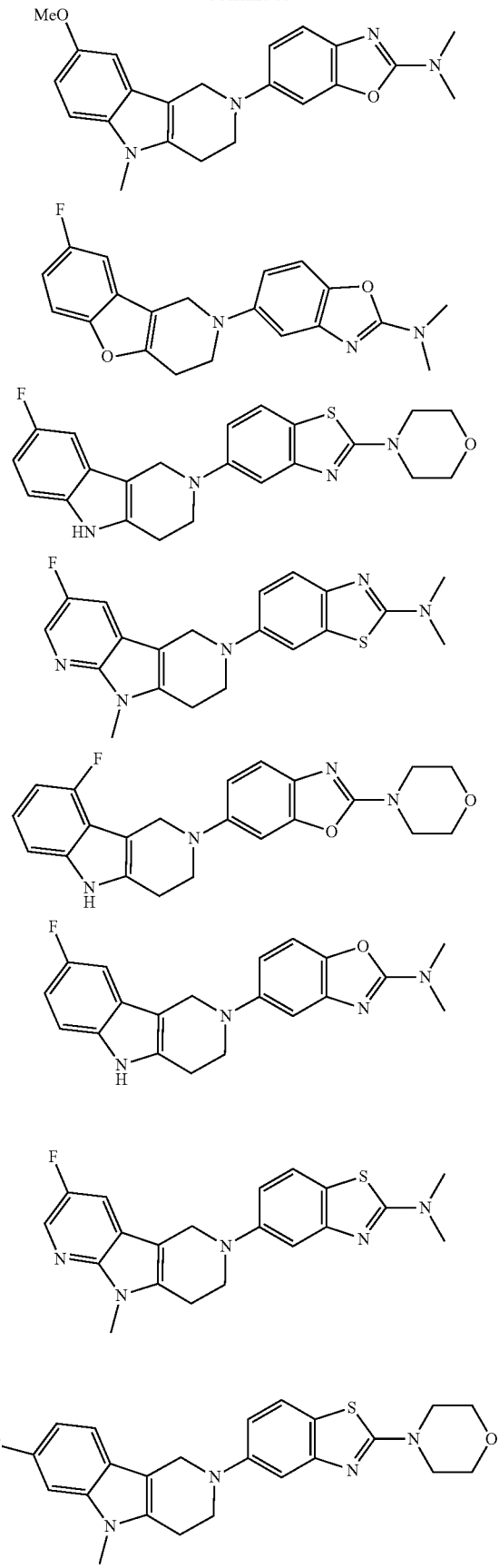

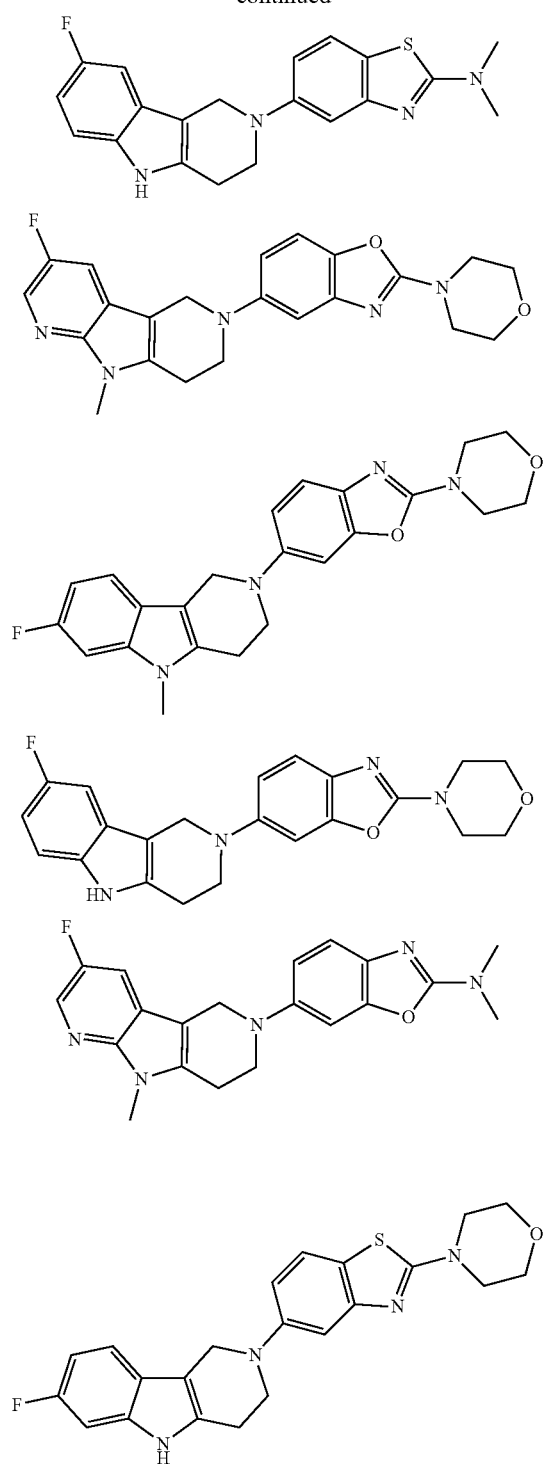
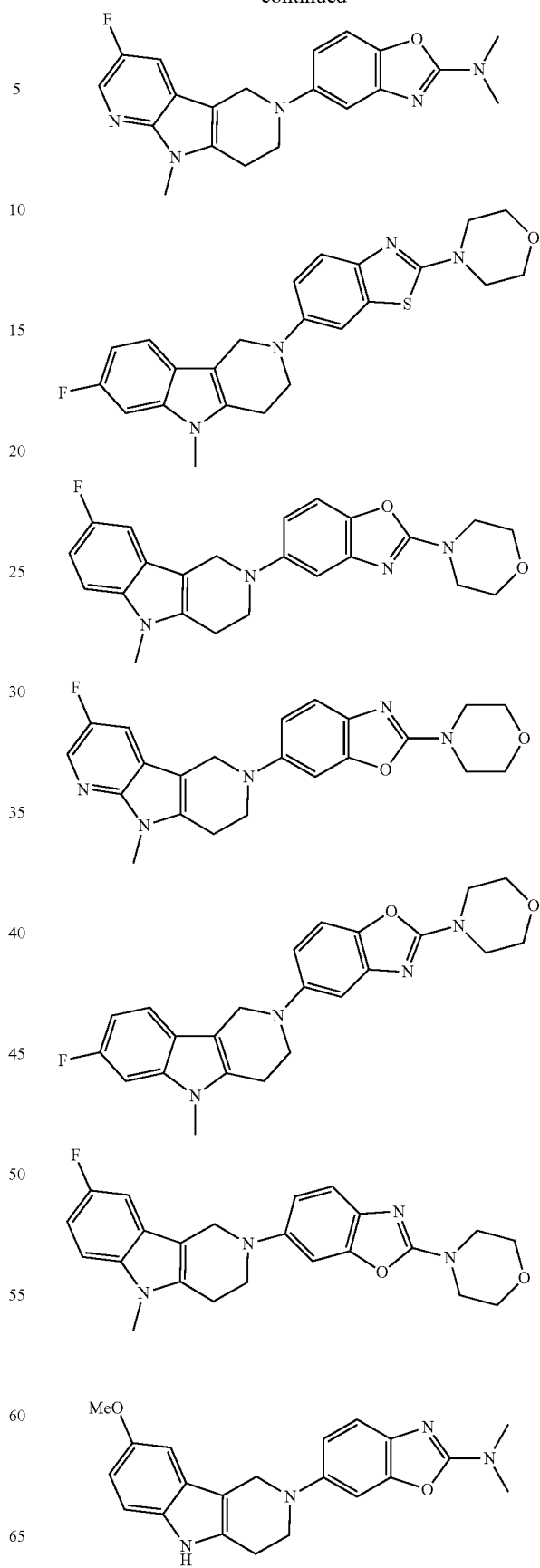

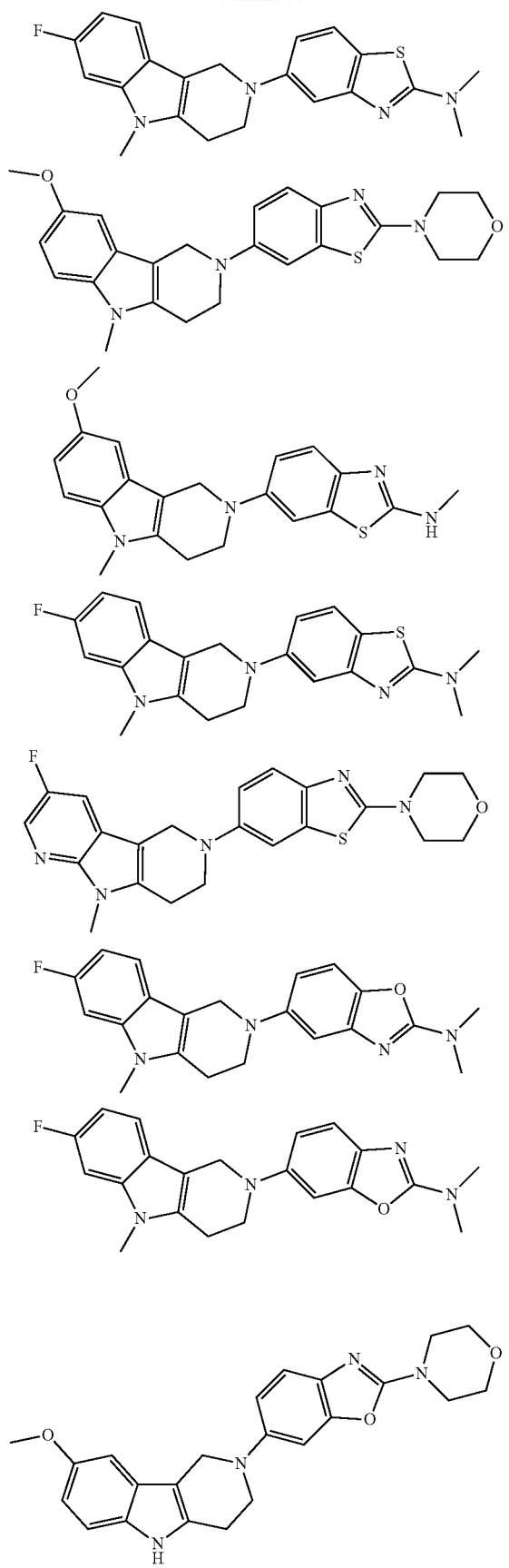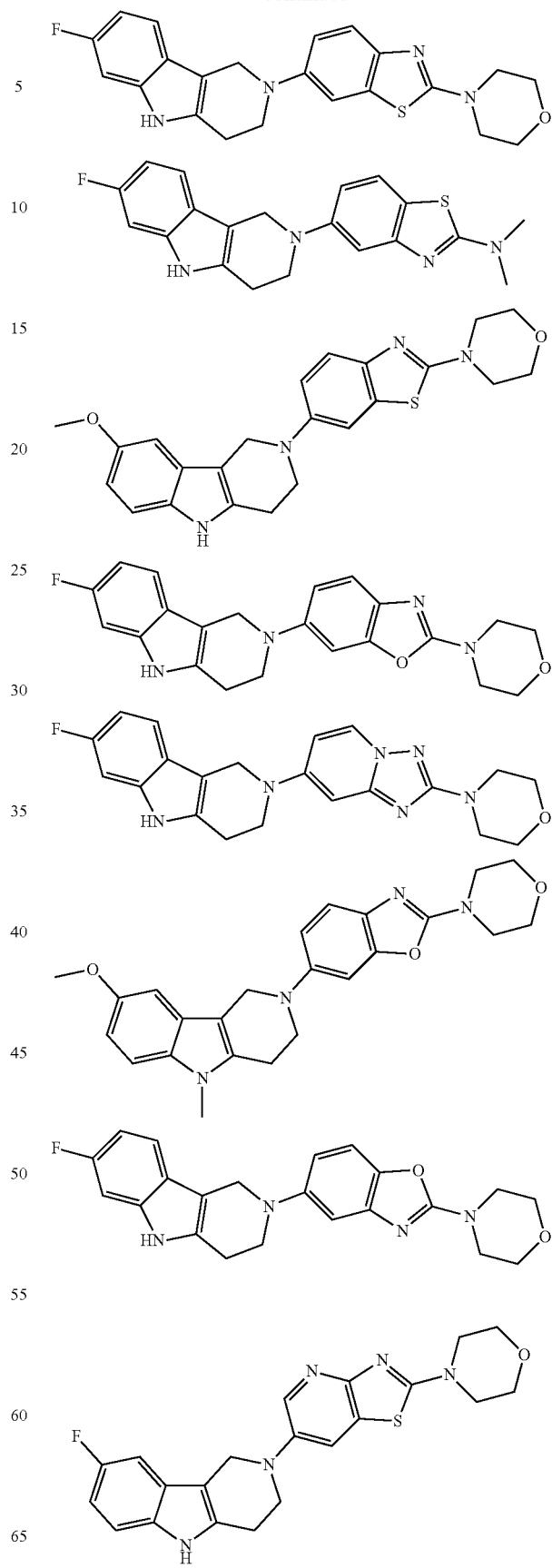

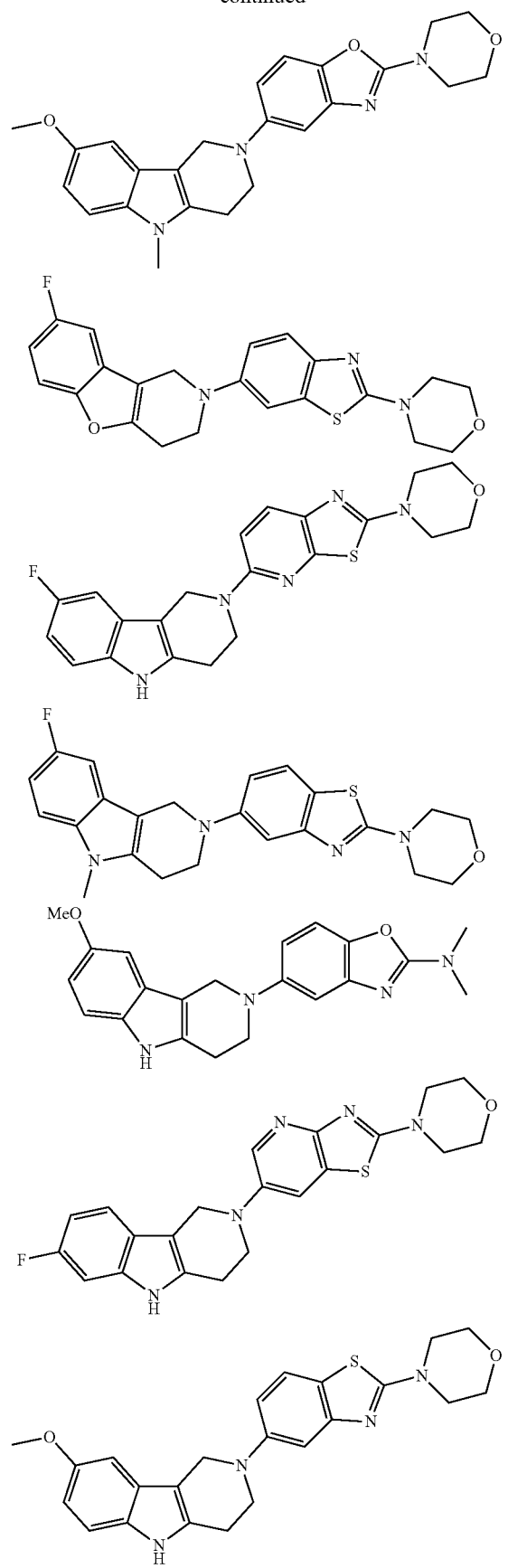
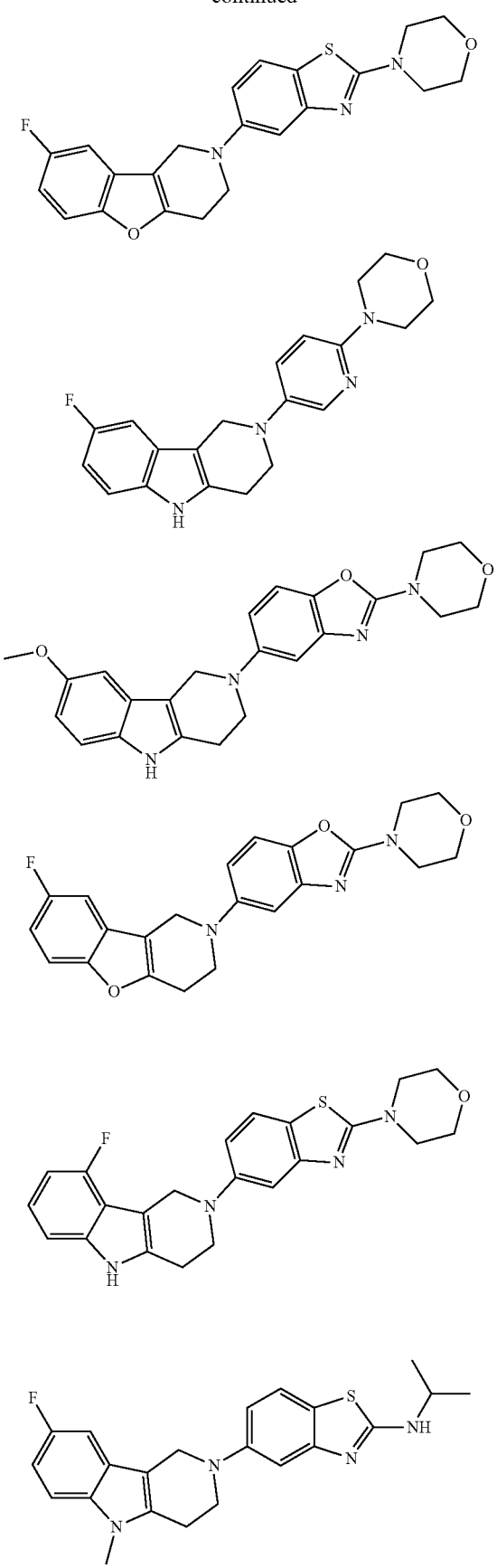

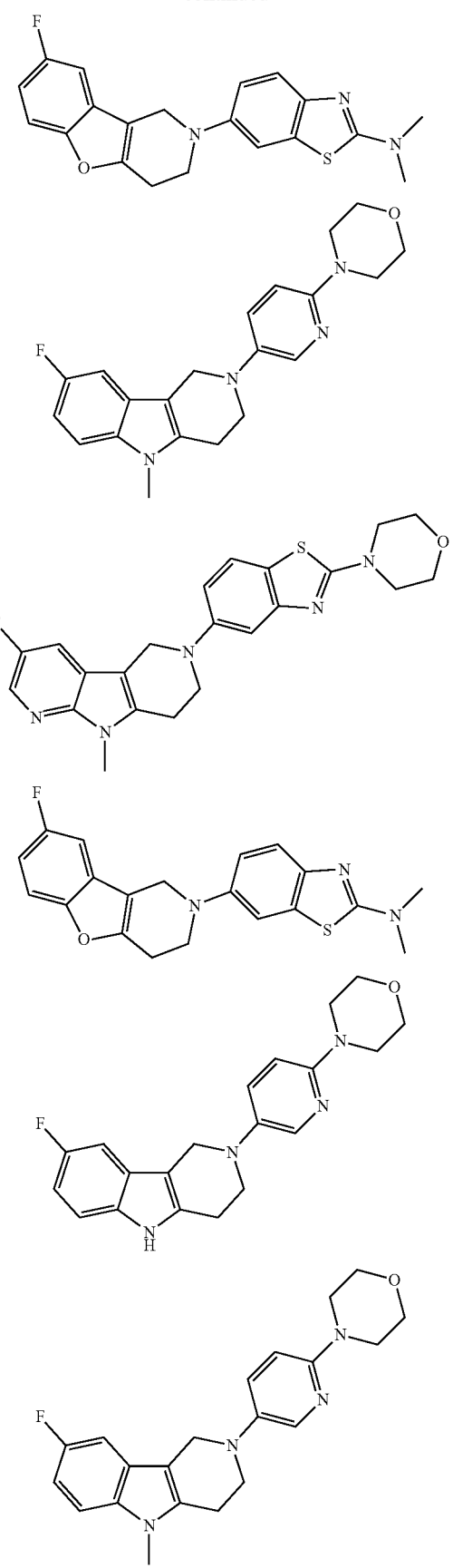
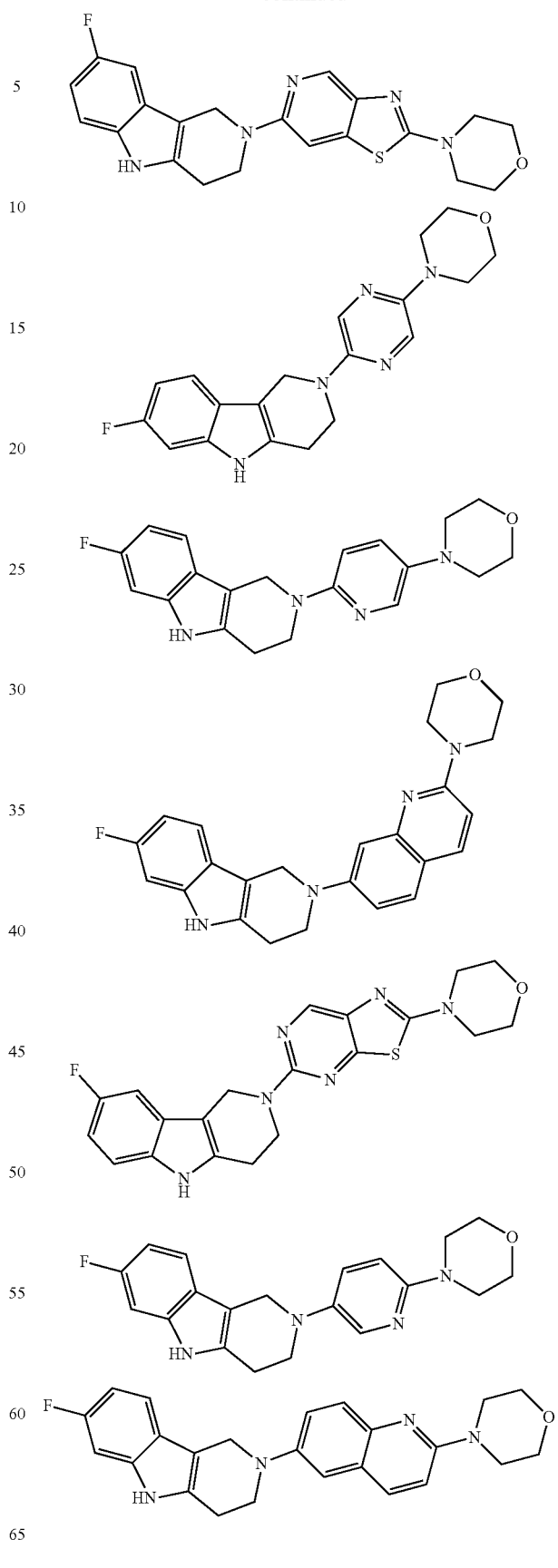

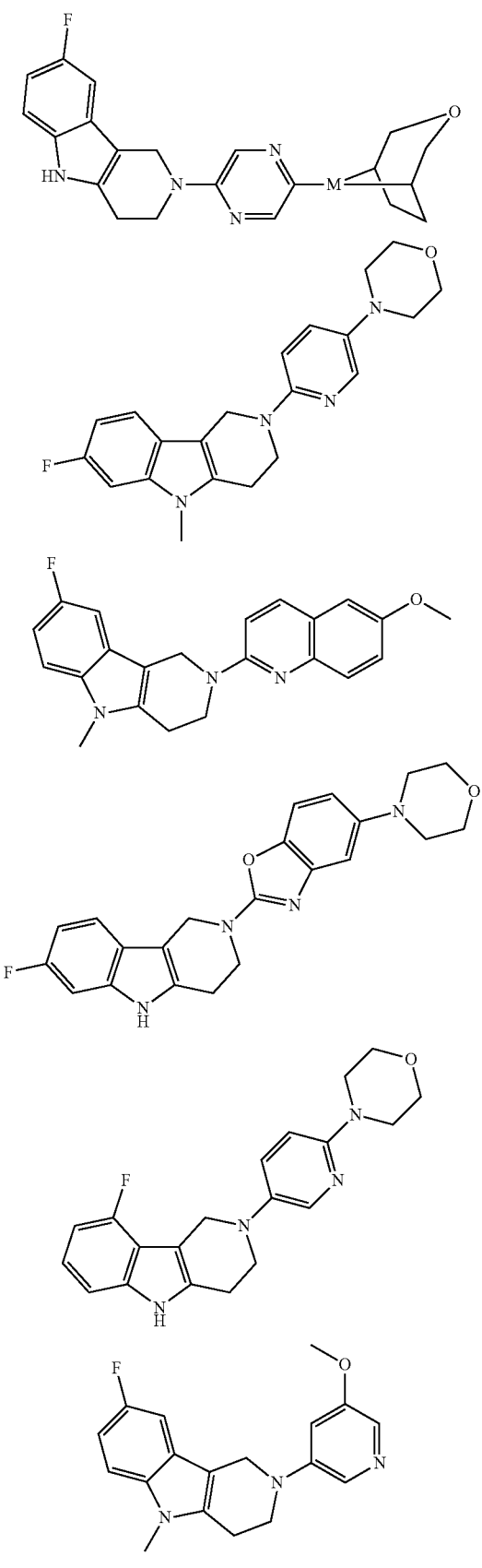
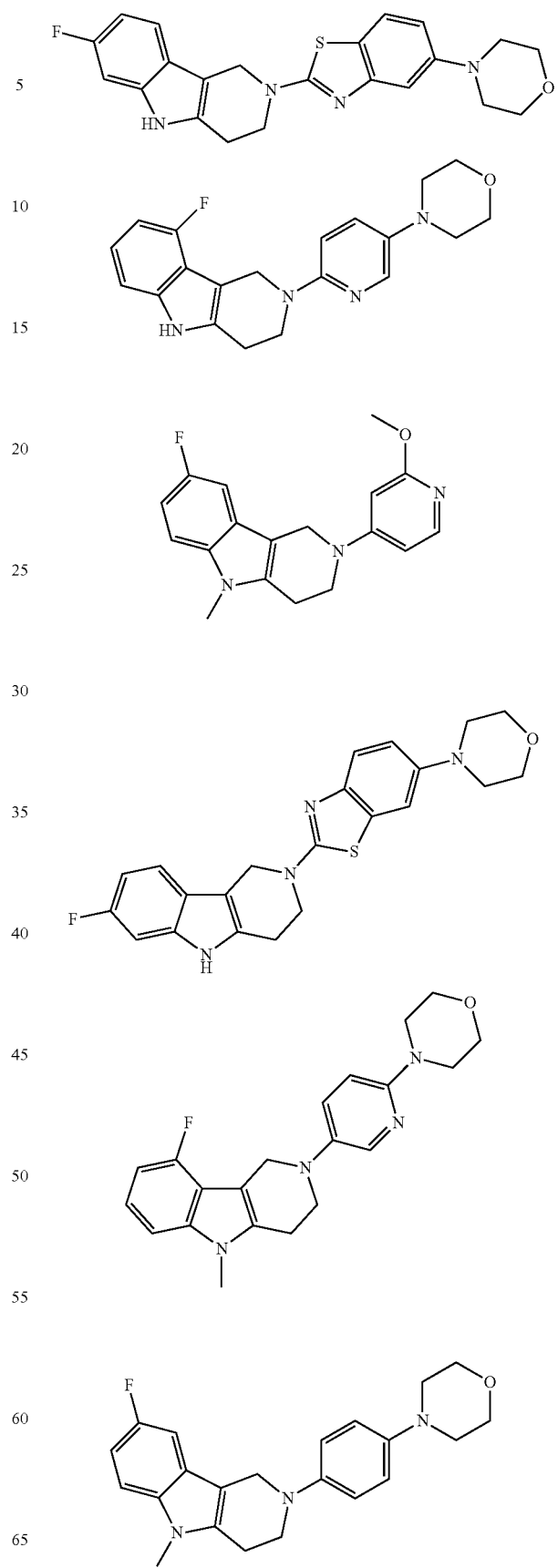

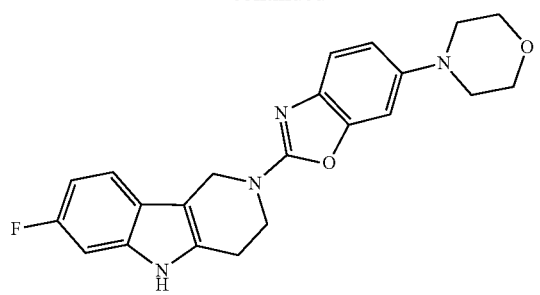
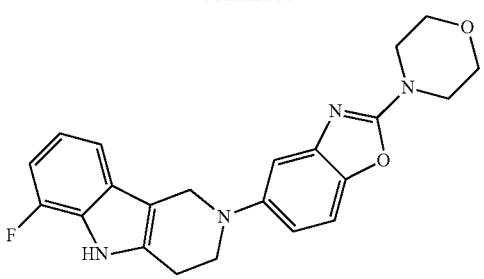
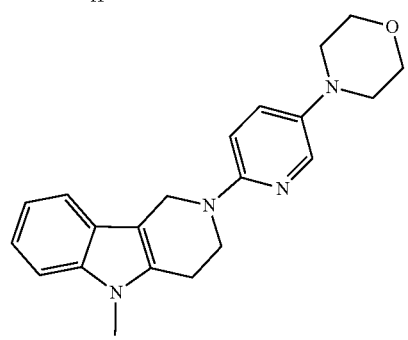
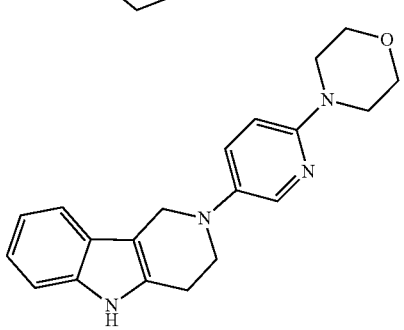
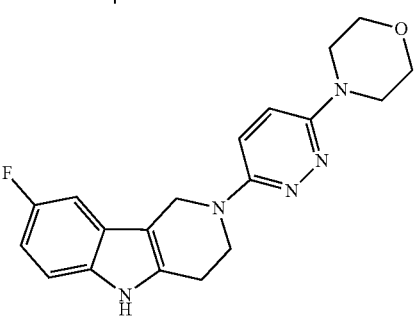
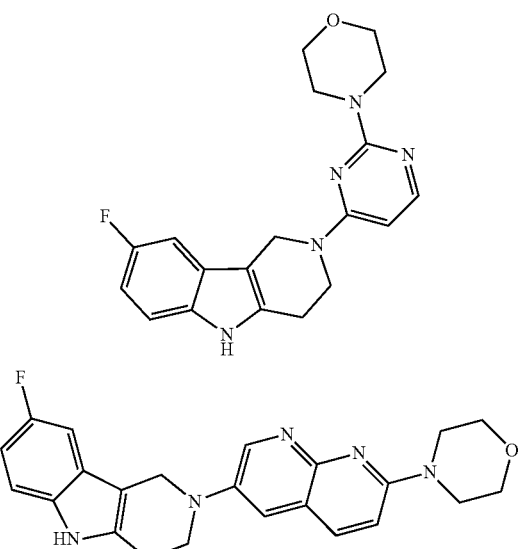
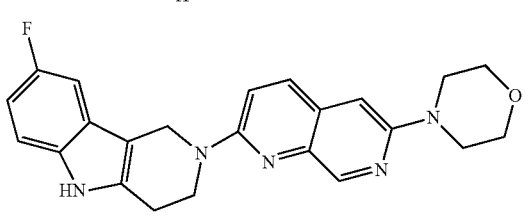
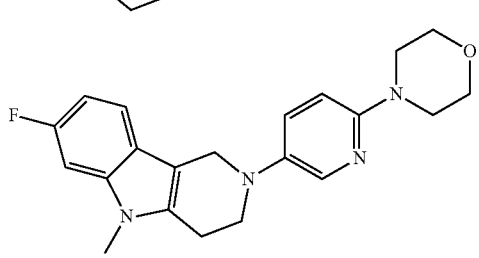
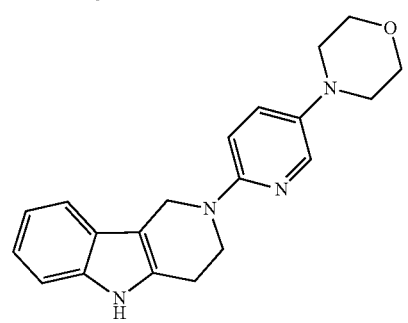
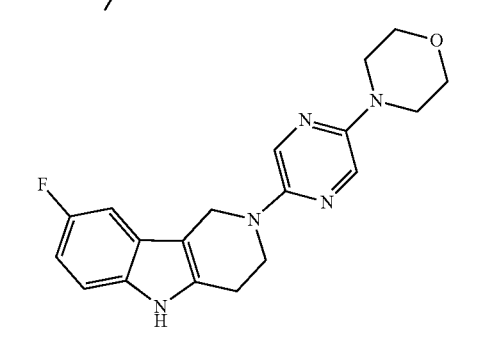
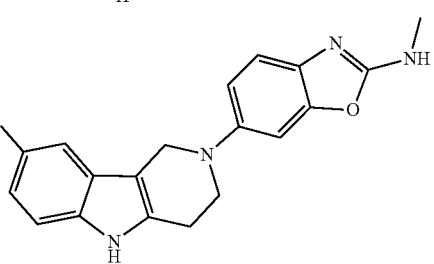

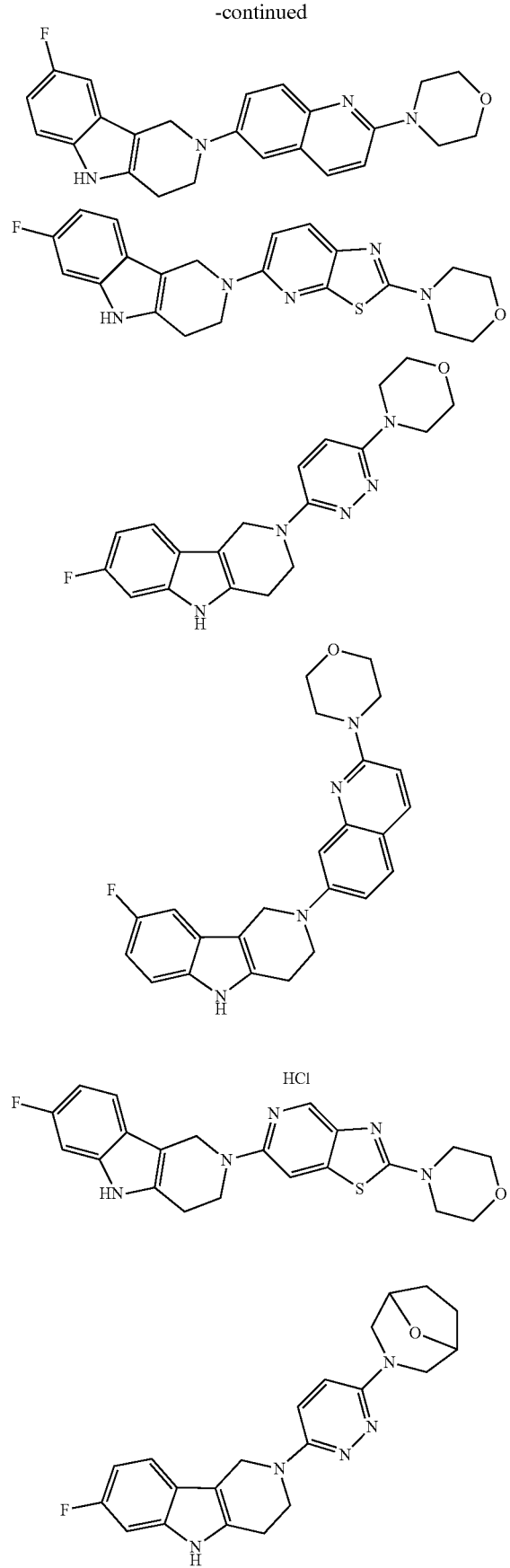
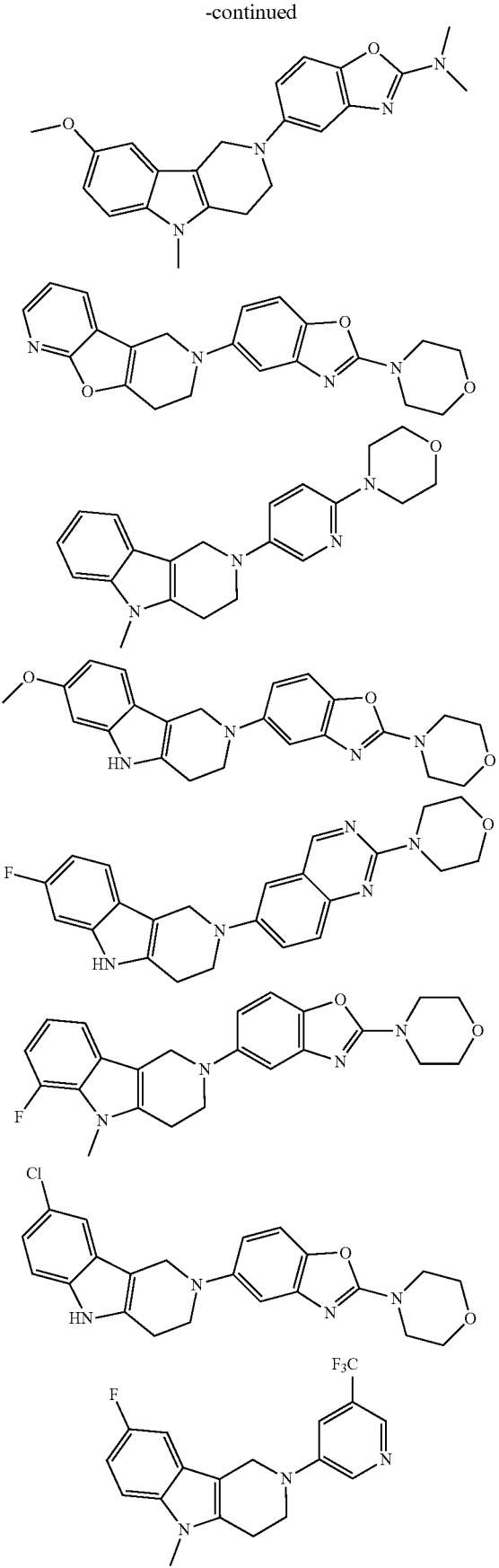

65
-continued
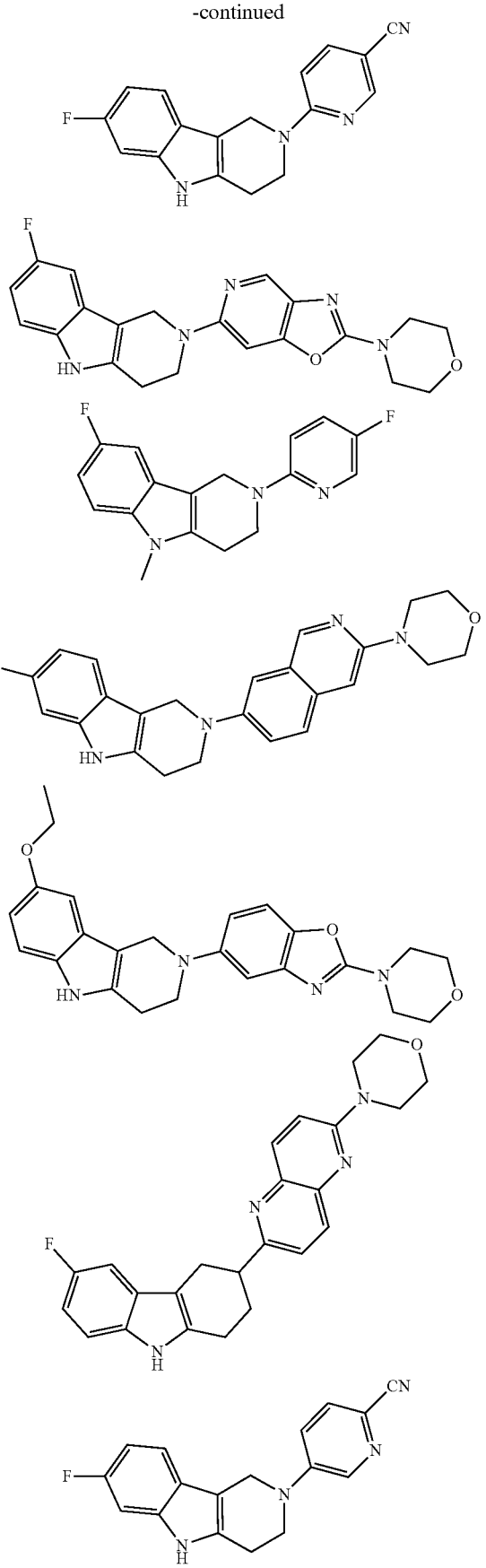
66
-continued
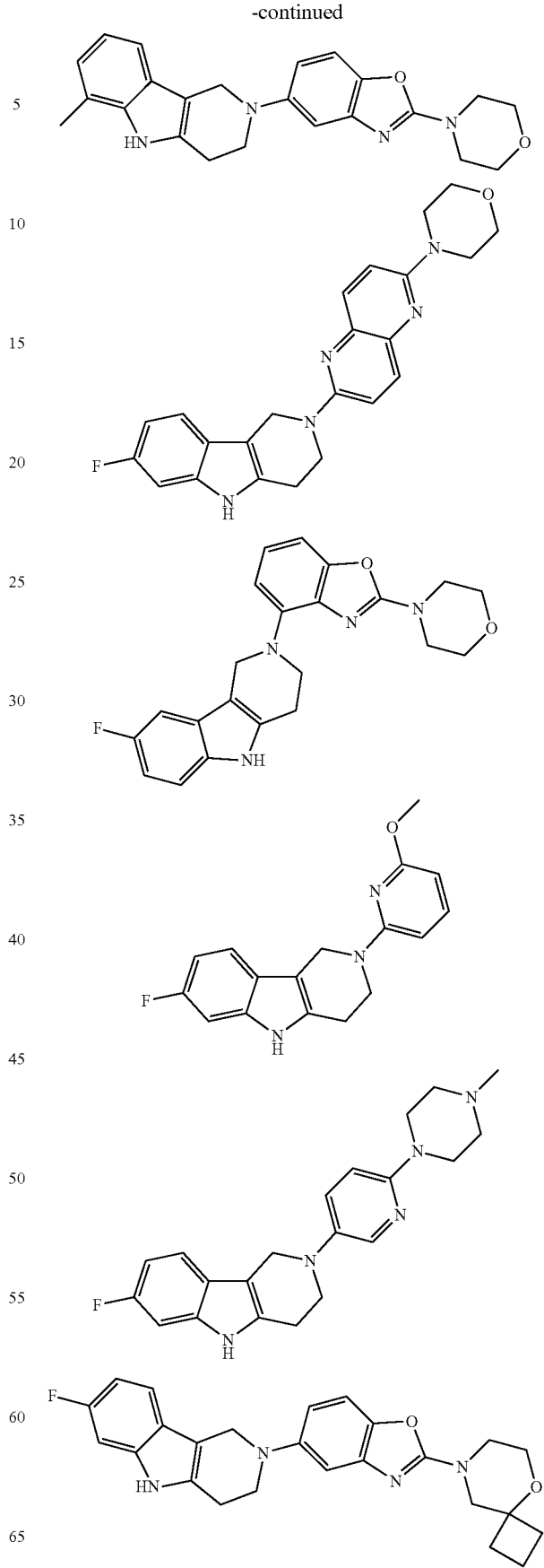

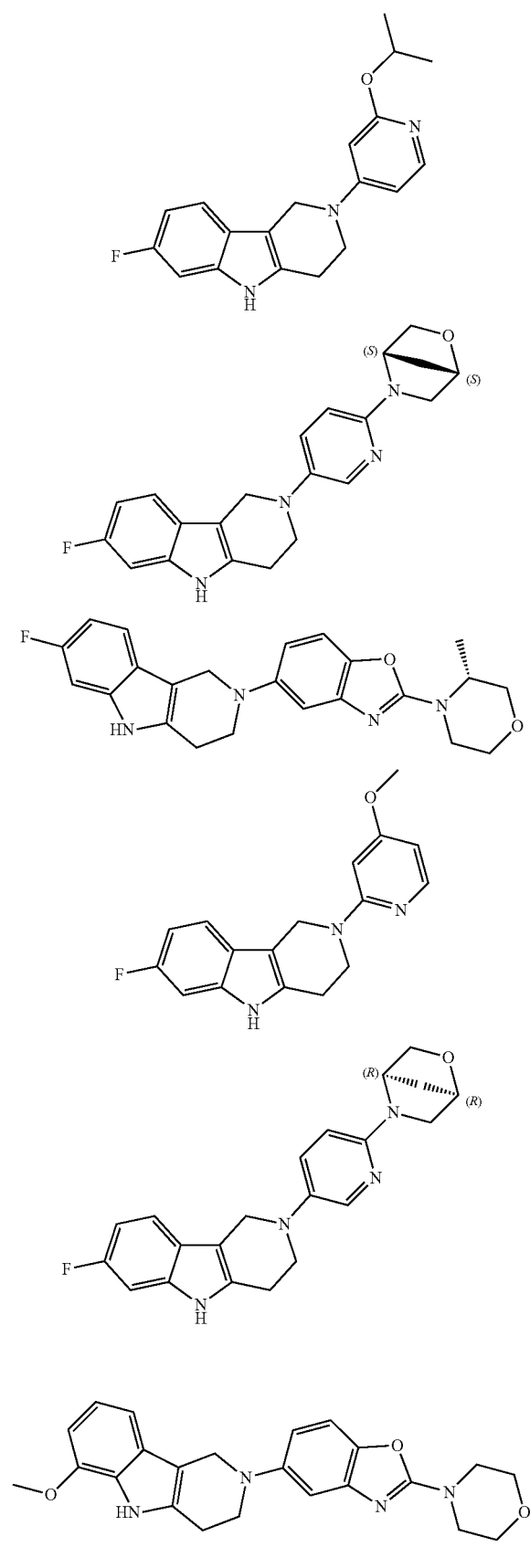
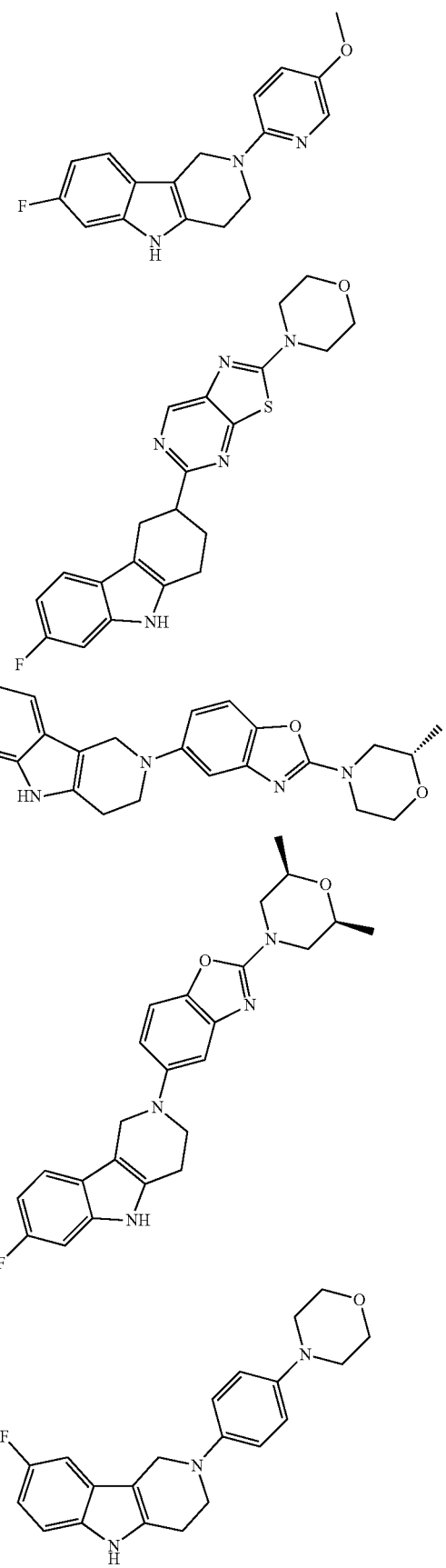

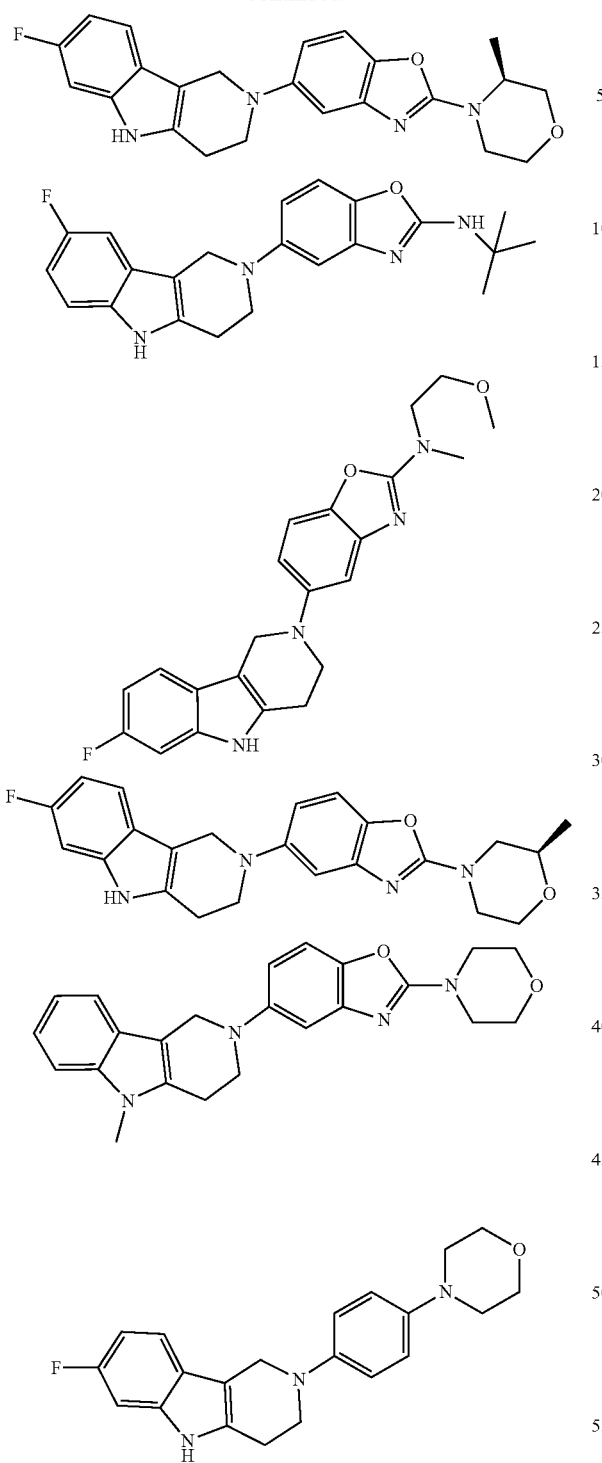
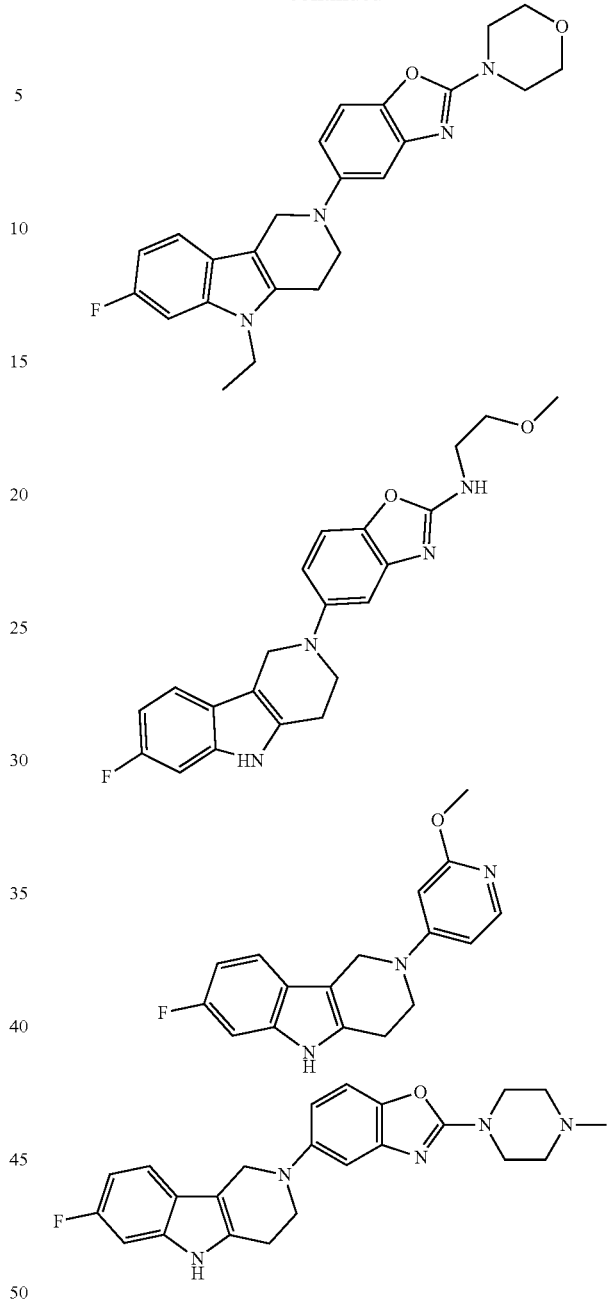

Preferred compounds are also illustrated in the examples.

Any combination of the embodiments, preferred embodiments and more preferred embodiments disclosed herein is also envisaged in the present invention.

Pharmaceutical Compositions

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formula (I) optionally in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e. g. as a tablet, capsule, or as an ingestible solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e. g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e. g. using a mixture of ethanol and the propellant as the solvent, which may additionally contain a lubricant, e. g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 3 g, 0.1 mg to 2 g, 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15$^{th}$ Ed., Mack Publishing Co., New Jersey (1975).

The diseases or conditions that can be treated, alleviated or prevented with the compounds of the present invention are disorders or abnormalities associated with Tau protein aggregates such as neurodegenerative disorders. Examples of diseases and conditions which can be treated, alleviated or prevented are caused by or associated with the formation of neurofibrillary lesions. This is the predominant brain pathology in tauopathy. The diseases and conditions comprise a heterogeneous group of neurodegenerative diseases or conditions including diseases or conditions which show co-existence of Tau and amyloid pathologies.

Examples of the diseases and conditions which can be treated, alleviated or prevented include, but are not limited, to Alzheimer's disease (AD), familial AD, PART (Primary Age-Related Tauopathy), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease. Preferably the diseases and conditions which can be treated, alleviated or prevented include Alzheimer's disease (AD), as well as other neurodegenerative tauopathies such as Creutzfeldt-Jacob disease, dementia pugilistica, amyotrophic lateral sclerosis (ALS), argyrophilic grain disease, corticobasal degeneration (CBD), frontotemporal dementia with Parkinsonism linked to chromosome 17 (FTDP-17), Pick's disease (PiD), progressive supranuclear palsy (PSP), tangle predominant dementia, Parkinson dementia complex of Guam, Hallervorden-Spatz disease, chronic traumatic encephalopathy (CTE), traumatic brain injury (TBI), and other frontotemporal lobar degeneration. More preferably Alzheimer's disease (AD), corticobasal degeneration (CBD), Pick's disease (PiD), and progressive supranuclear palsy (PSP).

The compounds of the present invention can also be employed to decrease protein aggregation, in particular Tau aggregation. The ability of a compound to decrease of Tau aggregation can, for example, be determined using the ThT assay (Hudson et al., FEBS J., 2009, 5960-72).

The compounds of the invention can be used in the treatment of a wide range of disorders in which the neuroinflammation process is associated with misfolding and/or pathologic aggregation of Tau protein.

The compounds of the present invention can be used as an analytical reference or an in vitro screening tool for characterization of tissue with Tau pathology and for testing of compounds targeting Tau pathology on such tissue.

The compounds of the present invention can be used as photoprobes for the crosslinking of the compound to the target, for use in in vitro screening assays for the identification and characterization of compound's mode of action, including mapping of binding site. Below are reported some examples of photoprobes of compounds of the present invention:

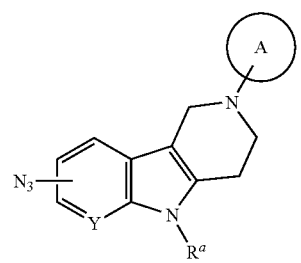

-continued

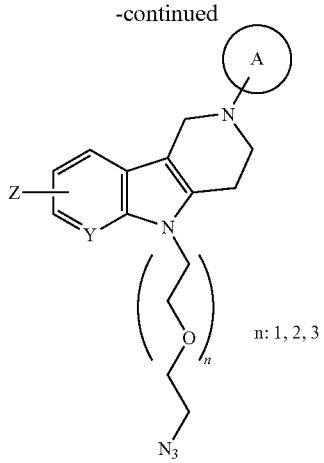

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholineesterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidosis, compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, glycogen synthase kinase 3 inhibitors, O-glcnacase (OGA) inhibitors, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or Tau modifying drug and nutritive supplements, an antibody, including any functionally equivalent antibody or functional parts thereof, or a vaccine.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 93) and prodrugs (pages 93 and 94), which document is incorporated herein by reference.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^2H$, $^3H$, $^{13}$, $^{14}O$, $^{15}N$, $^{17}O$, $^{18}O$, $^{35}S$, $^{18}F$ and $^{36}Cl$ respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and delectability. $^{18}F$-labeled compounds are particularly suitable for imaging applications such as PET. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

The compounds of the present invention can be synthesized by one of the general methods shown in the following schemes. These methods are only given for illustrative purposes and should not to be construed as limiting.

General Synthetic Schemes for the Preparation of Building Blocks of this Invention:

Scheme 1

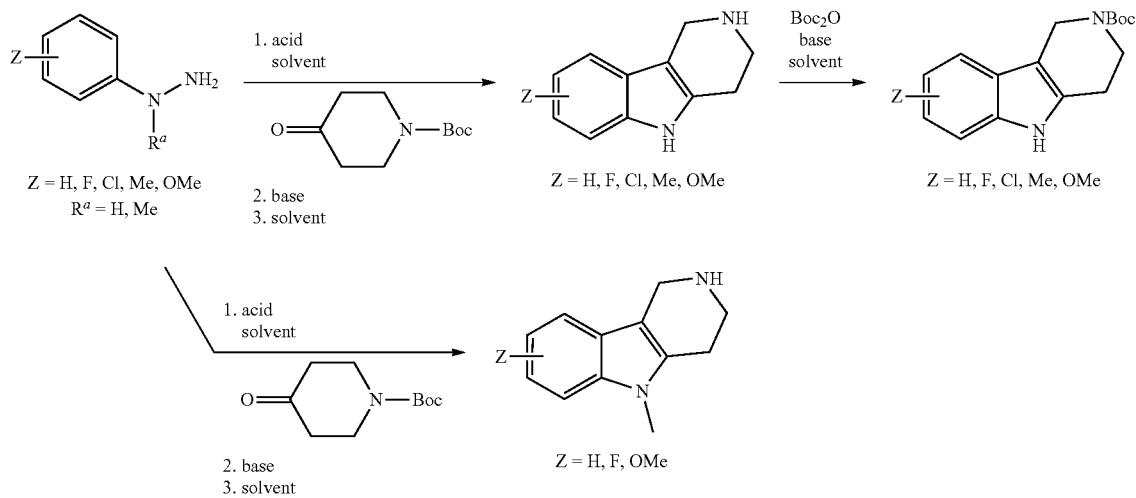

Heating of commercially available phenylhydrazine derivatives (Z=H, F, Cl, Me or OMe; $R^a$=H, $CH_3$) with commercially available tert.-butyl 4-oxopiperidine-1-carboxylate in a suitable solvent under acidic conditions (Fischer-Indole synthesis) afforded the tricyclic 2,3,4,5-tetrahydro-1H-pyrido[4,3-b]indole building blocks after purification. In case 2- or 3-substituted phenylhydrazine derivatives were used, the regioisomers were separated by supercritical fluid chromatography (SFC). Tricyclic building blocks bearing a NH-moiety at the indole ring are further treated with $Boc_2O$ to selectively protect the aliphatic, secondary amine moiety and were obtained after purification.

Scheme 2

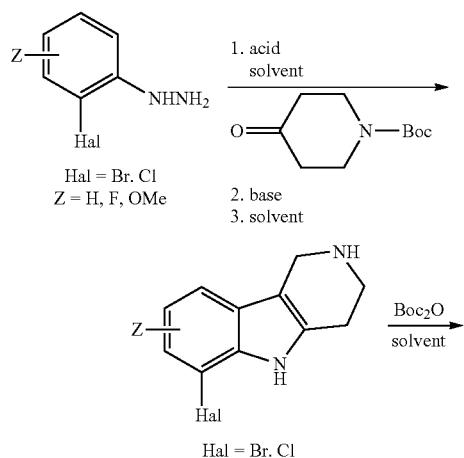

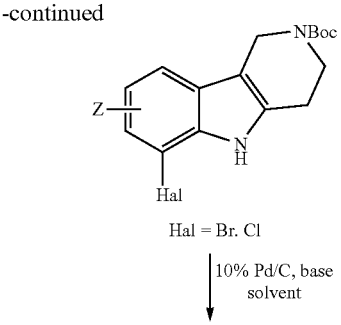

In order to avoid the regioisomer formation by employing 2- or 3-substituted phenylhydrazine derivatives, the corresponding phenylhydrazine derivatives having an additional halogen atom (Br, Cl) adjacent to the hydrazine moiety were used. Thus, Fischer indole synthesis with commercially available tert.-butyl 4-oxopiperidine-1-carboxylate in a suitable solvent under acidic conditions afforded only a single product with an additional halogen atom after purification. The aliphatic, secondary amine was Boc-protected and the products were obtained after purification. The additional halogen atom was then removed by hydrogenation with a palladium catalyst using a suitable base in an appropriate solvent to afford the desired tricyclic 2,3,4,5-tetrahydro-1H-pyrido[4,3-b]indole building blocks after purification.

Scheme 3

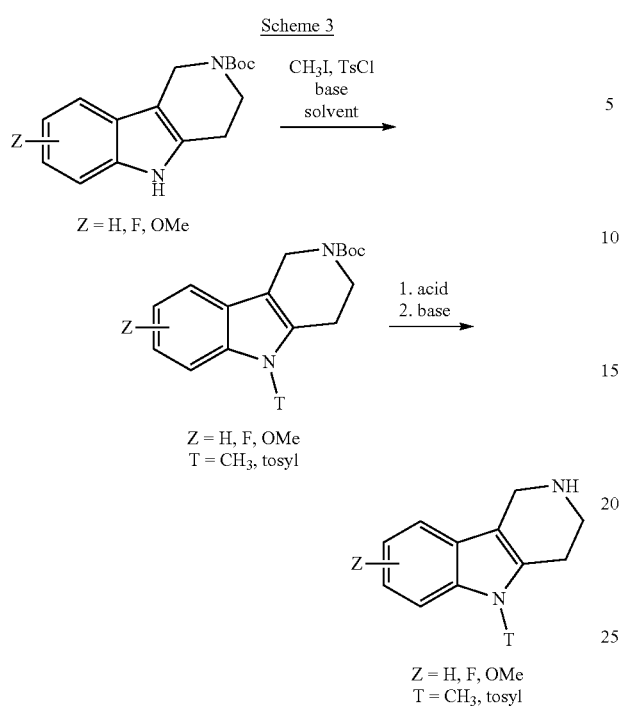

The NH-moiety of the indole moiety was then treated with either methyl iodide or tosyl chloride in an appropriate solvent using a suitable base to afford the N-methyl or N-tosyl derivatives after purification. The Boc-protecting group was removed by acid treatment in an appropriate solvent to afford the desired tricyclic 2,3,4,5-tetrahydro-1H-pyrido[4,3-b]indole building blocks after purification. In case there was no base treatment, the corresponding salts were obtained.

Scheme 4

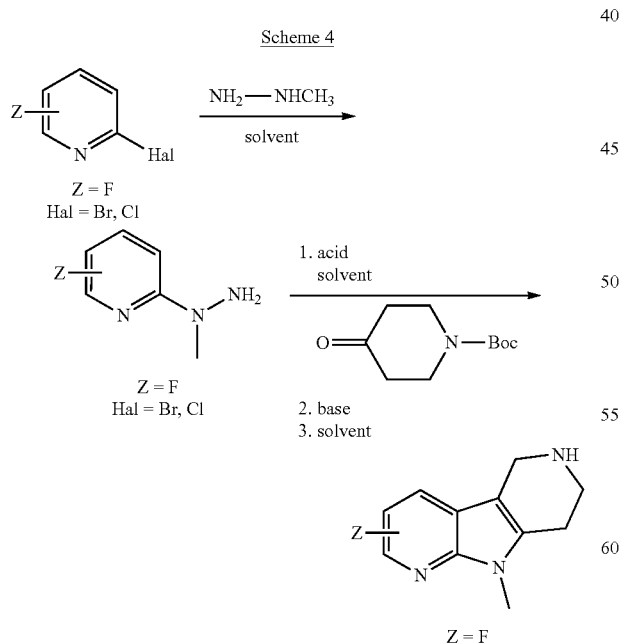

Commercially available fluoropyrdine derivatives with the F-atom in 3-, 4-, or 5-position and an additional halogen atom (Br, Cl) in 2-position were treated with methylhydrazine in an appropriate solvent to afford the corresponding N-methyl hydrazine derivatives after purification. Fischer indole synthesis with commercially available tert.-butyl 4-oxopiperidine-1-carboxylate in a suitable solvent under acidic conditions afforded the desired tricyclic 9-methyl-6,7,8,9-tetrahydro-5H-pyrrolo[2,3-b:4,5-c']dipyridine derivatives after purification.

Scheme 5

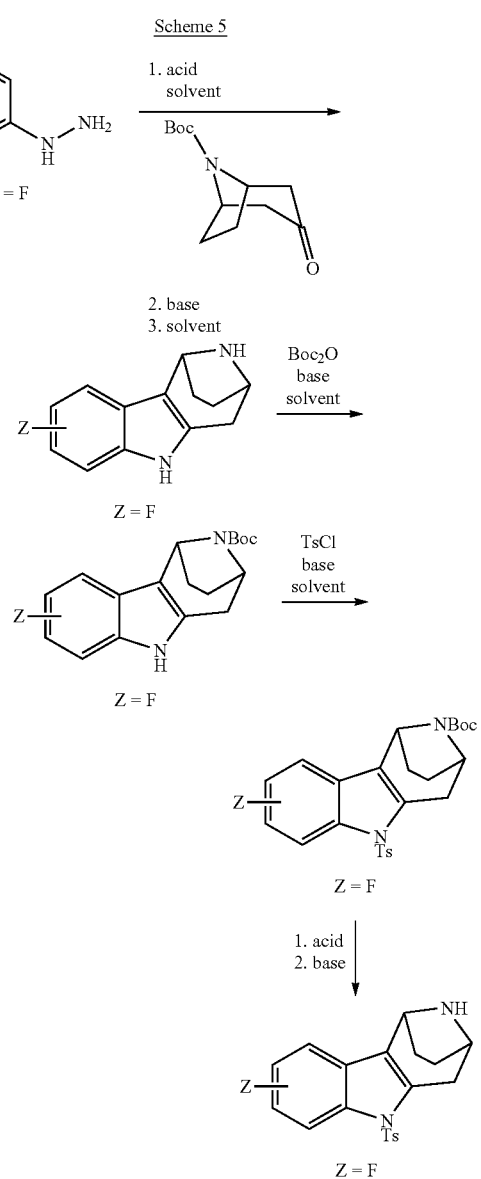

Heating of commercially available phenylhydrazine derivatives (Z=F) with commercially available tert.-butyl 3-oxo-8-azabicyclo[3.2.1]octane-8-carboxylate in a suitable solvent under acidic conditions (Fischer indole synthesis) afforded the tricyclic 5,6,7,8,9,10-hexahydro-7,10-epimino-cyclohepta[b]indole derivatives after purification. In case of 2- or 3-substituted phenylhydrazine derivatives, the regioisomers have to be separated by supercritical fluid chromatography (SFC). The aliphatic, secondary amine moiety was then Boc-protected and the products were obtained after purification. The NH-moiety of the indole moiety was then treated with tosyl chloride in an appropriate solvent using a suitable base to afford the N-tosyl derivatives after purification. The Boc-protecting group was removed by acid treatment in an appropriate solvent to afford the desired tricyclic 5,6,7,8,9,10-hexahydro-7,10-epiminocyclohepta[b] indole building blocks after purification. In case there was no base treatment, the corresponding salts were obtained.

Scheme 6

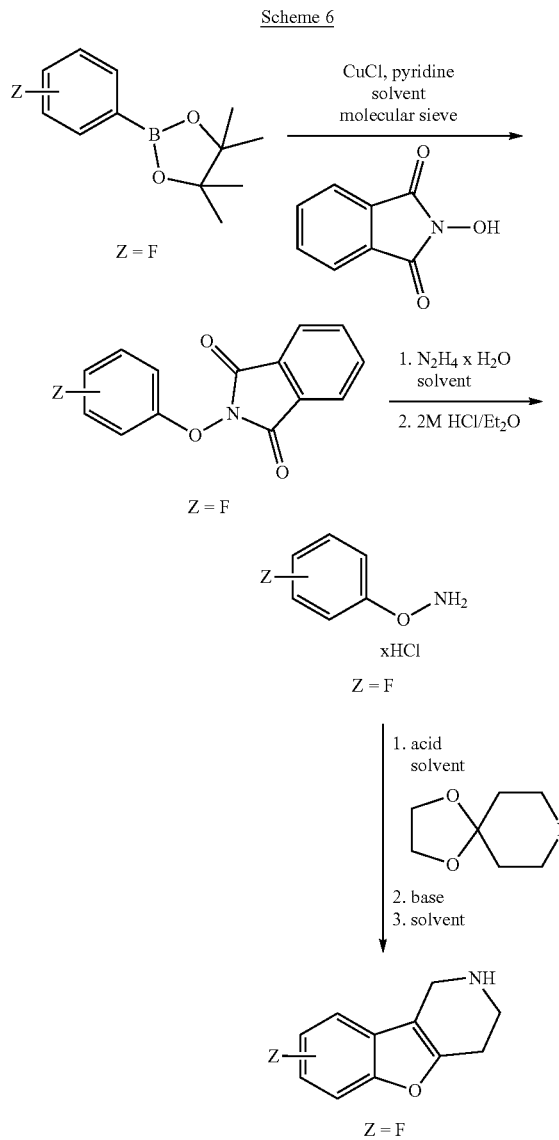

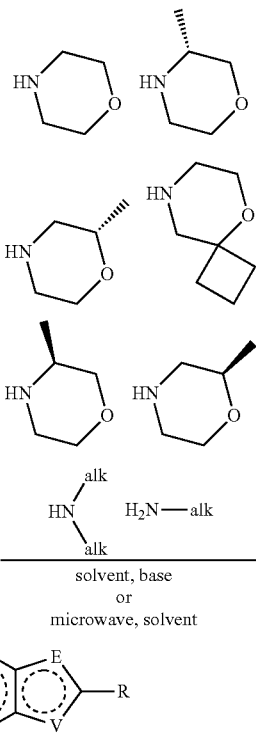

$R^x$, X = Hal
R = Morpholine,
(R/S)-2-methylmorpholine,
(R/S)-3-methylmorpholine,
———N(alk)$_2$, ———NH(alk),
5-oxa-8-azaspiro
[3.5] nonane
$R^x$ = Hal
E and V = N, O, S
G = Ph, Py, pyrimidine Commercially available phenyl boronic ester derivatives (Z=F) were treated with N-hydroxyphthalimide and copper (I)-chloride and pyridine in an appropriate solvent to afford the corresponding hydroxylamine derivatives containing a phthalimide protecting group after purification. The phthalimide protecting group was cleaved with hydrazine hydrate and the corresponding hydroxylamine derivatives were obtained as salts. Heating of the hydroxylamine derivatives with commercially available 1,4-dioxa-8-azaspiro[4.5]decane in a suitable solvent under acidic conditions (Fischer indole synthesis) afforded the tricyclic 1,2,3,4-tetrahydrobenzofuro[3,2-c]pyridine derivatives after purification.

Commercially available benzo[d]thiazole (G=Ph) or benzo[d]oxazole (G=Ph) derivatives containing two halogen (Br, Cl) atoms were treated with primary or secondary amines in an appropriate solvent and with an additional base. The leaving group X was replaced via nucleophilic substitution by the primary or secondary amines to afford the corresponding amino-substituted benzo[d]thiazole or benzo [d]oxazole derivatives after purification. In case of less reactive amines, the desired benzo[d]thiazole or benzo[d] oxazole derivatives were obtained by performing the nucleophilic substitution reaction under microwave conditions. The corresponding thiazolo[5,4-b]pyridine (G=Py) and thiazolo[4,5-b]pyridine (G=Py) derivatives containing two halogen (Br, Cl) atoms were treated with morpholinein an appropriate solvent and with an additional base to afford the corresponding morpholino-thiazolo[5,4-b]pyridine (G=Py) and morpholino-thiazolo[4,5-b]pyridine (G=Py) derivatives after purification. The corresponding thiazolo[5,4-d]pyrimidine (G=pyrimidine) derivatives containing two halogen (Br, Cl) atoms were treated with morpholine in an appropriate solvent and with an additional base to afford the corresponding morpholino-thiazolo[5,4-d]pyrimidine (G=pyrimidine) derivatives after purification.

Scheme 8

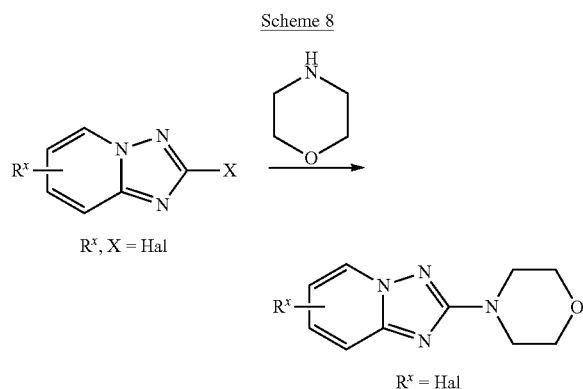

Commercially available [1,2,4]triazolo[1,5-a]pyridine derivatives containing two halogen (Br, Cl) atoms were treated with morpholine under microwave conditions to afford the nuleophilic displacement products after purification.

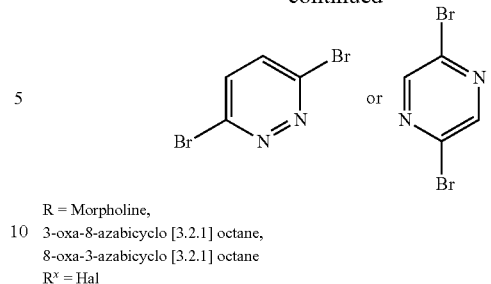

R = Morpholine,
3-oxa-8-azabicyclo [3.2.1] octane,
8-oxa-3-azabicyclo [3.2.1] octane
R$^x$ = Hal Commercially available 3,6-dibromopyridazine and 2,5-dibromopyrazine derivatives containing two bromo atoms were treated with morpholine, 3-oxa-8-azabicyclo[3.2.1]octane, or 8-oxa-3-azabicyclo[3.2.1]octane under microwave conditions to afford the nuleophilic displacement products after purification.

Scheme 8b

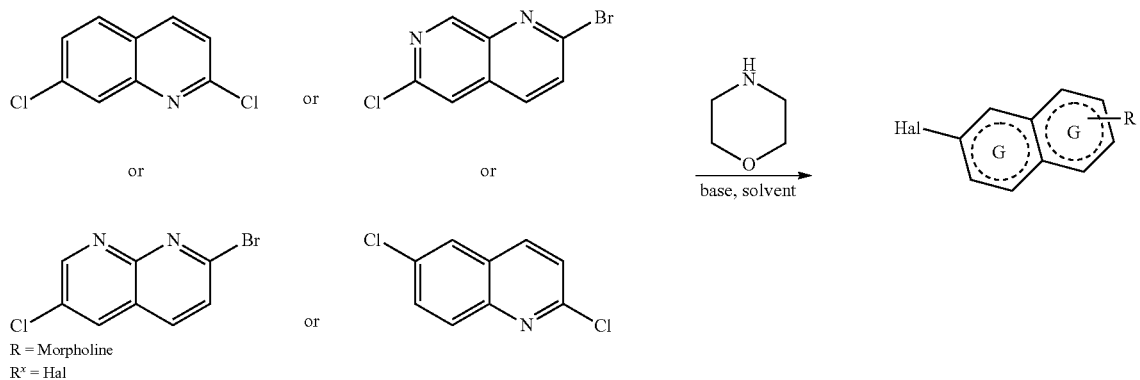

R = Morpholine
R$^x$ = Hal

Commercially available 2,7-dichloroquinoline, 2-bromo-6-chloro-1,7-naphthyridine, 2-bromo-6-chloro-1,8-naphthyridine and 2,6-dichloroquinoline derivatives containing two halogen (Br, Cl) atoms were treated with morpholine under microwave conditions to afford the nuleophilic displacement products after purification.

General Synthetic Scheme for the Preparation of Compounds of this Invention:

Scheme 8a

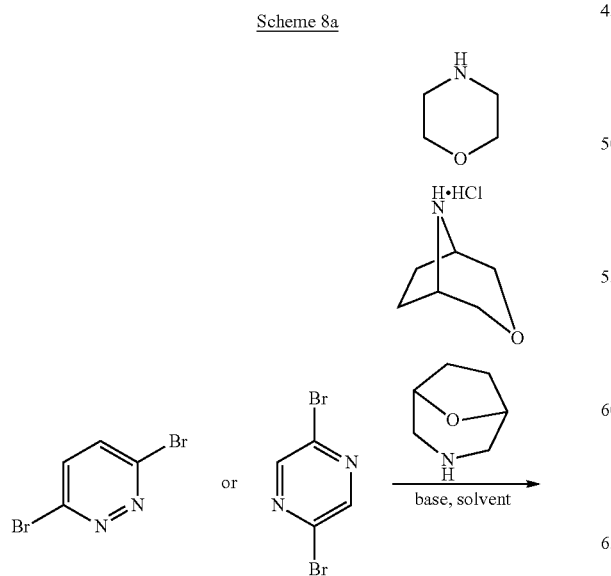

Scheme 9

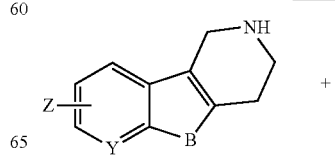

+

-continued

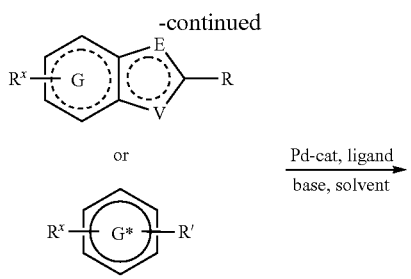

or

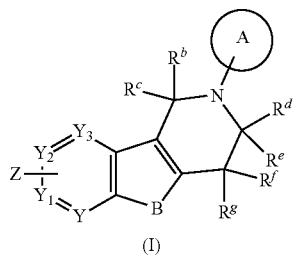

Pd-cat, ligand
———————————
base, solvent

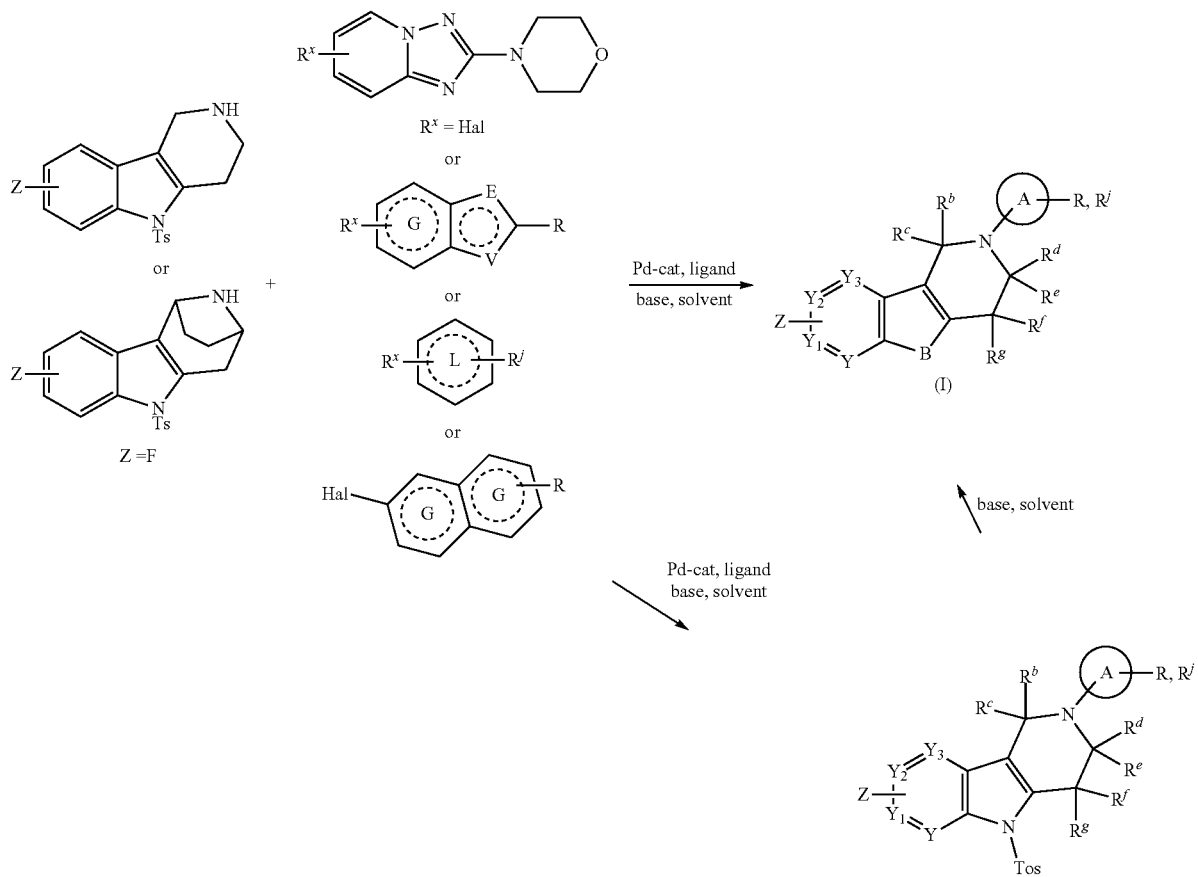

Y = N, CH
Z = H, F, OMe
B = NCH₃, O
R = Morpholine, —N(alk)₂, —NH(alk)
R' = Morpholine
R$^x$ = Hal
E and V = N, O, S
G = Ph, Py
G* = Py The tricyclic building blocks with B=NCH₃ or B=O were coupled with amino substituted benzo[d]thiazole or benzo[d]oxazole derivatives, or substituted pyridine derivatives via palladium chemistry with a suitable palladium catalyst (chloro-(2-dicyclohexylphosphino-2',6'-diisopropoxy-1,1'-biphenyl)[2-(2-aminoethyl)phenyl]palladium(II)-methyl-t-butyl ether adduct; Pd(RuPhos) G1), ligand (2-dicyclohexylphosphino-2',6'-diisopropoxybiphenyl; RuPhos) and base (lithium bis(trimethylsilyl)amide; LiHMDS) in a suitable solvent (tetrahydrofuran; THF) to afford the desired compounds of formula (I) after purification.

Scheme 10

R = Morpholine, (R/S)-2-methylmorpholine,
  (R/S)-3-methylmorpholine, -N(alk)₂, -NH(alk),
  5-oxa-8-azaspiro[3.5]nonane
R$^j$ = Morpholine, (1S,4S)-2-oxa-5-azabicyclo[2.2.1]heptane,
  (1R/4R)-2-oxa-5-azabicyclo[2.2.1]heptane,
  2-oxa-8-azabicyclo[3.2.1]octane,
  8-oxa-3-azabicyclo[3.2.1]octane
R$^X$ = Hal
E and V = N, O, S
G = Ph, Py, pyrimidine
L = Py, pyrazine, pyridazine, pyrimidine The tricyclic building blocks containing a N-tosyl group at the indole/azaindole moiety were coupled with amino substituted benzo[d]thiazole, benzo[d]oxazole, thiazolo[5,4-b]pyridine (G=Py), thiazolo[4,5-b]pyridine (G=Py) derivatives, thiazolo[5,4-d]pyrimidine (G=pyrimidine), or amino substituted [1,2,4]triazolo[1,5-a]pyridine derivatives, or amino substituted pyridine (L=Py), pyrazine (L=pyrazine), pyridazine (L=pyridazine), pyrimidine (L=pyrimidine) derivatives, or amino substituted isoquinoline, naphthyridine, quinazoline derivatives via palladium chemistry with a suitable palladium catalyst (tris(dibenzylideneacetone)dipalladium(0); Pd$_2$(dba)$_3$), ligand (2-dicyclohexylphosphino-2',6'-diisopropoxybiphenyl; RuPhos) and base (sodium tert.-butoxide; NaOtBu) in a suitable solvent (1,4-dioxane) to afford the desired compounds of formula (I) after purification. Alternatively, tricyclic building blocks containing a N-tosyl group at the indole/azaindole moiety were coupled with amino substituted benzo[d]thiazole, benzo[d]oxazole, thiazolo[5,4-b]pyridine (G=Py), thiazolo[4,5-b]pyridine (G=Py) derivatives, thiazolo[5,4-d]pyrimidine (G=pyrimidine), or amino substituted [1,2,4]triazolo[1,5-a] pyridine derivatives, or amino substituted pyridine (L=Py), pyrazine (L=pyrazine), pyridazine (L=pyridazine), pyrimidine (L=pyrimidine) derivatives, or amino substituted isoquinoline, naphthyridine, quinazoline derivatives via palladium chemistry with a suitable palladium catalyst (tris (dibenzylideneacetone)dipalladium(0); Pd$_2$(dba)$_3$), ligand (2-dicyclohexylphosphino-2',6'-diisopropoxybiphenyl; RuPhos) and a weaker base (caesium carbonate; Cs$_2$CO$_3$) in a suitable solvent (1,4-dioxane) to afford the N-tosyl protected compounds after purification. The tosyl-protecting group is then removed using a suitable base (caesium carbonate; Cs$_2$CO$_3$) in a suitable solvent (2-methyl THF, methanol) at elevated temperature (reflux) to afford the desired compounds of formula (I) after purification.

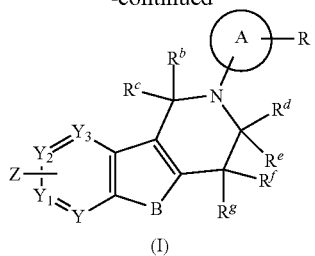

Z = F
R and R$^x$ = Hal
E and V = N, O, S
G = Ph, Py

The tricyclic building blocks containing a N-tosyl group at the indole moiety were coupled with di-halogenated benzo[d]thiazole and di-halogenated benzo[d]oxazole with a suitable base (potassium carbonate; K$_2$CO$_3$) in a suitable solvent (DMF) to afford the nuleophilic displacement products. He product was then coupled via palladium chemistry with a suitable palladium catalyst (tris(dibenzylideneacetone)dipalladium(0); Pd$_2$(dba)$_3$), ligand (2-dicyclohexylphosphino-2',6'-diisopropoxybiphenyl; RuPhos) and base (sodium tert.-butoxide; NaOtBu) in a suitable solvent (1,4-dioxane) to afford the desired compounds of formula (I) after purification.

General Synthetic Scheme for the Preparation of Tritium-Labeled Compounds of this Invention:

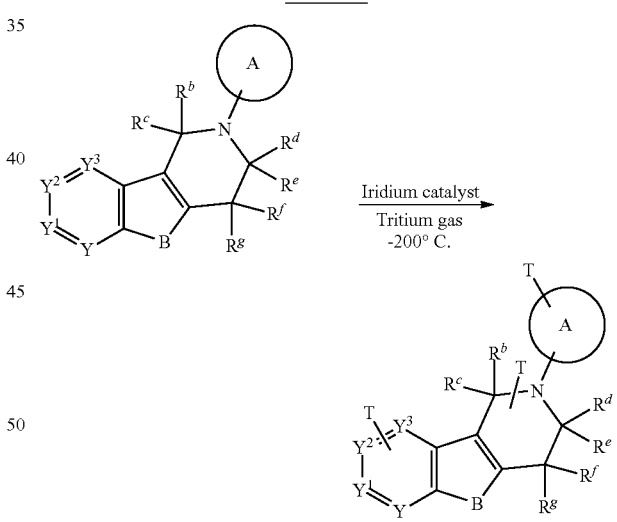

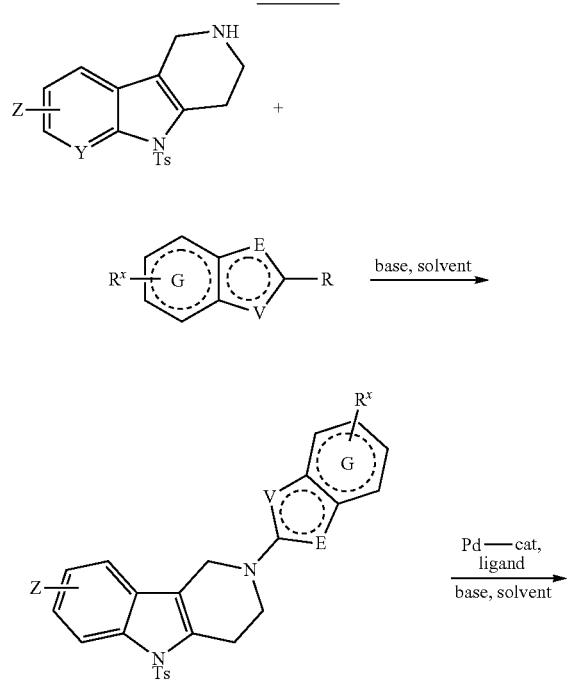

The catalyst was added to a tritium reaction vessel, followed by a solution of a compound of the present invention in dichloromethane. The vessel was attached to the tritium line and pressurized to the tritium gas at −200° C. The solution was stirred for 8 hours at room temperature, cooled to −200° C. and excess gas removed. The reaction flask was rinsed with methanol and the combined organic phase was evaporated under vacuum. The crude material was purified by HPLC, the mobile phase was evaporated under vacuum and the product was re-dissolved in absolute ethanol. The specific activity was determined by mass spectrometry.

The disaggregation of Tau K18 and full-length (fl) Tau may be measured using any suitable assay known in the art. A standard in vitro assay for measuring the disaggregation capacity is described.

EXAMPLES

All reagents and solvents were obtained from commercial sources and used without further purification. $^1$H NMR spectra were recorded on Bruker AV 300 and 400 MHz spectrometers in deuterated solvents. Chemical shifts (δ) are reported in parts per million and coupling constants (J values) in hertz. Spin multiplicities are indicated by the following symbols: s (singlet), d (doublet), t (triplet), q (quartet), m (multiplet), bs (broad singlet). Mass spectra were obtained on an Agilent 1290 Infinity II spectrometer with a 6130 Chemstation and an Agilent 1200 Infinity II spectrometer with a 6130 Chemstation. GC-MS data were collected using an Agilent 7890B gas chromatograph and 5977B mass spectrometer. Infrared spectra were obtained on a PerkinElmer spectrometer. Chromatography was performed using silica gel (Fluka: Silica gel 60, 0.063-0.2 mm) and suitable solvents as indicated in specific examples. Flash purification was conducted with a Biotage Isolera with HP-Sil or KP-NH SNAP cartridges (Biotage) and the solvent gradient indicated in specific examples. Thin layer chromatography (TLC) was carried out on silica gel plates with UV detection.

Preparative Example 1 phase was separated and dried over $Na_2SO_4$ and the solvent was removed to give the title compound as a pale yellow solid (950 mg, 59%).

MS: 191 (M+H)$^+$.

$^1$H-NMR (400 MHz, DMSO-d$_6$) δ=10.91 (s, 1H), 7.23-7.24 (m, 1H), 7.09-7.09 (m, 1H), 6.80-6.81 (m, 1H), 3.91 (s, 2H), 3.11 (t, J=5.56 Hz, 2H), 2.75 (d, J=4.96 Hz, 2H).

Step B

To a solution of the title compound from Step A above (0.95 g, 4.77 mmol) in THF (tetrahydrofuran) was added di-tert-butyl dicarbonate (Boc$_2$O) (1.5 g) and the mixture was stirred overnight. After the completion of the reaction as evidenced by TLC, the solvent was removed and the crude reaction mixture was purified on a silica gel column using a Biotage Isolera One purification system employing an EtOAc/heptane gradient (10/80=>80/20) to afford the title compound as a pale yellow gummy liquid (1.1 g, 78%).

MS: 291 (M+H)$^+$.

$^1$H-NMR (400 MHz, DMSO-d$_6$) δ=11.00 (s, 1H), 7.26 (q, J=4.52 Hz, 1H), 7.18 (t, J=8.12 Hz, 1H), 6.83-6.83 (m, 1H), 4.49 (s, 2H), 3.69 (t, J=5.64 Hz, 2H), 2.76 (s, 2H), 1.43 (s, 9H).

Step C

To a solution of the title compound from Step B above (0.41 g, 1.41 mmol) in THF (5 mL) was added sodium hydride (0.15 g, 6.25 mmol), followed by p-toluenesulfonyl chloride (TsCl) (0.29 g, 1.45 mmol). The reaction mixture was stirred for 10 min. The mixture was dissolved in EtOAc (20 ml) and washed with water and brine and dried over

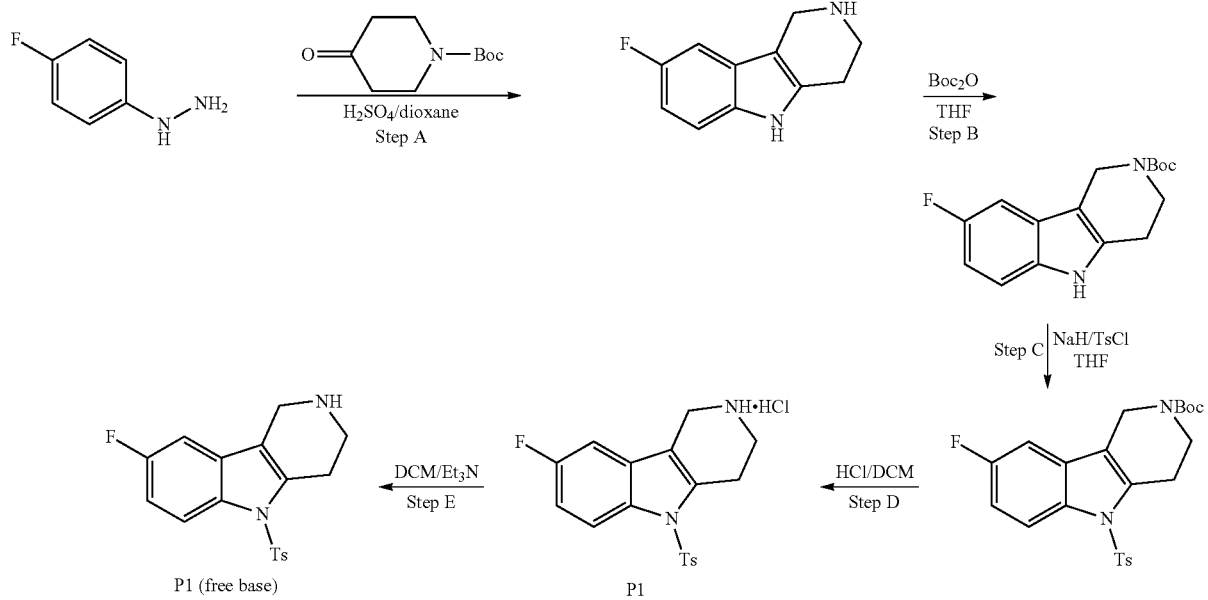

Step A

To a solution of 4-fluorophenyl hydrazine (1 g, 7.9 mmol) and tert-butyl 4-oxopiperidine-1-carboxylate (1.2 g, 8.3 mmol) in 1,4-dioxane (10 mL) was added conc. $H_2SO_4$ (1 mL) at ice bath temperature. Then the reaction mixture was heated at 110° C. for 3 h. The reaction mixture was cooled to room temperature, the precipitate was filtered off. The solid was dissolved in water basified with NaOH solution and extracted with DCM (dichloromethane). The organic $Na_2SO_4$. The crude product was purified on a silica gel column using a Biotage Isolera One purification system employing an EtOAc/heptane gradient (20/80=>80/20) to afford the title compound (0.45 g, 72%).

MS: 445 (M+H)$^+$.

$^1$H-NMR (400 MHz, DMSO-d$_6$) δ=8.03-8.04 (m, 1H), 7.77 (d, J=8.20 Hz, 2H), 7.36-7.38 (m, 3H), 7.15-7.16 (m, 1H), 4.43 (s, 2H), 3.69 (t, J=5.64 Hz, 2H), 3.08 (s, 2H), 2.32 (s, 3H), 1.43 (s, 9H).

Step D

To a solution of the title compound from Step C above (0.42 g, 0.915 mmol) in dichloromethane was added 2N HCl (5 mL) in 1,4-dioxane. The reaction mixture was stirred overnight. After the completion of the reaction, the reaction mixture was evaporated to remove the solvent and washed with diethyl ether to afford the title compound as an off white solid (0.2 g, 58%).

MS: 345 (M+H)$^+$.

$^1$H-NMR (400 MHz, DMSO-d$_6$) δ=9.61 (s, 1H), 8.01-8.02 (m, 1H), 7.82 (d, J=8.40 Hz, 1H), 7.45-7.45 (m, 1H), 7.39 (d, J=8.40 Hz, 2H), 7.20-7.21 (m, 1H), 4.25 (s, 2H), 3.49 (s, 2H), 3.35 (d, J=3.60 Hz, 2H), 2.34 (s, 3H).

Step E

To a solution of the title compound from Step D above (5.0 g, 13 mmol) in Dichloromethane (50 mL), was added triethylamine (5 mL) and stirred for 10 min. The reaction mixture was diluted with Dichloromethane (20 mL), washed with water (2×30 mL) and a saturated solution of NaCl (30 mL). The combined organic layer was dried over sodium sulfate and concentrated under vacuum to afford the title compound as free base (quantitative yield).

Preparative Example 2

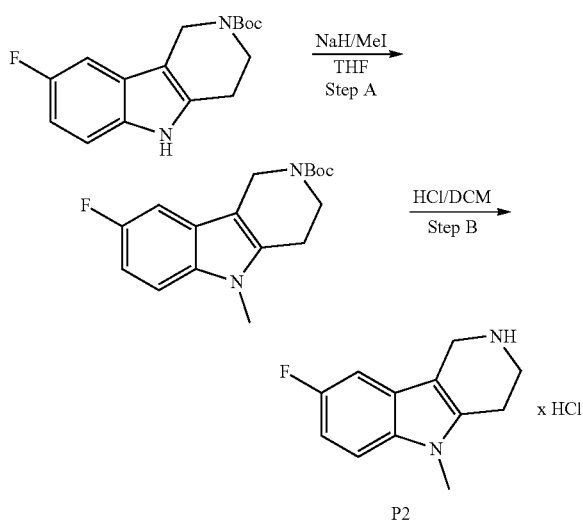

Step A

To a solution of the title compound from Preparative Example 1 Step B (0.41 g, 1.41 mmol) in THF (5 mL) was added sodium hydride (0.067 g, 2.82 mmol), the suspension was stirred at room temperature for 20 minutes. The reaction mixture was cooled again to 0° C. and methyl iodide (0.24 g, 1.45 mmol) was added. The reaction mixture was stirred for 3 h. The reaction mixture was dissolved in EtOAc (15 mL) and washed with water and brine and dried over Na$_2$SO$_4$. The crude product was purified on a silica gel column using a Biotage Isolera One purification system employing an EtOAc/hexane gradient (20/80=>80/20) to afford the title compound (0.3 g, 70%).

MS: 304 (M+H)$^+$.

$^1$H-NMR (400 MHz, DMSO-d$_6$) δ=7.38-7.39 (m, 1H), 7.22 (dd, J=2.40, 10.00 Hz, 1H), 6.90-6.91 (m, 1H), 4.49 (s, 2H), 3.71 (t, J=6.00 Hz, 2H), 3.62 (s, 3H), 2.79 (t, J=5.20 Hz, 2H), 1.40 (s, 9H).

Step B

To a solution of the title compound from Step A Above (0.3 mg, 0.986 mmol) in dichloromethane was added 2N HCl (5 mL) in 1,4-dioxane. The reaction mixture was stirred overnight. The reaction mixture was evaporated to remove the solvent and washed with diethyl ether to afford the title compound as an off white solid (0.12 g, 60%).

MS: 205.08 (M+H)$^+$.

$^1$H-NMR (400 MHz, DMSO-d$_6$) δ=9.45 (br, 1H), 7.45-7.46 (m, 1H), 7.30-7.31 (m, 1H), 6.98-7.00 (m, 1H), 4.26 (s, 2H), 3.66 (s, 3H), 3.49 (d, J=4.80 Hz, 2H), 3.06 (t, J=6.00 Hz, 2H), 2.50 (s, 9H).

Preparative Example 3

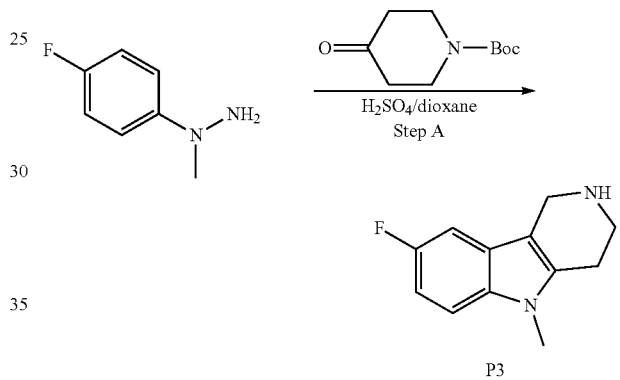

Step A

To a solution of 1-(4-fluorophenyl)-1-methylhydrazine (2 g, 14.0 mmol) and tert-butyl 4-oxopiperidine-1-carboxylate (2.84 g, 14.0 mmol) in 1,4-dioxane (10 mL) was added conc. H$_2$SO$_4$ (1 mL) at ice bath temperature. Then the reaction mixture was heated at 110° C. overnight. The reaction mixture was cooled to room temperature, the precipitate was filtered off. The filtrate was discarded. The solid was dissolved in water (10 mL), the pH was adjusted to 14 with NaOH solution, and the mixture was extracted with dichloromethane (150 mL). The organic phase was washed with water and brine and dried over Na$_2$SO$_4$. The solvent was removed to afford the title compound as free base (1.3 g, 46%).

MS: 205.08 (M+H)$^+$.

Preparative Example 4

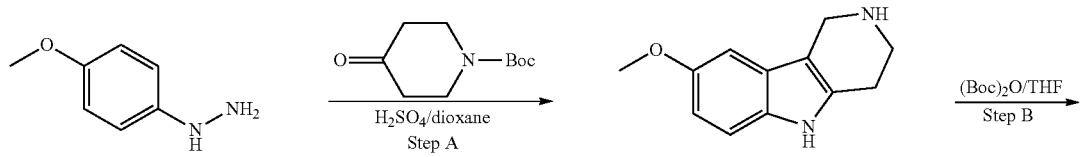

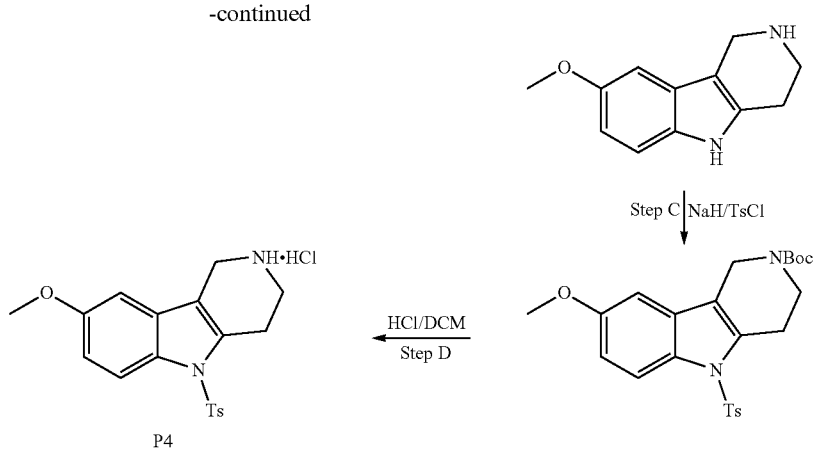

Step C | NaH/TsCl

Step D | HCl/DCM

P4

Step DA

To a solution of (4-methoxyphenyl)hydrazine (1 g, 5.6 mmol) and tert-butyl 4-oxopiperidine-1-carboxylate (1.13 g, 5.6 mmol) in 1,4-dioxane (10 mL) was added conc. $H_2SO_4$ (1 mL) at ice bath temperature. Then the reaction mixture was heated at 110° C. for 3 h. The reaction mixture was cooled to room temperature, the precipitate was filtered off. The solid was dissolved in water basified with NaOH solution and extracted with dichloromethane. The organic phase was separated and dried over $Na_2SO_4$, filtered and the solvent was removed to give the title compound as a pale yellow gummy liquid (0.60 g, 53%). The crude product as such was taken for the next step.

MS: 203 $(M+H)^+$.

Step B

To a solution of the title compound from Step A above (0.60 mg, 2.9 mmol) in THF was added di-tert-butyl dicarbonate (0.65 g, 2.9 mmol) and the mixture was stirred overnight. The solvent was removed and the crude product was purified on a silica gel column using a Biotage Isolera One purification system employing an EtOAc/hexane gradient (80/20) to afford the title compound as a pale yellow solid (0.55 g, 62%).

MS: 303 $(M+H)^+$.

$^1$H-NMR (400 MHz, DMSO-$d_6$) δ=10.71 (bs, 1H), 7.17 (d, J=8.40 Hz, 1H), 6.89 (s, 1H), 6.65-6.66 (m, 1H), 4.49 (s, 2H), 3.75 (s, 3H), 3.69 (t, J=5.60 Hz, 2H), 2.74 (t, J=5.60 Hz, 2H), 1.44 (s, 9H).

Step C

To a solution of the title compound from Step B above (0.55 g, 1.8 mmol) in THF (5 mL) was added sodium hydride (0.087 g, 3.6 mmol), followed by p-toluenesulfonyl chloride (0.342 g, 1.8 mmol). The reaction mixture was stirred for 45 minutes. After the completion of the reaction, the reaction mixture was dissolved in EtOAc (200 mL) and washed with water and brine and dried over $Na_2SO_4$. The crude product was purified on a silica gel column using a Biotage Isolera One purification system employing an EtOAc/hexane gradient (20/80) to afford the title compound as an off-white solid (0.45 g, 45%).

MS: 457 $(M+H)^+$.

$^1$H-NMR (400 MHz, DMSO-$d_6$) δ=7.92 (d, J=9.20 Hz, 1H), 7.71 (d, J=8.40 Hz, 2H), 7.35 (d, J=8.00 Hz, 2H), 7.01 (s, 1H), 6.91-6.92 (m, 1H), 4.42 (s, 2H), 3.77 (s, 3H), 3.68 (t, J=5.60 Hz, 2H), 3.05 (bs, 2H), 2.31 (s, 3H), 1.43 (s, 9H).

Step D

To a solution of the title compound from Step C above (0.450 g, 0.986 mmol) in dichloromethane was added 2N HCl (5 mL) in 1,4-dioxane. The reaction mixture was stirred overnight. After the completion of the reaction, the reaction mixture was evaporated to remove the solvent and washed with diethyl ether to afford the compound as an off white solid (0.23 g, 65%).

MS: 357 $(M+H)^+$.

$^1$H-NMR (400 MHz, DMSO-$d_6$) δ=9.67 (bs, 1H), 7.89 (d, J=9.20 Hz, 1H), 7.77 (d, J=8.40 Hz, 2H), 7.36 (d, J=8.00 Hz, 2H), 7.11 (d, J=2.40 Hz, 1H), 6.93-6.94 (m, 1H), 4.24 (s, 2H), 3.77 (s, 3H), 3.48-3.49 (m, 2H), 3.34-3.35 (m, 2H), 2.33 (s, 3H).

Preparative Example 5

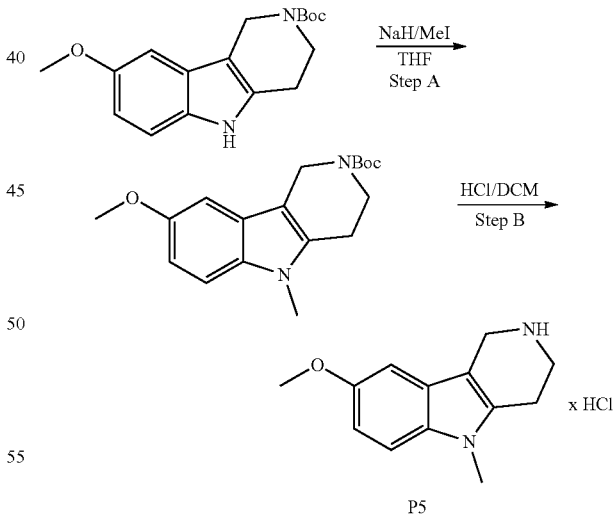

NaH/MeI, THF, Step A

HCl/DCM, Step B

P5

Step A

To a solution of the title compound from Preparative Example 4 Step B (0.55 g, 1.8 mmol) in THF (5 mL) was added sodium hydride (0.087 g, 3.6 mmol) at 0° C. The suspension was stirred at room temperature for 20 minutes. The reaction mixture was cooled again to 0° C. and methyl iodide (0.255 g, 1.8 mmol) was added. The reaction mixture was stirred for 45 minutes. After the completion of the reaction, the reaction mixture was dissolved in EtOAc (20 ml) and washed with water and brine and dried over Na₂SO₄, filtered and concentrated. The crude mixture was purified on a silica gel column using a Biotage Isolera One purification system employing an EtOAc/hexane gradient (80/20) to afford the title compound as a pale brown solid (0.40 g, 45%).

MS: 317 (M+H)$^+$.

$^1$H-NMR (400 MHz, DMSO-d$_6$) δ=7.29 (d, J=8.80 Hz, 2H), 6.93 (s, 1H), 6.72-6.73 (m, 1H), 4.50 (s, 2H), 3.76 (s, 3H), 3.70-3.72 (m, 2H), 3.59 (s, 3H), 2.78-2.79 (m, 2H), 1.44 (s, 9H).

Step B

To a solution of the title compound from Step A above (0.4 g, 1.26 mmol) in dichloromethane was added 2N HCl (5 mL) in 1,4-dioxane. The reaction mixture was stirred overnight. After the completion of the reaction, the reaction mixture was evaporated to remove the solvent and washed with diethyl ether to afford the title compound as a white solid (0.2 g, 73%).

MS: 217 (M+H)$^+$.

Step A

A mixture of 2-chloro-5-fluoropyridine (10 g, 76.34 mmol) and N-methylhydrazine (6 mL) was irradiated at 180° C. for 1 h in a microwave oven. After the completion of the reaction, the reaction mixture was cooled and the reaction mixture was poured in ice cold water and extracted with dichloromethane (2×50 mL). The organic phase was separated and dried over Na₂SO₄ and the solvent was removed to give the title compound as a pale brown solid (10 g, crude). The crude product was taken as such for the next step.

MS: 143 (M+H)$^+$.

Step B

To a solution of the title compound from Step A above (10 g, 70.84 mmol) in methanol (100 mL) was added tert-butyl 4-oxopiperidine-1-carboxylate (16.9 g, 85 mmol) and stirred overnight. The solvent was removed, the crude reaction mixture was purified on a silica gel column using a Biotage Isolera One purification system employing a methanol/DCM gradient (1/99) to afford the title compound as a brown gummy oil (5 g, 22%).

MS: 323 (M+H)$^+$.

$^1$H-NMR (400 MHz, DMSO-d$_6$) δ=7.82-7.84 (m, 1H), 7.13-7.14 (m, 1H), 6.72-6.73 (m, 1H), 4.51 (bs, 2H), 3.77 (s, 3H), 3.71-3.73 (m, 2H), 2.76-2.78 (m, 2H), 1.43 (s, 9H).

Step C

A mixture of the title compound from Step B above (5 g, 15.50 mmol) and diethylene glycol (5 mL) was irradiated at 180° C. for 1 h in a microwave oven. After the completion of the reaction, the reaction mixture was cooled and the reaction mixture was poured in ice cold water and extracted with dichloromethane (2×50 mL). The organic phase was separated and dried over Na₂SO₄ and the solvent was removed, the crude mixture was purified by preparative HPLC (Column: Phenomenex Gemini C18 (150*4.6) mm, 3.0 μm. Mobile Phase A: 10 mM ammonium acetate in Milli-Q water. Mobile phase B: Acetonitrile. Flow rate:1.0 ml\min), to afford the title compound as a brown solid (0.9 g, 29%).

MS: 206 (M+H)$^+$.

$^1$H-NMR (400 MHz, DMSO-d$_6$) δ=7.87-7.89 (m, 1H), 7.46-7.47 (m, 1H), 4.53 (bs, 2H), 3.77 (s, 3H), 3.71-3.73 (m, 2H), 2.76-2.78 (m, 2H).

Preparative Example 6

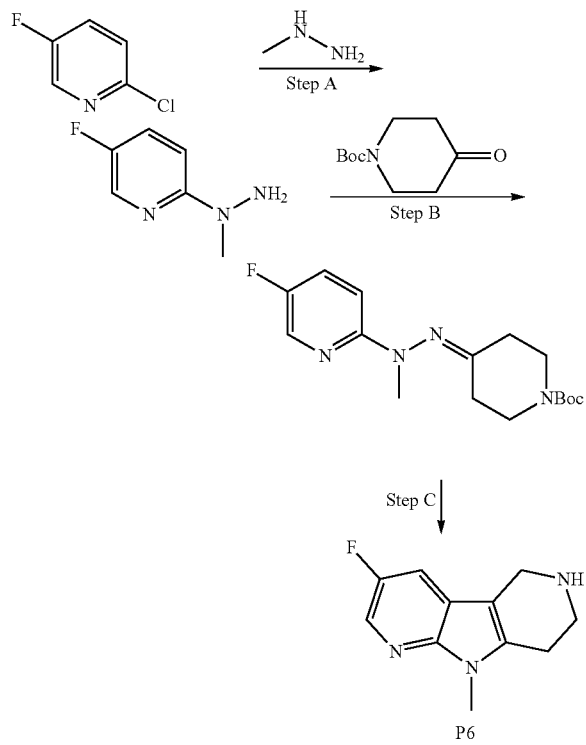

P6

Preparative Example 7

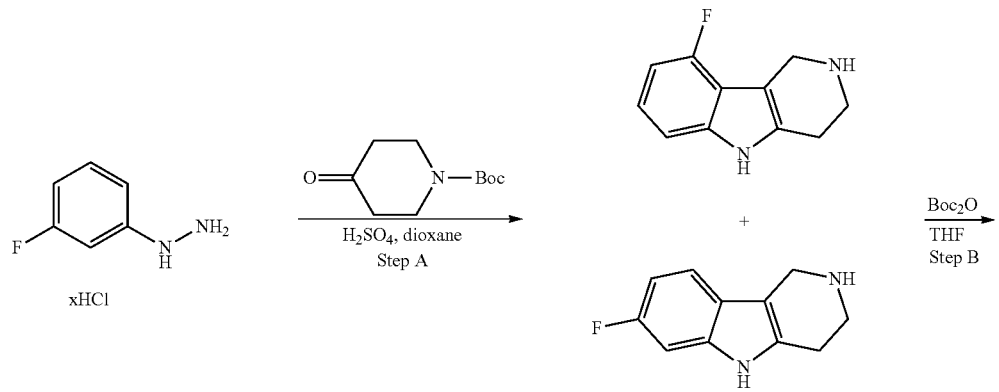

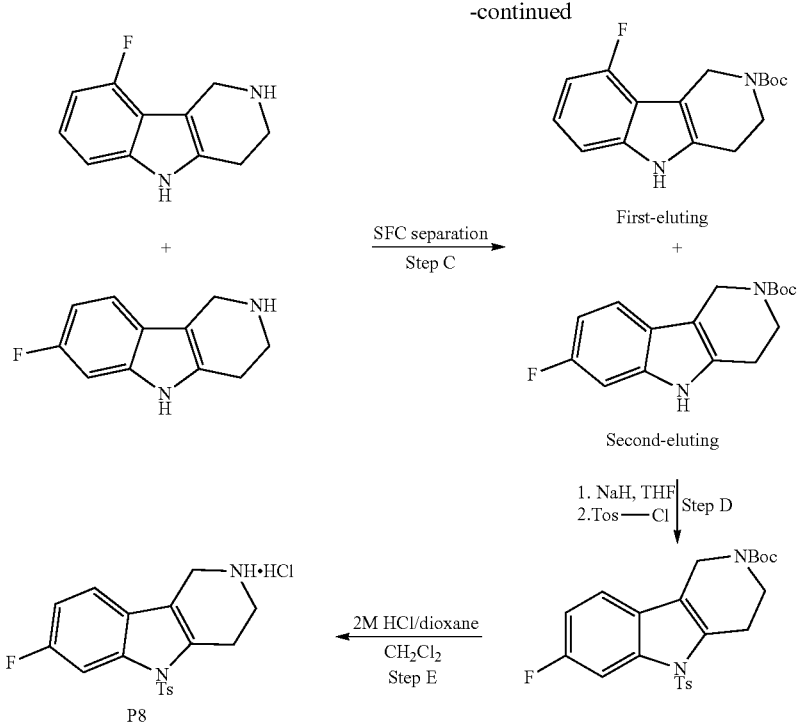

Step A

To a solution of 3-(fluorophenyl) hydrazine (1 g, 6.1 mmol) and tert-butyl 4-oxopiperidine-1-carboxylate (1.2 g, 6.1 mmol) in 1,4-dioxane (10 mL) was added conc. $H_2SO_4$ (1 mL) at 0° C. Then the reaction mixture was warmed to 25° C. and heated at 110° C. for 3 h. The reaction mixture was cooled to room temperature and the precipitate was filtered off. The solid was dissolved in water, basified with NaOH solution and extracted with dichloromethane. The organic phase was separated and dried over $Na_2SO_4$ and the solvent was removed to afford the mixture of regioisomers as a pale yellow solid (0.65 g, 56%).

MS: 191.1 $(M+H)^+$.

$^1$H-NMR (400 MHz, DMSO-$d_6$) δ=10.87 (bs, 1H), 7.26-7.30 (m, 1H), 7.02-7.05 (m, 1H), 6.74-6.79 (m, 1H), 3.83 (bs, 2H), 2.99-3.02 (m, 2H), 2.65-2.66 (m, 2H).

Step B

To a solution of the mixture of regioisomers (0.65 g, 3.15 mmol) in THF was added di-tert-butyl dicarbonate (0.757 g, 3.47 mmol) and the mixture was stirred for 12 h. After the completion of the reaction (monitored by TLC), the solvent was concentrated under reduced pressure to yield the crude product. It was purified by silica gel (60-120 mesh) column chromatography using hexane: EtOAc (70:30) to afford the mixture of the regioisomers tert-butyl 7-fluoro-1,3,4,5-tetrahydro-2H-pyrido[4,3-b]indole-2-carboxylate and tert-butyl 9-fluoro-1,3,4,5-tetrahydro-2H-pyrido[4,3-b]indole-2-carboxylate as a yellow solid (0.750 g, 61%) in a ratio of ~70:30, respectively.

MS: 291.2 $(M+H)^+$.

$^1$H-NMR (400 MHz, DMSO-$d_6$) δ=11.01 (bs, 1H), 7.36-7.39 (m, 1H), 7.06-7.09 (m, 1H), 6.79-6.84 (m, 1H), 4.51 (bs, 2H), 3.68-3.71 (m, 2H), 2.74-2.76 (m, 2H), 1.38 (s, 9H).

Step C

The mixture of regioisomers (0.750 mg, 70:30) was separated by a SFC chiral column (Chiracel OJ-H; Column: X-bridge C8 (50×4.6) mm, 3.5 µm, mobile Phase A: 0.1% TFA in water, mobile phase B: 0.1% TFA acetonitrile) to afford the second-eluting title compound tert-butyl 7-fluoro-1,3,4,5-tetrahydro-2H-pyrido[4,3-b]indole-2-carboxylate as a pale yellow solid with 100% chiral purity (0.4 mg, 53%). The first-eluting title compound tert-butyl 9-fluoro-1,3,4,5-tetrahydro-2H-pyrido[4,3-b]indole-2-carboxylate was isolated as a pale yellow solid with 100% chiral purity (0.25 g, 33%).

Second-Eluting Title Compound:

MS: 291.2 $(M+H)^+$.

$^1$H-NMR (400 MHz, DMSO-$d_6$) δ=11.01 (bs, 1H), 7.36-7.39 (m, 1H), 7.06-7.09 (m, 1H), 6.79-6.84 (m, 1H), 4.51 (bs, 2H), 3.68-3.71 (m, 2H), 2.74-2.77 (m, 2H), 1.44 (s, 9H).

RT=2.08 min.

First-Eluting Title Compound:

MS: 291.2 $(M+H)^+$.

$^1$H-NMR (400 MHz, DMSO-$d_6$) δ=11.22 (s, 1H), 7.13 (d, J=8.08 Hz, 1H), 6.96-6.97 (m, 1H), 6.69-6.71 (m, 1H), 4.63 (s, 2H), 3.69-3.70 (m, 2H), 2.68-2.76 (m, 2H), 1.44 (s, 9H).

RT=1.74 min.

Step D

To a solution of the second-eluting title compound from Step C above (0.4 g, 1.37 mmol) in THF (5 mL) was added sodium hydride (0.099 mg, 4.137 mmol), followed by p-toluenesulfonyl chloride (0.288 g, 1.51 mmol). The reaction mixture was stirred for 30 minutes. The mixture was dissolved in EtOAc (20 ml) and washed with water and brine and dried over $Na_2SO_4$. The crude product was purified on a silica gel column using a Biotage Isolera One purification system employing an EtOAc/heptane gradient (20/80=>80/20) to afford the title compound (0.3 g, 49%).

MS: 445 $(M+H)^+$.

$^1$H-NMR (400 MHz, chloroform-d) δ=7.92-7.94 (m, 1H), 7.68-7.70 (m, 1H), 7.25-7.29 (m, 4H), 7.00-7.04 (m, 1H), 4.50 (bs, 2H), 3.76 (bs, 2H), 3.12 (bs, 2H), 2.38 (s, 3H), 1.51 (s, 9H).

Step E

To a solution of the title compound from Step D above (0.3 g, 0.676 mmol) in dichloromethane was added 2N HCl (5 mL) in 1,4-dioxane. The reaction mixture was stirred for 12 h. After the completion of the reaction, the reaction mixture was evaporated to remove the solvent and washed with diethyl ether to afford the title compound as an off white solid (0.2 g 78%).

MS: 345 (M+H)$^+$.

$^1$H-NMR (400 MHz, DMSO-d$_6$) δ=9.50 (bs, 2H), 7.80-7.87 (m, 2H), 7.78 (d, J=2.00 Hz, 1H), 7.57-7.61 (m, 1H), 7.40 (d, J=8.16 Hz, 2H), 7.18-7.23 (m, 1H), 4.27 (bs, 2H), 3.56 (bs, 2H), 3.47 (bs, 2H), 2.34 (s, 3H).

Preparative Example 8

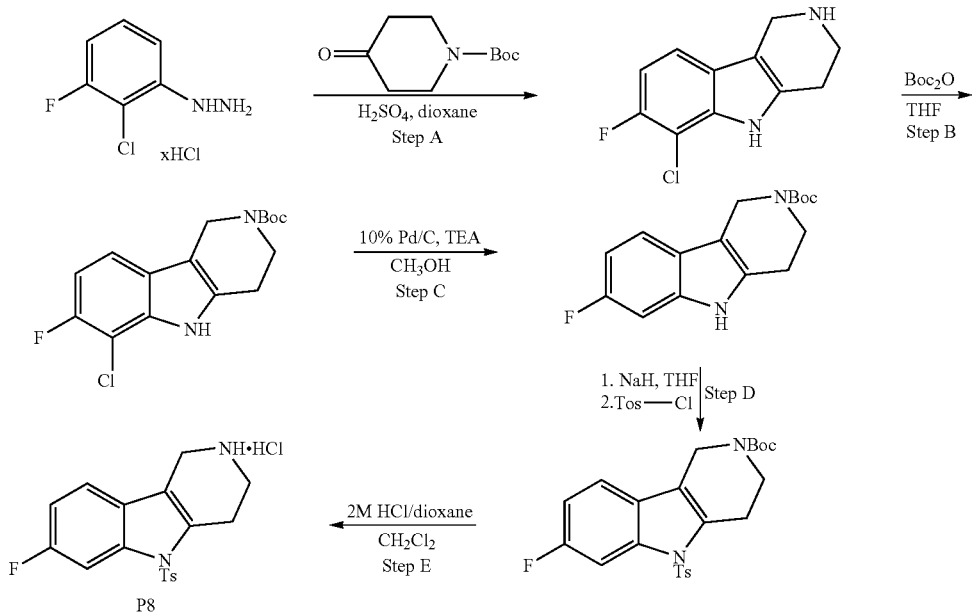

MS: 325.1 (M+H)$^+$.

$^1$H-NMR (400 MHz, DMSO-d$_6$) δ=11.43 (s, 1H), 7.36-7.38 (m, 1H), 6.97-7.00 (m, 1H), 4.51 (s, 2H), 3.68-3.69 (m, 2H), 2.76-2.78 (m, 2H), 1.43 (s, 9H).

Step C

To a solution of the title compound from Step B above (5 g, 15.3 mmol) in dry methanol (50 mL) was added triethylamine (6.74 mL, 46.18 mmol) and 10% Pd/C (0.2 mg, 20% wt). Hydrogenation was conducted under 10 bar pressure for 16 hours. The reaction mixture was filtered through a celite pad and concentrated under vacuum to afford the title compound (4 g, 90%).

MS: 291.2 (M+H)$^+$.

$^1$H-NMR (400 MHz, DMSO-d$_6$) δ=11.01 (bs, 1H), 7.36-7.39 (m, 1H), 7.06-7.09 (m, 1H), 6.79-6.84 (m, 1H), 4.51 (bs, 2H), 3.68-3.71 (m, 2H), 2.74-2.77 (m, 2H), 1.44 (s, 9H).

Step A

To a solution of (2-chloro-3-fluorophenyl)hydrazine (10 g, 62.5 mmol) and tert-butyl 4-oxopiperidine-1-carboxylate (12 g, 62.5 mmol) in 1,4-dioxane (100 mL) was added conc. H$_2$SO$_4$ (10 mL) at 0° C. Then the reaction mixture was warmed to 25° C. and heated at 110° C. for 3 h. The reaction mixture was cooled to room temperature and the precipitate was filtered off. The solid was dissolved in water, basified with NaOH solution and extracted with dichloromethane. The organic phase was separated and dried over Na$_2$SO$_4$ and the solvent was removed to give the title compound as a pale yellow solid (10 g, 72%).

MS: 225 (M+H)$^+$.

$^1$H-NMR (400 MHz, DMSO-d$_6$) δ=11.23 (bs, 1H), 7.27-7.28 (m, 1H), 6.94-6.96 (m, 1H), 3.82 (s, 2H), 2.98-3.00 (m, 2H), 2.68 (d, J=4.72 Hz, 2H).

Step B

To a solution of the title compound from Step A above (10 g, 44.5 mmol) in THF (100 mL) was added di-tert-butyl dicarbonate (10.5 g, 46.5 mmol) and the mixture was stirred for 12 h. After the completion of the reaction (monitored by TLC), the solvent was concentrated under reduced pressure to yield the crude product. It was purified by silica gel (60-120 mesh) column chromatography to afford the title compound as a yellow solid (12 g, 85%).

Step D

To a solution of the title compound from Step C above (4 g, 13.7 mmol) in THF (40 mL) was added sodium hydride (9.9 g, 41.23 mmol), followed by p-toluenesulfonyl chloride (2.88 g, 15.1 mmol). The reaction mixture was stirred for 30 min. The mixture was dissolved in EtOAc (200 ml) and washed with water and brine and dried over Na$_2$SO$_4$. The crude product was purified on a silica gel column using a Biotage Isolera One purification system employing an EtOAc/heptane gradient (20/80=>80/20) to afford the title compound (5 g, 82%).

MS: 445 (M+H)$^+$.

$^1$H-NMR (400 MHz, chloroform-d) δ=7.92-7.94 (m, 1H), 7.68-7.70 (m, 1H), 7.25-7.29 (m, 4H), 7.00-7.04 (m, 1H), 4.50 (bs, 2H), 3.76 (bs, 2H), 3.12 (bs, 2H), 2.38 (s, 3H), 1.51 (s, 9H).

Step E

To a solution of the title compound from Step D above (3 g, 6.76 mmol) in dichloromethane (30 mL) was added 2N HCl (15 mL) in 1,4-dioxane. The reaction mixture was stirred for 12 h. After the completion of the reaction, the reaction mixture was evaporated to remove the solvent and washed with diethyl ether to afford the title compound as an off white solid (2 g, 78%).

MS: 345 (M+H)⁺.

$^1$H NMR (400 MHz, DMSO-d$_6$) δ=9.50 (bs, 2H), 7.80-7.87 (m, 2H), 7.78 (d, J=2.00 Hz, 1H), 7.57-7.61 (m, 1H), 7.40 (d, J=8.16 Hz, 2H), 7.18-7.23 (m, 1H), 4.27 (bs, 2H), 3.56 (bs, 2H), 3.47 (bs, 2H), 2.34 (s, 3H).

Preparative Example 9

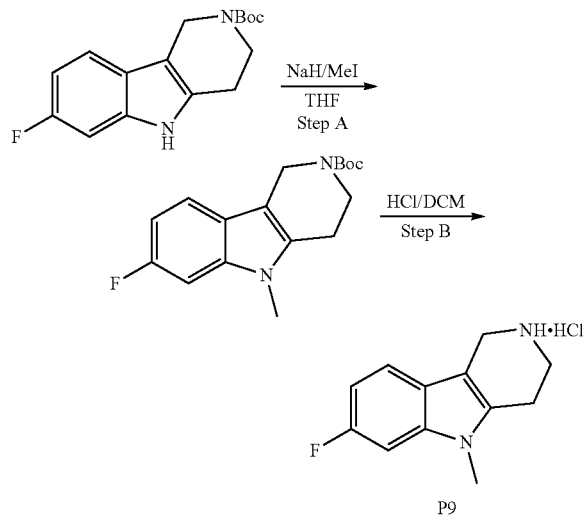

P9

Step A

To a solution of the title compound from Preparative Example 8 Step C (0.4 mg, 1.37 mmol) in THF (5 mL) was added sodium hydride (0.099 g, 4.137 mmol), followed by methyl iodide (0.102 ml, 1.64 mmol). The reaction mixture was stirred for 2 h. The mixture was dissolved in EtOAc (20 ml) and washed with water and brine and dried over Na$_2$SO$_4$. The crude product was purified on a silica gel column using a Biotage Isolera One purification system employing an EtOAc/heptane gradient (20/80=>80/20) to afford the title compound (0.3 mg, 73%).

MS: 305.37 (M+H)⁺.

Step B

To a solution of the title compound from Step A above (0.3 mg, 0.986 mmol) in dichloromethane was added 2N HCl (5 mL) in 1,4-dioxane. The reaction mixture was stirred overnight. After the completion of the reaction, the reaction mixture was evaporated to remove the solvent and washed with diethyl ether to afford the title compound as an off white solid (0.18 g 75%).

MS: 205 (M+H)⁺.

Preparative Example 10

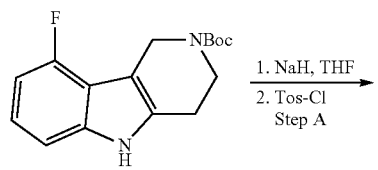

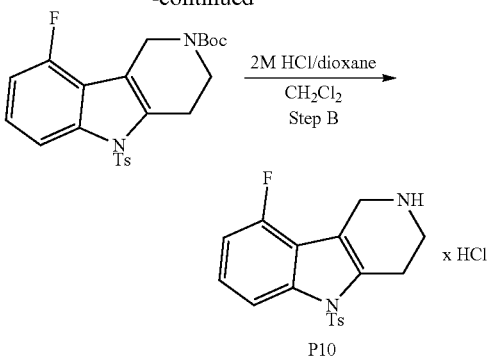

P10

Step A

To a solution of the first eluting title compound from Preparative Example 7 of Step C (0.2 mg, 0.67 mmol) in THF (5 mL) was added sodium hydride (0.048 g, 2.137 mmol), followed by p-toluenesulfonyl chloride (0.144 g, 0.76 mmol). The reaction mixture was stirred for 30 minutes. The mixture was dissolved in EtOAc (20 ml) and washed with water and brine and dried over Na$_2$SO$_4$. The crude product was purified on a silica gel column using a Biotage Isolera One purification system employing an EtOAc/heptane gradient (20/80=>80/20) to afford the title compound (0.155 g, 50%).

MS: 445 (M+H)⁺.

$^1$H-NMR (400 MHz, DMSO-d$_6$) δ=7.80-7.82 (m, 3H), 7.31-7.32 (m, 3H), 7.07-7.09 (m, 1H), 4.56 (s, 2H), 3.68-3.69 (m, 2H), 3.09 (bs, 2H), 2.33 (s, 3H), 1.43 (s, 9H).

Step B

To a solution of the title compound from Step A above (0.15 g, 0.337 mmol) in dichloromethane was added 2N HCl (5 mL) in 1,4-dioxane. The reaction mixture was stirred for 12 h. After the completion of the reaction, the reaction mixture was evaporated to remove the solvent and washed with diethyl ether to afford the title compound as an off white solid (0.1 g, 71%).

MS: 345 (M+H)⁺.

$^1$H-NMR (400 MHz, DMSO-d$_6$) δ=9.49 (bs, 2H), 7.85-7.87 (m, 3H), 7.35-7.36 (m, 3H), 7.12-7.14 (m, 1H), 4.39 (s, 2H), 3.48 (bs, 2H), 3.17 (bs, 2H), 2.35 (s, 3H).

Preparative Example 11

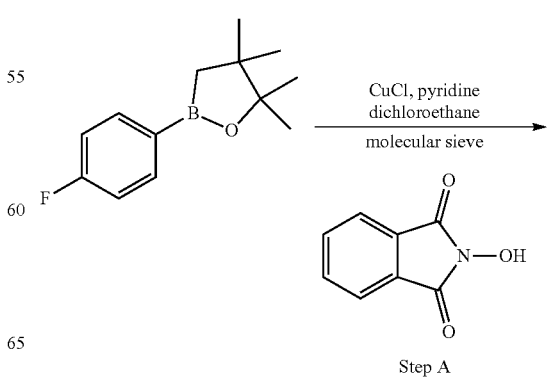

Step A

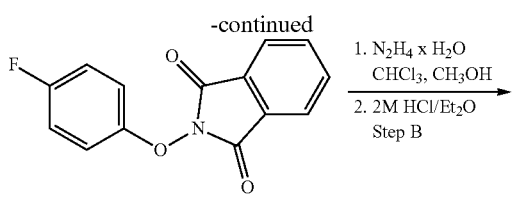

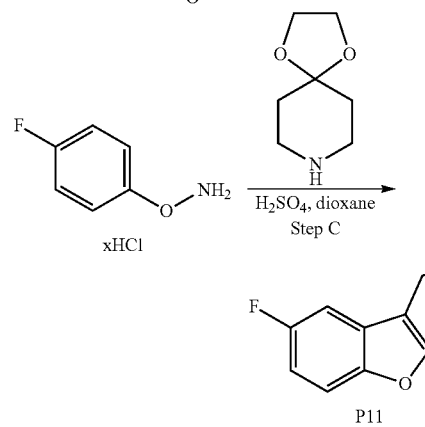

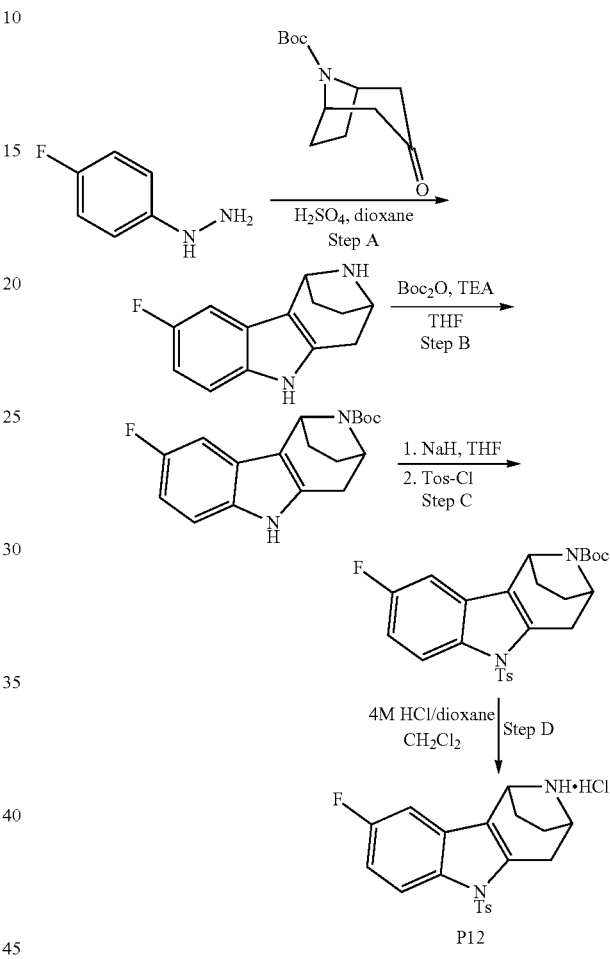

Step A

To a solution of 2-(4-fluorophenyl)-4,4,5,5-tetramethyl-1,3,2-dioxaborolane (5 g, 22.51 mmol) in dichloroethane (250 mL) was added N-hydroxyphthalimide (7.34 g, 45.03 mmol), copper(I) chloride (2.22 g, 22.51 mmol), pyridine (2.75 mL, 33.75 mmol), molecular sieves (5 g), and the reaction mixture was heated to 70° C. for 12 h. After the completion of the reaction, the reaction mixture was filtered through a Celite bed and washed with ethyl acetate. The ethyl acetate layer was concentrated and the crude product was purified on a silica gel using a Biotage Isolera One purification system employing a hexane/EtOAc gradient (90/10=>80/20) to afford the title compound as a white solid (1.4 g, 24%).

MS: 258.22 (M+H)$^+$.

$^1$H-NMR (400 MHz, DMSO-d$_6$) δ=7.92-7.93 (m, 4H), 7.33-7.34 (m, 2H), 7.20-7.22 (m, 2H).

Step B

To a solution of the title compound from Step A above (1.4 g, 5.44 mmol) in chloroform:methanol (9:1, 100 mL) was added hydrazine hydrate (0.81 g, 16.32 mmol) and the reaction mixture was allowed to stir at 25° C. for 12 h. After the completion of the reaction, the reaction mixture was filtered through a Celite bed and washed with dichloromethane. The dichloromethane layer was concentrated and the crude product was added to ether (5 mL) and 2N HCl in ether (2 mL) at 0° C., then the reaction mixture was allowed to stir at 25° C. for 30 min. After the completion of the reaction, the reaction mixture was filtered, dried under vacuum to get an off white solid (0.44 g, 50%).

MS: 128.12 (M+H)$^+$.

$^1$H-NMR (400 MHz, DMSO-d$_6$) δ=8.03-8.04 (m, 2H), 7.76-7.76 (m, 2H).

Step C

To a solution of the title compound from Step B above (0.44 g, 2.7 mmol) and 1,4-dioxa-8-azaspiro[4.5]decane (0.44 g, 3.07 mmol) in 1,4-dioxane (5 mL) was added conc. H$_2$SO$_4$ (0.5 mL) at 0° C. The reaction mixture was warmed to 25° C. and then further heated at 150° C. for 1 h under microwave conditions. The reaction mixture was cooled to 25° C. and the precipitate was filtered off. The solid was dissolved in water, basified with NaOH solution and extracted with dichloromethane. The organic phase was separated and dried over Na$_2$SO$_4$ and the solvent was concentrated, the crude product was taken as such for the next step (0.270 g, 52%).

MS: 192.21 (M+H)$^+$.

Preparative Example 12

Step A

To a solution of 4-(fluorophenyl) hydrazine hydrochloride (10 g, 0.061 mol) and tert-butyl 3-oxo-8-azabicyclo[3.2.1]octane-8-carboxylate (13.9 g, 0.61 mol) in 1,4-dioxane (100 mL) was added conc. H$_2$SO$_4$ (10 mL) at 0° C. and then the mixture was heated to 100° C. for 12 h. After completion of the reaction, the reaction mixture was cooled to room temperature and the solvent was removed by high vacuum to get the crude material. The crude material was basified using 30% sodium hydroxide solution and the solid was precipitated. The precipitated solid was filtered, washed with water (100 mL) and diethyl ether (100 mL), then the solid was dried under line vacuum for 16 h to afford the title compound as a pale brown solid (11 g, 83%).

MS: 216.10 (M+H)$^+$.

Step B

To a solution of the title compound from Step A above (11 g, 0.051 mol) in THF (50 mL) was added triethylamine (11 mL, 0.076 mol) and di-tert-butyl dicarbonate (11.13 g, 0.051 mol) at 0° C. and then stirred at room temperature for 12 h. After the completion of the reaction as evidenced by TLC, the solvent was removed and the crude reaction mixture was purified by a silica gel column using 40% to 50% of ethyl acetate in petroleum ether to afford the title compound as a pale yellow solid (7.4 g, 46%).

MS: 316.15 (M+H)$^+$.

$^1$H-NMR (400 MHz, DMSO-d$_6$) δ=10.94 (bs, 1H), 7.23-7.24 (m, 2H), 6.80-6.81 (m, 1H), 5.09-5.11 (m, 1H), 4.46 (bs, 1H), 3.23-3.27 (m, 1H), 2.51-2.57 (m, 1H), 2.22-2.26 (m, 1H), 2.00-2.07 (m, 1H), 1.59-1.60 (m, 1H), 1.41-1.44 (m, 2H), 1.20-1.27 (m, 9H).

Step C

To a solution of the title compound from Step B above (3 g, 0.009 mol) in THF (30 mL) was added sodium hydride (60% in mineral oil; 0.57 g, 0.014 mol) portionwise at 0° C. After the addition was completed, the reaction mixture was allowed to stir at room temperature for 30 minutes, and then the reaction mixture was again cooled to 0° C. To this mixture p-toluenesulfonyl chloride (2.16 g, 0.11 mol) dissolved in THF (20 mL) was added dropwise at 0° C. After the addition was completed, the reaction mixture was allowed to stir at room temperature for 2 h. After completion of the reaction as evidenced by TLC, the reaction mixture was cooled to 0° C. and quenched with ice water, followed by extraction using ethyl acetate (100 mL). The ethyl acetate layer was washed with water (30 mL) and brine solution (30 mL). The organic layer was dried over Na$_2$SO$_4$, filtered and evaporated to afford the crude product which was purified by a silica gel column using 15% to 25% of ethyl acetate in petroleum ether to afford the title compound as an off white solid (2.9 g, 65%).

MS: 470.16 (M+H)$^+$.

Step D

To a solution of the title compound from Step C above (2.9 g, 0.006 mol) in dichloromethane (10 mL) at 0° C. was added 4N HCl (20 mL) in 1,4-dioxane. The reaction mixture was allowed to stir at ambient temperature for 12 h. After the completion of the reaction, the reaction mixture was evaporated to remove the solvent and washed with diethyl ether (10 mL) to afford the title compound as an off white solid (2.4 g, 98%).

MS: 370.15 (M+H)$^+$.

$^1$H-NMR (400 MHz, DMSO-d$_6$) δ=8.07-8.08 (m, 1H), 7.78-7.80 (m, 1H), 7.30-7.31 (m, 3H), 7.10-7.11 (m, 1H), 5.13 (d, J=4.80 Hz, 1H), 4.52 (d, J=4.80 Hz, 1H), 3.64-3.65 (m, 4H), 3.30-3.30 (m, 1H), 2.22-2.24 (m, 7H), 1.92 (bs, 1H).

Preparative Example 13

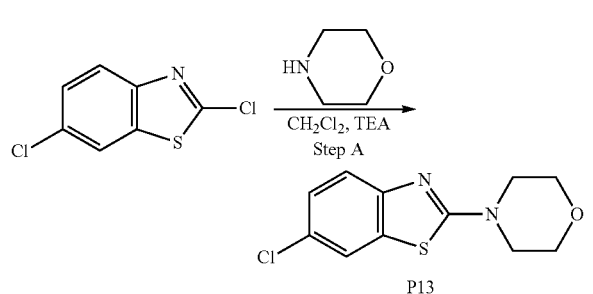

Step A

To a solution of 2,6-dichlorobenzo[d]thiazole (5 g, 24.5 mmol) in dry dichloromethane (50 mL) was added morpholine (3.19 g, 36.6 mmol), and the mixture was cooled to 0° C. To this cold reaction mixture was added triethylamine (3.71 g, 36.7 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (5 g, 96%).

MS: 213.4 (M+H)$^+$.

$^1$H-NMR (400 MHz, DMSO-d$_6$) δ=7.80 (d, J=8.00 Hz, 1H), 7.53 (d, J=2.00 Hz, 1H), 7.13-7.14 (m, 1H), 3.74-3.75 (m, 4H), 3.56-3.57 (m, 4H).

Preparative Example 14

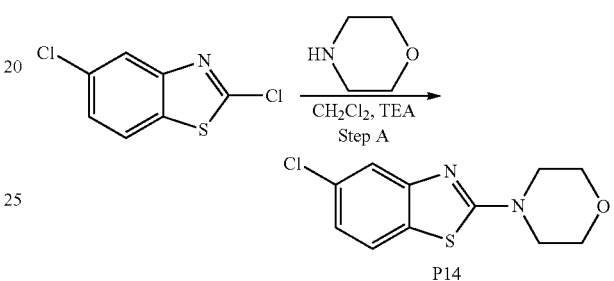

Step A

To a solution of 2,5-dichlorobenzo[d]thiazole (5 g, 24.5 mmol) in dry dichloromethane (50 mL) was added morpholine (3.19 g, 36.6 mmol), and the mixture was cooled to 0° C. To this cold reaction mixture was added triethylamine (3.71 g, 36.7 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (4.5 g, 86%).

MS: 255.4 (M+H)$^+$.

$^1$H-NMR (400 MHz, DMSO-d$_6$) δ=7.82 (d, J=8.00 Hz, 1H), 7.50 (d, J=2.00 Hz, 1H), 7.11-7.11 (m, 1H), 3.72-3.73 (m, 4H), 3.55-3.56 (m, 4H).

Preparative Example 15

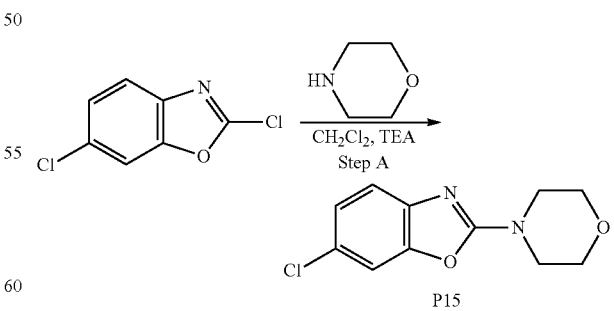

Step A

To a solution of 2,6-dichlorobenzo[d]oxazole (5 g, 26.8 mmol) in dry dichloromethane (50 mL) was added morpholine (3.50 g, 40.3 mmol), and the mixture was cooled to 0° C. To this cold reaction mixture was added triethylamine (4.0 g, 39.6 mmol) dropwise and the mixture was allowed to stir at room temperature for 4 h. After the completion of the reaction, the reaction mixture was treated with H$_2$O (2×20 mL) and extracted with dichlormethane. The organic layer was separated, dried over Na$_2$SO$_4$, filtered and evaporated to afford a white solid which was triturated with diethyl ether to afford the title compound (5 g, 78%).

MS: 239.2 (M+H)$^+$.

$^1$H-NMR (400 MHz, DMSO-d$_6$) δ=7.59 (d, J=2.80 Hz, 1H), 7.30 (d, J=11.20 Hz, 1H), 7.21 (dd, J=2.80, 11.20 Hz, 1H), 3.71-3.74 (m, 4H), 3.57-3.60 (m, 4H).

Preparative Example 16

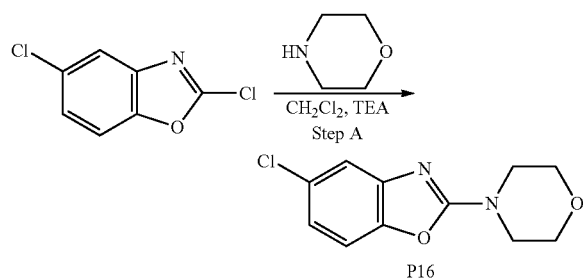

P16

Step A

To a solution of 2,5-dichlorobenzo[d]oxazole (5 g, 26.8 mmol) in dry dichloromethane (50 mL) was added morpholine (3.50 g, 40.3 mmol), and the mixture was cooled to 0° C. To this cold reaction mixture was added triethylamine (4.0 g, 39.6 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (5.2 g, 81%).

MS: 239.2 (M+H)$^+$.

$^1$H-NMR (400 MHz, DMSO-d$_6$) δ=7.44 (d, J=8.40 Hz, 1H), 7.36 (d, J=2.40 Hz, 1H), 7.06 (dd, J=2.00, 8.40 Hz, 1H), 3.71-3.73 (m, 4H), 3.59-3.61 (m, 4H).

Preparative Example 17

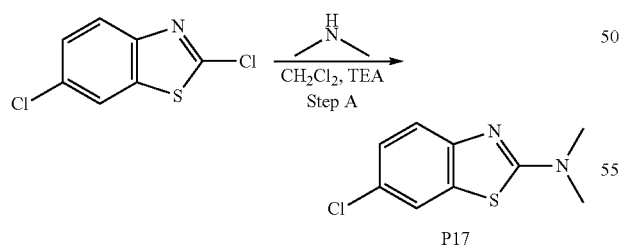

P17

Step A

To a solution of 2,6-dichlorobenzo[d]thiazole (5 g, 24.5 mmol) in dry dichloromethane (50 mL) was added 2M dimethylamine in THF (18.37 mL, 36.65 mol), and the mixture was cooled to 0° C. To this cold reaction mixture was added triethylamine (6.8 mL, 49 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (4.8 g, 94%).

MS: 213.4 (M+H)$^+$.

$^1$H-NMR (400 MHz, DMSO-d$_6$) δ=7.88 (d, J=2.10 Hz, 1H), 7.41 (d, J=8.70 Hz, 1H), 7.25-7.26 (m, 1H), 3.14 (s, 6H).

Preparative Example 18

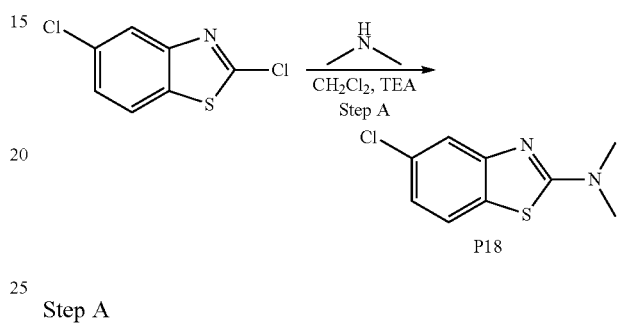

P18

Step A

To a solution of 2,5-dichlorobenzo[d]thiazole (5 g, 24.5 mmol) in dry dichloromethane (50 mL) was added 2M dimethylamine in THF (18.37 mL, 36.65 mol), and the mixture was cooled to 0° C. To this cold reaction mixture was added triethylamine (6.8 mL, 49 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (4.5 g, 88%).

MS: 213.4 (M+H)$^+$.

$^1$H-NMR (400 MHz, DMSO-d$_6$) δ=7.77 (d, J=11.20 Hz, 1H), 7.46 (d, J=2.40 Hz, 1H), 7.05-7.05 (m, 1H), 3.14 (s, 6H).

Preparative Example 19

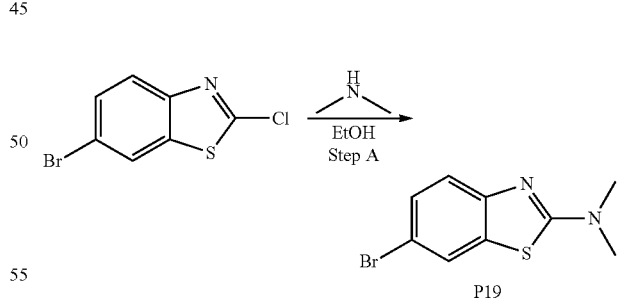

P19

Step A

To a solution of 6-bromo-2-chlorobenzo[d]thiazole (0.45 g, 1.81 mmol) in ethanol (12 mL), was added 2M dimethyl amine solution (3 mL) and the mixture was heated for 60 minutes using a Biotage microwave oven at 100° C. The reaction mixture was cooled to room temperature. The solvent was removed, the crude product was purified on a silica gel column using an ethyl acetate and heptane gradient (40/60=>60/40) to give the title compound as a solid (0.441 g, 95%).

$^1$H-NMR (400 MHz, Chloroform-d) δ=7.70 (d, J=1.9 Hz, 1H), 7.43-7.35 (m, 2H), 3.20 (s, 6H).

Preparative Example 20

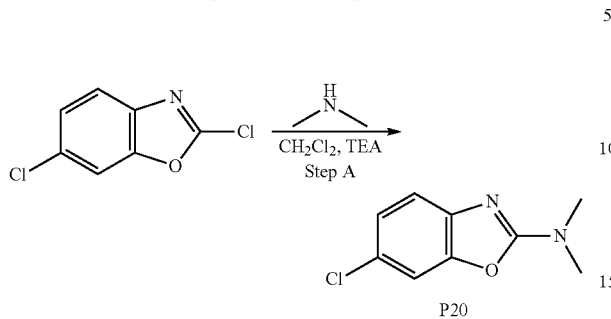

Step A

To a solution of 2,6-dichlorobenzo[d]oxazole (5 g, 26.6 mmol) in dry dichloromethane (50 mL) was added 2M dimethylamine in THF (26.6 mL, 53.2 mmol), and the mixture was cooled to 00° C. To this cold reaction mixture was added triethylamine (5.6 mL, 39.9 mmol) dropwise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (5 g, 96%).

MS: 197.2 (M+H)$^+$.

$^1$H-NMR (400 MHz, DMSO-d$_6$) δ=7.56 (s, 1H), 7.23-7.24 (m, 1H), 7.16-7.16 (m, 1H), 3.13 (s, 6H).

Preparative Example 21

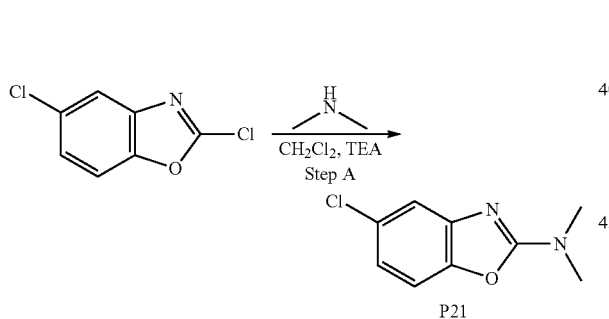

Step A

To a solution of 2,5-dichlorobenzo[d]oxazole (5 g, 26.6 mmol) in dry dichloromethane (50 mL) was added 2M dimethylamine in THF (26.6 mL, 53.2 mmol), and the mixture was cooled to 00° C. To this cold reaction mixture was added triethylamine (5.6 mL, 39.9 mmol) drop-wise and the mixture was allowed to stir at room temperature for 4 h. After the completion of the reaction, the reaction mixture was treated with H$_2$O (2×20 mL) and extracted with dichloromethane. The organic layer was separated, dried over Na$_2$SO$_4$, filtered and evaporated to afford a white solid which was triturated with diethyl ether to afford the title compound (4.9 g, 94%).

MS: 197.2 (M+H)$^+$.

$^1$H-NMR (400 MHz, DMSO-d$_6$) δ=7.40 (d, J=8.40 Hz, 1H), 7.30 (d, J=2.00 Hz, 1H), 6.99-6.99 (m, 1H), 3.13 (s, 6H).

Preparative Example 22

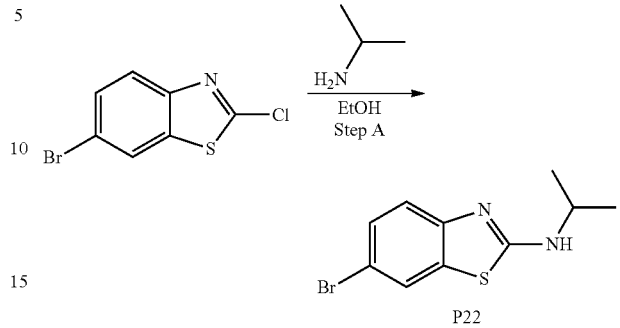

Step A

To a solution of 6-bromo-2-chlorobenzo[d]thiazole (0.8 g, 3.2 mmol) in ethanol (12 mL) was added isopropylamine solution (1 mL) and the mixture was heated for 45 minutes using a Biotage microwave oven at 100° C. The reaction mixture was cooled to room temperature. The solvent was removed, the crude product was crystallized from EtOAc and n-heptane mixture to afford the title compound as a solid (0.663 g, 75.8%).

$^1$H-NMR (400 MHz, Chloroform-d) δ=7.69 (t, J=1.3 Hz, 1H), 7.38 (d, J=1.3 Hz, 2H), 7.27 (s, 1H), 5.51-5.26 (m, 1H), 3.92 (h, J=6.5 Hz, 1H), 1.33 (d, J=6.4 Hz, 6H).

Preparative Example 23

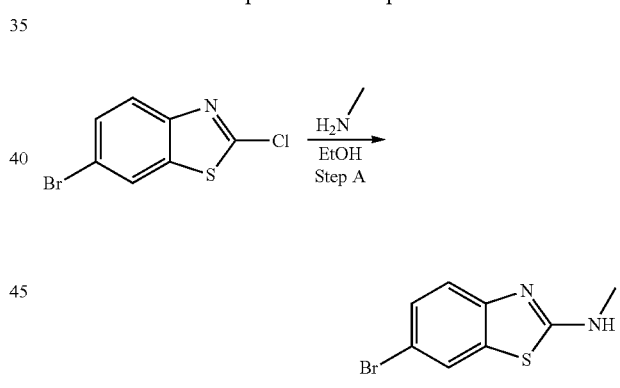

Step A

To a solution of 6-bromo-2-chlorobenzo[d]thiazole (1 g, 4.0 mmol) in ethanol (6 mL) was added isopropylamine solution (1.5 mL) and the mixture was heated for 90 minutes using a Biotage microwave oven at 100° C. The reaction mixture was cooled to room temperature. The solvent was removed, the crude product was dissolved in dichloromethane (150 mL) and washed with 1M NaOH solution, water and brine and dried over Na$_2$SO$_4$. The solvent was removed under reduced pressure to give a crude product, which was purified on a silica gel column using an EtOAc and heptane gradient (20/80=>50/50) to afford the title compound as a solid (0.35 g, 36%).

$^1$H-NMR (400 MHz, Chloroform-d) δ=7.72 (s, 1H), 7.41 (s, 1H), 7.29 (d, J=3.3 Hz, 1H), 5.40 (s, 1H), 3.13 (s, 3H).

Preparative Example 24

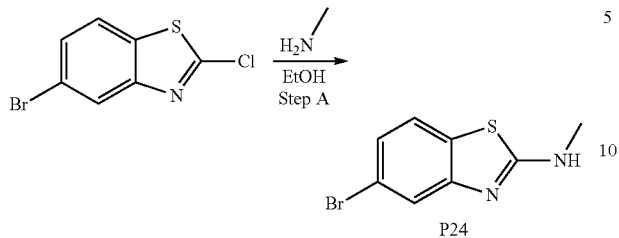

Step A

To a solution of 5-bromo-2-chlorobenzo[d]thiazole (0.9 g, 3.62 mmol) in ethanol (12 mL) was added 4M methylamine solution (1 mL) and the mixture was heated for 90 minutes using a Biotage microwave oven at 100° C. The reaction mixture was cooled to room temperature. The solvent was removed, the crude product was purified on a silica gel column using an EtOAc and heptane gradient (20/80=>50/50) to afford the title compound as a solid (0.57 g, 65%).

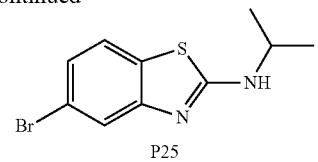

Step A

To a solution of 5-bromo-2-chlorobenzo[d]thiazole (0.87 g, 3.5 mmol) in ethanol (12 mL) was added isopropylamine solution (1.5 mL) and the mixture was heated for 60 minutes using a Biotage microwave oven at 100° C. The reaction mixture was cooled to room temperature. The solvent was removed, the crude product was dissolved in dichlormethane (150 mL) and washed with 1M NaOH solution, water and brine and dried over $Na_2SO_4$. The solvent was removed under reduced pressure to give a crude product, which was purified on a silica gel column using an EtOAc and heptane gradient (20/80=>50/50) to afford the title compound as a solid (0.75 g, 79%).

$^1$H-NMR (400 MHz, Chloroform-d) δ=7.67 (d, J=1.9 Hz, 1H), 7.43 (d, J=8.5 Hz, 1H), 7.19 (dd, J=8.3, 1.9 Hz, 1H), 5.47 (s, 1H), 4.04-3.79 (m, 1H), 1.34 (d, J=6.5 Hz, 6H).

Preparative Example 26

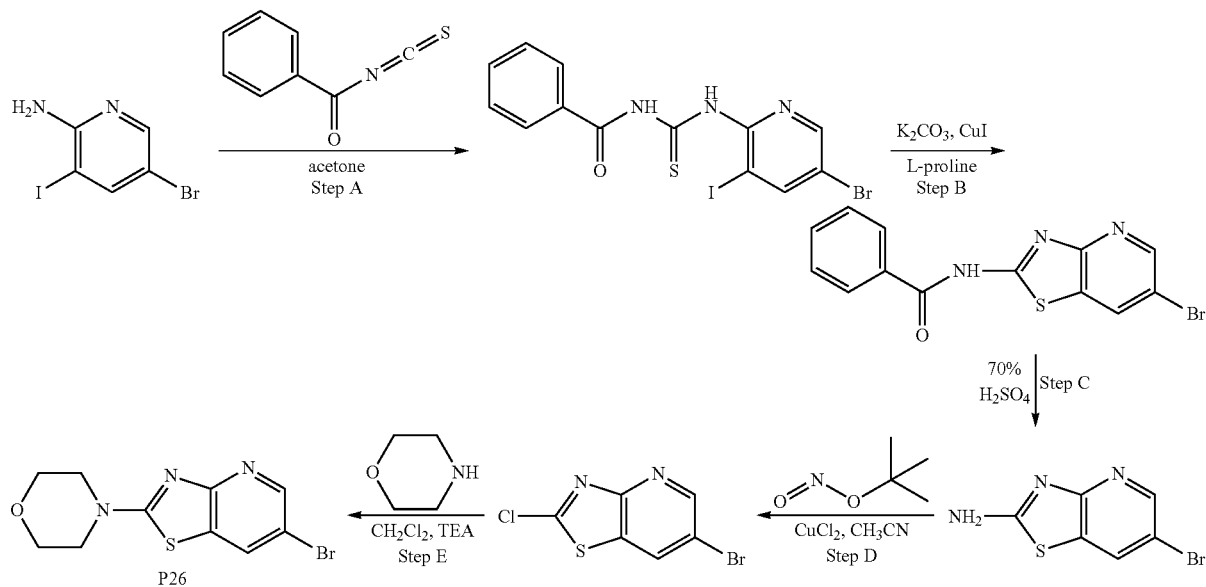

$^1$H-NMR (400 MHz, Chloroform-d) δ=7.68 (t, J=2.0 Hz, 1H), 7.46 (d, J=8.3 Hz, 1H), 7.22 (dd, J=8.4, 1.9 Hz, 1H), 5.90 (s, 1H), 3.13 (s, 3H).

Preparative Example 25

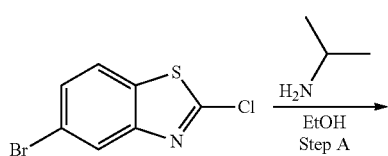

Step A

A solution of 5-bromo-3-iodopyridin-2-amine (5 g, 16.72 mmol) and benzoyl isothiocyanate (3.29, 20.07 mmol) in acetone (10 mL) was stirred at 60° C. for 12 hours, the reaction was monitored by TLC. The solvent was evaporated and the solid was filtered, washed with n-hexane (200 mL) and dried to give the title compound as an off-white solid (4 g, 52%).

MS: 461.5 (M+H)$^+$.

$^1$H-NMR (400 MHz, DMSO-d$_6$) δ=12.35 (s, 1H), 11.86 (s, 1H), 8.64-8.65 (m, 2H), 7.99-7.99 (m, 2H), 7.67 (s, 1H), 7.56 (d, J=9.40 Hz, 2H).

Step B

To a solution of the title compound from Step A above (4 g, 12.1 mmol) in 1,4-dioxane (60 mL) was added potassium carbonate (2.5 g, 18.15 mmol), L-proline (0.28 g, 2.43 mmol) and copper(I) iodide (0.462 g, 2.43 mmol). Then, the reaction mixture was stirred at 80° C. for 16 hours, the reaction was monitored by TLC. The reaction mixture was poured into 1.0 L of water and 1.0 L of aqueous saturated solution of NH₄Cl. The suspension was stirred at room temperature for 1 hour. The solid was filtered, washed with aqueous saturated solution of NH₄Cl (2×300 mL) and water (2×300 mL) and dried to give the title compound as an off-white solid (2.5 g, crude).

MS: 334.51 (M+H)⁺.

Step C A suspension of the title compound from Step B above (2 g, 5.98 mmol) in 70% $H_2SO_4$ (6, 3.0 vol) was heated at 120° C. for 2 hours. The reaction mixture was cooled to room temperature and the reaction mixture was slowly poured into 100 mL of cold water (0° C.). Then, the reaction mixture was adjusted to basic pH by addition of 50% aqueous NaOH. Then, the compound was extracted with EtOAc (6×150 mL). The combined organic layers were dried over with $Na_2SO_4$ and filtered, then the solution was concentrated to afford the title compound as a light yellow solid (0.3 g, 23%).

MS: 230.4 (M)⁺.

¹H-NMR (400 MHz, DMSO-d₆) δ=8.27-8.31 (m, 2H), 8.11 (s, 2H).

Step D

To a suspension of the title compound from Step C above (0.3 mg, 1.3 mmol) in acetonitrile (5 mL) at 0° C. was added tert-butyl nitrite (0.2 ml, 1.95 mmol) over a period of 10 min with a syringe. Then, copper (II) chloride (0.2 g, 1.56 mmol) was added portion wise. After 30 minutes at 0° C., the reaction mixture was allowed to warm to room temperature for 1 hour and heated to the 65° C., then stirred for 4 hours. The progress of the reaction was monitored by TLC. After completion of the reaction, the solvent was evaporated and the product was diluted with water (20 mL) and 5% MeOH/DCM (3×20 mL). The combined organics were washed with brine (10 mL), dried over Na₂SO₄, filtered and concentrated under reduced pressure. The crude compound was purified by silica gel (60-120) column chromatography, eluted with 1% methanol/dichloromethane to afford the title compound (0.15 g, 46%) as an off white solid.

MS: 250.9 (M+H)⁺.

¹H-NMR (400 MHz, DMSO-d₆) δ=8.91 (d, J=2.40 Hz, 1H), 8.82 (d, J=1.60 Hz, 1H).

Step E

To a solution of the title compound from Step D above (0.18 g, 0.72 mmol) in dry dichloromethane (5 mL) was added triethylamine (0.3 mL, 2.16 mmol) and morpholine (0.074 g, 0.86 mmol) and the mixture was stirred at room temperature for 6 hours. The reaction mixture was concentrated under vacuum. The crude compound was purified by silica gel (60-120) column chromatography, eluted with petroleum ether/ethyl acetate to afford the title compound (0.18 g, 83%) as an off yellow solid.

MS: 300.0 (M+H)⁺.

¹H-NMR (400 MHz, DMSO-d₆) δ=8.49 (d, J=2.00 Hz, 1H), 8.38 (d, J=1.60 Hz, 1H), 3.72-3.74 (m, 4H), 3.61-3.62 (m, 4H).

Preparative Example 27

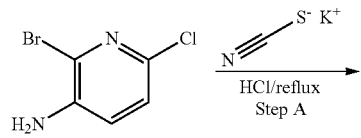

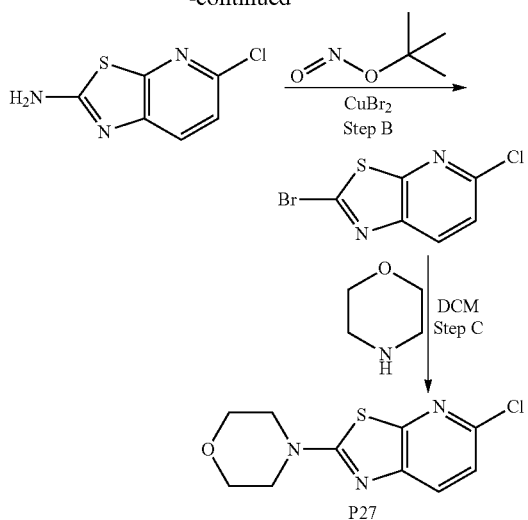

Step A

A solution of 2-bromo-6-chloropyridin-3-amine (5 g, 24.1 mmol) and potassium thiocyanate (7 g, 72.3 mmol) in ethanol (50 mL) and conc. hydrochloric acid (37%, 100 mL) was stirred at 100° C. for 40-45 h. The completion of the reaction was confirmed by TLC (PE/EA=7.5/2.5). The reaction mixture was cooled down to room temperature and concentrated to provide a brown solid, which was partitioned in dichloromethane (150 mL) and aqueous 1 N NaOH (50 mL). The solid was filtered and dried to afford the title compound (3.5 g, 79% yield) as a light yellow solid.

MS: 186.1 (M+H)⁺.

Step B

To a suspension of the title compound from Step A above (1.5 g, 8.08 mmol) in acetonitrile (25 mL) at 0° C. was added tert-butyl nitrite (1.4 ml, 12.12 mmol) over a period of 10 min with a syringe. Then, copper (II) bromide (2.16 g, 9.69 mmol) was added portion wise. After 30 minutes at 0° C., the reaction mixture was allowed to warm to room temperature for 2 hours. The progress of the reaction was monitored by TLC. After completion of the reaction, the solvent was evaporated and the mixture was diluted with water (20 mL) and 5% MeOH/DCM (3×20 mL). The combined organics were washed with brine (10 mL), dried over Na₂SO₄, filtered and concentrated under reduced pressure. The crude compound was purified by silica gel (60-120) column chromatography, and eluted with 1% methanol/dichloromethane to afford the title compound (0.65 g, 32%) as a pale yellow solid.

MS: 248.5 (M+H)⁺.

Step C

To a solution of the title compound from Step B above (0.65 g, 2.61 mmol) in dry dichloromethane (5 mL) was added triethylamine (1.1 mL, 7.83 mmol) and morpholine (0.34 g, 3.91 mmol) and the mixture was stirred at room temperature for 6 hours. The reaction mixture was concentrated under vacuum. The crude compound was purified by silica gel (60-120) column chromatography, eluted with petroleum ether/ethyl acetate to afford the title compound (0.6 g, 90%) as an off yellow solid.

MS: 256.0 (M+H)⁺.

¹H-NMR (400 MHz, DMSO-d₆) δ=7.83 (d, J=8.40 Hz, 1H), 7.41 (d, J=8.44 Hz, 1H), 3.72-3.74 (m, 2H), 3.59-3.60 (m, 2H).

Preparative Example 28

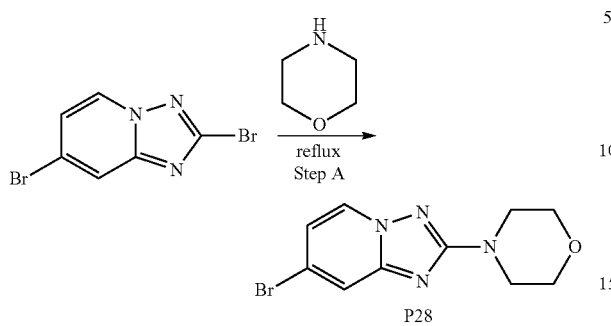

Step A

A mixture of 2,7-dibromo-[1,2,4]triazolo[1,5-a]pyridine (0.4 g, 1.44 mmol) and morpholine (4 mL) was refluxed for 4 hours under $N_2$ atmosphere. The reaction mixture was concentrated to dryness. The crude compound was purified by silica gel (60-120) column chromatography, eluted with petroleum ether/ethyl acetate 10-100 percent as an eluent affording the title compound (0.27 g, 66%) as a white solid.

MS: 285.0 $(M+H)^+$.

$^1$H-NMR (400 MHz, DMSO-$d_6$) δ=8.64 (d, J=7.08 Hz, 1H), 7.83 (s, 1H), 7.13-7.14 (m, 1H), 3.69-3.71 (m, 2H), 3.45-3.46 (m, 2H).

Preparative Example 29

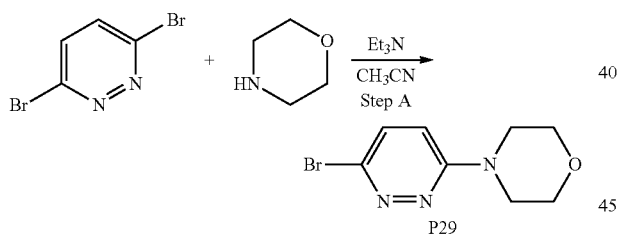

3,6-Dibromopyridazine (0.2 g, 0.841 mmol) was dissolved in acetonitrile (2.5 mL). Then morpholine (0.110 mL, 1.261 mmol) and triethylamine (0.176 mL, 1.261 mmol) were added and the suspension was irradiated in the microwave at 160° C. for 1 h and 20 minutes. The reaction mixture was diluted with dichloromethane and water. The organic layer was separated and the aqueous layer was extracted with dichloromethane twice. The combined organic layers were dried over $Na_2SO_4$, filtered and concentrated under reduced pressure. The crude product was purified on a silica gel column using a Biotage Isolera One purification system employing an n-heptane/ethyl acetate gradient (100/0→0/100) to afford the title compound as a white solid (0.168 g, 82%).

MS: 245.2 $(M+H)^+$.

$^1$H-NMR (400 MHz, Chloroform-d) δ=7.35 (d, J=9.5 Hz, 1H), 6.79 (d, J=9.5 Hz, 1H), 3.88-3.79 (m, 4H), 3.66-3.55 (m, 4H).

Preparative Example 30

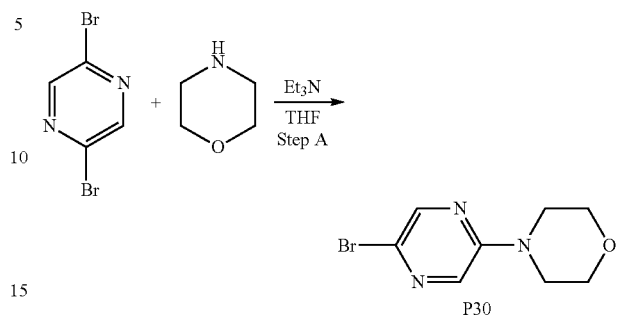

To a suspension of sodium hydride (0.0404 g, 1.682 mmol) in dry THF (3 mL), morpholine (0.146 mL, 1.682 mmol) was added under nitrogen at 0° C. The reaction mixture was stirred at 0° C. for 15 minutes, then 2,5-dibromopyrazine (0.400 g, 1.682 mmol) dissolved in dry THF (3 mL) was added. The reaction mixture was allowed to stir at reflux conditions overnight. It was quenched with water and the product was extracted with EtOAc three times. The combined organic layers were dried over $Na_2SO_4$, filtered and concentrated under reduced pressure. The crude product was purified on a silica gel column using a Biotage Isolera One purification system employing an n-heptane/ethyl acetate gradient (100/0→0/100) to afford the title compound as a white solid (0.245 g, 60%).

$^1$H-NMR (400 MHz, Chloroform-d) δ=8.15 (d, J=1.5 Hz, 1H), 7.86 (d, J=1.5 Hz, 1H), 3.89-3.76 (m, 4H), 3.60-3.45 (m, 4H).

Preparative Example 31

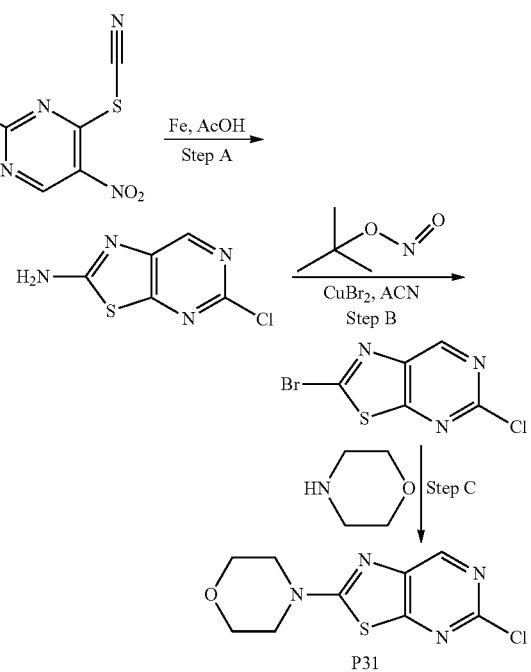

Step A

To a hot solution of 2-chloro-5-nitro-4-thiocyanatopyrimidine (10 g, 46.2 mmol) in acetic acid (264 mL, 4617 mmol) at 120° C. was added iron (15.47 g, 277 mmol). The mixture was stirred for 1 hour at the same temperature. The mixture was allowed to cool to room temperature and the insoluble material were removed by filtration and washed with acetic acid. The filtrate was concentrated under reduced pressure and dissolved in THF (200 mL) and EtOAc (400 mL) and washed with a saturated NH$_4$Cl aqueous solution (100 mL), a saturated NaHCO$_3$ solution (100 mL), dried over Na$_2$SO$_4$ and the solvent was removed under reduced pressure to afford the title compound (6.82 g, 79%).

$^1$H-NMR (400 MHz, DMSO-d$_6$) δ=9.42 (s, 1H).

Step B

To a suspension of the title compound from Step A above (8.2 g, 43 mmol) in acetonitrile (20 mL) at 0° C. was added tert-butyl nitrite (6.8 g, 65.9 mmol) over 30 minutes. Then, copper (II) bromide (11.78 g, 52.8 mmol) was added in portions. After 30 minutes at 0° C., the reaction mixture was allowed to warm to room temperature and stirred for 12 hours. Water (50 mL) and EtOAc (100 mL) were added and the phases were separated. The aqueous layer was extracted twice with EtOAc and the organic layers were combined, dried over Na$_2$SO$_4$ and the solvent was evaporated under reduced pressure. The residue was purified on HP-Sil SNAP cartridges using a Biotage Isolera One purification system employing EtOAc/n-heptane (20/80) to afford the title compound (4.94 g, 45%).

$^1$H-NMR (400 MHz, DMSO-d$_6$) δ=8.54 (s, 1H), 8.30 (s, 2H).

Step C

The title compound from Step B above (0.157 g, 0.627 mmol) was dissolved in morpholine (3 mL, 0.627 mmol) and stirred at room temperature for 2 h. The reaction mixture was diluted with dichloromethane and water. The organic layer was separated and the aqueous layer was extracted with dichloromethane twice. The combined organic layers were dried over Na$_2$SO$_4$, filtered and concentrated under reduced pressure. The crude product was purified on a silica gel column using a Biotage Isolera One purification system employing an n-heptane/ethyl acetate gradient (100/0→0/100) to afford the title compound as a white solid (0.048 g, 30%).

MS: 258.6 (M+H)$^+$.

$^1$H-NMR (400 MHz, DMSO-d$_6$) δ=8.71 (s, 1H), 3.74 (dd, J=6.0, 3.6 Hz, 4H), 3.70-3.58 (m, 4H).

Preparative Example 32

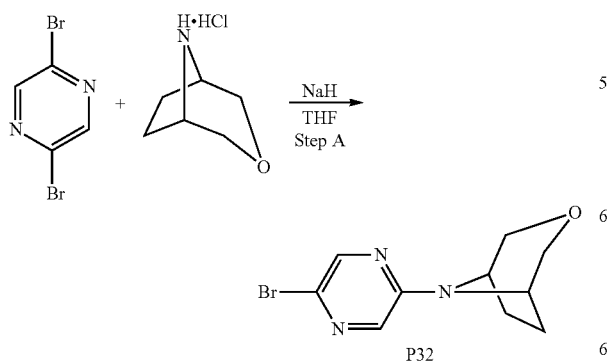

To a suspension of sodium hydride (0.077 g, 3.21 mmol) in dry THF (5 mL), (1R,5S)-3-oxa-8-azabicyclo[3.2.1]octane hydrochloride (0.457 g, 3.06 mmol) was added under nitrogen at 0° C. The reaction mixture was stirred for 15 minutes, then 2,5-dibromopyrazine (0.800 g, 3.36 mmol) dissolved in dry THF (5 mL) was added. The reaction mixture was allowed to stir at reflux conditions overnight. The reaction mixture was quenched with water and the product was extracted three times with ethyl acetate. The combined organic layers were dried over Na$_2$SO$_4$, filtered and concentrated under reduced pressure. The crude product was purified on a silica gel column using a Biotage Isolera One purification system employing an n-heptane/ethyl acetate gradient (100/0→0/100) to afford the title compound as a white solid (0.038 mg, 5%).

MS: 271.8 (M+H)$^+$.

$^1$H-NMR (400 MHz, DMSO-d$_6$) δ=8.24 (d, J=1.4 Hz, 1H), 8.11 (d, J=1.4 Hz, 1H), 4.49 (s, 2H), 3.62 (d, J=10.9 Hz, 2H), 3.52 (d, J=11.0 Hz, 2H), 2.02-1.95 (m, 2H), 1.91 (m, 2H).

Preparative Example 33

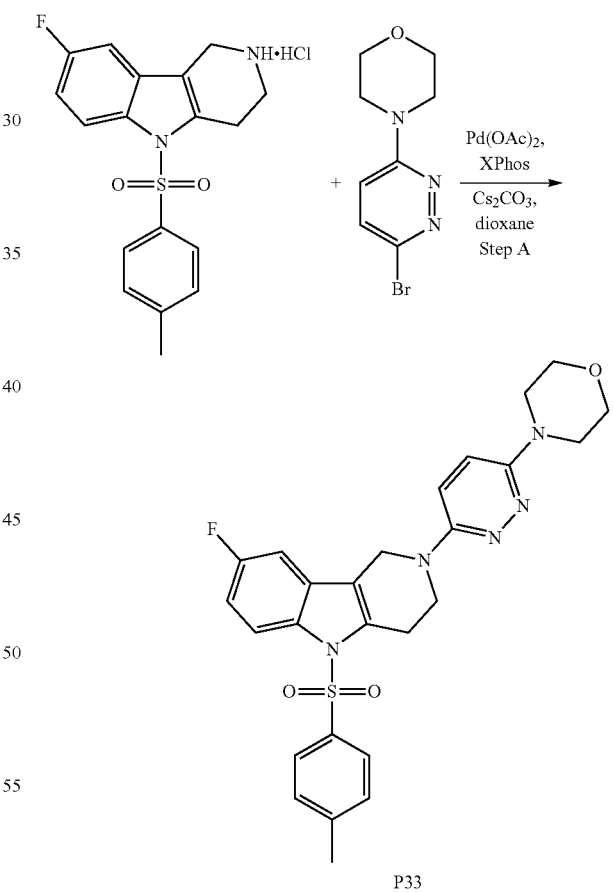

Step A

Palladium (II) acetate (0.00651 g, 0.029 mmol) and 2-dicyclohexylphosphino-2',4',6'-triisopropylbiphenyl (XPhos) (0.0415 g, 0.087 mmol) were placed in a reaction vial and degassed 1,4-dioxane (2 mL) was added. The resulting solution was degassed briefly. The suspension was heated at 100° C. (on a pre-heated heating block) for less than 1 minute until the color of the solution turned from orange to dark pink. Then, the vial was removed from the heating block and the title compound from Preparative Example 1 (0.110 g, 0.290 mmol) and the title compound from Preparative Example 29 (0.078 g, 0.319 mmol) and cesium carbonate (0.331 g, 1.015 mmol) were added. The reaction vial was filled with argon before closing it. The reaction mixture was heated at 100° C. for 12 h. The reaction mixture was diluted with ethyl acetate and water. The organic layer was separated and the aqueous layer was extracted with ethyl acetate two more times. The combined organic layers were dried over $Na_2SO_4$, filtered and the solvents were evaporated under reduced pressure. The crude product was purified on a silica gel column using a Biotage Isolera One purification system employing an n-heptane/ethyl acetate gradient (90/10→0/100) to afford the title compound as a yellow solid (0.072 g, 49%).

MS: 508.2 (M+H)$^+$.

$^1$H-NMR (400 MHz, DMSO-$d_6$) δ=8.03 (dd, J=9.1, 4.5 Hz, 1H), 7.70 (d, J=8.4 Hz, 2H), 7.42 (d, J=9.9 Hz, 1H), 7.38 (dd, J=8.9, 2.6 Hz, 1H), 7.32 (dd, J=9.0, 6.1 Hz, 2H), 7.17 (td, J=9.2, 2.6 Hz, 1H), 6.93 (s, 1H), 4.55 (s, 2H), 3.88 (t, J=5.6 Hz, 2H), 3.78-3.65 (m, 4H), 3.41-3.34 (m, 4H), 3.21-3.14 (m, 2H), 2.30 (s, 3H).

Preparative Examples 34 to 41f

Following the palladium coupling procedure as described in Preparative Example 33, except using the tricyclic amino- and bromo/chloro-derivatives indicated in the table below, the following compounds were prepared:

TABLE 1

| Preparative Example | Tricyclic amino derivative | Bromo or Chloro derivative | Product | 1. Yield<br>2. $^1$H-NMR<br>3. MH$^+$ (ESI) |
| --- | --- | --- | --- | --- |
| 34 | [structure] | [structure] | [structure] | 1. 68%<br>2.<br>3. 645.1 |
| 35 | [structure] | [structure] | [structure] | 1. 80%<br>2. $^1$H-NMR (400 MHz, DMSO-$d_6$) δ = 8.08-7.99 (m, 1H), 7.96 (d, J = 5.9 Hz, 1H), 7.75 (d, J = 8.4 Hz, 2H), 7.44 (dd, J = 8.9, 2.7 Hz, 1H), 7.34 (d, J = 8.2 Hz, 2H), 7.18 (td, J = 9.2, 2.7 Hz, 1H), 6.28 (d, J = 6.0 Hz, 1H), 4.62 (s, 2H), 4.01-3.96 (m, 2H), 3.76-3.53 (m, 8H), 3.15 (s, 2H), 2.30 (s, 3H).<br>3. 508.1 |
| 36 | [structure] | [structure] | [structure] | 1. 52%<br>2. $^1$H-NMR (400 MHz, DMSO-$d_6$) δ = 8.09 (d, J = 1.5 Hz, 1H), 8.03 (dd, J = 9.1, 4.4 Hz, 1H), 7.93 (d, J = 1.5 Hz, 1H), 7.71 (d, J = 8.4 Hz, 2H), 7.40 (dd, J = 8.9, 2.7 Hz, 1H), 7.33 (d, J = 8.1 Hz, 2H), 7.17 (td, J = 9.2, 2.7 Hz, 1H), 4.46 (s, 2H), 3.85 (t, J = 5.7 Hz, 2H), 3.77-3.67 (m, 4H), 3.30-3.28 (m, 4H), 3.20-3.15 (m, 2H), 2.30 (s, 3H).<br>3. 508.5 |

TABLE 1-continued

| Preparative Example | Tricyclic amino derivative | Bromo or Chloro derivative | Product | 1. Yield 2. ¹H-NMR 3. MH⁺ (ESI) |
|---|---|---|---|---|
| 37 | | | | 1. 62% 3. 354.5 |
| 38 | | | | 1. 22% 3. 534.7 |
| 39 | | | | 1. 45% 2. ¹H-NMR (400 MHz, DMSO-$d_6$) δ = 8.10 (d, J = 1.5 Hz, 1H), 7.92 (d, J = 1.5 Hz, 1H), 7.80 (dd, J = 10.3, 2.4 Hz, 2H), 7.78-7.74 (m, 2H), 7.58 (dd, J = 8.6, 5.5 Hz, 1H), 7.46-7.27 (m, 2H), 7.18 (ddd, J = 9.4, 8.6, 2.4 Hz, 1H), 4.49 (s, 2H), 3.84 (t, J = 5.6 Hz, 2H), 3.72 (t, J = 4.9 Hz, 4H), 3.29 (d, J = 4.9 Hz, 4H), 3.16 (s, 2H), 2.31 (s, 3H). 3. 508.6 |
| 40 | | | | 1. 24% 2. ¹H-NMR (400 MHz, DMSO-$d_6$) δ = 8.53 (s, 1H), 8.04 (dd, J = 9.1, 4.4 Hz, 1H), 7.74 (d, J = 8.4 Hz, 2H), 7.48 (dd, J = 8.9, 2.7 Hz, 1H), 7.32 (d, J = 8.2 Hz, 2H), 7.17 (td, J = 9.2, 2.7 Hz, 1H), 4.75 (s, 2H), 4.14 (t, J = 5.6 Hz, 2H), 3.72 (t, J = 5.0 Hz, 4H), 3.53 (t, J = 4.9 Hz, 4H), 3.22-3.11 (m, 2H), 2.29 (s, 3H). 3. 508.5 |
| 41 | | | | 1. 39% 2. ¹H-NMR (400 MHz, DMSO-$d_6$) δ = 8.07-7.99 (m, 2H), 7.95 (d, J = 1.5 Hz, 1H), 7.71 (d, J = 8.4 Hz, 2H), 7.40 (dd, J = 8.9, 2.7 Hz, 1H), 7.33 (d, J = 8.1 Hz, 2H), 7.17 (td, J = 9.2, 2.7 Hz, 1H), 4.45 (s, 2H), 4.34 (d, J = 4.6 Hz, 2H), 3.85 (t, J = 5.6 Hz, 2H), 3.67 (d, J = 10.7 Hz, 2H), 3.55-3.46 (m, 2H), 3.17 (t, |

TABLE 1-continued

| Preparative Example | Tricyclic amino derivative | Bromo or Chloro derivative | Product | 1. Yield 2. ¹H-NMR 3. MH⁺ (ESI) |
|---|---|---|---|---|
| | | | | J = 6.2 Hz, 2H), 2.30 (s, 3H), 1.95-1.87 (m, 2H), 1.85-1.74 (m, 2H). 3. 508.5 |
| 41a | | | | 1. 29% 2. ¹H-NMR (400 MHz, DMSO-d₆) δ = 8.54 (s, 1H), 7.82 (dd, J = 9.3, 6.4 Hz, 3H), 7.65 (dd, J = 8.7, 5.4 Hz, 1H), 7.36 (d, J = 8.1 Hz, 2H), 7.26-7.13 (m, 1H), 4.79 (s, 2H), 4.15 (t, J = 5.6 Hz, 2H), 3.74 (t, J = 4.9 Hz, 4H), 3.55 (d, J = 4.9 Hz, 4H), 3.18 (s, 2H), 2.31 (s, 3H). 3. 565.21 |
| 41b | | | | 1. 31 % 2. ¹H-NMR (400 MHz, DMSO-d₆) δ = 8.06 (dd, J = 9.1, 4.4 Hz, 1H), 7.91-7.80 (m, 2H), 7.73 (d, J = 8.3 Hz, 1H), 7.57-7.41 (m, 3H), 7.39-7.27 (m, 3H), 6.94 (s, 1H), 4.71 (s, 2H), 4.09 (t, J = 5.6 Hz, 2H), 3.75 (t, J = 4.7 Hz, 4H), 3.57 (t, J = 4.8 Hz, 4H), 3.25 (d, J = 5.7 Hz, 2H), 2.28 (s, 3H). 3. 558.28 |
| 41c | | | | 1. 13% 2. ¹H-NMR (400 MHz, DMSO-d₆) δ = 7.87-7.82 (m, 2H), 7.79 (d, J = 8.4 Hz, 2H), 7.63 (dd, J = 8.6, 5.5 Hz, 1H), 7.55-7.43 (m, 2H), 7.33 (dd, J = 8.9, 4.0 Hz, 3H), 6.94 (s, 1H), 4.74 (s, 2H), 4.12-4.04 (m, 2H), 3.74 (t, J = 4.8 Hz, 4H), 3.56 (t, J = 4.8 Hz, 4H), 3.22 (s, 2H), 2.29 (s, 3H). 3. 558.28 |

TABLE 1-continued

| Preparative Example | Tricyclic amino derivative | Bromo or Chloro derivative | Product | 1. Yield<br>2. ¹H-NMR<br>3. MH⁺ (ESI) |
|---|---|---|---|---|
| 41d | F-[tricyclic indole]-NH·HCl, N-Ts | 5-Bromo-2-(4-methylpiperazin-1-yl)pyridine | Coupled product | 1. 42%<br>2. ¹H-NMR (400 MHz, DMSO-d₆) δ = 7.97 (d, J = 2.9 Hz, 1H), 7.79 (dd, J = 10.3, 2.3 Hz, 1H), 7.75 (d, J = 8.2 Hz, 2H), 7.56 (dd, J = 8.6, 5.5 Hz, 1H), 7.42 (dd, J = 9.1, 3.0 Hz, 1H), 7.36 (d, J = 8.1 Hz, 2H), 7.18 (td, J = 9.1, 2.3 Hz, 1H), 6.79 (d, J = 9.1 Hz, 1H), 4.18 (s, 2H), 3.48 (t, J = 5.7 Hz, 2H), 3.41-3.33 (m, 4H), 3.14 (d, J = 5.7 Hz, 2H), 2.40 (t, J = 5.0 Hz, 4H), 2.32 (s, 3H), 2.21 (s, 3H).<br>3. 520.33 |
| 41e | F-[tricyclic indole]-NH·HCl, N-Ts | 5-Chloro-2-[(1S,4S)-2-oxa-5-azabicyclo[2.2.1]heptan-5-yl]pyridine | Coupled product (S,S) | 1. 67%<br>2. ¹H-NMR (400 MHz, DMSO-d₆) δ = 7.93 (d, J = 2.9 Hz, 1H), 7.81 (dd, J = 10.3, 2.3 Hz, 1H), 7.78-7.74 (m, 2H), 7.55 (dd, J = 8.6, 5.5 Hz, 1H), 7.44-7.39 (m, 1H), 7.40-7.32 (m, 2H), 7.18 (td, J = 9.1, 2.4 Hz, 1H), 6.53 (d, J = 9.0 Hz, 1H), 4.73 (d, J = 2.0 Hz, 1H), 4.61 (s, 1H), 4.16 (s, 2H), 3.75 (dd, J = 7.4, 1.5 Hz, 1H), 3.62 (d, J = 7.4 Hz, 1H), 3.52-3.39 (m, 3H), 3.24-3.08 (m, 3H), 2.33 (s, 3H), 1.93-1.78 (m, 2H).<br>3. 519.14 |
| 41f | F-[tricyclic indole]-NH·HCl, N-Ts | 5-Chloro-2-[(1R,4R)-2-oxa-5-azabicyclo[2.2.1]heptan-5-yl]pyridine | Coupled product (R,R) | 1. 95%<br>2. ¹H-NMR (400 MHz, DMSO-d₆) δ = 7.93 (d, J = 2.9 Hz, 1H), 7.80 (dd, J = 10.3, 2.4 Hz, 1H), 7.77 (d, J = 8.4 Hz, 2H), 7.55 (dd, J = 8.6, 5.6 Hz, 1H), 7.43 (dd, J = 9.1, 3.0 Hz, 1H), 7.37 (d, J = 8.2 Hz, 2H), 7.18 (td, J = 9.0, 2.3 Hz, 1H), 6.53 (d, J = 9.0 Hz, 1H), 4.72 (s, 1H), 4.61 (s, 1H), 4.16 (s, 2H), 3.79-3.71 (m, 1H), 3.62 (d, J = 7.3 Hz, 1H), 3.50-3.40 (m, 3H), 3.22-3.09 (m, 3H), 2.33 (s, 3H), 1.93-1.76 (m, 2H).<br>3. 519.14 |

Preparative Example 42

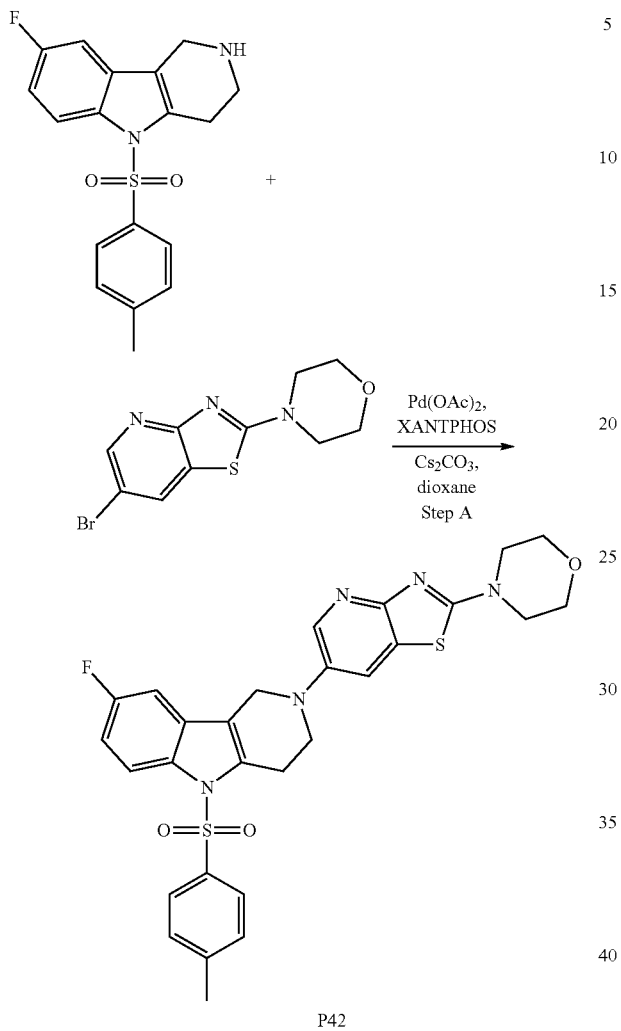

P42

Step A

Palladium (II) acetate (0.0045 g, 0.020 mmol) and 4,5-Bis(diphenylphosphino)-9,9-dimethylxanthene (XANTPHOS) (0.035 g, 0.061 mmol) were placed in a reaction vial and degassed 1,4-dioxane (4 mL) was added. The resulting solution was degassed briefly. The suspension was heated at 100° C. (on a pre-heated heating block) for less than 1 minute until the color of the solution turned from orange to dark pink. Then, the vial was removed from the heating block and the title compound from Preparative Example 1 Step E (70 mg, 0.203 mmol) and the title compound from Preparative Example 26 (0.067 g, 0.224 mmol) and cesium carbonate (0.232 g, 0.771 mmol) were added. The reaction vial was filled with argon before closing it. The reaction mixture was heated at 100° C. for 18 h. The reaction mixture was diluted with ethyl acetate and water. The organic layer was separated and the aqueous layer was extracted with ethyl acetate two more times. The combined organic layers were dried over $Na_2SO_4$, filtered and the solvents were evaporated under reduced pressure. The crude product was purified on a silica gel column using a Biotage Isolera One purification system employing an dichloromethane/methanol (100/00→95/05) to afford the title compound as a yellow solid (0.052 g, 45%).

$^1$H NMR (400 MHz, Chloroform-d) δ=8.24 (d, J=2.7 Hz, 1H), 8.16-8.03 (m, 1H), 7.64-7.59 (m, 2H), 7.55 (d, J=2.7 Hz, 1H), 7.18 (d, J=8.2 Hz, 2H), 7.02 (dd, J=8.6, 1.9 Hz, 2H), 4.23 (d, J=2.0 Hz, 2H), 3.84-3.78 (m, 4H), 3.69-3.63 (m, 4H), 3.59 (t, J=5.6 Hz, 2H), 3.48 (s, 1H), 3.25 (dq, J=5.7, 3.5, 2.8 Hz, 2H), 2.33 (s, 3H).

Preparative Example 43

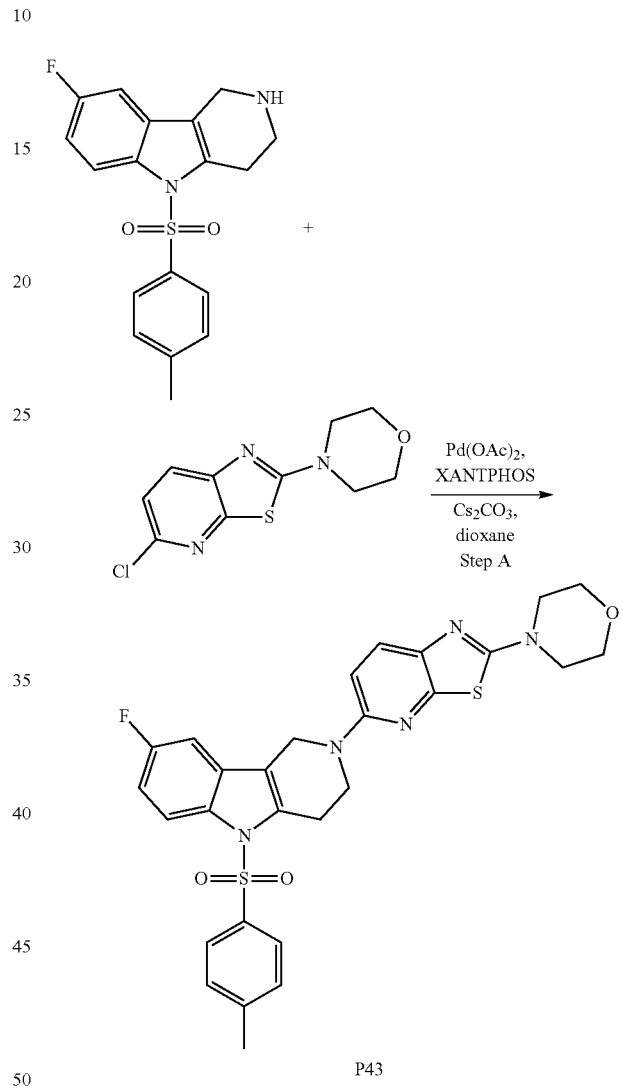

P43

Step A

Palladium (II) acetate (0.0045 g, 0.020 mmol) and 4,5-Bis(diphenylphosphino)-9,9-dimethylxanthene (XANTPHOS) (0.035 g, 0.061 mmol) were placed in a reaction vial and degassed 1,4-dioxane (4 mL) was added. The resulting solution was degassed briefly. The suspension was heated at 100° C. (on a pre-heated heating block) for less than 1 minute until the color of the solution turned from orange to dark pink. Then, the vial was removed from the heating block and the title compound from Preparative Example 1 Step E (70 mg, 0.203 mmol) and the title compound from Preparative Example 27 (0.067 g, 0.224 mmol) and cesium carbonate (0.232 g, 0.771 mmol) were added. The reaction vial was filled with argon before closing it. The reaction mixture was heated at 100° C. for 18 h. The reaction mixture was diluted with ethyl acetate and water. The organic layer was separated and the aqueous layer was extracted with ethyl acetate two more times. The combined organic layers were dried over Na$_2$SO$_4$, filtered and the solvents were evaporated under reduced pressure. The crude product was purified on a silica gel column using a Biotage Isolera One purification system employing an dichloromethane/methanol (100/00→95/05) to afford the title compound as a yellow solid (0.048 g, 42%).

$^1$H NMR (400 MHz, Chloroform-d) δ=8.10 (dd, J=9.0, 4.4 Hz, 1H), 7.65 (d, J=8.9 Hz, 1H), 7.63-7.57 (m, 2H), 7.15 (d, J=8.2 Hz, 2H), 7.09-6.97 (m, 2H), 6.75 (d, J=8.9 Hz, 1H), 4.51 (d, J=2.0 Hz, 2H), 3.94 (t, J=5.6 Hz, 2H), 3.82 (q, J=5.2 Hz, 4H), 3.57 (dd, J=5.8, 4.0 Hz, 4H), 3.25 (td, J=5.5, 2.7 Hz, 2H), 2.31 (s, 3H).

Preparative Example 44

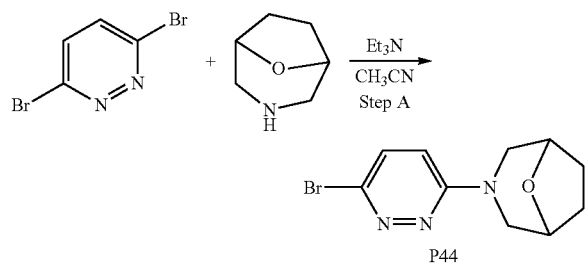

Step A 3,6-Dibromopyridazine (0.2 g, 0.841 mmol) was dissolved in acetonitrile (2.5 mL). Then 8-oxa-3-azabicyclo[3.2.1]octane (0.105 g, 0.925 mmol) and triethylamine (0.176 mL, 1.261 mmol) were added and the suspension was irradiated in the microwave to 160° C. for 1 h and 20 minutes. The reaction mixture was diluted with dichloromethane and water. The organic layer was separated and the aqueous layer was extracted with dichloromethane twice. The combined organic layers were dried over Na$_2$SO$_4$, filtered and concentrated under reduced pressure. The crude product was purified on a silica gel column using a Biotage Isolera One purification system employing an n-heptane/ethyl acetate gradient (100/0→0/100) to afford the title compound as a beige solid (0.152 g, 67%).

MS: 271.5 (M+H)$^+$.

$^1$H-NMR (400 MHz, Chloroform-d) δ=7.32 (d, J=9.5 Hz, 1H), 6.70 (d, J=9.5 Hz, 1H), 4.60-4.43 (m, 2H), 3.83 (d, J=12.8 Hz, 2H), 3.23 (dd, J=12.4, 2.7 Hz, 2H), 2.08-1.94 (m, 2H), 1.90-1.76 (m, 2H).

Preparative Example 45

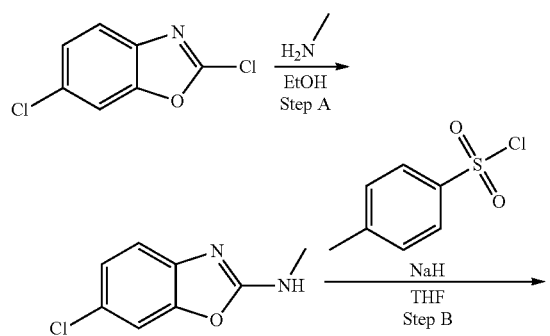

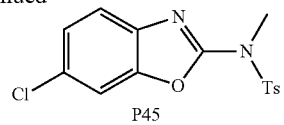

Step A

To a solution of 2,6-dichlorobenzo[d]oxazole (1.2 g, 6.3 mmol) was added Methylamine solution 33 wt. % in absolute ethanol (8 mL) and the mixture was heated for 30 minutes at 100° C. using a Biotage microwave oven. The reaction mixture was cooled to room temperature and dissolved in dichloromethane (150 mL). The organic phase was washed with water, 1 N NaOH solution and brine and then dried over Na$_2$SO$_4$. The solvent was removed and the title compound was obtained (1.08 g, 94%).

$^1$H NMR (400 MHz, Chloroform-d) δ 7.30-7.24 (m, 2H), 7.16 (dd, J=8.4, 1.9 Hz, 1H), 5.35 (s, 1H), 3.14 (s, 3H).

Step B

To a stirred suspension of title compound from Step A above (39 mg, 1.643 mmol) in dry THF (1.5 mL) at 0° C., a solution of 6-chloro-N-methylbenzo[d]oxazol-2-amine (100 mg, 0.548 mmol) in dry THF (2 mL) was added slowly and stirred at the same temperature for 30 min. Then a solution of 4-methylbenzene-1-sulfonyl chloride (107 mg, 0.561 mmol) in dry THF (1.5 mL) was added dropwise at 0° C., and the reaction mixture was stirred at 0° C. for 2 h. The reaction mixture was quenched at 0° C. with ice water (4 mL). Then the product was extracted with ethyl acetate three times. The combined organic extracts were washed with water, brine, dried over Na$_2$SO$_4$, filtered and evaporated under reduced pressure to afford the title compound as a beige solid (154 mg, 83%).

MS: 337.14 (M+H)$^+$.

$^1$H-NMR (400 MHz, DMSO-d$_6$) δ=7.93-7.89 (m, 2H), 7.88 (d, J=2.0 Hz, 1H), 7.58 (d, J=8.5 Hz, 1H), 7.49-7.44 (m, 2H), 7.36 (dd, J=8.5, 2.0 Hz, 1H), 3.49 (s, 3H), 2.39 (s, 3H).

Preparative Example 46

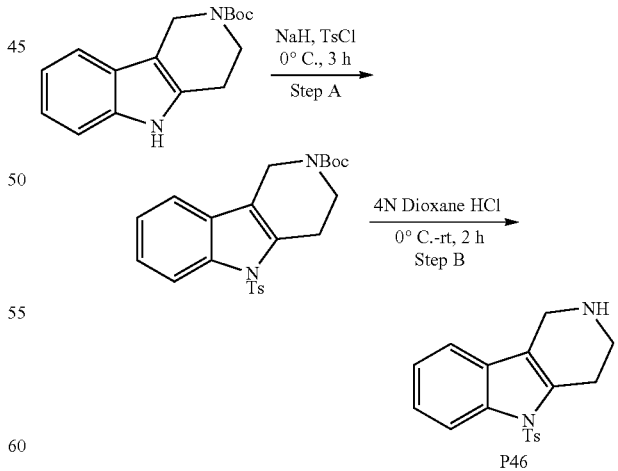

Step A

To suspension of NaH (0.47 g, 19.55 mmol) in THF (20 mL) was added commercially available tert-butyl 1,3,4,5-tetrahydro-2H-pyrido[4,3-b]indole-2-carboxylate (2.0 g, 7.35 mmol) (dissolved in THF) dropwise at 0° C. The mixture was then stirred at room temperature for 1 h. After that tosyl chloride (1.5 g, 7.82 mmol) (dissolved in THF) was added at 0° C. and then the mixture was stirred at room temperature for 2 h. After completion of the reaction as checked by TLC, the reaction mixture was quenched with ice water followed by extraction using ethyl acetate. The organic layer was concentrated to afford the title compound (1.8 g, 65%). The product was taken as such for the next step.

MS: 427.1 (M+H)$^+$.

Step B

To a solution of the title compound from Step A above (1.8 g, 4.22 mmol) in DCM (20 mL) was added 4M HCl (5 mL) in dioxane. The reaction mixture was stirred overnight. After the completion of the reaction, the reaction mixture was evaporated to remove the solvent and the residue was washed with diethyl ether to afford the title compound as an off-white solid (1.0 g, 66%).

MS: 361.3 (M+H)$^+$.

Preparative Example 47 mmol) at room temperature. The mixture was stirred for 12 h. After completion of the reaction as evidenced by TLC, the solvent was removed and the crude reaction mixture was purified on a silica gel column using a Biotage Isolera One purification system employing an EtOAc/heptane gradient (10/80=>80/20) to afford the title compound as a pale yellow solid (700 mg, 27%).

MS: 291.1 (M+H)$^+$.

$^1$H-NMR (400 MHz, DMSO-d$_6$) δ=11.38 (bs, 1H), 7.22 (d, J=7.60 Hz, 1H), 6.96-6.85 (m, 2H), 4.53 (s, 2H), 3.70-3.71 (m, 2H), 2.78 (bs, 2H), 1.44 (s, 9H).

Step C

To suspension of NaH (144 mg, 3.61 mmol) in THF (15 mL) was added the title compound from Step B above (700 mg, 2.41 mmol) (dissolved in THF) dropwise at 0° C. Then the mixture was stirred at room temperature for 1 h. After that tosyl chloride (549 mg, 2.89 mmol) (dissolved in THF) was added at 0° C. and then the mixture was stirred at room temperature for 2 h. After completion of the reaction as evidenced by TLC, the reaction mixture was quenched with ice water, followed by extraction using ethyl acetate. The

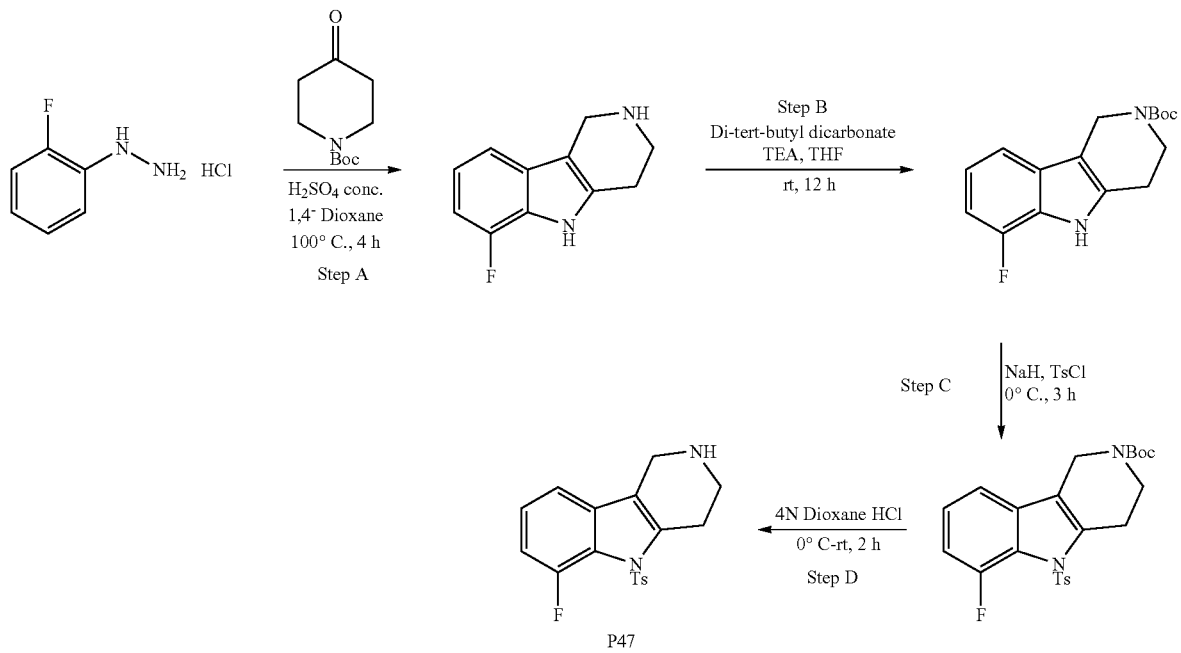

P47

Step A

To a solution of commercially available (2-fluorophenyl) hydrazine hydrochloride (2 g, 12.34 mmol) and tert-butyl 4-oxopiperidine-1-carboxylate (2.45 g, 12.34 mmol) in dioxane (20 mL) was added concentrated H$_2$SO$_4$ (2 mL), 0° C. Then the reaction mixture was heated at 100° C. for 4 h. After completion of the reaction as evidenced by TLC, the reaction mixture was cooled to 25° C. and then concentrated. The crude mixture was basified by 10% NaOH solution and the precipitate was filtered off. The solid was washed with water and dried under vacuum to get the title compound (1.7 g, 75%).

MS: 191.0 (M+H)$^+$.

Step B

To a stirred solution of title compound from Step A above (1.7 g, Crude) in THF (20 mL) was added TEA (3.76 mL, 26.82 mmol) and di-tert-butyl dicarbonate (2.34 mL, 10.73 organic layer was concentrated and the crude reaction mixture was purified on a silica gel column using a Biotage Isolera One purification system employing an EtOAc/hexane gradient (10/80=>80/20) to afford the title compound (900 mg, 84%).

MS: 345.1 (M-Boc).

$^1$H-NMR (400 MHz, DMSO-d$_6$) δ=7.79 (d, J=8.04 Hz, 2H), 7.41 (d, J=8.24 Hz, 2H), 7.34 (d, J=7.68 Hz, 2H), 7.22-7.23 (m, 1H), 7.07-7.09 (m, 1H), 4.50 (s, 2H), 3.70-3.72 (m, 2H), 3.17 (bs, 2H), 2.36 (s, 3H), 1.40 (s, 9H).

Step D

To a solution of the title compound from Step C above (900 mg, 2.02 mmol) in DCM (10 mL) was added 2N HCl (5 mL) in dioxane. The reaction mixture was stirred at room temperature for 2 h. After the completion of the reaction, the reaction mixture was evaporated to remove the solvent and the residue was washed with diethyl ether to afford the title compound as a pale brown solid (450 mg, 65%).

MS: 345.1 (M+H)⁺.

Preparative Example 48

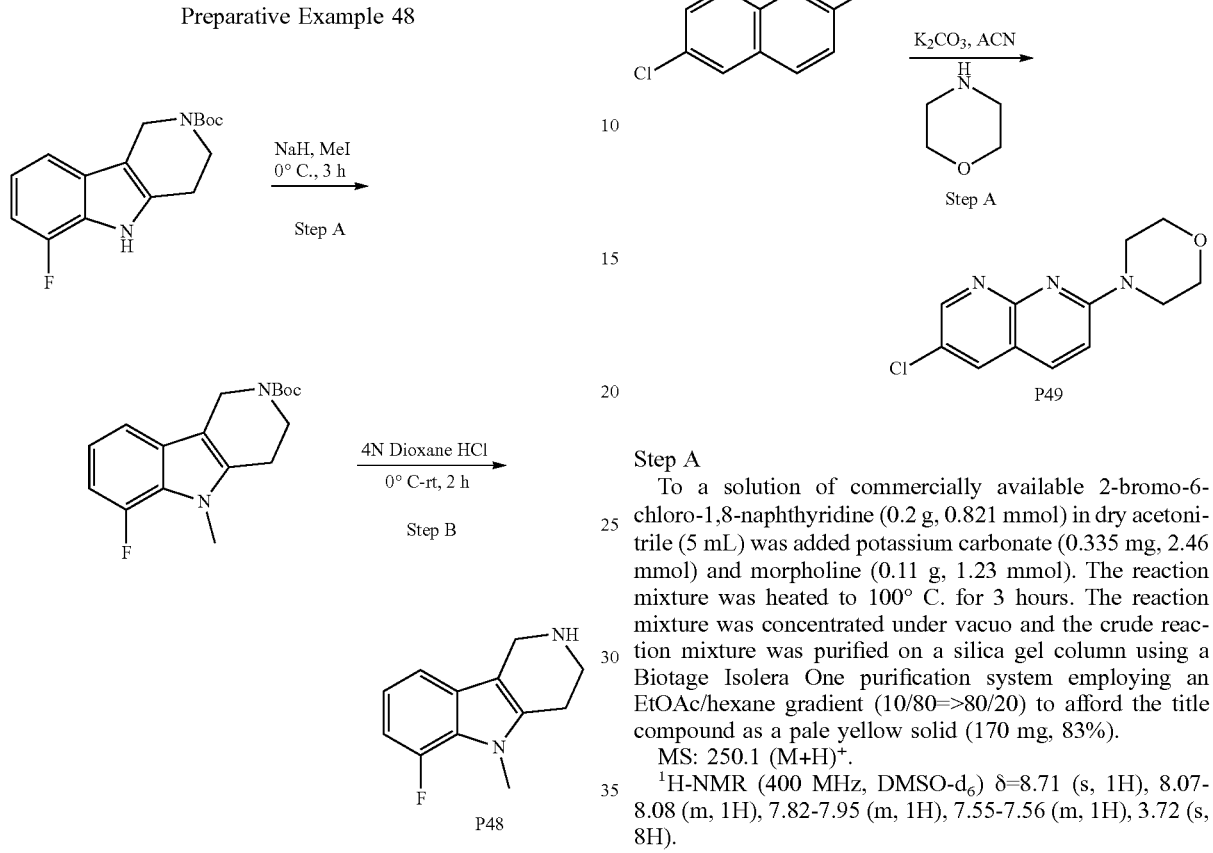

P48

Step A

To suspension of NaH (300 mg, 12.39 mmol) in THF (15 mL) was added the title compound from Preparative Example 47, Step B (1.2 g, 4.13 mmol) (dissolved in THF) dropwise at 0° C. Then the reaction mixture was stirred at room temperature for 1 h. After that iodomethane (0.5 mL, 8.26 mmol) was added at 0° C. and then the mixture was stirred at room temperature for 2 h. After competition, the reaction mixture was quenched with ice water, followed by extraction using ethyl acetate. The organic layer was concentrated and the crude reaction mixture was purified on a silica gel column using a Biotage Isolera One purification system employing an EtOAc/hexane gradient (10/80=>80/20) to afford the title compound (900 mg, 72%).

MS: 305.3 (M+H)⁺.

$^1$H-NMR (400 MHz, DMSO-$d_6$) δ=7.23 (d, J=9.60 Hz, 1H), 6.88-6.91 (m, 2H), 4.51 (s, 2H), 3.71-3.73 (m, 5H), 2.73-2.77 (m, 2H), 1.50 (s, 9H).

Step B

To a solution of the title compound from Step A above (900 mg, 2.96 mmol) in DCM (10 mL) was added 4M HCl (5 mL) in dioxane. The reaction mixture was stirred at room temperature for 2 h. After the completion of the reaction, the reaction mixture was evaporated to remove the solvent and the residue was washed with diethyl ether to afford the title compound as a pale brown solid (500 mg, 83%).

MS: 205.1 (M+H)⁺.

Preparative Example 49

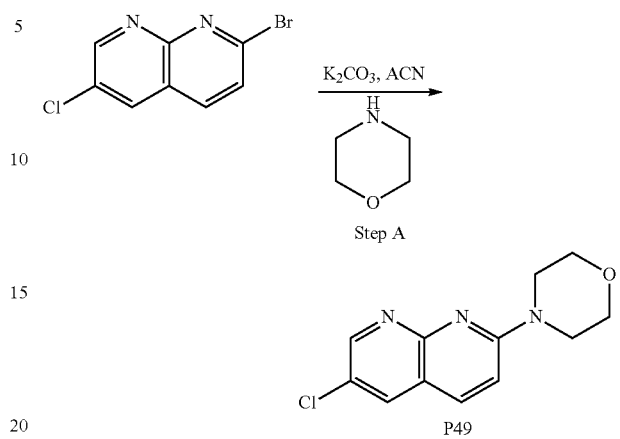

Step A

To a solution of commercially available 2-bromo-6-chloro-1,8-naphthyridine (0.2 g, 0.821 mmol) in dry acetonitrile (5 mL) was added potassium carbonate (0.335 mg, 2.46 mmol) and morpholine (0.11 g, 1.23 mmol). The reaction mixture was heated to 100° C. for 3 hours. The reaction mixture was concentrated under vacuo and the crude reaction mixture was purified on a silica gel column using a Biotage Isolera One purification system employing an EtOAc/hexane gradient (10/80=>80/20) to afford the title compound as a pale yellow solid (170 mg, 83%).

MS: 250.1 (M+H)⁺.

$^1$H-NMR (400 MHz, DMSO-$d_6$) δ=8.71 (s, 1H), 8.07-8.08 (m, 1H), 7.82-7.95 (m, 1H), 7.55-7.56 (m, 1H), 3.72 (s, 8H).

Preparative Example 50

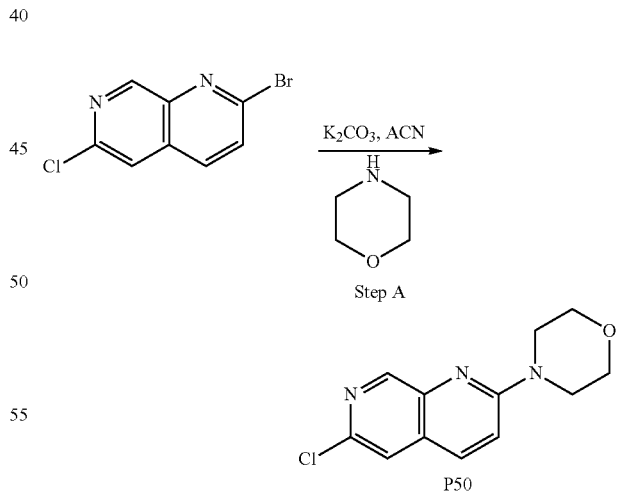

Step A

To a solution of commercially available 2-bromo-6-chloro-1,7-naphthyridine (0.5 g, 2.05 mmol) in dry acetonitrile (5 mL) was added potassium carbonate (0.837 mg, 6.16 mmol) and morpholine (0.27 g, 3.08 mmol). The reaction mixture was heated to 100° C. for 3 hours. The reaction mixture was concentrated under vacuo and the crude reaction mixture was purified on a silica gel column using a Biotage Isolera One purification system employing an EtOAc/hexane gradient (10/80=>80/20) to afford the title compound as a pale yellow solid (270 mg, 53%).

MS: 250.1 (M+H)⁺.

¹H-NMR (400 MHz, DMSO-d$_6$) δ=9.01 (s, 1H), 7.91-7.93 (m, 2H), 6.92-6.93 (m, 1H), 3.71 (s, 8H).

Preparative Example 51

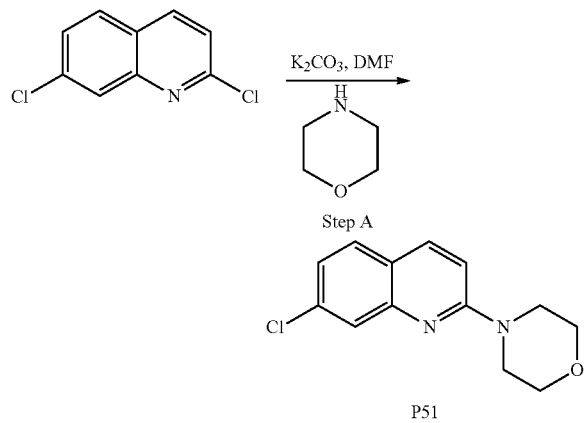

Step A

To a solution of commercially available 2,7-dichloroquinoline (0.5 g, 2.52 mmol) in dry DMF (5 mL) was added potassium carbonate (1 g, 7.52 mmol) and morpholine (0.32 g, 3.78 mmol). The reaction mixture was heated to 100° C. for 3 hours. The reaction mixture was concentrated under vacuo to afford the title compound as a pale yellow solid (500 mg, 80%).

MS: 249.1 (M+H)⁺.

Preparative Example 52

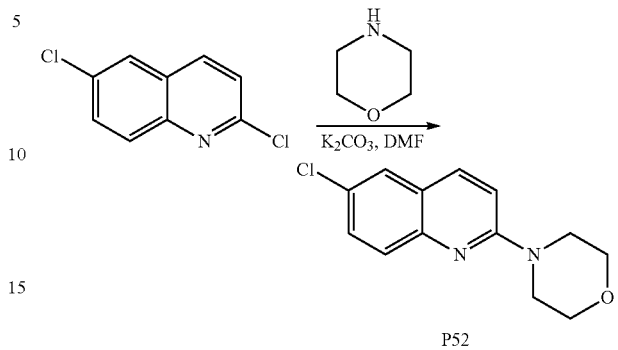

Step A

To a solution of commercially available 2,6-dichloroquinoline (0.5 g, 2.52 mmol) in dry DMF (5 mL) was added potassium carbonate (1 g, 7.52 mmol) and morpholine (0.32 g, 3.78 mmol). The reaction mixture was heated to 100° C. for 3 hours. The reaction mixture was concentrated under vacuo and the crude reaction mixture was purified on a silica gel column using a Biotage Isolera One purification system employing an EtOAc/hexane gradient (10/80=>80/20) to afford the title compound as a pale yellow solid (500 mg, 80%).

MS: 249.1 (M+H)⁺

¹H-NMR (400 MHz, DMSO-d$_6$) δ=8.06 (d, J=12.40 Hz, 1H), 7.84 (d, J=2.40 Hz, 1H), 7.51-7.52 (m, 2H), 7.31 (d, J=12.40 Hz, 1H), 3.66-3.67 (m, 8H).

Preparative Example 53

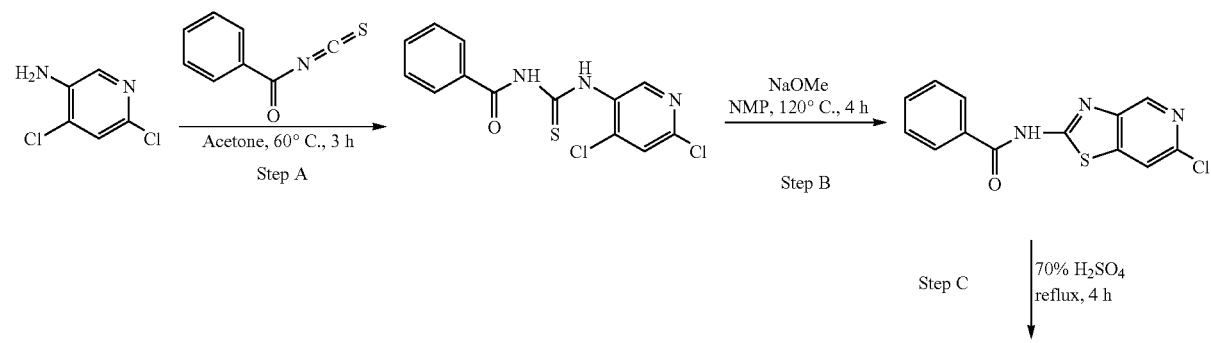

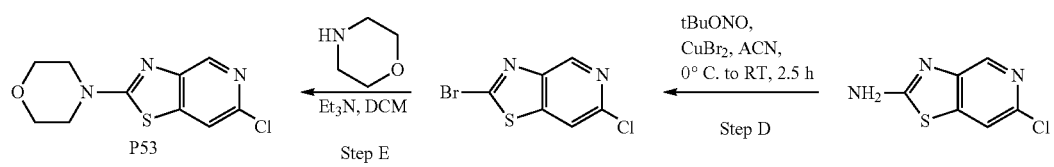

Step A

A solution of commercially available 4,6-dichloropyridin-3-amine (8.0 g, 49.07 mmol) and benzoyl isothiocyanate (7.3 mL, 53.98 mmol) in acetone (120 mL) was stirred at 60° C. for 3 hours. The reaction was monitored by the TLC. The solvent was evaporated and the solid was filtered, washed with n-hexane (100 mL) and dried to give the desired product as an off-white solid (14.0 g, 87%).

MS: 328.0 (M+H)$^+$.

$^1$H-NMR (400 MHz, DMSO-d$_6$) δ=12.39 (s, 1H), 12.02 (s, 1H), 8.74 (s, 1H), 7.98-7.99 (m, 3H), 7.67-7.68 (m, 1H), 7.56 (t, J=7.60 Hz, 2H).

Step B

To a solution of the title compound from Step A above (14.0 g, 42.94 mmol) in N-methyl-2-pyrrolidone (NMP) (70 mL) was added sodium methoxide (NaOMe) (4.6 g, 85.88 mmol) at 0° C. The mixture was then heated to 120° C. and stirring was continued for 4 hours. The reaction was monitored by TLC. The reaction mixture was poured into cold water (300 mL) and a white precipitate was obtained. The solid was filtered, washed with water (300 mL) and n-hexane (200 mL). The compound was dried under vacuum for 6 h to give the desired product as a white solid (14.0 g, crude). The product was taken as such for next step.

MS: 290.0 (M+H)$^+$

Step C

A suspension of the title compound from Step B above (14.0 g, 48.4 mmol) in 70% H$_2$SO$_4$ (50.0 mL) was heated at 110° C. for 4 hours. The reaction mixture was cooled to room temperature and the reaction mixture was slowly poured into 200 mL of cold water (0° C.). Then, the reaction mixture was adjusted to basic pH by addition of 50% aq. NaOH. Then, the compound was extracted with EtOAc (6×100 mL). The combined organic layers were dried over with Na2SO4 and filtered, then the solvent was concentrated to give the desired product as a light yellow solid (6 g, 67%).

MS: 186.1 (M+H)$^+$ $^1$H-NMR (400 MHz, DMSO-d$_6$) δ=8.30 (s, 1H), 7.86 (s, 1H).

Step D

To a suspension of the title compound from Step C above (5.0 g, 27.02 mmol) in acetonitrile (120 mL) at 0° C. was added tert-butyl nitrite (4.8 mL, 40.54 mmol) over a period of 10 min with a syringe. Then, copper(II) bromide (9.0 g, 40.54 mmol) was added portionwise. After 30 minutes at 0° C., the reaction mixture was allowed to warm to room temperature for 2.5 hours, the progress of the reaction was monitored by TLC. After completion of the reaction, solvent was evaporated and diluted with water (200 mL) and 5% MeOH/DCM (3×200 mL). The combined organics were washed with brine (50 mL), dried over Na$_2$SO$_4$, filtered and concentrated under reduced pressure to afford the title compound as a white solid (6.5 g). The product was taken as such for the next step.

MS: 250.9 (M+H)$^+$

Step E

To a solution of the title compound from Step D above (6.5 g, 26.09 mmol) in dry DCM (100 mL) was added triethylamine (11.2 mL, 81.5 mmol) and morpholine (2.8 mL, 28.13 mmol). The reaction mixture was stirred at room temperature for 4 hours. The reaction mixture was concentrated under vacuo. The crude reaction mixture was purified on a silica gel column using a Biotage Isolera One purification system employing an EtOAc/hexane gradient (10/80=>80/20) to afford the title compound as a pale yellow solid (4.7 g, 71%).

MS: 256.1 (M+H)$^+$.

$^1$H-NMR (400 MHz, DMSO-d$_6$) δ=8.48 (s, 1H), 8.05 (s, 1H), 3.73-3.74 (m, 4H), 3.60-3.61 (m, 4H).

Preparative Example 54

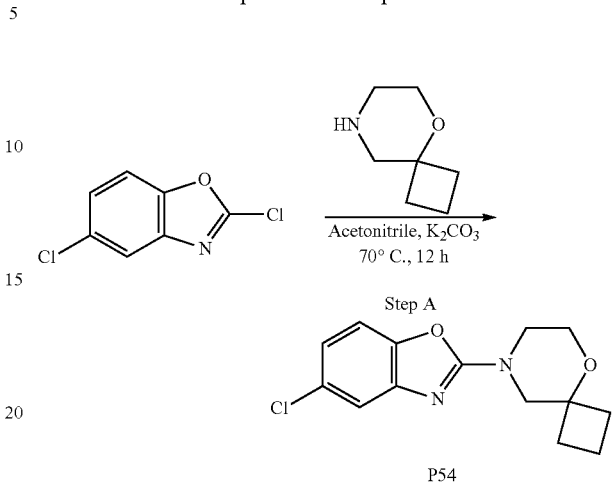

P54

To a stirred solution of 2,5-dichloro-1,3-benzoxazole (0.25 g, 0.0013 mol) in acetonitrile (15 mL) K$_2$CO$_3$ (0.538 g, 0.0039 mol) and 5-oxa-8-azaspiro[3.5]nonane (0.178 g, 0.0014 mol) were added. After that the reaction mixture was heated to 70° C. for 12 h. After completion of the reaction by TLC, the reaction mixture was added DCM and water (50 mL). The organic layer was separated, dried over sodium sulphate filtered and then concentrated to get the title compound (0.30 g, 80.21%) as a white solid.

MS: 279.1 (M+H)$^+$.

$^1$H-NMR (400 MHz, DMSO-d$_6$) δ=7.44 (d, J=8.40 Hz, 1H), 7.36-7.37 (m, 1H), 7.06 (dd, J=2.00, 8.40 Hz, 1H), 3.64-3.65 (m, 2H), 3.60 (s, 2H), 3.54-3.55 (m, 2H), 1.96-1.97 (m, 4H), 1.71-1.74 (m, 2H).

Preparative Example 55

P55

To a stirred solution of 2,5-dichloro-1,3-benzoxazole (0.60 g, 0.0032 mol) in acetonitrile (15 mL) K$_2$CO$_3$ (1.32 g, 0.0096 mol) and 2-methoxyethane-1-amine (0.266 g, 0.0035 mol) were added. After that the reaction mixture was heated to 70° C. for 12 h. After completion of the reaction by TLC, the reaction mixture was added DCM and water (50 mL). The organic layer was separated, dried over sodium sulphate filtered and then concentrated to get the title compound (0.41 g, 56.24%) as a brown solid.

MS: 226.9 (M+H)$^+$.

$^1$H-NMR (400 MHz, DMSO-d$_6$) δ=8.26 (s, 1H), 7.35 (d, J=11.20 Hz, 1H), 7.28 (d, J=2.80 Hz, 1H), 6.99 (dd, J=2.80, 11.20 Hz, 1H), 3.48 (d, J=7.20 Hz, 4H), 3.27 (s, 3H).

Preparative Example 56

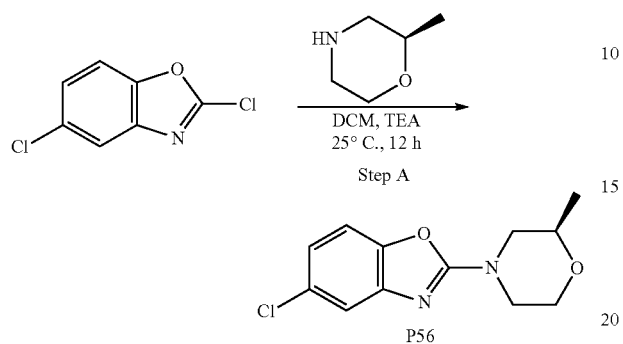

To a stirred solution of 2,5-dichloro-1,3-benzoxazole (0.719 g, 0.0038 mol) in DCM (15 mL) TEA (2.67 ml, 0.0191 mol) and (2R)-2-methylmorpholine (0.5 g, 0.00494 mol) were added and stirred for 12 h at 25° C. After completion of the reaction by TLC, the reaction mixture was added DCM and water (50 mL). The organic layer was separated, dried over sodium sulphate filtered and then concentrated to get the title compound (0.6 g, 45.4%) as a white solid.

MS: 253.2 (M+H)$^+$.

$^1$H-NMR (400 MHz, DMSO-d$_6$) δ=7.43 (d, J=11.20 Hz, 1H), 7.35 (d, J=2.40 Hz, 1H), 7.05 (dd, J=2.80, 11.20 Hz, 1H), 3.89-3.90 (m, 3H), 3.56-3.59 (m, 2H), 3.17-3.18 (m, 1H), 2.86-2.89 (m, 1H), 1.15 (d, J=8.40 Hz, 3H).

Preparative Example 57

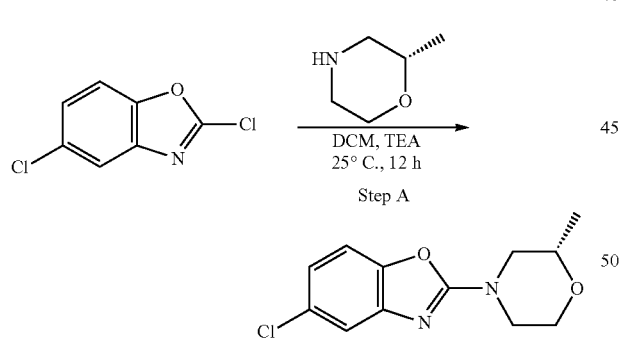

To a stirred solution of 2,5-dichloro-1,3-benzoxazole (0.360 g, 0.0019 mol) in DCM (15 mL) TEA (1.33 ml, 0.0095 mol) and (2S)-2-methylmorpholine (0.25 g, 0.00247 mol) were added and stirred for 12 h at 25° C. After completion of the reaction by TLC, the reaction mixture was added DCM and water (50 mL). The organic layer was separated, dried over sodium sulphate filtered and then concentrated. The crude reaction mixture was purified on a silica gel column using a Biotage Isolera One purification system employing 20-25% of ethyl acetate in petroleum ether to afford the title compound as a white solid (0.3 g, 45.5%).

MS: 253.1 (M+H)$^+$.

$^1$H-NMR (400 MHz, DMSO-d$_6$) δ=7.43 (d, J=8.48 Hz, 1H), 7.34-7.35 (m, 1H), 7.05 (dd, J=2.08, 8.46 Hz, 1H), 3.90-3.90 (m, 3H), 3.61-3.62 (m, 2H), 3.24-3.25 (m, 1H), 2.87-2.89 (m, 1H), 1.15 (d, J=6.20 Hz, 3H).

Preparative Example 58

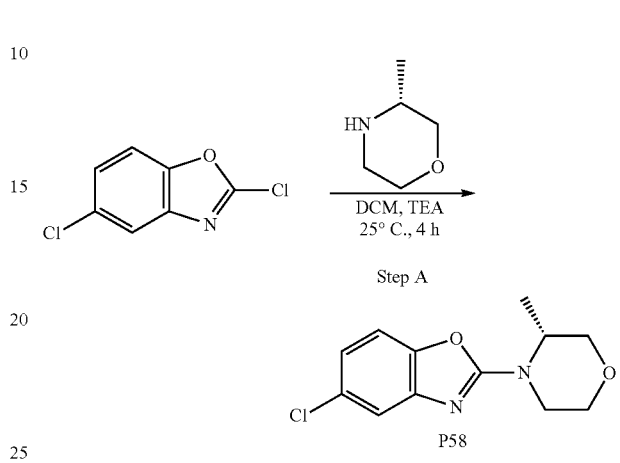

To a solution of 2,5-dichloro-1,3-benzoxazole (1.20 g, 6.38 mmol) in dry DCM (50 mL) at 0° C., (3R)-3-methylmorpholine (0.775 g, 7.65 mmol) and Et$_3$N (1.94 g, 19.10 mmol) were added, and stirred at 25° C. for 4 h. After the completion of the reaction (monitored by TLC), the reaction mixture was diluted with water (20 mL) and extracted with DCM (20 mL×2). The combined organic extracts were dried over Na$_2$SO$_4$, filtered and evaporated under reduced pressure.

The crude reaction mixture was purified on a silica gel column using a Biotage Isolera One purification system employing 10-20% of ethyl acetate in petroleum ether to afford the title compound (1.0 g, 59.9%).

MS: 252.9 (M+H)$^+$.

$^1$H-NMR (400 MHz, DMSO-d$_6$) δ=7.43 (d, J=11.20 Hz, 1H), 7.35 (d, J=2.80 Hz, 1H), 7.04 (dd, J=2.80, 11.40 Hz, 1H), 4.17-4.19 (m, 1H), 3.69-3.76 (m, 3H), 3.42-3.43 (m, 5H), 1.30 (d, J=9.20 Hz, 3H).

Preparative Example 59

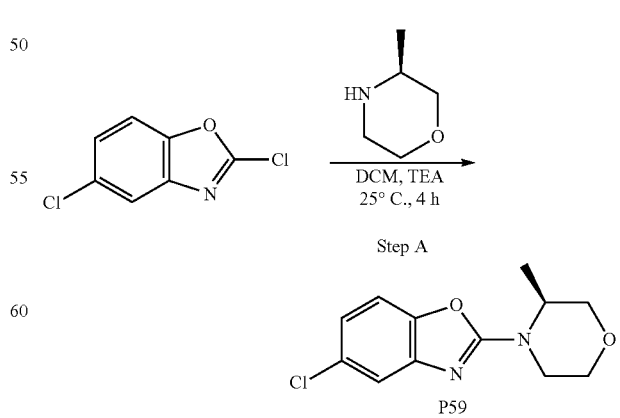

To a solution of 2,5-dichloro-1,3-benzoxazole (1.20 g, 6.38 mmol) in dry DCM (50 mL) at 0° C., (3S)-3-methylmorpholine (0.775 g, 7.65 mmol) and Et₃N (1.94 g, 19.10 mmol) were added, and stirred at 25° C. for 4 h. After the completion of the reaction (monitored by TLC), the reaction mixture was diluted with H₂O (20 mL) and extracted with DCM (20 mL×2). The combined organic extracts were dried over Na₂SO₄, filtered and evaporated under reduced pressure.

The crude reaction mixture was purified on a silica gel column using a Biotage Isolera One purification system employing 10-20% of ethyl acetate in petroleum ether to afford the title compound (0.8 g, 49.6%).

MS: 252.9 (M+H)⁺.

¹H-NMR (400 MHz, DMSO-d₆) δ=7.43 (d, J=11.20 Hz, 1H), 7.35 (d, J=2.80 Hz, 1H), 7.04 (dd, J=2.80, 11.20 Hz, 1H), 4.17-4.19 (m, 1H), 3.73-3.75 (m, 4H), 3.46-3.47 (m, 2H), 1.30 (d, J=9.20 Hz, 3H).

Preparative Example 60

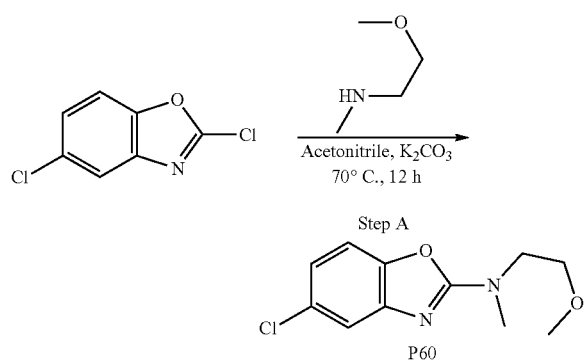

To a stirred solution of 2,5-dichloro-1,3-benzoxazole (0.5 g, 0.00265 mol) in acetonitrile (10 mL) K₂CO₃ (1.1 g, 0.00797 mol) and 2-methoxy-N-methylethane-1-amine (0.284 g, 0.00319 mol) were added. After that the reaction mixture was heated to 70° C. for 12 h. After completion of the reaction by TLC, the reaction mixture was added DCM and water (50 mL). The organic layer was separated, dried over sodium sulphate filtered and then concentrated to get the title compound (0.61 g, 95%) as a brown liquid.

MS: 241.1 (M+H)⁺.

¹H-NMR (400 MHz, DMSO-d₆) δ=7.40 (d, J=11.20 Hz, 1H), 7.30 (d, J=2.80 Hz, 1H), 7.00 (dd, J=2.80, 11.20 Hz, 1H), 3.68 (t, J=6.40 Hz, 2H), 3.58 (t, J=7.20 Hz, 2H), 3.27 (s, 3H), 3.16 (s, 3H).

Preparative Example 61

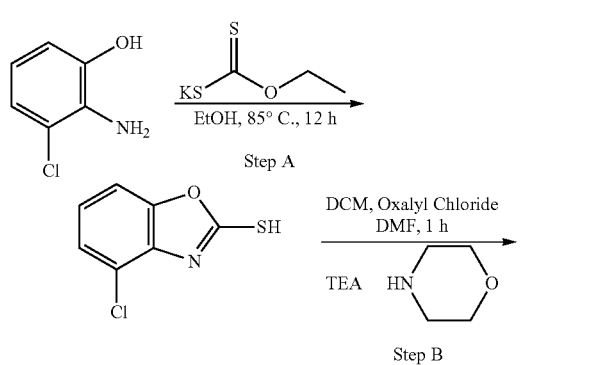

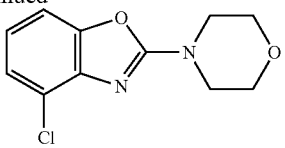

Step A

To a stirred solution of 2-amino-3-chlorophenol (4 g, 0.0280 mol) in ethanol (80 mL) potassium O-ethyl carbonodithioate (4.49 g, 0.0280 mol) was added, then heated to 85° C. for 12 h under N₂. After completion of the reaction by LCMS, the reaction mixture was concentrated, the crude product was acidified by using acetic acid (pH=5) and the solid was filtered washed with water, dried under vacuum for 6 h to get 4-chlorobenzo[d]oxazole-2-thiol (4.6 g, 89%) as a pale brown solid.

MS: 186.0 (M+H)⁺.

¹H-NMR (400 MHz, DMSO-d₆) δ=14.44 (bs, 1H), 7.46 (d, J=10.80 Hz, 1H), 7.35 (d, J=11.20 Hz, 1H), 7.23 (t, J=10.80 Hz, 1H).

Step B

To a solution of the title compound from Step A above (4.6 g, 0.0244 mol) in DCM (90 mL) oxalyl chloride (3.20 mL, 0.0374 mol) was added followed by DMF (1 mL) at 0° C., then stirred at 25° C. for 1 h. Then TEA (10 mL, 0.0734 mol) and morpholine (2.5 mL, 0.0293 mol) were added at 0° C. and stirred at 25° C. for 2 h under nitrogen. After completion of the reaction followed by TLC, water (40 mL) was added and extracted with DCM (2×50 mL). The organic layer was concentrated and the crude was purified on a silica gel column using a Biotage Isolera One purification system employing 10-15% of ethyl acetate in petroleum ether to afford the title compound (3.4 g, 58%) as a pale yellow solid.

MS: 239.1 (M+H)⁺.

¹H-NMR (400 MHz, DMSO-d₆) δ=7.40 (d, J=10.80 Hz, 1H), 7.23 (d, J=10.40 Hz, 1H), 7.03 (t, J=10.80 Hz, 1H), 3.71-3.73 (m, 4H), 3.60-3.62 (m, 4H).

Preparative Example 62

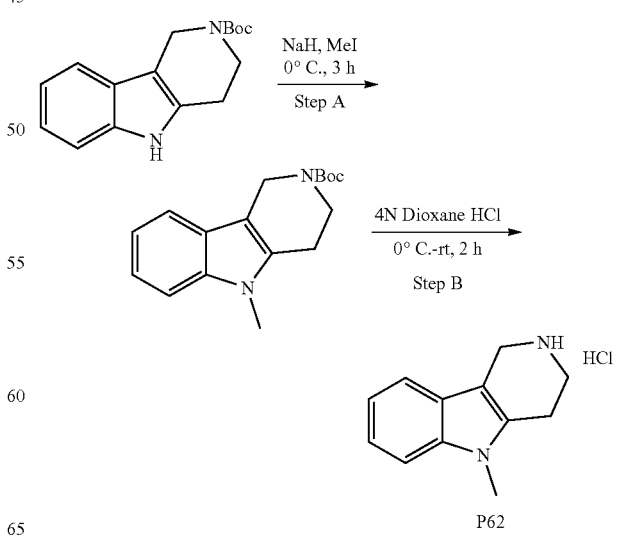

Step A

To suspension of NaH (0.47 g, 19.8 mmol) in THF (10 mL) tert-butyl 1,3,4,5-tetrahydro-2Hpyrido[4,3-b]indole-2-carboxylate (1.8 g, 6.61 mmol) (dissolved in THF) was added dropwise at 0° C., and then stirred at room temperature for 1 h. After that iodomethane (0.7 mL, 11.76 mmol) was added at 0° C. and then stirred at rt for 2 h. After completion of the reaction monitored by TLC, the reaction mixture was quenched with ice water followed by extraction using ethyl acetate. The organic layer was concentrated to afford the crude reaction mixture tert-butyl 5-methyl-1,3,4,5-tetrahydro-2H-pyrido[4,3-b]indole-2-carboxylate (1.5 g, crude). The product was taken as such for next step.

MS: 287.2 (M+H)$^+$.

Step B

To a solution of the title compound from Step A above (1.5 g, 5.24 mmol) in DCM (20 mL) was added 4.0 M HCl (5 mL) in dioxane. The reaction mixture was stirred overnight. After the completion of the reaction, the reaction mixture was evaporated to remove the solvent and washed with diethyl ether to afford the title compound as brown solid (800 mg, crude).

MS: 187.1 (M+H)$^+$.

Preparative Example 63

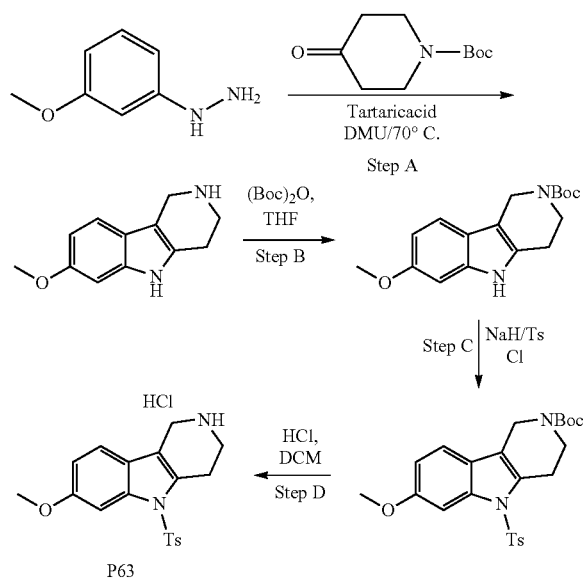

P63

To a solution of (3-methoxy phenyl)hydrazine hydrochloride (10 g, 57.4 mmol) and tert-butyl 4-oxopiperidine-1-carboxylate (11.3 g, 57.4 mmol) in ethanol (100 mL), tartaric acid was added. Dimethyl urea (30:70, 10 g) was added and heated at 70° C. for 16 h. The reaction mixture was cooled to 25° C. and concentrated under vacuo. The residue was dissolved in water and basified to pH=14 with NaOH solution (30%) and extracted with DCM. The organic phase was separated and dried over Na$_2$SO$_4$ filtered and the solvent was evaporated under reduced pressure to give 7-methoxy-2,3,4,5-tetrahydro-1H-pyrido[4,3-b]indole as a pale yellow gum (2.5 g, 21%). The crude product was taken as such for next step.

MS: 203.0 (M+H)$^+$.

Step B

To a solution of the title compound from Step A above (600 mg, 2.9 mmol) in THF (6 mL) at 25° C., triethylamine (0.8 mL, 5.8 mmol) and Boc anhydride (650 mg, 3 mmol) were added and stirred for 12 h. After completion of the reaction (monitored by TLC), the reaction mixture was concentrated under reduced pressure and the crude product was purified by flash column chromatography using hexane: EtOAc (80:20) to afford tert-butyl 7-methoxy-1,3,4,5-tetrahydro-2H-pyrido[4,3-b]indole-2-carboxylate as a pale yellow solid (610 mg, 68%).

MS: 303.2 (M+H)$^+$.

$^1$H-NMR (400 MHz, DMSO-d$_6$) δ=10.69 (bs, 1H), 7.25 (d, J=11.60 Hz, 1H), 6.80 (d, J=2.80 Hz, 1H), 6.61 (dd, J=2.80, 11.60 Hz, 1H), 4.48 (s, 2H), 3.81 (s, 3H), 3.67-3.68 (m, 2H), 2.73 (bs, 2H), 1.44 (s, 9H).

MS: 187.1 (M+H)$^+$.

Step C

To a solution of the title compound from Step B above (550 mg, 1.8 mmol) in THF (5 mL) 0° C., NaH (60% mineral oil, 0.14 g, 3.6 mmol) was added and stirred for 30 min. Then p-toluenesulfonyl chloride (342 mg, 1.8 mmol) was added and stirred for 45 min. After the completion of the reaction (monitored by TLC), the reaction mixture was quenched with water and extracted with EtOAc (20 mL×3). The combined organic extracts were washed with water, brine and dried over Na$_2$SO$_4$. Filtered and the solvents were evaporated under reduced pressure to yield tert-butyl 7-methoxy-5-tosyl-1,3,4,5-tetrahydro-2H-pyrido[4,3-b]indole-2-carboxylate as an off-White Solid (550 mg, 66%). The product was taken as such for next step.

MS: 357.0 (M+H)$^+$-Boc.

Step D

To a solution of the title compound from Step C above (550 mg, 1.204 mmol) in dry DCM (5 mL) at 0° C., HCl (g) in dioxane (2M, 5 mL) was added slowly and stirred at 25° C. for 12 h. After the completion of the reaction (monitored by TLC), the reaction mixture was evaporated under reduced pressure to yield the crude product. It was washed with diethyl ether to afford 7-methoxy-5-tosyl-2,3,4,5-tetrahydro-1H-pyrido[4,3-b]indole as an off white solid (350 mg, 81%).

MS: 357.2 (M+H)$^+$.

$^1$H-NMR (400 MHz, DMSO-d$_6$) δ=7.73 (d, J=8.40 Hz, 1H), 7.56 (s, 1H), 7.37 (d, J=8.00 Hz, 2H), 7.27 (d, J=8.40 Hz, 1H), 6.85-6.86 (m, 1H), 3.82 (s, 3H), 3.72 (s, 2H), 2.90-2.97 (m, 4H), 2.32 (s, 3H).

Preparative Example 64

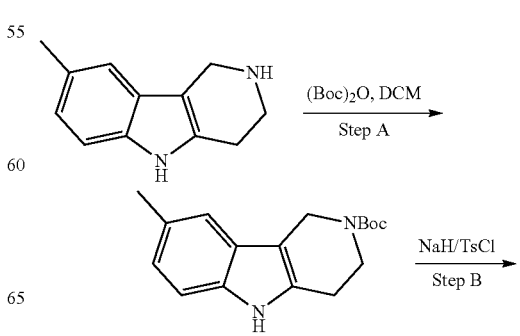

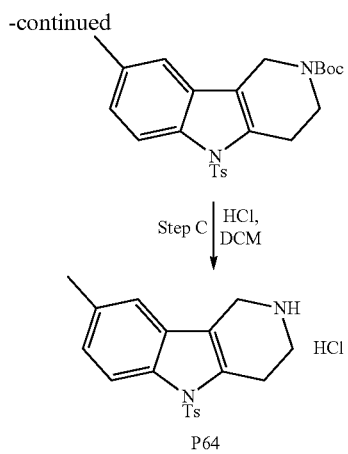

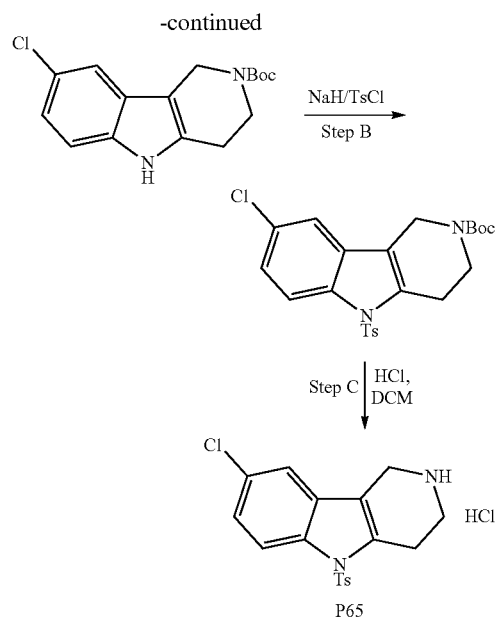

Step A

To a stirred solution of 8-methyl-2,3,4,5-tetrahydro-1H-pyrido[4,3-b]indole (1 g, 5.37 mmol) in DCM (20 mL) TEA (2.25 mL, 16.1 mmol) and BOC anhydride (1.85 mL, 8.05 mol) at 0° C. were added, then stirred at 25° C. for 12 h. After completion of the reaction by TLC, the reaction mixture water was added followed by extraction using DCM. The organic layer was separated and washed with brine solution, concentrated and washed with hexane to get the title compounds (1.1 g, 71%) as an off-white solid.

MS: 287.1 (M+H)$^+$.

$^1$H-NMR (400 MHz, DMSO-d$_6$) δ=10.74 (s, 1H), 7.16 (d, J=8.44 Hz, 1H), 6.85 (d, J=8.28 Hz, 1H), 4.49 (s, 2H), 3.69 (t, J=5.64 Hz, 2H), 2.74 (t, J=5.28 Hz, 2H), 2.35 (s, 3H), 1.47 (s, 9H).

Step B

To a suspension of Sodium hydride (0.125 g, 3.13 mmol) in THF (10 mL) the title compound from Step A above (0.6 g, 2.08 mmol) was added drop wise (dissolved in THF 20 mL) at 0° C., then stirred at room temperature for 30 min. After that Tosyl chloride (1.19 g, 6.25 mmol) was added at 0° C. dropwise (dissolved in THF 20 mL) and then stirred at room temperature for 3 h. After completion of the reaction by TLC, the reaction mixture was quenched with ice water formed solid was filtered and washed with water and dried to get the title compound (0.550 g, 57%) as a white solid.

MS: 341.1 (M+H)$^+$-Boc.

$^1$H-NMR (400 MHz, DMSO-d$_6$) δ=7.91 (d, J=8.52 Hz, 1H), 7.73 (d, J=8.20 Hz, 2H), 7.34 (d, J=8.40 Hz, 2H), 7.26 (s, 1H), 7.15 (d, J=8.56 Hz, 1H), 4.41 (s, 2H), 3.68 (t, J=5.60 Hz, 2H), 3.06 (s, 2H), 2.29-2.30 (m, 6H), 1.43 (s, 9H),

Step C

To a solution of the title compound from Step B above (0.55 g, 1.20 mmol) in DCM 4M HCl (4 mL) in dioxane at 0° C. was added. The reaction mixture was stirred 2 h. After the completion of the reaction, the reaction mixture was evaporated to remove the solvent and filtered with diethyl ether to afford the title compound as white solid (0.40 g, 85.9%).

Preparative Example 65

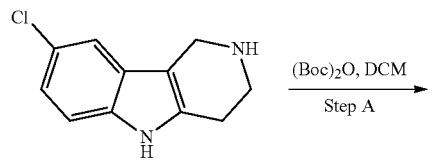

Step A

To a stirred solution of 8-chloro-2,3,4,5-tetrahydro-1H-pyrido[4,3-b]indole (1 g, 4.84 mmol) in DCM (20 mL) TEA (2.02 mL, 14.5 mmol) and BOC anhydride (1.67 mL, 7.26 mmol) at 0° C. were added, then stirred at 25° C. for 12 h. After completion of the reaction by TLC, the reaction mixture water was added followed by extraction using DCM. The organic layer was separated and washed with brine solution, concentrated to get as tert-butyl 8-chloro-1,3,4,5-tetrahydropyrido[4,3-b]indole-2-carboxylate (1 g, 66.5%) as a white solid.

MS: 305.1 (M+H)$^+$.

$^1$H-NMR (400 MHz, DMSO-d$_6$) δ=11.12 (bs, 1H), 7.46 (d, J=1.68 Hz, 1H), 7.30 (d, J=8.56 Hz, 1H), 7.03 (dd, J=1.96, 8.52 Hz, 1H), 4.51 (s, 2H), 3.70 (t, J=5.64 Hz, 2H), 2.77 (t, J=5.32 Hz, 2H), 1.47 (s, 9H).

Step B

To a suspension of Sodium hydride (0.096 g, 2.42 mmol) in THF (10 mL) cooled to 0° C., the title compound from Step A above (0.5 g, 1.61 mol) was added drop wise (dissolved in THF 20 mL) at 0° C., then stirred at room temperature for 30 min. After that Tosyl chloride (0.921 g, 48.3 mol) was added dropwise at 0° C. (dissolved in THF 20 mL) and then stirred at room temperature for 3 h. After completion of the reaction by TLC, the reaction mixture was quenched with ice water followed by extraction using ethyl acetate (100 mL). The organic layer was separated, dried over sodium sulphate, filtered and then concentrated. The product was purified by silica gel column chromatography using pet ether in ethyl acetate (75:25) to get tert-butyl 8-chloro-5-(p-tolylsulfonyl)-3,4-dihydro-1H-pyrido[4,3-b]indole-2-carboxylate (0.450 g, 60%) as a white solid.

MS: 361.1 (M+H)$^+$-Boc.

$^1$H-NMR (400 MHz, DMSO-d$_6$) δ=8.05 (d, J=8.88 Hz, 1H), 7.78 (d, J=8.16 Hz, 2H), 7.64 (d, J=1.96 Hz, 1H), 7.35-7.36 (m, 3H), 4.44 (s, 2H), 3.68 (t, J=5.60 Hz, 2H), 3.08 (bs, 2H), 2.32 (s, 3H), 1.43 (s, 9H).

Step C

To a solution of the title compound from Step B above (0.45 g, 0.97 mol) in DCM 4M HCl (3 mL) in dioxane at 0° C. was added. The reaction mixture was stirred 2 h. After the completion of the reaction, the reaction mixture was evaporated to remove the solvent and concentrated with diethyl ether to afford the title compound as white solid (0.32 g, 91%). The product was taken as such for next step.

MS: 361.1 (M+H)+.

Preparative Example 66

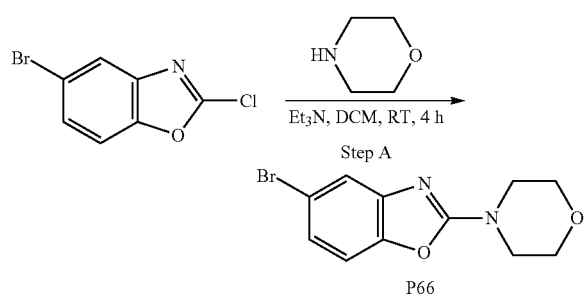

Step A

To a solution of 5-bromo-2-chlorobenzo[d]oxazole (1 g, 4.30 mmol) in dry DCM (10 mL) at 0° C., morpholine (0.56 g, 6.42 mmol) and Et₃N (1.7 mL, 12.9 mmol) were added and stirred at 25° C. for 4 h. After the completion of the reaction (monitored by TLC), the reaction mixture was diluted with H₂O (10 mL) and extracted with DCM (10 mL×2). The combined organic extracts were dried over Na₂SO₄, filtered and evaporated under reduced pressure to yield the crude product. It was triturated with diethyl ether (100 mL), filtered, washed with diethyl ether (5 mL) and dried to afford the title compound (0.85 g, 71%) as an off-white solid.

$^1$H-NMR (400 MHz, DMSO-$d_6$) δ=7.48 (d, J=2.40 Hz, 1H), 7.34-7.38 (m, 1H), 7.16-7.17 (m, 1H), 3.70-3.72 (m, 4H), 3.58-3.59 (m, 4H).

Preparative Example 67

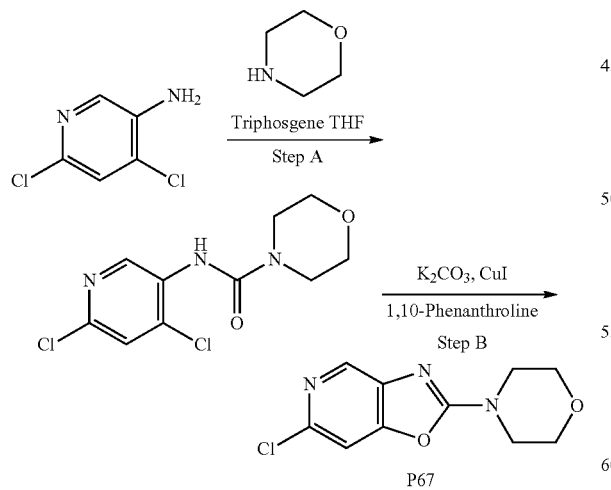

Step A

To a stirred solution of 4,6-dichloropyridin-3-amine (2.5 g, 15.3 mmol) in THF (50 mL) was added triphosgene (4.55 g, 15.3 mol) in THF was added dropwise followed by addition of TEA (4.28 mL, 30.7 mol) and heated to reflux for 2 h. The reaction mixture was concentrated under vacuum. The residue was dissolved in acetonitrile (50 mL) and toluene (50 mL) and morpholine (1.34 g, 15.3 mmol) were added and heated to 110° C. for 12 h. After that TLC was checked, crude was concentrated and purified by silica gel column chromatography using pet ether: ethylacetate (20: 80) to get N-(4,6-dichloro-3-pyridyl)morpholine-4-carboxamide (3.0 g, 70.1%) as white solid.

MS: 276.0 (M+H)+.

$^1$H-NMR (400 MHz, DMSO-$d_6$) δ=8.55 (s, 1H), 8.38-8.40 (m, 1H), 7.78-7.79 (m, 1H), 3.57-3.58 (m, 4H), 3.40-3.42 (m, 4H).

Step B

To a solution of the title compound from Step A above (3.0 g, 10.8 mmol) in 1,4-dioxane (5 mL) Cs₂CO₃ (10.5 g, 32.4 mol), 1,10-phenanthroline (0.972 g, 5.40 mol) and copper iodide (1.03 g, 5.40 mol) were added, then heated to 120° C. for 12 h. The reaction mixture was filtered through celite and washed with DCM/MeOH, concentrated and the crude was purified on silica gel column using Biotage Isolera One purification system employing an EtOAc/hexane gradient (40/60) to afford the title compound as an off-white solid (0.150 g, crude). The crude product was taken as such for next step.

MS: 240.1 (M+H)+.

Preparative Example 68

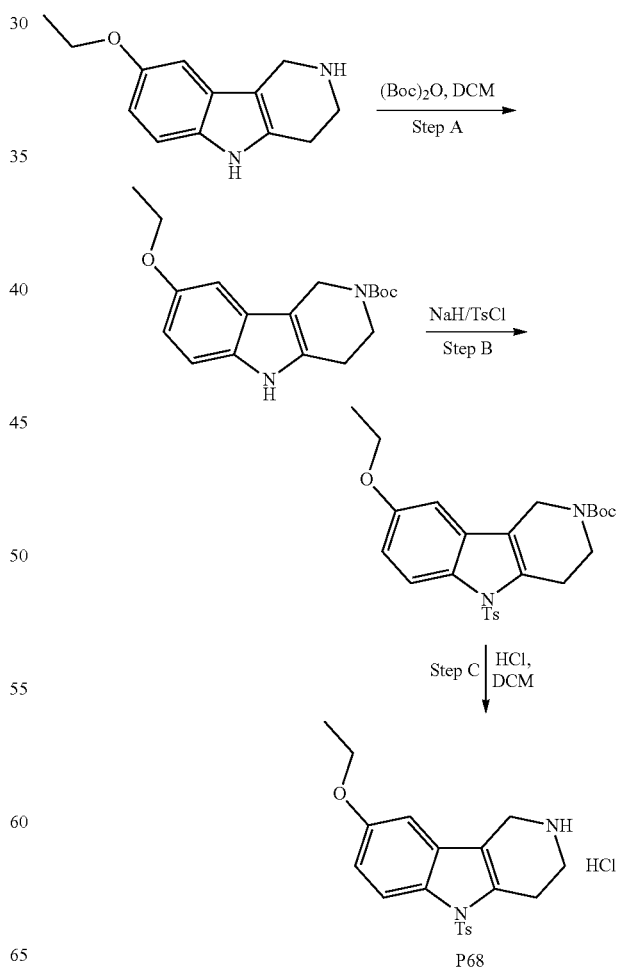

Step A

To a stirred solution of 8-ethoxy-2,3,4,5-tetrahydro-1H-pyrido[4,3-b]indole (1 g, 4.62 mmol) in DCM (20 mL) TEA (1.97 mL, 13.87 mmol) and BOC anhydride (1.5 mL, 6.93 mol) at 0° C. were added, then stirred at 25° C. for 12 h. After completion of the reaction by TLC, to the reaction mixture water was added followed by extraction using DCM. The organic layer was separated and washed with brine solution, concentrated and washed with hexane to obtain tert-butyl 8-ethoxy-1,3,4,5-tetrahydro-2H-pyrido[4,3-b]indole-2-carboxylate (0.8 g, 54%) as brown solid.

MS: 317.2 (M+H)$^+$.

$^1$H-NMR (400 MHz, DMSO-d$_6$) δ=10.69 (bs, 1H), 7.16 (d, J=8.68 Hz, 1H), 6.87 (s, 1H), 6.66 (t, J=6.76 Hz, 1H), 4.48 (s, 1H), 3.97-3.99 (m, 2H), 3.69 (t, J=5.48 Hz, 2H), 2.74 (bs, 2H), 1.44 (s, 9H), 1.23 (t, J=6.84 Hz, 3H).

Step B

To a suspension of Sodium hydride (0.136 g, 2.84 mmol) in THF (5 mL) the title compound from Step A above (0.3 g, 0.95 mmol) was added drop wise (dissolved in THF 10 mL) at 0° C., then stirred at room temperature for 30 min. After that tosyl chloride (0.27 g, 1.42 mmol) was added at 0° C. dropwise (dissolved in THF 10 mL) and then stirred at room temperature for 3 h. After completion of the reaction by TLC, the reaction mixture was quenched with ice water formed solid was filtered and washed with water and dried to get tert-butyl 8-ethoxy-5-tosyl-1,3,4,5-tetrahydro-2H-pyrido[4,3-b]indole-2-carboxylate (0.32 g, 72%) as a white solid. The product was taken as such for next step.

MS: 371.2 (M+H)$^+$-Boc.

Step C

To a solution of the title compound from Step B above (0.32 g, 0.68 mmol) in DCM 4M HCl (4 mL) in Dioxane at 0° C. was added. The reaction mixture was stirred 2 h. After the completion of the reaction, the reaction mixture was evaporated to remove the solvent and filtered with diethyl ether to afford the title compound as brown solid (0.13 g, 56%). The product was taken as such for next step.

MS: 371.2 (M+H)$^+$.

Preparative Example 69

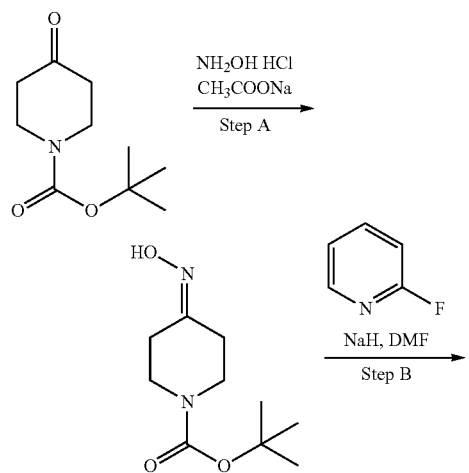

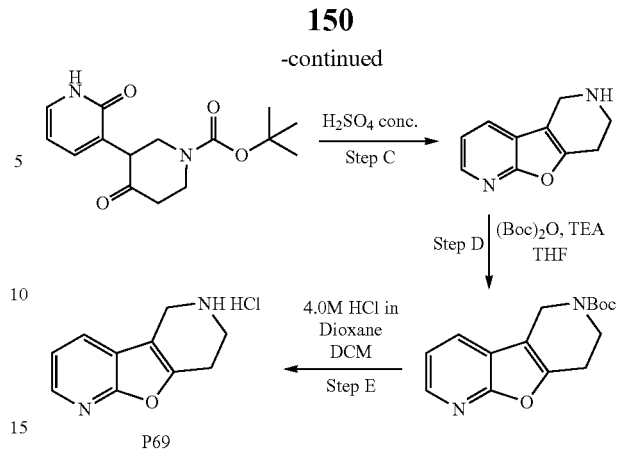

Step A

To a stirred solution of tert-butyl 4-oxopiperidine-1-carboxylate (10.00 g, 0.0502 mol) in ethanol (100 mL) hydroxylamine hydrochloride (6.98 g, 0.100 mol) and CH$_3$COONa (8.23 g, 0.100 mol) were added, then heated to 90° C. for 12 h under nitrogen atmosphere. After completion of the reaction by LCMS, the reaction mixture was concentrated and to the crude material water (100 mL) was added followed by extraction by using dichloromethane (250 mL). The organic layer was concentrated and the crude product was purified by silica gel column (Biotage) using 18-30% of ethyl acetate in pet ether to obtain tert-butyl-4-(hydroxyimino)piperidine-1-carboxylate (5 g, 46.4%) as a white solid.

MS: 159.1 (M+H)$^+$-t-butyl $^1$H-NMR (400 MHz, DMSO-d$_6$) δ=10.45 (s, 1H), 3.33-3.36 (m, 4H), 2.42-2.44 (m, 2H), 2.20-2.22 (m, 2H), 1.41 (s, 9H).

Step B

To a suspension of sodium hydride (0.268 g, 7.00 mmol) in DMF (3 mL) the title compound from Step A above (0.500 g, 2.33 mmol) was added drop wise (dissolved in DMF 5 mL) at 0° C., then stirred at room temperature for 60 min. After that 2-fluoropyridine (0.340 g, 3.50 mmol) was added dropwise at 0° C. (dissolved in DMF 2 mL) and then stirred at room temperature for 3 h. After completion of the reaction by TLC, the reaction mixture was quenched with ice water followed by extraction using ethyl acetate (30 mL). The organic layer was separated, dried over sodium sulphate, filtered and then concentrated to obtain tert-butyl 4-oxo-3-(2-oxo-1,2-dihydropyridin-3-yl)piperidine-1-carboxylate (300 mg, crude) as a pale brown solid. The crude product was taken as such for next step.

MS: 293.2 (M+H)$^+$.

Step C

A suspension of the title compound from Step B above (0.5 g, 1.71 mmol) in concentrated H$_2$SO$_4$ (2.0 mL) was stirred at room temperature for 16 h under nitrogen atmosphere. After that LCMS was checked which indicated only starting material, then the reaction mixture was heated to 60° C. for 16 h under nitrogen atmosphere. After that LCMS was checked which indicated 80% of product mass. The reaction mixture was cooled to room temperature, to this 10% of acetonitrile in water (20.0 mL) was added and the reaction mixture was basified by using solid K$_2$CO$_3$, then the solid was filtered. The filtrate was concentrated to get the title compound (250 mg, crude) as a brown gummy oil. The product was taken as such for next step.

MS: 175.1 (M+H)$^+$.

Step D

To a stirred solution of the title compound from Step C above (0.6 g, 3.15 mmol) in Tetrahydrofuran (10.0 mL) TEA (1.32 mL, 9.46 m0mol) and BOC anhydride (0.869 mL, 3.78 mmol) at 0° C. were added, then stirred at 25° C. for 12 h under nitrogen atmosphere. After completion of the reaction by TLC, the reaction mixture was concentrated and the crude product was purified by silica gel column (Biotage) using 15-20% of ethyl acetate in pet ether to get tert-butyl-7,8-dihydrofuro[2,3-b:4,5-c]dipyridine-6(5H)-carboxylate (500 mg, 53%) as an off white solid.

MS: 275.2 (M+H)$^+$.

$^1$H-NMR (400 MHz, DMSO-d$_6$) δ=8.21-8.22 (m, 1H), 8.05-8.06 (m, 1H), 7.30-7.31 (m, 1H), 4.51 (s, 2H), 3.76 (t, J=5.60 Hz, 2H), 2.86 (t, J=5.60 Hz, 2H), 1.44 (s, 9H).

Step E

To a stirred solution of the title compound from Step D above (0.5 g, 1.67 mmol) in dichloromethane (5 mL) 4.0 M HCl in dioxane (2 mL) at 0° C. was added, then stirred for 2 h at 0° C.-20° C. After completion of the reaction by TLC and LCMS, the reaction mixture was concentrated to get the title compound (350 mg, Quantitative) as an off white solid.

MS: 175.1 (M+H)$^+$.

Preparative Example 70

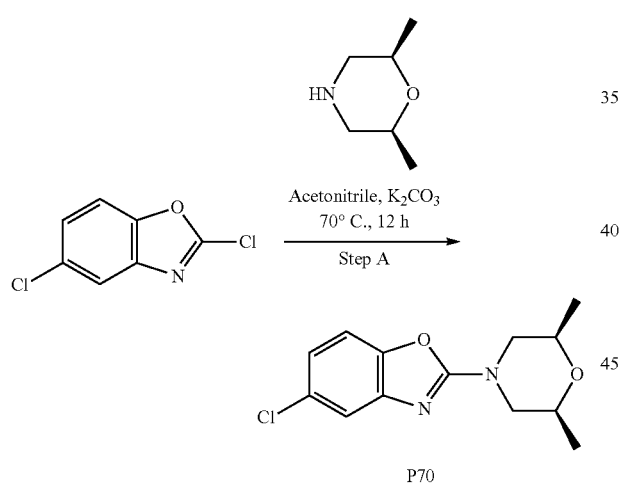

P70

Step A

To a stirred solution of 2,5-dichloro-1,3-benzoxazole (0.25 g, 0.0013 mol) in acetonitrile (15 mL) K$_2$CO$_3$ (0.55 g, 0.0040 mol) and (2S,6R)-2,6-dimethylmorpholine (0.17 g, 0.0014 mol) were added. After that the reaction mixture was heated to 70° C. for 12 h. After completion of the reaction by TLC, the reaction mixture was added DCM and water (50 mL). The organic layer was separated, dried over sodium sulphate filtered and then concentrated to title compound (0.2 g, 56%) as a white solid.

MS: 267.0 (M+H)$^+$.

$^1$H-NMR (400 MHz, DMSO-d$_6$) δ=7.43 (d, J=8.44 Hz, 1H), 7.34 (d, J=1.96 Hz, 1H), 7.04-7.04 (m, 1H), 3.99 (d, J=13.16 Hz, 2H), 3.66-3.67 (m, 2H), 2.82 (t, J=10.84 Hz, 2H), 1.00 (d, J=6.28 Hz, 6H).

Preparative Example 71

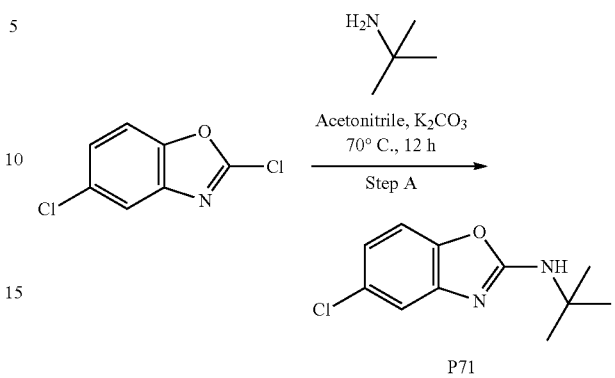

P71

Step A

To a stirred solution of 2,5-dichloro-1,3-benzoxazole (0.6 g, 0.0032 mol) in acetonitrile (15 mL) K$_2$CO$_3$ (1.32 g, 0.0096 mol) and tert-butyl amine (0.255 g, 0.0035 mol) were added. After that the reaction mixture was heated to 70° C. for 12 h.

After completion of the reaction by TLC, the reaction mixture DCM and water (50 mL) were added. The organic layer was separated, dried over sodium sulphate filtered and then concentrated to get title compound (0.4 g, 55%) as a brown solid.

MS: 225.0 (M+H)$^+$.

$^1$H-NMR (400 MHz, DMSO-d$_6$) δ=7.97 (s, 1H), 7.31-7.32 (m, 2H), 6.96-6.97 (m, 1H), 1.40 (s, 9H).

Preparative Example 72

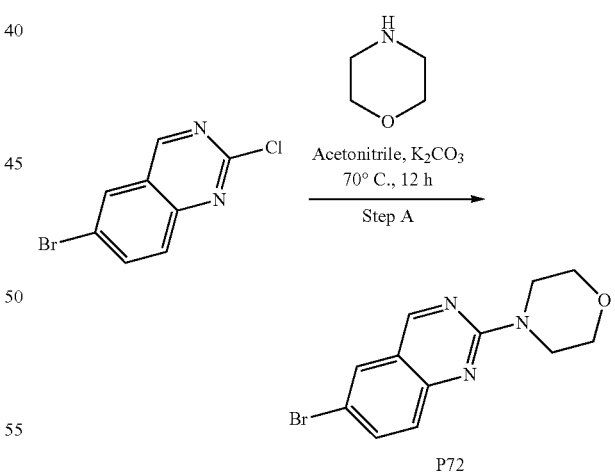

P72

Step A

To a stirred solution of 6-bromo-2-chloroquinazoline (0.3 g, 1.234 mmol) in acetonitrile (10 mL) K$_2$CO$_3$ (0.34 g, 2.467 mmol) and morpholine (0.17 g, 1.85 mmol) were added. After that the reaction mixture was heated to 70° C. for 12 h.

After completion of the reaction by TLC, to the reaction mixture DCM and water (50 mL) were added. The organic layer was separated, dried over sodium sulphate filtered and then concentrated to get the title compound (0.25 g, 69%) as a pale yellow solid. The product was taken as such for next step.

MS: 294.0 (M+H)⁺.

Preparative Example 73

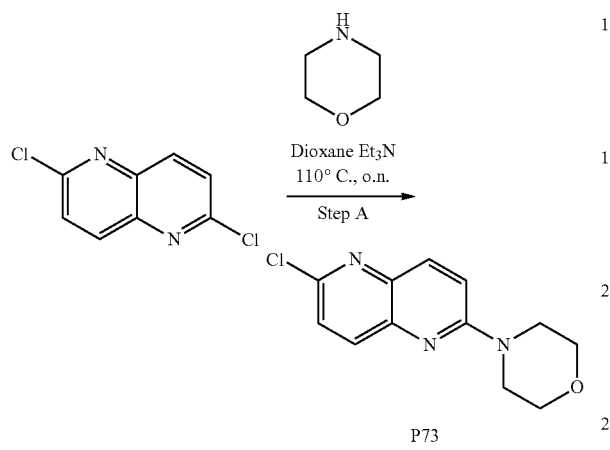

Step A

To a stirred solution of 2,6-dichloro-1,5-naphthyridine (100 mg, 0.502 mmol) in dioxane (3 mL), triethylamine (0.210 ml, 1.507 mmol) and morpholine (0.052 ml, 0.603 mmol) were added. Then the reaction mixture was stirred at 110 CC. After 4 h, the reaction was not complete, therefore, triethylamine (0.210 ml, 1.507 mmol) was added and the reaction mixture was further stirred at 110° C. overnight. The reaction mixture was concentrated to dryness and was then dissolved in dichloromethane and washed with a saturated NH₄Cl aqueous solution. The aqueous layer was extracted twice with dichloromethane. The combined organic layers were dried over Na₂SO₄, filtered and evaporated under reduced pressure to afford the title product as a beige solid (93 mg, 74%).

MS: 250.02 (M+H)⁺.

¹H-NMR (400 MHz, DMSO-d₆) δ=8.05 (d, J=9.4 Hz, 1H), 7.98 (d, J=8.8 Hz, 1H), 7.59 (d, J=8.7 Hz, 1H), 7.53 (d, J=9.5 Hz, 1H), 3.71 (hept, J=3.3, 2.6 Hz, 8H).

Preparative Example 74

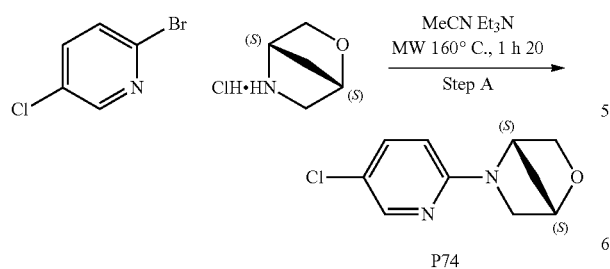

Step A 2-bromo-5-chloropyridine (200 mg, 1.039 mmol) was dissolved in acetonitrile (2.5 mL), to this (1S,4S)-2-oxa-5-azabicyclo[2.2.1]heptane hydrochloride (211 mg, 1.559 mmol) and triethylamine (0.362 mL, 2.60 mmol) were added and the suspension was irradiated in the microwave to 1600 for 1 h 20. The sample was then extracted between water (20 mL) and dichloromethane (20 mL). The aqueous layer was washed twice with dichloromethane. The combined organic layers were dried over Na₂SO₄, filtered and concentrated under reduced pressure. The crude was purified on a silica gel column using a Biotage Isolera One purification system with a dichloromethane/methanol gradient (100/0→90/10) to get the product as a beige solid (57 mg, 26%).

MS: 211.03 (M+H)⁺.

¹H-NMR (400 MHz, DMSO-d₆) δ=8.06 (d, J=2.6 Hz, 1H), 7.56 (dd, J=9.0, 2.7 Hz, 1H), 6.57 (d, J=9.0 Hz, 1H), 4.80 (d, J=2.3 Hz, 1H), 4.65 (d, J=2.4 Hz, 1H), 3.76 (dd, J=7.3, 1.5 Hz, 1H), 3.61 (d, J=7.3 Hz, 1H), 3.43 (dd, J=10.1, 1.5 Hz, 1H), 3.20 (d, J=10.3 Hz, 1H), 1.90 (dd, J=9.7, 2.3 Hz, 1H), 1.87-1.81 (m, 1H).

Preparative Example 75

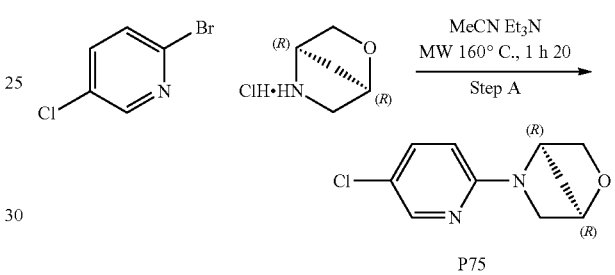

Step A 2-bromo-5-chloropyridine (200 mg, 1.039 mmol) was dissolved in acetonitrile (2.5 mL), to this (1R,4R)-2-oxa-5-azabicyclo[2.2.1]heptane hydrochloride (211 mg, 1.559 mmol) and triethylamine (0.362 mL, 2.60 mmol) were added and the suspension was irradiated in the microwave to 160° C. for 1 h 20. The sample was then extracted between water (20 mL) and dichloromethane (20 mL). The aqueous layer was washed twice with dichloromethane. The combined organic layers were dried over Na₂SO₄, filtered and concentrated under reduced pressure. The crude was purified on a silica gel column using a Biotage Isolera One purification system with a dichloromethane/methanol gradient (100/0→90/10) to get the product as a beige solid (51 mg, 23%).

MS: 211.04 (M+H)⁺.

¹H-NMR (400 MHz, DMSO-d₆) δ=8.06 (dd, J=2.7, 0.7 Hz, 1H), 7.56 (dd, J=9.0, 2.7 Hz, 1H), 6.63-6.50 (m, 1H), 4.80 (s, 1H), 4.64 (s, 1H), 3.75 (dd, J=7.3, 1.5 Hz, 1H), 3.61 (d, J=7.3, 0.9 Hz, 1H), 3.43 (dd, J=10.1, 1.6 Hz, 1H), 3.20 (d, J=10.1, 1.1 Hz, 1H), 1.94-1.78 (m, 2H).

Example 1

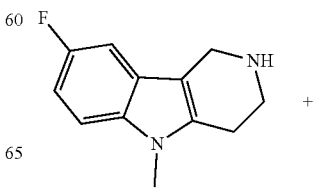

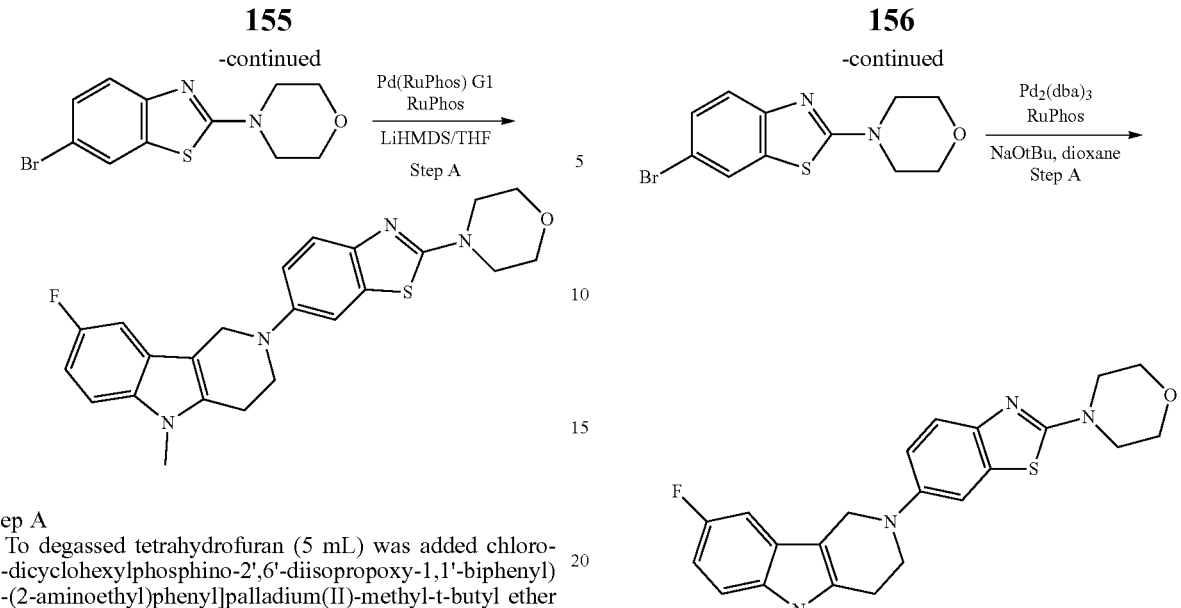

Step A

To degassed tetrahydrofuran (5 mL) was added chloro-(2-dicyclohexylphosphino-2',6'-diisopropoxy-1,1'-biphenyl)[2-(2-aminoethyl)phenyl]palladium(II)-methyl-t-butyl ether adduct (PdRuPhos G1) (0.017 g, 0.024 mmol), 2-dicyclohexylphosphino-2',6'-diisopropoxybiphenyl (RuPho) (0.011 g, 0.024 mmol), the title compound from Preparative Example 2 (0.05 g, 0.024 mmol), and the commercially available 4-(6-bromobenzo[d]thiazol-2-yl)morpholine (0.073 g, 0.029 mmol). Then, a 1 M solution of lithium bis(trimethylsilyl)amide (LiHMDS) in tetrahydrofuran (1 mL, 1 mmol) was added. The resulting reaction mixture was heated at reflux for 2 hours. The reaction mixture was cooled to room temperature, dissolved in dichloromethane (100 mL). The organic phase was washed with water and brine and dried over $Na_2SO_4$. The solvent was removed under reduced pressure. The crude product was purified on a silica gel column using a Biotage Isolera One purification system employing an ethyl acetate/n-heptane gradient (80/20=>100/0) to afford the title compound (0.070 g, 69%).

$^1$H-NMR (400 MHz, Chloroform-d) δ=7.51 (d, J=8.8 Hz, 1H), 7.31 (d, J=2.4 Hz, 1H), 7.27 (s, 1H), 7.20 (dd, J=8.8, 4.2 Hz, 1H), 7.14 (td, J=8.6, 2.4 Hz, 2H), 6.94 (td, J=9.1, 2.5 Hz, 1H), 4.40 (s, 2H), 3.88-3.81 (m, 4H), 3.70 (t, J=5.7 Hz, 2H), 3.64 (s, 3H), 3.59 (t, J=4.9 Hz, 4H), 2.92 (t, J=5.7 Hz, 2H).

Example 2

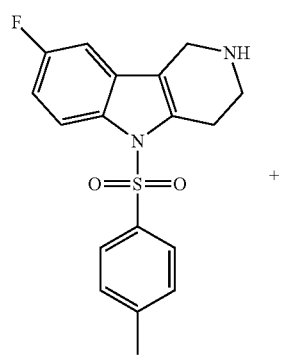

Step A

To a stirred solution of the title compound of Preparative Example 1 (0.150 g, 1 eq) in dry 1,4-dioxane (5 mL) was added the commercially available 4-(6-bromobenzo[d]thiazol-2-yl)morpholine (1 eq), sodium tert-butoxide (3 eq) and the mixture was degassed for 10 minutes under $N_2$ atmosphere. To this reaction mixture was added $Pd_2(dba)_3$ (0.05 eq) and Ru-Phos (0.1 eq) and the mixture was heated to 100° C. until the completion of the reaction. After the completion of the reaction, the reaction mixture was filtered through a celite bed, and washed with EtOAc. The filtrate was concentrated and the crude product was purified by column chromatography or preparative HPLC to afford title compound 6 as indicated in table 2.

Examples 3 to 96e

Following the palladium coupling procedures as described in Examples 1 and 2, except using the tricyclic amino- and bromo/chloro-derivatives indicated in the table below, the following compounds were prepared. Examples 71 and 72 were prepared following the procedures as described in Preparative Examples 42 and 43, respectively, followed by the deprotection procedure described in Example 97.

TABLE 2

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 3 | | | | 1. 63% 2. ¹H-NMR (400 MHz, Chloroform-d) δ = 7.50 (d, J = 8.8 Hz, 1H), 7.31 (d, J = 2.5 Hz, 1H), 7.27 (s, 1H), 7.23-7.08 (m, 3H), 6.93 (td, J = 9.1, 2.5 Hz, 1H), 4.47-4.20 (m, 2H), 3.68 (t, J = 5.7 Hz, 2H), 3.64 (s, 2H), 3.19 (s, 6H), 2.92 (dq, J = 5.3, 2.9, 1.7 Hz, 2H). 4. Example 1 |
| 4 | | | | 1. 49% 2. ¹H-NMR (400 MHz, DMSO-d₆) δ = 7.59 (d, J = 7.4 Hz, 1H), 7.43-7.35 (m, 2H), 7.26 (dd, J = 9.3, 2.1 Hz, 2H), 7.02 (dd, J = 8.8, 2.5 Hz, 1H), 6.92 (td, J = 9.2, 2.6 Hz, 1H), 4.30 (s, 2H), 4.05-3.80 (m, 1H), 3.63 (d, J = 4.3 Hz, 5H), 2.99-2.79 (m, 2H), 1.19 (d, J = 6.5 Hz, 6H). 4. Example 1 |
| 5 | | | | 1. 33% 2. ¹H-NMR (400 MHz, Chloroform-d) δ = 7.51 (d, J = 8.8 Hz, 1H), 7.32 (d, J = 2.5 Hz, 1H), 7.22 (dd, J = 8.8, 4.3 Hz, 1H), 7.15 (ddd, J = 12.9, 9.1, 2.5 Hz, 2H), 6.96 (td, J = 9.1, 2.6 Hz, 1H), 5.13 (s, 1H), 4.41 (t, J = 1.7 Hz, 2H), 3.72 (t, J = 5.7 Hz, 2H), 3.67 (s, 3H), 3.12 (s, 3H), 2.94 (dd, J = 6.5, 4.7 Hz, 2H). 4. Example 1 |

TABLE 2-continued

| Example | Tricyclic amino derivative | Bromo or Chloro derivative | Product | 1. Yield  2. ¹H-NMR  3. MH⁺ (ESI)  4. Synthesis procedure |
|---|---|---|---|---|
| 6 | | | | 1. 20%  2. ¹H-NMR (400 MHz, DMSO-d₆) δ = 10.96 (s, 1H), 7.51-7.51 (m, 1H), 7.37-7.40 (m, 1H), 7.22- 7.29 (m, 2H), 7.10- 7.13 (m, 1H), 6.88- 6.88 (m, 1H), 4.33 (s, 2H), 3.73 (t, J = 5.20 Hz, 4H), 3.63 (t, J = 5.60 Hz, 2H), 3.48 (t, J = 4.80 Hz, 4H), 2.90 (s, 2H).  3. 410.5  4. Example 2 |
| 7 | | | | 1. 16%  2. ¹H-NMR (400 MHz, DMSO-d₆) δ = 10.95 (s, 1H), 7.48 (s, 1H), 7.33-7.36 (m, 1H), 7.21-7.33 (m, 2H), 7.07-7.09 (m, 1H), 6.82-6.88 (m, 1H), 4.31 (m, 2H), 3.60 (s, 2H), 3.10 (m,6H), 2.90 (s, 2H).  3. 367.5  4. Example 2 |
| 8 | | | | 1. 24%  2. ¹H-NMR (400 MHz, DMSO-d₆) δ = 7.29-7.23 (m, 3H), 7.04 (d, J = 1.8 Hz, 1H), 6.88-6.83 (m, 1H), 6.80-6.77 (m, 1H), 4.31 (s, 2H), 3.73-3.71 (m, 4H), 3.64-3.61 (m, 2H), 3.56 (t, J = 9.2 Hz, 4H), 2.88-2.87 (m, 2H).  3. 393.4  4. Example 2 |
| 9 | | | | 1. 20%  2. ¹H-NMR (400 MHz, DMSO-d₆) δ = 10.95 (s, 1H), 7.59 (d, J = 8.40 Hz, 1H), 7.30-7.25 (m, 2H), 3.52 (d, J = 2.00 Hz, 1H), 6.93 (dd, J = 2.40, 8.80 Hz, 1H), 6.88-6.83 (m, 1H), 4.37 (s, 2H), 3.74-3.68 (m, 6H), 3.51 (t, J = 4.80 Hz, 4H), 2.88 (t, J = 4.80 Hz, 2H).  3. 409.5 |

TABLE 2-continued

| Example | Tricyclic amino derivative | Bromo or Chloro derivative | Product | 1. Yield  2. ¹H-NMR  3. MH⁺ (ESI)  4. Synthesis procedure |
|---|---|---|---|---|
| 10 | | | | 1. 12%  2. ¹H-NMR (400 MHz, DMSO-$d_6$) δ = 10.95 (s, 1H), 7.28–7.22 (m, 3H), 7.00 (s, 1H), 6.72 (d, J = 8.92 Hz, 1H), 3.52 (t, J = 8.68 Hz, 1H), 3.12 (s, 2H), 3.61 (t, J = 4.72 Hz, 2H), 3.10 (d, J = 1.24 Hz, 6H), 2.88 (s, 2H).  3. 351.4  4. Example 2 |
| 11 | | | | 1. 32%  2. ¹H-NMR (400 MHz, DMSO-$d_6$) δ = 10.95 (s, 1H), 7.54 (d, J = 8.68 Hz, 1H), 7.30–7.25 (m, 2H), 3.52 (d, J = 2.00 Hz, 1H), 6.89–6.85 (m, 2H), 3.12 (s, 2H), 3.68 (t, J = 5.44 Hz, 2H), 3.12 (s, 6H), 2.89 (d, J = 5.00 Hz, 2H).  3. 367.5  4. Example 2 |
| 12 | | | | 1. 27%  2. ¹H-NMR (400 MHz, DMSO-$d_6$) δ = 10.96 (s, 1H), 7.29–7.18 (m, 3H), 6.95 (dd, J = 2.08, 8.58 Hz, 1H), 3.52 (t, J = 2.32 Hz, 1H), 4.31 (s, 2H), 3.12 (t, J = 5.00 Hz, 4H), 3.62 (t, J = 5.52 Hz, 2H), 3.53 (t, J = 4.52 Hz, 4H), 2.89 (t, J = 5.16 Hz, 2H).  3. 393.4  4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 13 | (fluoro-tetrahydro-β-carboline with N-Ts, as NH·HCl) | 6-chloro-2-(dimethylamino)benzoxazole | fluoro-tetrahydro-β-carboline coupled to 2-(dimethylamino)benzoxazol-6-yl | 1. 28%<br>2. ¹H-NMR (400 MHz, DMSO-d₆) δ = 10.94 (s, 1H), 7.28-7.11 (m, 4H), 6.92- 6.84 (m, 2H), 3.52 (s, 2H), 3.59 (s, 2H), 3.12 (d, J = 2.00 Hz, 6H), 2.88 (s, 2H).<br>3. 351.4<br>4. Example 2 |
| 14 | (8-fluoro-N-methyl-tetrahydro-β-carboline) | 6-chloro-2-morpholinobenzoxazole | 8-fluoro-N-methyl-tetrahydro-β-carboline coupled to 2-morpholinobenzoxazol-6-yl | 1. 22%<br>2. ¹H-NMR (400 MHz, DMSO-d₆) δ = 7.42-7.39 (m, 1H), 7.31-7.26 (m, 2H), 7.05 (s, 1H), 6.95- 6.91 (m, 1H), 6.79 (d, J = 8.6 Hz, 1H), 4.33 (s, 2H), 3.72-3.71 (m, 4H), 3.67-3.64 (m, 5H), 3.57-3.57 (m, 4H), 2.90-2.98 (m, 2H).<br>3. 407.5<br>4. Example 2 |
| 15 | (7-fluoro-N-methyl-tetrahydro-β-carboline) | 6-chloro-2-morpholinobenzoxazole | 7-fluoro-N-methyl-tetrahydro-β-carboline coupled to 2-morpholinobenzoxazol-6-yl | 1. 30%<br>2. ¹H-NMR (400 MHz, DMSO-d₆) δ = 7.42-7.39 (m, 1H), 7.30-7.27 (m, 1H), 7.22-7.18 (m, 2H), 6.97-6.91 (m, 2H), 4.33 (s, 2H), 3.72- 3.64 (m, 9H), 3.53- 3.50 (m, 4H), 2.91-2.89 (m, 2H).<br>3. 407.5<br>4. Example 2 |
| 16 | (methoxy-N-methyl-tetrahydro-β-carboline) | 6-chloro-2-morpholinobenzothiazole | methoxy-N-methyl-tetrahydro-β-carboline coupled to 2-morpholinobenzothiazol-6-yl | 1. 33%<br>2. ¹H-NMR (400 MHz, DMSO-d₆) δ = 7.53 (s, 1H), 7.39 (d, J = 8.8 Hz, 1H), 7.29 (d, J = 8.7 Hz, 1H), 7.13 (d, J = 8.7 Hz, 1H), 7.04 (d, J = 1.7 Hz, 1H), 6.74 (d, J = 8.8 Hz, 1H), 4.34 (s, 2H), 3.78 (s, 3H), 3.74-3.73 (m, 4H), 3.67-3.65 (m, 2H), 3.61 (s, 3H), 3.49- 3.48 (m, 4H), 2.91-2.89 (m, 2H).<br>3. 435.6<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 17 | (structure) | (structure) | (structure) | 1. 18%<br>2. ¹H-NMR (400 MHz, DMSO-d₆) δ = 8.16 (s, 1H), 7.82 (d, J = 8.5 Hz, 1H), 7.52 (s, 1H), 7.40 (d, J = 8.8 Hz, 1H), 7.12 (d, J = 8.7 Hz, 1H), 4.36 (s, 2H), 3.78-3.74 (m, 7H), 3.64-3.61 (m, 5H), 3.04-3.02 (m, 4H), 2.89-2.87 (m, 2H).<br>3. 424.5<br>4. Example 2 |
| 18 | (structure) | (structure) | (structure) | 1. 45%<br>2. ¹H-NMR (400 MHz, DMSO-d₆) δ = 7.20-7.16 (m, 3H), 7.00-7.00 (m, 1H), 6.97-6.94 (m, 1H), 6.67-6.65 (m, 1H), 4.31 (s, 2H), 3.76 (s, 3H), 3.73-3.70 (m, 4H), 3.61 (t, J = 11.2 Hz, 2H), 3.54-3.51 (m, 4H), 2.86-2.88 (m, 2H).<br>3. 405.5<br>4. Example 2 |
| 19 | (structure) | (structure) | (structure) | 1. 38%<br>2. ¹H-NMR (400 MHz, DMSO-d₆) δ = 7.51 (s, 1H), 7.38 (d, J = 8.80 Hz, 1H), 7.17 (d, J = 8.80 Hz, 1H), 7.11 (d, J = 8.00 Hz, 1H), 6.99 (s, 1H), 6.66 (d, J = 7.20 Hz, 1H), 4.33 (s, 2H), 3.73-3.77 (m, 7H), 3.62 (s, 2H), 3.48 (s, 4H), 2.88 (s, 2H).<br>3. 421.5<br>4. Example 2 |

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 20 | | | | 1. 13%<br>2. ¹H-NMR (400 MHz, DMSO-d₆) δ = 7.28 (d, J = 8.80 Hz, 1H), 7.17-7.21 (m, 2H), 7.03 (d, J = 2.40 Hz, 1H), 6.94-6.97 (m, 1H), 6.71-6.74 (m, 1H), 4.32 (s, 2H), 3.77 (s, 3H), 3.63-3.72 (m, 6H), 3.59 (s, 3H), 3.50-3.53 (m, 4H), 2.86-2.87 (m, 2H).<br>3. 419.0<br>4. Example 2 |
| 21 | | | | 1. 15%<br>2. ¹H-NMR (400 MHz, DMSO-d₆) δ = 7.24-7.29 (m, 2H), 7.04 (s, 2H), 6.71-6.79 (m, 2H), 4.32 (bs, 2H), 3.77 (s, 3H), 3.71 (bs, 4H), 3.64 (bs, 2H), 3.59 (s, 3H), 3.55 (bs, 4H), 2.86 (bs, 2H).<br>3. 419.0<br>4. Example 2 |
| 22 | | | | 1. 24%<br>2. ¹H-NMR (400 MHz, DMSO-d₆) δ = 7.58 (d, J = 8.80 Hz, 1H), 7.32-7.41 (m, 2H), 7.18 (d, J = 2.00 Hz, 1H), 6.90-6.96 (m, 2H), 4.39 (bs, 2H), 3.71-3.73 (m, 6H), 3.63 (s, 3H), 3.49-3.51 (m, 4H), 2.87-2.89 (m, 2H).<br>3. 422.8<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 23 | | | | 1. 13%<br>2. ¹H-NMR (400 MHz, DMSO-d₆) δ = 10.65 (bs, 1H), 7.58 (d, J = 8.84 Hz, 1H), 7.17 (d, J = 8.68 Hz, 2H), 7.05 (s, 1H), 6.94 (d, J = 8.64 Hz, 1H), 6.66 (d, J = 8.76 Hz, 1H), 4.37 (bs, 2H), 3.79 (s, 3H), 3.68-3.77 (m, 6H), 3.50 (bs, 4H), 2.86 (bs, 2H).<br>3. 420.8<br>4. Example 2 |
| 24 | | | | 1. 16%<br>2. ¹H-NMR (400 MHz, DMSO-d₆) δ = 10.65 (bs, 1H), 7.26 (d, J = 8.80 Hz, 1H), 7.17 (d, J = 8.40 Hz, 1H), 7.00-7.04 (m, 2H), 6.79 (dd, J = 2.40, 8.80 Hz, 1H), 6.67 (d, J = 2.00 Hz, 1H), 4.31 (bs, 2H), 3.77 (s, 3H), 3.70-3.73 (m, 4H), 3.60-3.63 (m, 2H), 3.55-3.57 (m, 4H), 2.84-2.86 (m, 2H).<br>3. 405.2<br>4. Example 2 |
| 25 | | | | 1. 42%<br>2. ¹H-NMR (400 MHz, Chloroform-d) δ = 7.46 (d, J = 8.6 Hz, 1H), 7.29 (s, 1H), 7.20 (dd, J = 8.8, 4.3 Hz, 1H), 7.15 (dd, J = 9.5, 2.5 Hz, 1H), 6.93 (ddd, J = 18.8, 8.9, 2.6 Hz, 2H), 5.10 (s, 1H), 4.46 (s, 2H), 3.97 (dd, J = 13.1, 6.6 Hz, 1H), 3.77 (t, J = 5.6 Hz, 2H), 3.65 (s, 3H), 2.94 (t, J = 5.5 Hz, 2H), 1.35 (d, J = 6.5 Hz, 6H).<br>4. Example 1 |

TABLE 2-continued

| Example | Tricyclic amino derivative | Bromo or Chloro derivative | Product | 1. Yield  2. 1H-NMR  3. MH+ (ESI)  4. Synthesis procedure |
|---|---|---|---|---|
| 26 | | | | 1. 13%  2. 1H-NMR (400 MHz, DMSO-d6) δ = 8.16 (s, 1H), 7.86-7.89 (m, 1H), 7.58-7.60 (m, 1H), 7.19 (s, 1H), 6.94 (d, J = 8.80 Hz, 1H), 4.40 (bs, 2H), 3.68-3.76 (m, 9H), 3.50-3.51 (m, 4H), 2.93-2.95 (m, 2H).  3. 424.0  4. Example 2 |
| 27 | | | | 1. 40%  2. 1H-NMR (400 MHz, Chloroform-d) δ = 7.48 (d, J = 8.6 Hz, 1H), 7.31 (d, J = 2.5 Hz, 1H), 7.21 (dd, J = 8.8, 4.3 Hz, 1H), 7.15 (dd, J = 9.5, 2.5 Hz, 1H), 6.99-6.90 (m, 2H), 5.22 (s, 1H), 4.47 (t, J = 1.6 Hz, 2H), 3.78 (t, J = 5.7 Hz, 2H), 3.66 (s, 3H), 3.13 (s, 3H), 2.95 (tt, J = 5.7, 1.8 Hz, 2H).  4. Example 1 |
| 28 | | | | 1. 39%  2. 1H-NMR (400 MHz, DMSO-d6) δ = 7.52-7.55 (m, 1H), 7.38-7.41 (m, 1H), 7.32-7.35 (m, 1H), 7.15 (d, J = 2.04 Hz, 1H), 6.87-6.95 (m, 2H), 4.38 (bs, 2H), 3.72-3.73 (m, 2H), 3.64 (s, 3H), 3.11 (s, 6H), 2.89 (bs, 2H).  3. 381.2  4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 29 | (8-fluoro-9-methyl-2,3,4,9-tetrahydro-1H-pyrido[3,4-b]indole with NH) | 6-chloro-N,N-dimethylbenzo[d]oxazol-2-amine | coupled product | 1. 17%<br>2. ¹H-NMR (400 MHz, DMSO-d₆) δ = 7.38-7.42 (m, 1H), 7.27-7.30 (m, 1H), 7.23 (d, J = 8.80 Hz, 1H), 7.00 (d, J = 2.00 Hz, 1H), 6.91-6.95 (m, 1H), 6.72-6.74 (m, 1H), 4.31 (bs, 2H), 3.62-3.64 (m, 5H), 3.10 (s, 6H), 2.87-2.89 (m, 2H).<br>3. 365.0<br>4. Example 2 |
| 30 | (7-methoxy-9-tosyl-2,3,4,9-tetrahydro-1H-pyrido[3,4-b]indole with NH) | 6-chloro-N,N-dimethylbenzo[d]thiazol-2-amine | coupled product | 1. 15%<br>2. ¹H-NMR (400 MHz, DMSO-d₆) δ = 10.65 (bs, 1H), 7.54 (d, J = 8.80 Hz, 1H), 7.15-7.18 (m, 2H), 7.05 (s, 1H), 6.88 (dd, J = 2.00, 8.60 Hz, 1H), 6.66 (dd, J = 2.40, 8.60 Hz, 1H), 4.37 (bs, 2H), 3.77 (s, 3H), 3.66-3.69 (m, 2H), 3.11 (s, 6H), 2.84-2.86 (m, 2H).<br>3. 379.0<br>4. Example 2 |
| 31 | (7-methoxy-9-methyl-2,3,4,9-tetrahydro-1H-pyrido[3,4-b]indole with NH) | 6-chloro-N,N-dimethylbenzo[d]thiazol-2-amine | coupled product | 1. 27%<br>2. ¹H-NMR (400 MHz, DMSO-d₆) δ = 7.49 (d, J = 2.40 Hz, 1H), 7.34 (d, J = 8.80 Hz, 1H), 7.28 (d, J = 8.80 Hz, 1H), 7.08- 7.10 (m, 1H), 7.03 (d, J = 2.40 Hz, 1H), 6.72-6.74 (m, 1H), 4.32 (bs, 2H), 3.77 (s, 3H), 3.60-3.64 (m, 5H), 3.10 (s, 6H), 2.87-2.90 (m, 2H).<br>3. 393.0<br>4. Example 2 |

TABLE 2-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 32 | | | | 1. 21% 2. ¹H-NMR (400 MHz, DMSO-d₆) δ = 7.53 (d, J = 8.40 Hz, 1H), 7.28 (d, J = 8.80 Hz, 1H), 7.15 (s, 1H), 7.09 (s, 1H), 6.89 (d, J = 8.00 Hz, 1H), 6.72 (d, J = 8.80 Hz, 1H), 4.38 (bs, 2H), 3.78 (s, 3H), 3.69-3.71 (m, 2H), 3.59 (s, 3H), 3.11 (s, 6H), 2.87 (bs, 2H). 3. 393.0 4. Example 2 |
| 33 | | | | 1. 28% 2. ¹H-NMR (400 MHz, DMSO-d₆) δ = 7.28 (d, J = 8.80 Hz, 1H), 7.20 (d, J = 2.40 Hz, 1H), 7.12-7.14 (m, 1H), 7.04 (d, J = 2.40 Hz, 1H), 6.92 (dd, J = 2.40, 8.60 Hz, 1H), 6.73 (dd, J = 2.80, 8.60 Hz, 1H), 4.31 (bs, 2H), 3.78 (s, 3H), 3.62-3.65 (m, 2H), 3.60 (s, 3H), 3.08 (s, 6H), 2.86-2.89 (m, 2H). 3. 377.2 4. Example 2 |
| 34 | | | | 1. 16% 2. ¹H-NMR (400 MHz, DMSO-d₆) δ = 8.16 (s, 1H), 7.82 (dd, J = 2.60, 9.58 Hz, 1H), 7.48 (d, J = 2.08 Hz, 1H), 7.35 (d, J = 8.80 Hz, 1H), 7.09 (dd, J = 2.32, 8.82 Hz, 1H), 4.34 (bs, 2H), 3.69 (s, 3H), 3.65-3.68 (m, 2H), 3.10 (s, 6H), 2.96 (bs, 2H). 3. 382.3 4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 35 | | | | 1. 27%<br>2. ¹H-NMR (400 MHz, DMSO-d₆) δ = 8.16 (d, J = 1.72 Hz, 1H), 7.87 (dd, J = 2.52, 9.60 Hz, 1H), 7.54-7.56 (m, 1H), 7.16 (d, J = 1.96 Hz, 1H), 6.89 (dd, J = 1.96, 8.58 Hz, 1H), 4.40 (bs, 2H), 3.75- 3.76 (m, 2H), 3.70 (s, 3H), 3.12 (s, 6H), 2.94-2.96 (m, 2H).<br>3. 382.0<br>4. Example 2 |
| 36 | | | | 1. 13%<br>2. ¹H-NMR (400 MHz, DMSO-d₆) δ = 8.15-8.16 (m, 1H), 7.84 (dd, J = 2.72, 9.54 Hz, 1H), 7.25- 7.29 (m, 1H), 7.05 (d, J = 2.32 Hz, 1H), 6.79 (dd, J = 2.40, 8.76 Hz, 1H), 4.34 (bs, 2H), 3.67-3.73 (m, 9H), 3.55-3.57 (m, 4H), 2.94-2.97 (m, 2H).<br>3. 408.0<br>4. Example 2 |
| 37 | | | | 1. 22%<br>2. ¹H-NMR (400 MHz, DMSO-d₆) δ = 8.16 (bs, 1H), 7.82 (dd, J = 2.80, 9.40 Hz, 1H), 7.20 (d, J = 2.00 Hz, 1H), 7.14 (d, J = 8.40 Hz, 1H), 6.92 (dd, J = 2.00, 8.60 Hz, 1H), 4.33 (bs, 2H), 3.69 (s, 3H), 3.65-3.67 (m, 2H), 3.08 (s, 6H), 2.95-2.97 (m, 2H).<br>3. 366.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 38 | | | | 1. 19%<br>2. ¹H-NMR (400 MHz, DMSO-d₆) δ = 8.15-8.16 (m, 1H), 7.83 (dd, J = 2.80, 9.60 Hz, 1H), 7.24 (d, J = 8.80 Hz, 1H), 7.00 (d, J = 2.40 Hz, 1H), 6.73 (dd, J = 2.80, 8.60 Hz, 1H), 4.33 (bs, 2H), 3.69 (s, 3H), 3.65-3.67 (m, 2H), 3.10 (s, 6H), 2.94-2.97 (m, 2H).<br>3. 366.0<br>4. Example 2 |
| 39 | | | | 1. 13%<br>2. ¹H-NMR (400 MHz, DMSO-d₆) δ = 8.15-8.16 (m, 1H), 7.82 (dd, J = 2.40, 9.60 Hz, 1H), 7.18-7.22 (m, 2H), 6.96 (dd, J = 2.00, 8.60 Hz, 1H), 4.34 (bs, 2H), 3.66-3.73 (m, 9H), 3.51-3.54 (m, 4H), 2.95-2.97 (m, 2H).<br>3. 408.0<br>4. Example 2 |
| 40 | | | | 1. 12%<br>2. ¹H-NMR (400 MHz, DMSO-d₆) δ = 10.66 (bs, 1H), 7.12-7.20 (m, 3H), 7.00 (d, J = 2.28 Hz, 1H), 6.92 (d, J = 8.48 Hz, 1H), 6.66 (dd, J = 2.40, 8.68 Hz, 1H), 4.30 (bs, 2H), 3.77 (s, 3H), 3.59-3.61 (m, 2H), 3.09 (s, 6H), 2.86 (bs, 2H).<br>3. 363.2<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 41 | (structure) | (structure) | (structure) | 1. 15%<br>2. ¹H-NMR (400 MHz, Chloroform-d) δ = 7.50 (d, J = 8.8 Hz, 1H), 7.32 (d, J = 2.5 Hz, 1H), 7.21 (dd, J = 8.8, 0.6 Hz, 1H), 7.15 (dd, J = 8.8, 2.5 Hz, 1H), 6.98 (d, J = 2.4 Hz, 1H), 6.87 (dd, J = 8.8, 2.5 Hz, 1H), 5.21 (s, 1H), 4.44 (t, J = 1.6 Hz, 2H), 3.90 (s, 4H), 3.71 (t, J = 5.7 Hz, 2H), 3.64 (s, 4H), 2.93 (td, J = 5.6, 2.7 Hz, 3H).<br>4. Example 1 |
| 42 | (structure) | (structure) | (structure) | 1. 11%<br>2. ¹H-NMR (400 MHz, DMSO-d₆) δ = 7.46-7.50 (m, 1H), 7.21-7.30 (m, 2H), 7.00 (d, J = 2.40 Hz, 1H), 6.83-6.89 (m, 1H), 6.73 (dd, J = 2.40, 8.60 Hz, 1H), 4.33 (bs, 2H), 3.61-3.65 (m, 5H), 3.10 (s, 6H), 2.88-2.89 (m, 2H).<br>3. 365.2<br>4. Example 2 |
| 43 | (structure) | (structure) | (structure) | 1. 14%<br>2. ¹H-NMR (400 MHz, DMSO-d₆) δ = 10.96 (bs, 1H), 7.37-7.51 (m, 3H), 7.07-7.12 (m, 2H), 6.84-6.83 (m, 1H), 4.35 (bs, 2H), 3.73 (bs, 4H), 3.61 (bs, 2H), 3.48 (bs, 4H), 2.89 (bs, 2H).<br>3. 409.0<br>4. Example 2 |
| 44 | (structure) | (structure) | (structure) | 1. 19%<br>2. ¹H-NMR (400 MHz, DMSO-d₆) δ = 10.95 (bs, 1H), 7.43-7.47 (m, 1H), 7.18-7.21 (m, 2H), 7.06-7.09 (m, 1H), 6.81-6.97 (m, 2H), 4.33 (bs, 2H), 3.71-3.73 (m, 4H), 3.60-3.62 (m, 2H), 3.52-3.54 (m, 4H), 2.87-2.88 (m, 2H).<br>3. 393.2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 45 | (structure) | (structure) | (structure) | 1. 15%<br>2. ¹H-NMR (400 MHz, DMSO-d₆) δ = 10.94 (bs, 1H), 7.4-7.45 (m, 1H), 7.27 (d, J = 8.80 Hz, 1H), 7.04-7.08 (m, 2H), 6.77-6.85 (m, 2H), 4.33 (bs, 2H), 3.72 (bs, 4H), 3.56-3.61 (m, 6H), 2.86 (bs, 2H).<br>3. 393.2<br>4. Example 2. Example 45 can be also prepared by the procedure reported in Preparative Example 33 and Example 97. |
| 46 | (structure) | (structure) | (structure) | 1. 23%<br>2. ¹H-NMR (400 MHz, DMSO-d₆) δ = 7.53-7.57 (m, 2H), 7.33-7.43 (m, 2H), 7.06-7.14 (m, 2H), 4.32 (bs, 2H), 3.67-3.74 (m, 6H), 3.47-3.50 (m, 4H), 2.93-2.96 (m, 2H).<br>3. 410.0<br>4. Example 2 |
| 47 | (structure) | (structure) | (structure) | 1. 15%<br>2. ¹H-NMR (400 MHz, DMSO-d₆) δ = 10.64 (bs, 1H), 7.16-7.24 (m, 2H), 7.00 (s, 2H), 6.66-6.74 (m, 2H), 4.31 (bs, 2H), 3.77 (s, 3H), 3.59-3.61 (m, 2H), 3.11 (s, 6H), 2.84-2.86 (m, 2H).<br>3. 363.3<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 48 | (fluoro-tetrahydro-dibenzofuran-amine) | (6-chloro-2-morpholinobenzothiazole) | (product) | 1. 12%<br>2. ¹H-NMR (400 MHz, DMSO-d₆) δ = 7.61 (d, J = 8.40 Hz, 1H), 7.54-7.57 (m, 1H), 7.46-7.49 (m, 1H), 7.20-7.21 (m, 1H), 7.07-7.12 (m, 1H), 6.93-6.96 (m, 1H), 4.37 (bs, 2H), 3.72-3.76 (m, 6H), 3.50-3.52 (m, 4H), 2.91-2.93 (m, 2H).<br>3. 410.0<br>4. Example 2 |
| 49 | (fluoro-tetrahydro-dibenzofuran-amine) | (6-chloro-2-morpholinobenzoxazole) | (product) | 1. 10%<br>2. ¹H-NMR (400 MHz, DMSO-d₆) δ = 7.54-7.57 (m, 1H), 7.44-7.46 (m, 1H), 7.29 (d, J = 8.80 Hz, 1H), 7.07-7.12 (m, 2H), 6.80 (d, J = 8.80 Hz, 1H), 4.31 (bs, 2H), 3.66-3.73 (m, 6H), 3.56-3.58 (m, 4H), 2.91-2.93 (m, 2H).<br>3. 394.2<br>4. Example 2 |
| 50 | (fluoro-tetrahydro-dibenzofuran-amine) | (6-chloro-N,N-dimethylbenzothiazol-2-amine) | (product) | 1. 23%<br>2. ¹H-NMR (400 MHz, DMSO-d₆) δ = 7.54-7.58 (m, 2H), 7.48 (dd, J = 2.40, 8.80 Hz, 1H), 7.18 (d, J = 2.00 Hz, 1H), 7.09-7.10 (m, 1H), 6.89 (dd, J = 2.40, 9.00 Hz, 1H), 4.37 (bs, 2H), 3.73-3.75 (m, 2H), 3.12 (s, 6H), 2.93-2.95 (m, 2H).<br>3. 368.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 51 | | | | 1. 5%<br>2. ¹H-NMR (400 MHz, DMSO-d₆) δ = 7.54-7.57 (m, 1H), 7.50 (d, J = 2.40 Hz, 1H), 7.42 (dd, J = 2.80, 9.00 Hz, 1H), 7.36 (d, J = 8.80 Hz, 1H), 7.07-7.12 (m, 2H), 4.30 (bs, 2H), 3.65-3.67 (m, 2H), 3.10 (s, 6H), 2.93- 2.94 (m, 2H).<br>3. 368.0<br>4. Example 2 |
| 52 | | | | 1. 14%<br>2. ¹H-NMR (400 MHz, DMSO-d₆) δ = 11.19 (bs, 1H), 7.60 (d, J = 8.80 Hz, 1H), 7.13-7.14 (m, 2H), 6.98-7.00 (m, 1H), 6.92 (d, J = 8.80 Hz, 1H), 6.71-6.76 (m, 1H), 4.50 (bs, 2H), 3.70-3.73 (m, 6H), 3.51-3.52 (m, 4H), 2.89-2.88 (m, 2H).<br>3. 409.0<br>4. Example 2 |
| 53 | | | | 1. 8%<br>2. ¹H-NMR (400 MHz, DMSO-d₆) δ = 11.17 (bs, 1H), 7.27 (d, J = 8.76 Hz, 1H), 7.13 (d, J = 8.00 Hz, 1H), 6.98-7.01 (m, 2H), 6.70-6.78 (m, 2H), 4.44 (bs, 2H), 3.70-3.73 (m, 4H), 3.61-3.63 (m, 2H), 3.56-3.57 (m, 4H), 2.86-2.88 (m, 2H).<br>3. 393.0<br>4. Example 2 |
| 54 | | | | 1. 23%<br>2. ¹H-NMR (400 MHz, DMSO-d₆) δ = 10.96 (bs, 1H), 7.43-7.48 (m, 2H), 7.35 (d, J = 8.80 Hz, 1H), 7.07-7.09 (m, 2H), 6.81-6.86 (m, 1H), 4.33 (bs, 2H), 3.59-3.60 (m, 2H), 3.10 (s, 6H), 2.87-2.89 (m, 2H).<br>3. 367.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 55 | [F-substituted tetrahydro-β-carboline with N-Ts, NH·HCl] | [6-chloro-2-(dimethylamino)benzoxazole] | [F-substituted tetrahydro-β-carboline coupled with 2-(dimethylamino)benzoxazole] | 1. 20%<br>2. ¹H-NMR (400 MHz, DMSO-d₆) δ = 10.95 (s, 1H), 7.42-7.46 (m, 1H), 7.19 (d, J = 2.40 Hz, 1H), 3.52 (d, J = 8.40 Hz, 1H), 7.06 (d, J = 2.40 Hz, 1H), 6.85-6.86 (m, 1H), 6.80-6.84 (m, 1H), 4.31 (s, 2H), 3.59 (t, J = 5.60 Hz, 2H), 3.09 (s, 6H), 2.86 (t, J = 5.20 Hz, 2H).<br>3. 351.1<br>4. Example 2 |
| 56 | [F-substituted tetrahydro-β-carboline with N-Ts, NH·HCl] | [5-chloro-2-(dimethylamino)benzoxazole isomer] | [F-substituted tetrahydro-β-carboline coupled with 2-(dimethylamino)benzoxazole] | 1. 27%<br>2. ¹H-NMR (400 MHz, DMSO-d₆) δ = 10.95 (bs, 1H), 7.43-7.46 (m, 1H), 7.20 (s, 1H), 7.09-7.14 (m, 1H), 7.06-7.09 (m, 1H), 6.86-6.93 (m, 1H), 6.81-6.85 (m, 1H), 4.31 (bs, 2H), 3.59 (bs, 2H), 3.09 (s, 6H), 2.85-2.87 (m, 2H).<br>3. 351.0<br>4. Example 2 |
| 57 | [F-substituted dibenzofuran amino derivative, NH] | [6-chloro-2-morpholinobenzoxazole] | [F-substituted dibenzofuran coupled with 2-morpholinobenzoxazole] | 1. 16%<br>2. ¹H-NMR (400 MHz, DMSO-d₆) δ = 10.95 (bs, 1H), 7.43-7.46 (m, 1H), 7.23 (d, J = 8.40 Hz, 1H), 7.06-7.09 (m, 1H), 7.00 (s, 1H), 6.81-6.86 (m, 1H), 6.73 (d, J = 8.80 Hz, 1H), 4.32 (bs, 2H), 3.60 (bs, 2H), 3.10 (s, 6H), 2.85-2.87 (m, 2H).<br>3. 351.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 58 | | | | 1. 7%<br>2. ¹H-NMR (400 MHz, DMSO-d₆) δ = 7.54-7.58 (m, 1H), 7.43 (dd, J = 2.80, 8.80 Hz, 1H), 7.20-7.24 (m, 2H), 7.09-7.12 (m, 1H), 6.96 (dd, J = 2.00, 8.60 Hz, 1H), 4.31 (bs, 2H), 3.66-3.73 (m, 6H), 3.52-3.55 (m, 4H), 2.90-2.93 (m, 2H).<br>3. 394.0<br>4. Example 2 |
| 59 | | | | 1. 16%<br>2. ¹H-NMR (400 MHz, DMSO-d₆) δ = 7.54-7.58 (m, 1H), 7.43 (dd, J = 2.40, 8.80 Hz, 1H), 7.23 (d, J = 2.00 Hz, 1H), 7.07-7.16 (m, 2H), 6.93 (dd, J = 2.00, 8.40 Hz, 1H), 4.29 (bs, 2H), 3.64-3.67 (m, 2H), 3.09 (s, 6H), 2.92-2.93 (m, 2H).<br>3. 352.0<br>4. Example 2 |
| 60 | | | | 1. 16%<br>2. ¹H-NMR (400 MHz, DMSO-d₆) δ = 7.54-7.57 (m, 1H), 7.45 (d, J = 8.80 Hz, 1H), 7.25 (dd, J = 1.60, 8.60 Hz, 1H), 7.02-7.12 (m, 2H), 6.73-6.75 (m, 1H), 4.30 (bs, 2H), 3.65-3.68 (m, 2H), 3.11 (s, 6H), 2.92-2.93 (m, 2H).<br>3. 352.0<br>4. Example 2 |
| 61 | | | | 1. 16%<br>2. ¹H-NMR (400 MHz, DMSO-d₆) δ = 10.96 (s, 1H), 7.51 (d, J = 2.00 Hz, 1H), 7.39 (d, J = 9.20 Hz, 1H), 7.27-7.29 (m, 2H), 7.10-7.13 (m, 1H), 6.83-6.88 (m, 1H), 4.33 (s, 2H), 3.73 (t, J = 5.20 Hz, 4H), 3.63 (t, J = 5.60 Hz, 2H), 3.48 (t, J = |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 62 | (6-fluoro-9-methyl-2,3,4,9-tetrahydro-1H-β-carboline with NH) | 6-chloro-2-morpholinobenzoxazole | morpholino-benzoxazole linked to 6-fluoro-9-methyl tetrahydro-β-carboline | 1. 23%<br>2. ¹H-NMR (400 MHz, DMSO-d₆) δ = 7.47-7.50 (m, 1H), 7.27-7.30 (m, 1H), 7.18-7.22 (m, 2H), 6.95-6.97 (m, 1H), 6.84-6.89 (m, 1H), 3.12 (s, 2H), 3.72 (t, J = 5.20 Hz, 4H), 3.65 (t, J = 5.60 Hz, 2H), 3.62 (s, 3H), 3.52 (t, J = 4.40 Hz, 4H), 2.89 (t, J = Hz, 2H).<br>3. 407.2<br>4. Example 2 |
| 63 | (6-fluoro-9-Ts-2,3,4,9-tetrahydro-1H-β-carboline with NH·HCl) | 6-chloro-2-morpholinobenzothiazole | morpholino-benzothiazole linked to 6-fluoro tetrahydro-β-carboline (NH) | 1. 35%<br>2. ¹H-NMR (400 MHz, DMSO-d₆) δ = 10.95 (bs, 1H), 7.58 (d, J = 8.80 Hz, 1H), 7.47-7.50 (m, 1H), 7.17 (s, 1H), 7.06-7.09 (m, 1H), 6.93 (d, J = 8.80 Hz, 1H), 6.81-6.86 (m, 1H), 4.39 (bs, 2H), 3.68-3.72 (m, 6H), 3.51-3.52 (m, 4H), 2.86 (bs, 2H).<br>3. 409.0<br>4. Example 2 |
| 64 | (6-fluoro-9-methyl-2,3,4,9-tetrahydro-1H-β-carboline with NH) | 6-chloro-2-morpholinobenzothiazole | morpholino-benzothiazole linked to 6-fluoro-9-methyl tetrahydro-β-carboline | 1. 21%<br>2. ¹H-NMR (400 MHz, DMSO-d₆) δ = 7.51 (d, J = 2.40 Hz, 1H), 7.45-7.48 (m, 1H), 7.37 (d, J = 8.40 Hz, 1H), 7.26-7.29 (m, 1H), 7.09-7.12 (m, 1H), 6.83-6.69 (m, 1H), 4.35 (s, 2H), 3.72 (t, J = 5.20 Hz, 4H), 3.65 (t, J = 5.60 Hz, 2H), 3.61 (s, 3H), 3.47 (t, J = 4.80 Hz, 4H), 2.90 (s, 2H).<br>3. 423.3<br>4. Example 2 |

TABLE 2-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 65 | | | | 1. 40% 2. ¹H-NMR (400 MHz, DMSO-d₆) δ = 7.47-7.51 (m, 1H), 7.25-7.30 (m, 2H), 7.05 (s, 1H), 6.84-6.89 (m, 1H), 6.79 (d, J = 8.40 Hz, 1H), 4.34 (bs, 2H), 3.70-3.72 (m, 4H), 3.64-3.66 (m, 2H), 3.61 (s, 3H), 3.56-3.57 (m, 4H), 2.80-2.88 (m, 2H). 3. 407.2 4. Example 2 |
| 66 | | | | 1. 24% 2. ¹H-NMR (400 MHz, DMSO-d₆) δ = 7.50-7.55 (m, 2H), 7.26-7.30 (m, 1H), 7.15 (d, J = 2.40 Hz, 1H), 6.84-6.90 (m, 2H), 4.40 (bs, 2H), 3.71-3.72 (m, 2H), 3.61 (s, 3H), 3.11 (s, 6H), 2.88 (bs, 2H). 3. 381.2 4. Example 2 |
| 67 | | | | 1. 23% 2. ¹H-NMR (400 MHz, DMSO-d₆) δ = 7.46-7.50 (m, 2H), 7.27-7.35 (m, 2H), 7.07-7.10 (m, 1H), 6.85-6.89 (m, 1H), 4.34 (bs, 2H), 3.64-3.65 (m, 2H), 3.62 (s, 3H), 3.10 (s, 6H), 2.88-2.91 (m, 2H). 3. 381.2 4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 68 | | | | 1. 34%<br>2. ¹H-NMR (400 MHz, DMSO-d₆) δ = 7.46-7.50 (m, 1H), 7.27-7.30 (m, 1H), 7.20 (d, J = 2.16 Hz, 1H), 7.13 (d, J = 8.52 Hz, 1H), 6.84-6.93 (m, 2H), 4.33 (bs, 2H), 3.62-3.64 (m, 5H), 3.09 (s, 6H), 2.88-2.90 (m, 2H).<br>3. 365.1<br>4. Example 2 |
| 69 | | | | 1. 10%<br>2. 1H-NMR (400 MHz, DMSO-d₆) δ = 10.96 (bs, 1H), 7.47- 7.55 (m, 2H), 7.15 (d, J = 1.60 Hz, 1H), 7.06-7.09 (m, 1H), 6.84-6.89 (m, 2H), 4.38 (bs, 2H), 3.66-3.69 (m, 2H), 3.12 (s, 6H), 2.87 (bs, 2H).<br>3. 367.2<br>4. Example 2 |
| 70 | | | | 1. 15%<br>2. ¹H-NMR (400 MHz, DMSO-d₆) δ = 11.02 (s, 1H), 8.38(d, J = 7.56 Hz, 1H), 7.47-7.51 (m, 1H), 7.07-7.10 (m, 1H), 6.80-6.90 (m, 3H), 4.52 (s, 2H), 3.80-3.82 (m, 2H), 3.68-3.70 (m, 4H), 3.37-3.40 (m, 4H), 2.90 (t, J = 4.72 Hz, 2H).<br>3. 392.17<br>4. Example 2 |

TABLE 2-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 71 | | | | 1. 27% 2. ¹H-NMR (400 MHz, DMSO-d₆) δ = 10.98 (s, 1H), 8.23 (d, 1H), 8.00 (d, 1H), 7.25 (m, 2H), 6.886 (m, 1H), 4.37 (s, 2H), 3.74 (t, 4H), 3.67 (t, 2H), 3.55 (t, 4H), 2.91 (t, 2H). 3. 410.15. |
| 72 | | | | 1. 34% 2. ¹H-NMR (400 MHz, DMSO-d₆) δ = 10.98 (s, 1H), 7.69 (d, 1H), 7.27 (dt, 2H), 6.98 (d, 1H), 6.86 (td, 1H), 4.62 (s, 2H), 3.97 (t, 2H), 3.73 (t, 4H), 3.48 (t, 4H), 2.89 (t, 2H). 3. 410.16. |
| 73 | | | | 1. 17% 2. ¹H-NMR (400 MHz, DMSO-d₆) δ = 10.99 (bs, 1H), 8.23(d, J = 2.68 Hz, 1H), 8.01 (d, J = 2.68 Hz, 1H), 7.43-7.44 (m, 1H), 7.07-7.08 (m, 1H), 6.82-6.82 (m, 1H), 4.39 (s, 2H), 3.73-3.74 (m, 4H), 3.64-3.66 (m, 2H), 3.54-3.55 (m, 4H), 2.90 (bs, 2H). 3. 410.1. 4. Example 2 |

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 74 | | | | 1. 25%<br>2. ¹H-NMR (400 MHz, DMSO-d₆) δ = 1H NMR (400 MHz, DMSO-d₆) δ 10.95 (bs, 1H), 8.00-8.02 (m, 1H), 7.43-7.45 (m, 1H), 7.20-7.28 (m, 2H), 6.79-6.87 (m, 2H), 4.24-4.26 (m, 2H), 3.69-3.71 (m, 4H), 3.52-3.54 (m, 2H), 3.29-3.36 (m, 4H), 2.50-2.52 (m, 2H).<br>3. 353.0<br>4. Example 2 |
| 75 | | | | 1. 19%<br>2. ¹H-NMR (400 MHz, DMSO-d₆) δ = 7.86-7.87 (m, 1H), 7.60-7.68 (m, 1H), 7.39-7.43 (m, 1H), 7.28 (dd, J = 2.40, 10.00 Hz, 1H), 6.91-6.99 (m, 2H), 4.31 (bs, 2H), 3.58-3.73 (m, 9H), 3.36-3.43 (m, 4H), 2.90 (bs, 2H).<br>3. 367.0<br>4. Example 2 |
| 76 | | | | 1. 11%<br>2. ¹H-NMR (400 MHz, DMSO-d₆) δ = 10.95 (bs, 1H), 7.86- 7.87 (m, 1H), 7.34 (d, J = 9.08 Hz, 1H), 7.21-7.27 (m, 2H), 6.93 (d, J = 8.88 Hz, 1H), 6.82-6.89 (m, 1H), 4.54 (bs, 2H), 3.86-3.89 (m, 2H), 3.73 (bs, 4H), 2.98 (bs, 4H), 2.85 (bs, 2H).<br>3. 353.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 77 | (5-fluoro-9-methyl-2,3,4,9-tetrahydro-1H-carbazol-3-amine) | 4-(6-chloropyridin-3-yl)morpholine | morpholine-pyridine-tetrahydrocarbazole (N-methyl, F) | 1. 12%<br>2. ¹H-NMR (400 MHz, DMSO-d₆) δ = 7.87 (d, J = 3.20 Hz, 1H), 7.38-7.41 (m, 1H), 7.32-7.35 (m, 1H), 7.26-7.29 (m, 1H), 6.90-6.96 (m, 2H), 4.57 (bs, 2H), 3.91-3.94 (m, 2H), 3.71-3.74 (m, 4H), 3.63 (s, 3H), 2.96-2.98 (m, 4H), 2.87-2.89 (m, 2H).<br>3. 367.0<br>4. Example 2 |
| 78 | (NH·HCl, F, N-Ts) | 4-(5-bromopyridin-2-yl)morpholine | morpholine-pyridine-tetrahydrocarbazole (NH, F) | 1. 29%<br>2. ¹H-NMR (400 MHz, DMSO-d₆) δ = 10.94 (s, 1H), 7.87 (d, J = 3.60 Hz, 1H), 7.43-7.46 (m, 1H), 7.32-7.36 (m, 1H), 7.04-7.08 (m, 1H), 3.12 (d, J = 12.40 Hz, 1H), 6.79-6.85 (m, 1H), 4.56 (s, 2H), 3.89 (t, J = 7.60 Hz, 2H), 3.73 (t, J = 6.00 Hz, 4H), 2.97 (t, J = 6.00 Hz, 4H).<br>3. 353.2<br>4. Example 2 |
| 79 | (NH·HCl, F, N-Ts) | 4-(6-bromopyridin-3-yl)morpholine | morpholine-pyridine-tetrahydrocarbazole (NH, F) | 1. 25%<br>2. ¹H-NMR (400 MHz, DMSO-d₆) δ = 10.94 (s, 1H), 8.00 (d, J = 2.80 Hz, 1H), 7.40-7.46 (m, 2H), 7.05-7.08 (m, 1H), 6.79-6.85 (m, 2H), 3.12 (s, 2H), 3.69 (t, J = 5.20 Hz, 4H), 3.51 (t, J = 5.20 Hz, 2H), 3.28 (t, J = 4.80 Hz, 4H), 2.84 (s, 2H).<br>3. 353.2<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 80 | | | | 1. 27%<br>2. ¹H-NMR (400 MHz, DMSO-d₆) δ = 7.87 (d, J = 2.64 Hz, 1H), 7.45-7.47 (m, 1H), 7.26-7.27 (m, 2H), 6.95 (d, J = 9.08 Hz, 1H), 6.83-6.83 (m, 1H), 4.59 (s, 2H), 3.90-3.91 (m, 2H), 3.71-3.73 (m, 4H), 3.62 (s, 3H), 2.96-2.97 (m, 4H), 2.86 (s, 2H), 1.08-1.10 (m, 2H).<br>3. 367.1<br>4. Example 2 |
| 81 | | | | 1. 23%<br>2. ¹H-NMR (400 MHz, DMSO-d₆) δ = 11.18 (bs, 1H), 7.99 (s, 1H), 7.43-7.43 (m, 1H), 7.13 (d, J = 8.08 Hz, 1H), 6.95-6.97 (m, 1H), 6.80-6.82 (m, 1H), 6.70-6.71 (m, 1H), 4.38 (s, 2H), 3.69-3.70 (m, 4H), 3.51-3.53 (m, 2H), 3.28-3.29 (m, 4H), 2.85-2.86 (m, 2H).<br>3. 353.2<br>4. Example 2 |
| 82 | | | | 1. 27%<br>2. ¹H-NMR (400 MHz, DMSO-d₆) δ = 11.16 (bs, 1H), 7.88 (d, J = 2.68 Hz, 1H), 7.32-7.33 (m, 1H), 7.12 (d, J = 7.92 Hz, 1H), 6.91-6.93 (m, 2H), 6.69-6.71 (m, 1H), 4.71 (s, 2H), 3.88 (t, J = 5.12 Hz, 2H), 3.73-3.74 (m, 4H), 2.97-2.98 (m, 4H), 2.85 (bs, 2H).<br>3. 353.2<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 83 | (tricyclic amine with F, N-methyl) | 4-bromo-(6-morpholino)pyridine | product structure | 1. 26%<br>2. ¹H-NMR (400 MHz, DMSO-d₆) δ = 7.99 (d, J = 2.80 Hz, 1H), 7.45 (dd, J = 2.96, 9.16 Hz, 1H), 7.26 (d, J = 8.24 Hz, 1H), 7.05-7.06 (m, 1H), 6.75-6.76 (m, 2H), 4.39 (s, 1H), 3.69-3.70 (m, 4H), 3.65 (s, 3H), 3.56-3.57 (m, 2H), 3.28-3.29 (m, 4H), 2.88 (bs, 2H).<br>3. 367.2<br>4. Example 2 |
| 84 | (tricyclic amine, N-methyl) | 5-bromo-(2-morpholino)pyridine | product structure | 1. 23%<br>2. ¹H-NMR (400 MHz, DMSO-d₆) δ = 7.85 (d, J = 2.80 Hz, 1H), 7.47 (d, J = 8.00 Hz, 1H), 7.37 (d, J = 8.00 Hz, 1H), 7.30-7.31 (m, 1H), 7.06-7.06 (m, 1H), 6.93-6.95 (m, 2H), 4.59 (s, 2H), 3.89-3.90 (m, 2H), 3.70-3.71 (m, 4H), 3.61 (s, 3H), 2.94-2.95 (m, 4H), 2.85-2.86 (m, 2H).<br>3. 349.1<br>4. Example 2 |

TABLE 2-continued

| Example | Tricyclic amino derivative | Bromo or Chloro derivative | Product | 1. Yield  2. ¹H-NMR  3. MH⁺ (ESI)  4. Synthesis procedure |
|---|---|---|---|---|
| 85 | (tetrahydro-β-carboline, N-Tos) | 2-bromo-5-morpholinopyridine | morpholinopyridyl-tetrahydro-β-carboline | 1. 24%  2. ¹H-NMR (400 MHz, DMSO-$d_6$) δ = 10.84 (s, 1H), 7.88 (d, J = 2.92 Hz, 1H), 7.45 (d, J = 7.68 Hz, 1H), 7.32-7.33 (m, 1H), 7.28 (d, J = 7.92 Hz, 1H), 6.93-6.95 (m, 3H), 3.91 (t, J = 5.56 Hz, 2H), 3.72- 3.73 (m, 4H), 2.96-2.97 (m, 4H), 2.84-2.85 (m, 2H).  3. 335.1  4. Example 2 |
| 86 | (tetrahydro-β-carboline, N-Tos) | 5-bromo-2-morpholinopyridine | morpholinopyridyl-tetrahydro-β-carboline | 1. 53%  2. ¹H-NMR (400 MHz, DMSO-$d_6$) δ = 10.85 (s, 1H), 8.02 (d, J = 2.72 Hz, 1H), 7.43-7.45 (m, 2H), 7.28-7.30 (m, 1H), 6.95-6.97 (m, 2H), 6.80-6.81 (m, 1H), 4.28-0.00 (m, 2H), 3.69-3.71 (m, 4H), 3.53-3.54 (m, 2H), 3.28-3.29 (m, 4H), 2.87 (bs, 2H).  3. 335.2  4. Example 2 |
| 87 | (8-fluoro-N-methyl-tetrahydro-β-carboline) | 5-bromo-2-morpholinopyridine | 8-fluoro-N-methyl-morpholinopyridyl-tetrahydro-β-carboline | 1. 23%;  2. ¹H-NMR (400 MHz, DMSO-$d_6$): δ 8.01 (d, J = 2.40 Hz, 1H), 7.46-7.48 (m, 2H), 7.27-7.30 (m, 1H), 6.79-6.89 (m, 2H), 4.28 (s, 2H), 3.12 (t, J = 4.40 Hz, 4H), 3.61 (s, 3H), 3.56 (t, J = 5.60 Hz, 2H), 3.29 (t, J = 4.40 Hz, 4H), 2.87 (s, 2H).  3. 367.3  4. Example 2 |

TABLE 2-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 88 | (6-fluoro-2,3,4,5-tetrahydro-1H-pyrido[4,3-b]indole, N-Ts) | 6-chloro-2-morpholinothiazolo[5,4-b]pyridine | corresponding coupled product | 1. 17%<br>2. ¹H-NMR (400 MHz, DMSO-d₆): δ 11.00 (bs, 1H), 7.69 (d, J = 8.88 Hz, 1H), 7.47 (t, J = 5.88 Hz, 1H), 7.08 (d, J = 10.12 Hz, 1H), 6.99 (d, J = 8.68 Hz, 1H), 6.84 (t, J = 8.52 Hz, 1H), 4.64 (s, 2H), 3.95-3.96 (m, 2H), 3.72 (d, J = 4.08 Hz, 4H), 3.48 (d, J = 3.96 Hz, 4H), 2.87 (bs, 2H).<br>3. 410.1<br>4. Example 2 |
| 89 | (6-fluoro tricyclic) | 6-chloro-2-morpholinothiazolo[4,5-c]pyridine | coupled product | 1. 15%<br>2. ¹H-NMR (400 MHz, DMSO-d₆): δ 10.98 (bs, 1H), 8.35 (s, 1H), 7.42-7.43 (m, 2H), 7.06-7.07 (m, 1H), 6.81-6.82 (m, 1H), 4.62 (s, 2H), 3.98 (bs, 2H), 3.71-3.73 (m, 4H), 3.51(bs, 4H), 2.87 (bs, 2H).<br>3. 410.1<br>4. Example 2 |
| 90 | (8-fluoro tricyclic) | 6-chloro-2-morpholinothiazolo[5,4-c]pyridine | coupled product | 1. 21%<br>2. ¹H-NMR (400 MHz, DMSO-d₆): δ 10.96 (s, 1H), 8.34 (s, 1H), 7.45 (s, 1H), 7.19-7.22 (m, 2H), 6.85 (s, 1H), 4.60 (s, 2H), 3.98 (bs, 2H), 3.71 (bs, 4H), 3.50 (bs, 4H), 2.87 (bs, 2H).<br>3. 410.1<br>4. Example 2 |

TABLE 2-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 91 | 7-fluoro-N-tosyl-tetrahydro-β-carboline with NH | 7-chloro-2-morpholinoquinoline | 7-fluoro-tetrahydro-β-carboline coupled to 2-morpholinoquinolin-7-yl | 1. 15%<br>2. ¹H-NMR (400 MHz, DMSO-d₆): δ 10.98 (s, 1H), 7.87 (d, J = 8.96 Hz, 1H), 7.51-7.52 (m, 2H), 7.20-7.21 (m, 1H), 7.06-7.07 (m, 1H), 7.00 (s, 1H), 6.92 (d, J = 8.96 Hz, 1H), 6.81-6.82 (m, 1H), 4.49 (s, 2H), 3.77-3.79 (m, 2H), 3.70-3.71 (m, 4H), 3.59-3.60 (m, 4H), 2.90 (bs, 2H)<br>3. 403.2<br>4. Example 2 |
| 92 | 7-fluoro-N-tosyl-tetrahydro-β-carboline with NH | 6-chloro-2-morpholinoquinoline | 7-fluoro-tetrahydro-β-carboline coupled to 2-morpholinoquinolin-6-yl | 1. 16%<br>2. ¹H-NMR (400 MHz, DMSO-d₆): δ 10.99 (s, 1H), 7.96 (d, J = 9.12 Hz, 1H), 7.45-7.47 (m, 3H), 7.22 (s, 1H), 7.17 (d, J = 9.12 Hz, 1H), 7.08-7.08 (m, 1H), 6.82-6.83 (m, 1H), 4.42 (s, 2H), 3.68-3.70 (m, 6H), 3.54-3.56 (m, 4H), 2.92 (bs, 2H).<br>3. 403.2<br>4. Example 2 |
| 93 | 7-fluoro-N-methyl-tetrahydro-β-carboline with NH | 2-bromo-6-methoxyquinoline | 7-fluoro-N-methyl-tetrahydro-β-carboline coupled to 6-methoxyquinolin-2-yl | 1. 78%<br>2. ¹H NMR (400 MHz, DMSO-d₆) δ 8.48 (d, J = 9.6 Hz, 1H), 8.42-8.33 (m, 1H), 7.79 (d, J = 9.7 Hz, 1H), 7.54-7.45 (m, 3H), 7.35-7.25 (m, 1H), 7.07-6.95 (m, 1H), 5.14 (s, 2H), 4.50-4.30 (m, 2H), 3.89 (s, 3H), 3.70 (s, 3H), 3.24-3.07 (m, 2H).<br>4. Example 1 |

| Example | Tricyclic amino derivative | Bromo or Chloro derivative | Product | 1. Yield  2. ¹H-NMR  3. MH⁺ (ESI)  4. Synthesis procedure |
|---|---|---|---|---|
| 94 | (tricyclic amino derivative with F and N-Me) | 5-bromo-3-methoxypyridine | (product) | 1. 47%  2. ¹H NMR (400 MHz, Chloroform-d) δ 8.12 (d, J = 2.5 Hz, 1H), 7.84 (d, J = 2.5 Hz, 1H), 7.22 (dd, J = 8.8, 4.3 Hz, 1H), 7.17 (dd, J = 9.5, 2.5 Hz, 1H), 6.97 (td, J = 9.1, 2.5 Hz, 1H), 6.84 (t, J = 2.4 Hz, 1H), 4.47 (t, J = 1.6 Hz, 2H), 3.90 (s, 3H), 3.80 (t, J = 5.7 Hz, 2H), 3.67 (s, 3H), 3.00-2.93 (m, 2H).  4. Example 1 |
| 95 | (tricyclic amino derivative with F and N-Me) | 4-bromo-2-methoxypyridine | (product) | 1. 58%  2. 1H NMR (400 MHz, DMSO-d₆) δ 8.04-7.85 (m, 1H), 7.50-7.39 (m, 1H), 7.31 (d, J = 9.8 Hz, 1H), 7.12-7.01 (m, 1H), 6.96 (t, J = 9.3 Hz, 1H), 6.63 (s, 1H), 4.84 (s, 2H), 4.22-3.99 (m, 5H), 3.65 (s, 3H), 3.10-2.97 (m, 2H).  4. Example 1 |
| 96 | (tricyclic amino derivative with F and N-Me) | 4-(4-bromophenyl)morpholine | (product) | 1. 83%  2. 1H NMR (400 MHz, DMSO-d₆) δ 7.58 (d, J = 8.5 Hz, 2H), 7.57-7.52 (m, 0H), 7.46 (dt, J = 7.5, 3.2 Hz, 1H), 7.30 (d, J = 9.8 Hz, 1H), 7.23 (d, J = 8.6 Hz, 2H), 6.99 (t, J = 9.3 Hz, 1H), 4.67 (s, 2H), 3.96 (t, J = 6.0 Hz, 2H), 3.80 (d, J = 5.6 Hz, 4H), 3.66 (d, J = 5.2 Hz, 3H), 3.27 (d, J = 5.6 Hz, 4H), 3.20 (s, 2H)  4. Example 1 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 96a | | | | 1. 15%<br>2. ¹H-NMR (400 MHz, DMSO-d₆): δ 7.28 (d, J = 8.80 Hz, 1H), 7.22 (d, J = 8.40 Hz, 1H), 7.02 (dd, J = 2.40, 16.40 Hz, 2H), 6.71-6.71 (m, 2H), 4.31 (s, 2H), 3.77 (s, 3H), 3.64 (t, J = 5.60 Hz, 2H), 3.59 (s, 3H), 3.10 (s, 6H), 2.85-2.85 (m, 2H).<br>3. 377.1<br>4. Example 2 |
| 96b | | | | 1. 22%<br>2. ¹H-NMR (400 MHz, DMSO-d₆) δ 8.22-8.23 (m, 1H), 8.06-8.06 (m, 1H), 7.33-7.34 (m, 1H), 7.29 (d, J = 8.72 Hz, 1H), 7.08 (d, J = 2.48, 8.74 Hz, 1H), 6.80 (dd, J = 2.48, 8.74 Hz, 1H), 4.34 (s, 2H), 3.67-3.69 (m, 6H), 3.55-3.56 (m, 4H), 2.96 (bs, 2H).<br>3. 377.2<br>4. Example |
| 96c | | | | 1. 29%<br>2. ¹H-NMR (400 MHz, DMSO-d₆): δ 11.00 (bs, 1H), 9.11 (s, 1H), 7.78-7.79 (m, 1H), 7.45-7.46 (m, 2H), 7.31 (d, J = 2.80 Hz, 1H), 7.08-7.09 (m, 1H), 6.82-6.83 (m, 1H), 4.44 (s, 2H), 3.70-3.71 (m, 10H), 2.93-2.94 (m, 2H).<br>3. 404.0<br>4. Example 2 |

TABLE 2-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 96d | | | | 1. 66%<br>2. 1H NMR (400MHz, Chloroform-d) δ 8.60 (d, J = 2.9 Hz, 1H), 8.34 (s, 1H), 7.22 7.52 -7.43 (m, 1H), (ddd, J = 16.3, 9.1, 3.4 Hz, 2H), 6.99 (td, J = 9.1, 2.6 Hz, 2H), 4.54 (d, J = 1.9 Hz, 2H), 3.87 (t, J = 5.7 Hz, 2H), 3.69 (s, 3H), 3.00 (d, J = 5.6 Hz, 1H).<br>4. Example 1 |
| 96e | | | | 1. 62%<br>2. 1H NMR (400 MHz, DMSO-d₆) δ8.10 (d, J = 3.0 Hz, 1H), 7.61 (t, J = 8.9 Hz, 1H), 7.38 (dd, J = 8.9, 4.4 Hz, 1H), 7.24 (dd, J = 9.8, 2.5 Hz,1H), 7.10 (d, J = 9.4 Hz, 1H), 6.92 (td, J = 9.2, 2.5 Hz, 1H), 4.63 (s, 2H), 3.97 (t, J = 5.7 Hz, 2H), 3.60 (s, 3H), 2.89 (t, J = 5.6 Hz, 2H).<br>4. Example 1 |

Example 97

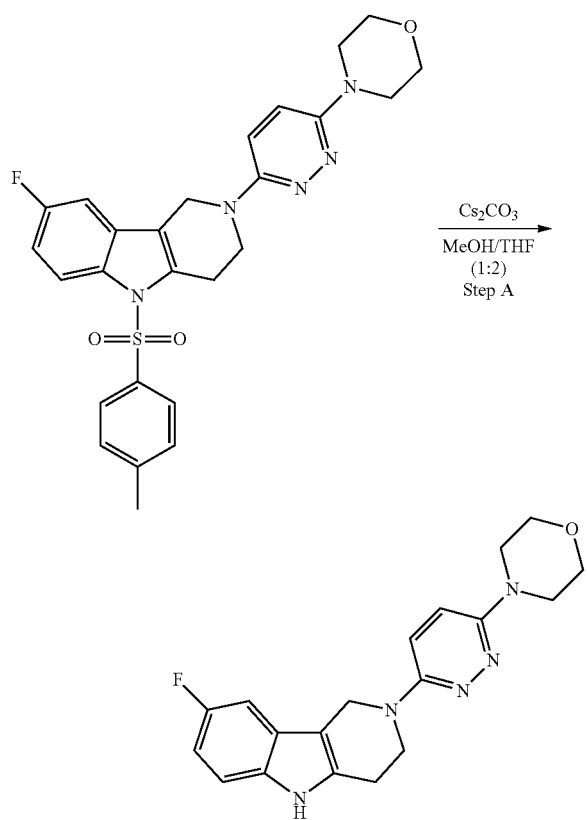

The title compound from Preparative Example 33 (0.072 g, 0.142 mmol) and cesium carbonate (0.107 g, 0.328 mmol) were placed into a microwave tube followed by MeOH (1.5 mL) and THF (3 mL). The reaction mixture was irradiated in a microwave to 110° C. for 30 minutes and then allowed to cool down to room temperature. The solvents were removed under reduced pressure and the residue was purified on a silica gel column using a Biotage Isolera One purification system with a gradient of n-heptane/ethyl acetate (80/20→0/100) to afford the title compound as a yellow solid (0.027 g, 53%).

MS: 354.2 $(M+H)^+$.

$^1$H-NMR (400 MHz, DMSO-$d_6$) δ=10.96 (s, 1H), 7.39 (d, J=9.9 Hz, 1H), 7.28 (s, 1H), 7.26 (t, J=4.4 Hz, 1H), 7.20 (dd, J=10.0, 2.6 Hz, 1H), 6.85 (td, J=9.2, 2.6 Hz, 1H), 4.62 (s, 2H), 3.91 (t, J=5.7 Hz, 2H), 3.79-3.67 (m, 4H), 3.37-3.32 (m, 4H), 2.88 (t, J=5.6 Hz, 2H).

Examples 98 to 105f

Following the tosylate-cleavage procedure as described in Example 97, except using the tosyl-protected-precursors indicated in the table below, the following compounds were prepared:

TABLE 3

| Example | Tosyl-protected precursor | Product | 1. Yield<br>2. $^1$H-NMR<br>3. MH$^+$ (ESI) |
|---|---|---|---|
| 98 | | | 1. 11%<br>2. $^1$H-NMR (400 MHz, Chloroform-d) δ = 7.95 (s, 1H), 7.29-7.24 (m, 1H), 7.22 (dd, J = 8.8, 4.3 Hz, 1H), 7.12 (dd, J = 9.5, 2.5 Hz, 1H), 7.04 (d, J = 2.3 Hz, 1H), 6.96 (dd, J = 8.6, 2.3 Hz, 1H), 6.89 (td, J = 9.1, 2.5 Hz, 1H), 5.31 (s, 1H), 4.36 (s, 2H), 3.64 (t, J = 5.6 Hz, 2H), 3.10 (s, 3H), 2.94 (td, J = 5.7, 4.9, 2.8 Hz, 2H).<br>3. 337.0 |

TABLE 3-continued

| Example | Tosyl-protected precursor | Product | 1. Yield<br>2. ¹H-NMR<br>3. MH⁺ (ESI) |
|---|---|---|---|
| 99 | | | 1. 47%<br>2. ¹H-NMR (400 MHz, DMSO-d$_6$) δ = 11.00 (s, 1H), 7.93 (d, J = 6.0 Hz, 1H), 7.35-7.18 (m, 2H), 6.86 (td, J = 9.3, 2.6 Hz, 1H), 6.26 (d, J = 6.0 Hz, 1H), 4.67 (s, 2H), 4.00 (s, 2H), 3.64 (s, 8H), 2.84 (t, J = 5.7 Hz, 2H).<br>3. 354.2 |
| 100 | | | 1. 92%<br>2. ¹H-NMR (400 MHz, DMSO-d$_6$) δ = 10.96 (s, 1H), 8.07 (d, J = 1.5 Hz, 1H), 7.92 (d, J = 1.5 Hz, 1H), 7.26 (dd, J = 8.8, 4.6 Hz, 1H), 7.22 (dd, J = 9.9, 2.6 Hz, 1H), 6.85 (td, J = 9.2, 2.6 Hz, 1H), 4.55 (s, 2H), 3.88 (t, J = 5.7 Hz, 2H), 3.77-3.66 (m, 4H), 3.28 (q, J = 4.9, 4.0 Hz, 4H), 2.87 (t, J = 5.7 Hz, 2H).<br>3. 354.5 |
| 101 | | | 1. 22%<br>2. ¹H-NMR (400 MHz, DMSO-d$_6$) δ = 10.98 (s, 1H), 7.46-7.36 (m, 2H), 7.26 (d, J = 9.9 Hz, 1H), 7.07 (dd, J = 10.2, 2.4 Hz, 1H), 6.83 (ddd, J = 9.9, 8.6, 2.4 Hz, 1H), 4.64 (s, 2H), 3.89 (t, J = 5.6 Hz, 2H), 3.71 (t, J = 4.8 Hz, 4H), 3.38-3.32 (m, 4H), 2.86 (t, J = 5.7 Hz, 2H).<br>3. 354.5 |
| 102 | | | 1. 39%<br>2. ¹H-NMR (400 MHz, DMSO-d$_6$) δ = 10.95 (s, 1H), 7.44-7.34 (m, 2H), 7.15 (d, J = 9.9 Hz, 1H), 7.06 (dd, J = 10.1, 2.3 Hz, 1H), 6.82 (t, J = 9.2 Hz, 1H), 4.62 (s, 2H), 4.42 (s, 2H), 3.87 (t, J = 5.7 Hz, 2H), 3.68 (d, J = 11.8 Hz, 2H), 2.96-2.80 (m, 4H), 1.91-1.73 (m, 4H).<br>3. 380.5 |

TABLE 3-continued

| Example | Tosyl-protected precursor | Product | 1. Yield<br>2. ¹H-NMR<br>3. MH⁺ (ESI) |
|---|---|---|---|
| 103 | | | 1. 67%<br>2. ¹H-NMR (400 MHz, DMSO-d₆) δ = 10.98 (s, 1H), 8.08 (d, J = 1.5 Hz, 1H), 7.91 (d, J = 1.5 Hz, 1H), 7.43 (dd, J = 8.6, 5.5 Hz, 1H), 7.07 (dd, J = 10.2, 2.4 Hz, 1H), 6.82 (ddd, J = 9.9, 8.6, 2.4 Hz, 1H), 4.57 (s, 2H), 3.87 (t, J = 5.7 Hz, 2H), 3.76-3.66 (m, 4H), 3.30-3.24 (m, 4H), 2.85 (t, J = 5.7 Hz, 2H).<br>3. 354.5 |
| 104 | | | 1. 16%<br>2. ¹H-NMR (400 MHz, DMSO-d₆) δ = 11.01 (s, 1H), 8.51 (s, 1H), 7.31-7.20 (m, 2H), 6.85 (td, J = 9.2, 2.6 Hz, 1H), 4.84 (s, 2H), 4.15 (t, J = 5.7 Hz, 2H), 3.76-3.66 (m, 4H), 3.52 (t, J = 4.9 Hz, 4H), 2.87 (s, 2H).<br>3. 354.5 |
| 105 | | | 1. 48%<br>2. ¹H-NMR (400 MHz, DMSO-d₆) δ = 10.98 (s, 1H), 8.04 (d, J = 1.5 Hz, 1H), 7.94 (d, J = 1.5 Hz, 1H), 7.26 (dd, J = 8.8, 4.6 Hz, 1H), 7.21 (dd, J = 10.0, 2.6 Hz, 1H), 6.89-6.82 (m, 1H), 4.53 (s, 2H), 4.32 (s, 2H), 3.87 (t, J = 5.7 Hz, 2H), 3.67 (d, J = 10.7 Hz, 2H), 3.49 (dd, J = 10.8, 1.8 Hz, 2H), 2.87 (t, J = 5.7 Hz, 2H), 1.94-1.86 (m, 2H), 1.83-1.73 (m, 2H).<br>3. 354.5 |
| 105a | | | 1. 18%<br>2. ¹H-NMR (400 MHz, DMSO-d₆) δ = 10.99 (s, 1H), 7.81 (d, J = 9.2 Hz, 2H), 7.44 (d, 1H), 7.36-7.19 (m, 3H), 6.92-6.78 (m, 1H), 4.77 (s, 2H), 4.09 (t, 2H), 3.73 (t, J = 4.7 Hz, 4H), 3.53 (t, J = 4.7 Hz, 4H), 2.92 (t, J = 5.8 Hz, 2H).<br>3. 404.19 |

TABLE 3-continued

| Example | Tosyl-protected precursor | Product | 1. Yield 2. ¹H-NMR 3. MH+ (ESI) |
|---|---|---|---|
| 105b | 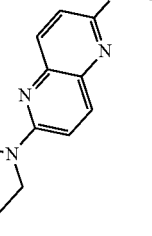 | 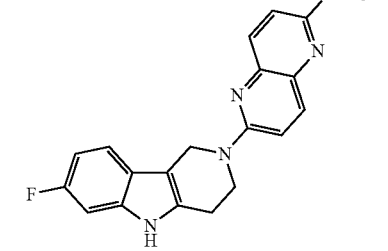 | 1. 8% 2. ¹H-NMR (400 MHz, DMSO-d₆) δ = 10.99 (s, 1H), 7.81 (dd, J = 9.4, 3.9 Hz, 2H), 7.51-7.41 (m, 2H), 7.29 (d, J = 9.3 Hz, 1H), 7.08 (d, J = 10.1 Hz, 1H), 6.84 (t, J = 9.3 Hz, 1H), 4.79 (s, 2H), 4.08 (t, J = 5.8 Hz, 2H), 3.72 (t, J = 4.6 Hz, 4H), 3.53 (t, J = 4.7 Hz, 4H), 2.90 (t, J = 5.9 Hz, 2H). 3. 404.19 |
| 105c | 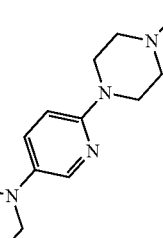 | 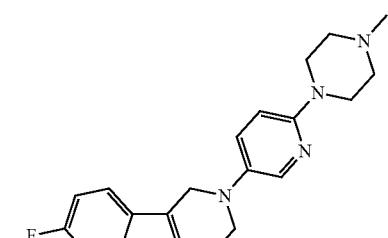 | 1. 4% 2. ¹H-NMR (400 MHz, DMSO-d₆) δ = 10.94 (s, 1H), 7.98 (d, J = 3.0 Hz, 1H), 7.46-7.36 (m, 2H), 7.06 (dd, J = 10.2, 2.4 Hz, 1H), 6.87-6.75 (m, 2H), 4.24 (s, 2H), 3.50 (t, J = 5.6 Hz, 2H), 3.37-3.32 (m, 4H), 2.89-2.79 (m, 2H), 2.39 (t, J = 5.1 Hz, 4H), 2.21 (s, 3H). 3. 366.19 |
| 105d | 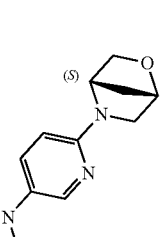 | 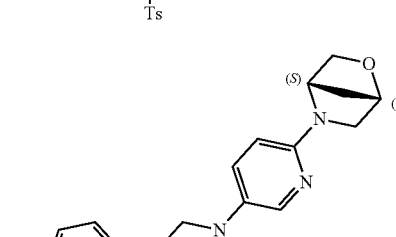 | 1. 52% 2. ¹H-NMR (400 MHz, DMSO-d₆) δ = 10.94 (s, 1H), 7.93 (d, J = 2.9 Hz, 1H), 7.47-7.35 (m, 2H), 7.07 (dd, J = 10.2, 2.4 Hz, 1H), 6.81 (s, 1H), 6.51 (d, J = 9.0 Hz, 1H), 4.70 (s, 1H), 4.59 (s, 1H), 4.21 (d, J = 1.6 Hz, 2H), 3.74 (dd, J = 7.3, 1.5 Hz, 1H), 3.62 (d, J = 7.2 Hz, 1H), 3.46 (t, J = 5.7 Hz, 2H), 3.42 (dd, J = 9.8, 1.5 Hz, 1H), 3.16 (d, J = 9.8 Hz, 1H), 2.93-2.78 (m, 2H), 1.88 (dd, J = 9.6, 2.2 Hz, 1H), 1.84-1.76 (m, 1H). 3. 365.15 |
| 105e |  | 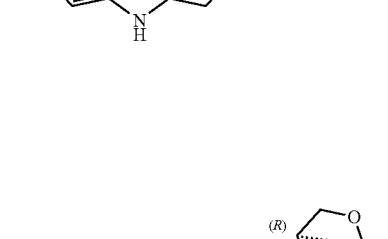 | 1. 37% 2. ¹H-NMR (400 MHz, DMSO-d₆) δ = 10.94 (s, 1H), 7.93 (d, J = 2.9 Hz, 1H), 7.47-7.31 (m, 2H), 7.06 (dd, J = 10.2, 2.4 Hz, 1H), 6.81 (ddd, J = 10.0, 8.6, 2.4 Hz, 1H), 6.51 (d, J = 9.0 Hz, 1H), 4.70 (s, 1H), 4.59 (s, 1H), 4.21 (s, 2H), 3.74 (dd, J = 7.3, 1.5 Hz, 1H), 3.62 (d, J = 7.2 Hz, 1H), 3.46 (t, J = 5.7 Hz, 2H), 3.42 (dd, J = 9.8, 1.5 Hz, 1H), 3.16 (d, J = 9.8 Hz, 1H), 2.84 (t, J = 5.7 Hz, 2H), 1.88 (dd, J = 9.6, 2.2 Hz, 1H), 1.83-1.77 (m, 1H). 3. 365.14 |

TABLE 3-continued

| Example | Tosyl-protected precursor | Product | 1. Yield<br>2. ¹H-NMR<br>3. MH⁺ (ESI) |
|---|---|---|---|
| 105f | | | 1. 29%<br>2. ¹H-NMR (400 MHz, DMSO-d₆) δ = 8.54 (s, 1H), 7.82 (dd, J = 9.3, 6.4 Hz, 3H), 7.65 (dd, J = 8.7, 5.4 Hz, 1H), 7.36 (d, J = 8.1 Hz, 2H), 7.26-7.13 (m, 1H), 4.79 (s, 2H), 4.15 (t, J = 5.6 Hz, 2H), 3.74 (t, J = 4.9 Hz, 4H), 3.55 (d, J = 4.9 Hz, 4H), 3.18 (s, 2H), 2.31 (s, 3H).<br>3. 565.21 |

Example 106

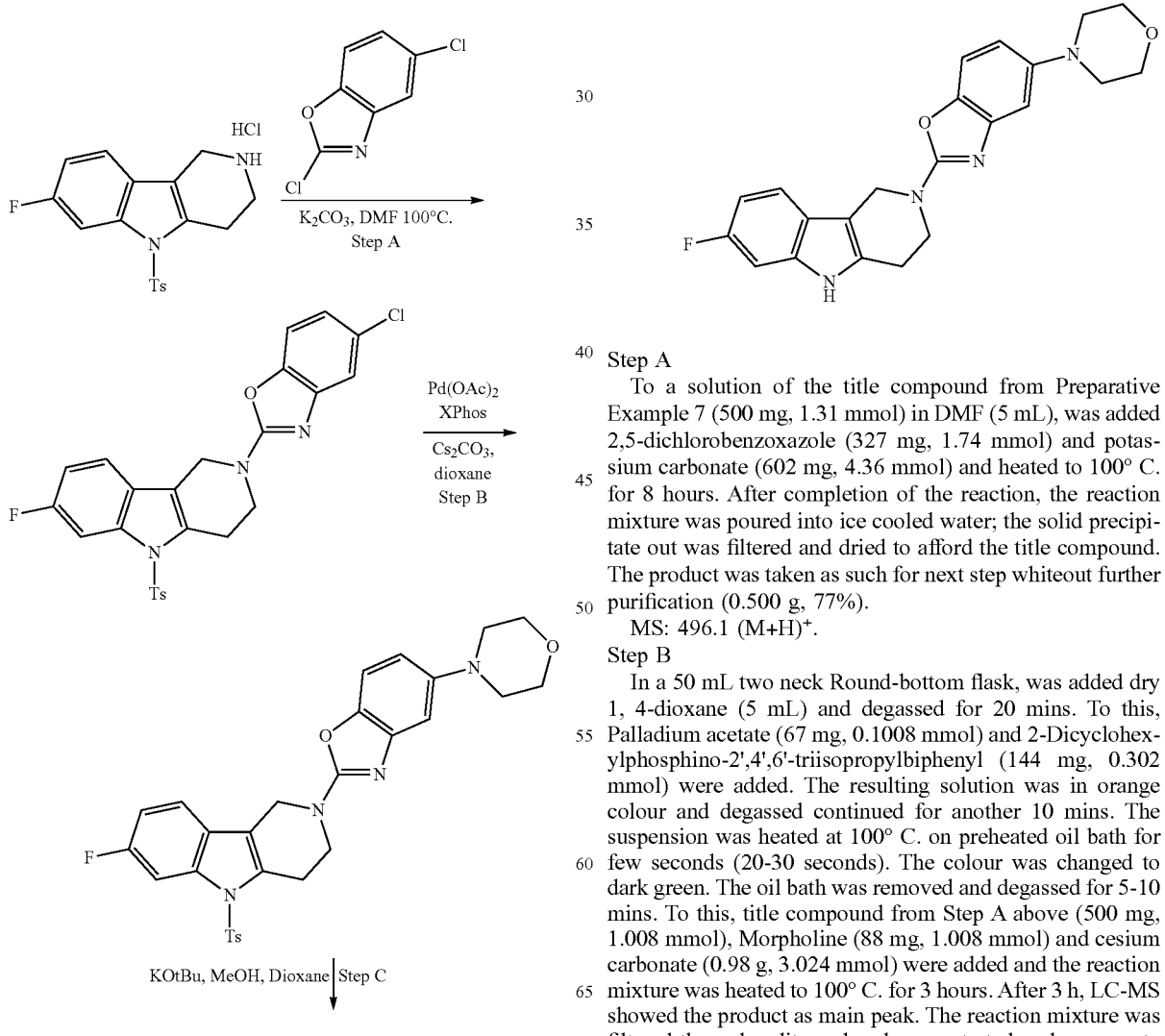

Step A

To a solution of the title compound from Preparative Example 7 (500 mg, 1.31 mmol) in DMF (5 mL), was added 2,5-dichlorobenzoxazole (327 mg, 1.74 mmol) and potassium carbonate (602 mg, 4.36 mmol) and heated to 100° C. for 8 hours. After completion of the reaction, the reaction mixture was poured into ice cooled water; the solid precipitate out was filtered and dried to afford the title compound. The product was taken as such for next step whiteout further purification (0.500 g, 77%).

MS: 496.1 (M+H)⁺.

Step B

In a 50 mL two neck Round-bottom flask, was added dry 1, 4-dioxane (5 mL) and degassed for 20 mins. To this, Palladium acetate (67 mg, 0.1008 mmol) and 2-Dicyclohexylphosphino-2',4',6'-triisopropylbiphenyl (144 mg, 0.302 mmol) were added. The resulting solution was in orange colour and degassed continued for another 10 mins. The suspension was heated at 100° C. on preheated oil bath for few seconds (20-30 seconds). The colour was changed to dark green. The oil bath was removed and degassed for 5-10 mins. To this, title compound from Step A above (500 mg, 1.008 mmol), Morpholine (88 mg, 1.008 mmol) and cesium carbonate (0.98 g, 3.024 mmol) were added and the reaction mixture was heated to 100° C. for 3 hours. After 3 h, LC-MS showed the product as main peak. The reaction mixture was filtered through celite pad and concentrated under vacuo to afford title compound. The product was taken as such for next step whiteout further purification (0.450 g, 82%).

MS: 547.3 (M+H)$^+$.

Step C

To a solution of the title compound from Step B above (450 mg, 0.82 mmol) in 1,4-dioxane:Methanol (1:1; 5 mL), was added sodium tert-butoxide (230 mg, 2.4 mmol) and heated to 70° C. for 16 hours. The reaction mixture was concentrated under vacuo. The purification was performed on silica gel column using a Biotage Isolera One purification system employing a Pet-ether/EtOAc gradient (0-100%) to afford title compound as solid (0.270 g, 84%).

MS: 393.2 (M+H)$^+$.

$^1$H-NMR (400 MHz, DMSO-d$_6$) δ=11.10 (s, 1H), 7.47-7.48 (m, 1H), 7.28 (d, J=8.72 Hz, 1H), 7.08-7.09 (m, 1H), 6.92 (d, J=2.20 Hz, 1H), 6.83-6.84 (m, 1H), 6.62-6.63 (m, 1H), 4.81 (s, 2H), 3.98-4.00 (m, 2H), 3.73-3.74 (m, 4H), 3.04-3.05 (m, 4H), 2.94-2.95 (m, 2H).

Example 107

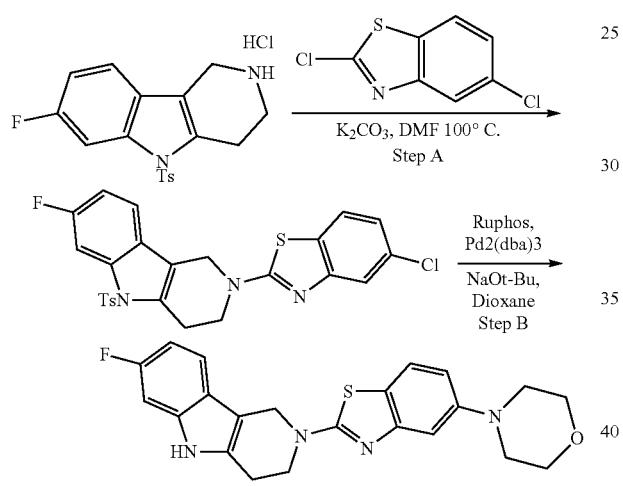

Step A

To a solution of the title compound from Preparative Example 7 (500 mg, 1.318 mmol) in DMF (5 mL), was added 2,5-dichlorobenzothiazole (268 mg, 1.32 mmol) and potassium carbonate (545 mg, 3.95 mmol) and heated to 100° C. for 8 hours. After completion of the reaction, the reaction mixture was poured into ice cooled water, the solid precipitate out was filtered and dried to afford title compound (500 mg, 74%). The product was taken as such for next step whiteout further purification.

MS: 513.1 (M+H)$^+$.

Step B

To a stirred solution of title compound from Step A above (200 mg, 0.39 mmol) in dry dioxane (5 mL), was added Morpholine (51 mg, 0.58 mmol), Sodium tert-Butoxide (112 mg, 1.17 mmol) and degassed for 10 min under N$_2$ atmosphere. To this reaction mixture was added Tris(dibenzylideneacetone)dipalladium(0) (17.9 mg, 0.019 mmol) and 2-dicyclohexylphosphino-2',6'-diisopropoxybiphenyl (18.2 mg, 0.039 mmol) and heated to 100° C. until the completion of the reaction. After the completion of the reaction (monitored by LCMS), the reaction mixture was filtered through celite and washed with EtOAc. The filtrate was concentrated under reduced pressure to yield the crude product. The purification was performed on silica gel column using a Biotage Isolera One purification system employing a Pet-ether/EtOAc gradient (0-100%) to afford title compound as solid (50 mg, 33%).

MS: 409.1 (M+H)$^+$.

$^1$H-NMR (400 MHz, DMSO-d$_6$) δ=11.11 (s, 1H), 7.60 (d, J=8.68 Hz, 1H), 7.48-7.49 (m, 1H), 7.07-7.08 (m, 2H), 6.86-6.88 (m, 2H), 4.77 (s, 2H), 3.97-3.98 (m, 2H), 3.74-3.76 (m, 4H), 3.11-3.12 (m, 4H), 2.95-2.96 (m, 2H).

Example 108

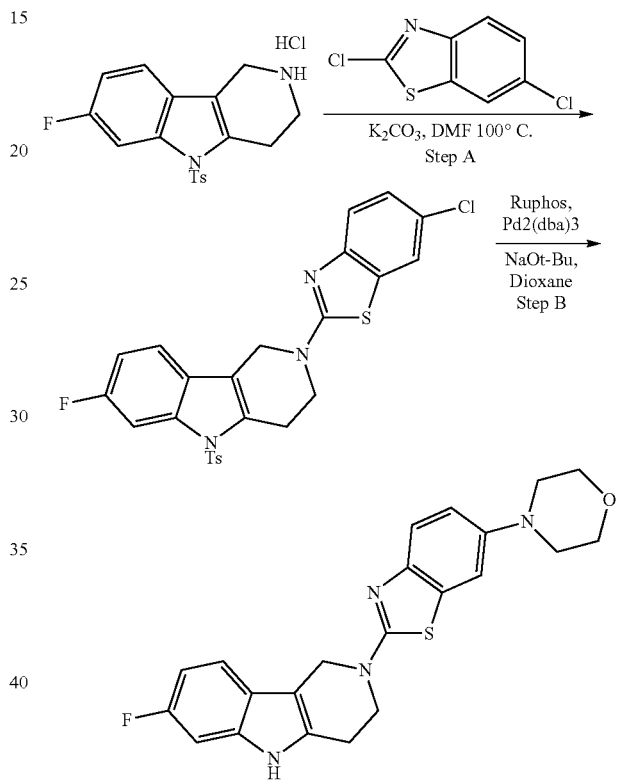

Step A

To a solution of the title compound from Preparative Example 7 (1 g, 2.63 mmol) in DMF (10 mL), was added 2,6-dichlorobenzothiazole (0.537 g, 2.63 mmol) and potassium carbonate (1.09 g, 7.89 mmol) and heated to 100° C. for 8 hours. After completion of the reaction, the reaction mixture was poured into ice cooled water, the solid precipitate out was filtered and dried to afford title compound (1.0 g, 74%). The product was taken as such for next step whiteout further purification.

MS: 513.2 (M+H)$^+$.

Step B

To a stirred solution of title compound from Step A above (150 mg, 0.293 mmol) in dry dioxane (5 mL), was added Morpholine (39 mg, 0.44 mmol), Sodium tert-Butoxide (85 mg, 0.87 mmol) and degassed for 10 min under N2 atmosphere. To this reaction mixture was added Tris(dibenzylideneacetone)dipalladium(0) (13.4 mg, 0.0015 mmol) and 2-Dicyclohexylphosphino-2',6'-diisopropoxybiphenyl (13.65 mg, 0.029 mmol) and heated to 100° C. until the completion of the reaction. After the completion of the reaction (monitored by LCMS), the reaction mixture was filtered through celite and washed with EtOAc. The filtrate was concentrated under reduced pressure to yield the crude product. The purification was performed on silica gel column using a Biotage Isolera One purification system employing a Pet-ether/EtOAc gradient (0-100%) to afford title compound as solid (60 mg, 50%).

MS: 409.1 (M+H)$^+$.

$^1$H-NMR (400 MHz, DMSO-d$_6$) δ=11.10 (s, 1H), 7.48-7.50 (m, 1H), 7.36-7.38 (m, 2H), 7.08-7.09 (m, 1H), 6.96-6.97 (m, 1H), 6.85-6.86 (m, 1H), 4.74 (s, 2H), 3.94-3.95 (m, 2H), 3.74-3.75 (m, 4H), 3.06-3.07 (m, 4H), 2.94-2.95 (m, 2H).

Example 109

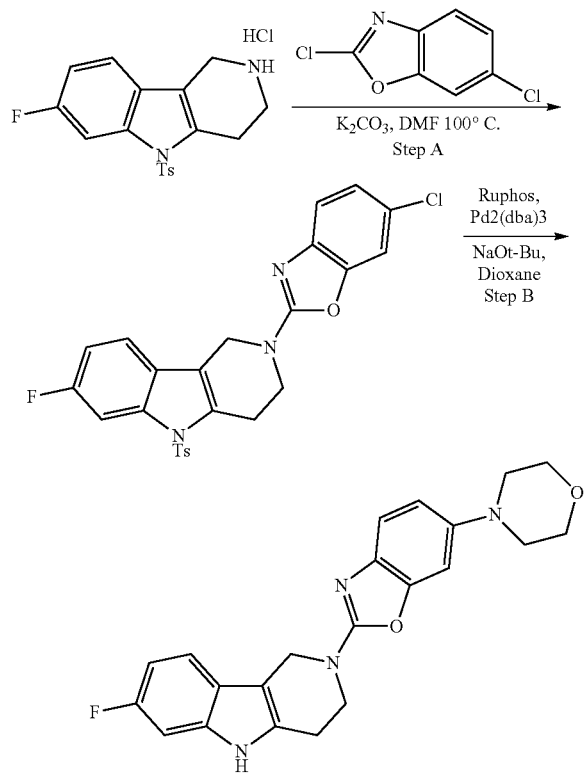

Step A

To a solution of the title compound from Preparative Example 7 (250 mg, 0.725 mmol) in DMF (5 mL), was added 2,6-dichlorobenzoxazole (166 mg, 0.88 mmol) and potassium carbonate (326 mg, 2.36 mmol) and heated to 100° C. for 8 hours. After completion of the reaction, the reaction mixture was poured into ice cooled water, the solid precipitate out was filtered and dried to afford title compound (250 mg, 70%). The product was taken as such for next step whiteout further purification.

MS: 496.1 (M+H)$^+$.

Step B

To a stirred solution of title compound from Step A above (250 mg, 0.505 mmol) in dry dioxane (5 mL), was added Morpholine (53 mg, 0.60 mmol), Sodium Tert-Butoxide (145 mg, 1.52 mmol) and degassed for 10 min under N2 atmosphere. To this reaction mixture was added Tris(dibenzylideneacetone)dipalladium(0) (23.1 mg, 0.0252 mmol) and 2-Dicyclohexylphosphino-2',6'-diisopropoxybiphenyl (23.53 mg, 0.051 mmol) and heated to 100° C. until the completion of the reaction. After the completion of the reaction (monitored by LCMS), the reaction mixture was filtered through celite and washed with EtOAc. The filtrate was concentrated under reduced pressure to yield the crude product. The purification was performed on silica gel column using a Biotage Isolera One purification system employing a Pet-ether/EtOAc gradient (0-100%) to afford title compound as solid (50 mg, 25%).

MS: 393.2 (M+H)$^+$.

$^1$H-NMR (400 MHz, DMSO-d$_6$) δ=11.09 (s, 1H), 7.45-7.46 (m, 1H), 7.17 (d, J=8.56 Hz, 1H), 7.08-7.09 (m, 2H), 6.87-6.79 (m, 2H), 4.77 (s, 2H), 3.95-3.96 (m, 2H), 3.72-3.74 (m, 4H), 3.03-3.04 (m, 4H), 2.91-2.93 (m, 2H).

Example 110

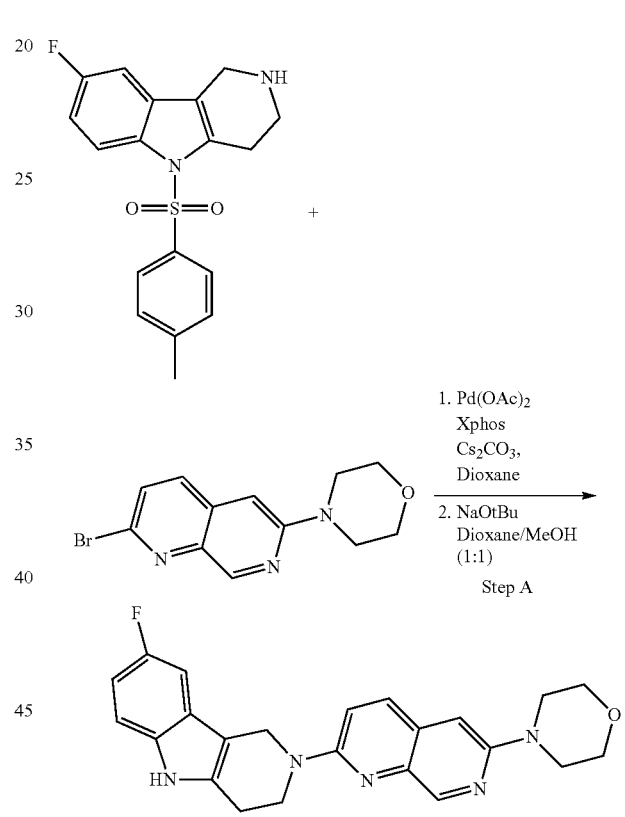

Step A

To a stirred solution of the title compound from Preparative Example 1 (0.15 g, 0.43 mmol) in dry 1,4-dioxane (5 mL), was added the title compound from Preparative Example 50 (0.17 g, 0.43 mmol) and Cs$_2$CO$_3$ (0.420 g, 1.29 mmol). The reaction mixture was degassed for 10 min under N2 atmosphere. Then Pd(OAc)$_2$; (0.009 g, 0.043 mmol) and 2-Dicyclohexylphosphino-2',4',6'-triisopropylbiphenyl (0.062 g; 0.129 mmol) were added and the reaction mixture was heated to 100° C. until the completion of the reaction. After the completion of the reaction (monitored by LCMS), the reaction mixture was filtered through celite and washed with ethyl acetate. The filtrate was concentrated under reduced pressure to yield the crude product. The crude material was purified by flash column chromatography or preparative HPLC to afford the Tosyl protected compound. To a solution of tosyl compound (1.0 eq) in Dioxane:MeOH (1:1, 10 vol), was added NaOtBu (3 eq) and heated to 70° C. for 6 hours. The reaction mixture was concentrated under vacuum and the crude product was column purified to afford desired product. The crude material was purified by flash column.

$^1$H-NMR (400 MHz, DMSO-d$_6$): δ 11.00 (bs, 1H), 8.70 (s, 1H), 7.96 (d, J=9.60 Hz, 1H), 7.45-7.46 (m, 1H), 7.39 (d, J=9.20 Hz, 1H), 7.07-7.08 (m, 2H), 6.82-6.83 (m, 1H), 4.64 (s, 2H), 4.02-4.04 (m, 2H), 3.73 (d, J=4.80 Hz, 4H), 3.59 (d, J=4.40 Hz, 4H), 2.90 (bs, 2H).

MS: 404.2 (M+H)$^+$.

Examples 111 and 112

Following the palladium coupling procedure followed by Tosyl deprotection as described in Example 110 the following compounds were prepared:

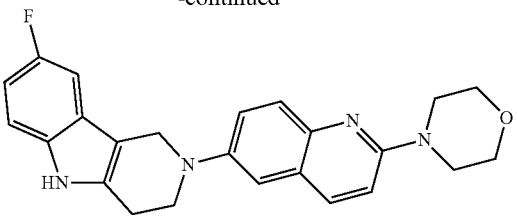

Step A

Palladium (II) acetate (0.013 g, 0.058 mmol) and 4,5-bis (diphenylphosphino)-9,9-dimethylxanthene (XANTPHOS) (0.101 g, 0.174 mmol) were placed in a reaction vial and degassed. 1,4-Dioxane (6 mL) was added. The resulting solution was degassed briefly. The suspension was heated at

TABLE 4

| Example | Tricyclic amino derivative | Bromo or Chloro derivative | Product | 1. Yield 2. $^1$H-NMR 3. MH$^+$ (ESI) |
|---|---|---|---|---|
| 111 | F-[tricyclic with TsN, NH·HCl] | Cl-[benzoxazole-morpholine] | F-[HN-tricyclic-N-benzoxazole-morpholine] | 1. 29% 2. $^1$H-NMR (400 MHz, DMSO-d$_6$): δ 11.29 (s, 1H), 7.25-7.27 (m, 2H), 7.04 (d, J = 2.40 Hz, 1H), 6.77-6.94 (m, 3H), 4.34 (s, 2H), 3.70-3.71 (m, 4H), 3.61-3.62 (m, 2H), 3.54-3.55 (m, 4H), 2.87-2.89 (m, 2H). 3. 393.2 |
| 112 | F-[tricyclic with TsN, NH·HCl] | Cl-[naphthyridine-morpholine] | F-[HN-tricyclic-N-naphthyridine-morpholine] | 1. 51% 2. $^1$H-NMR (400 MHz, DMSO-d$_6$): δ 11.01 (s, 1H), 8.81 (s, 1H), 8.07 (d, J = 9.04 Hz, 1H), 7.88 (s, 1H), 7.44-7.46 (m, 1H), 7.35 (d, J = 8.68 Hz, 1H), 7.07-7.08 (m, 1H), 6.85-6.87 (m, 1H), 4.48 (s, 2H), 3.70-3.72 (m, 10H), 2.94-2.95 (m, 2H). 3. 404.2 |

Example 113

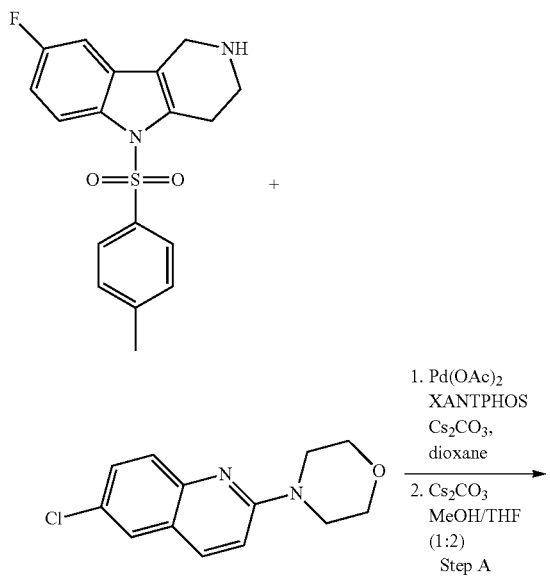

Step A

100° C. (on a pre-heated heating block) for less than 1 minute until the color of the solution turned from orange to dark pink. Then, the vial was removed from the heating block and the title compound from Preparative Example 52 (148 mg, 0.581 mmol), the title compound from Preparative Example 1 (0.200 g, 0.581 mmol) and cesium carbonate (0.662 g, 2.033 mmol) were added. The reaction vial was filled with argon before closing it. The reaction mixture was heated at 100° C. for 18 h. The reaction mixture was diluted with ethyl acetate and water. The organic layer was separated and the aqueous layer was extracted with ethyl acetate two more times. The combined organic layers were dried over Na$_2$SO$_4$, filtered and the solvents were evaporated under reduced pressure. The crude product was purified on a silica gel column using a Biotage Isolera One purification system employing an n-heptane/ethyl acetate (100/00→50/ 50) gradient. The obtained crude reaction mixture (0.261 g, 0.469 mmol) and cesium carbonate (0.214 g, 0.658 mmol) were placed into a microwave tube, followed by MeOH (4 mL) and THF (8 mL). The reaction mixture was irradiated in a microwave to 110° C. for 30 minutes and then allowed to cool down to room temperature. The solvents were removed under reduced pressure and the residue was purified on a silica gel column using a Biotage Isolera One purification system with a gradient of dichloromethane/methanol (100/00→95/05) to afford the title compound as a yellow solid (0.020 g, 9%).

¹H NMR (400 MHz, DMSO-d₆) δ 10.97 (s, 1H), 7.95 (d, 1H), 7.54 (d, 2H), 7.33-7.10 (m, 4H), 6.86 (td, 1H), 4.41 (s, 2H), 3.72 (dt, 6H), 3.55 (t, 4H), 2.95 (d, 2H). MS: 403.19 (M+H)⁺.

Example 114

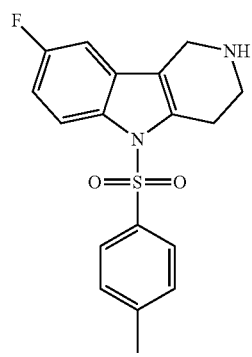

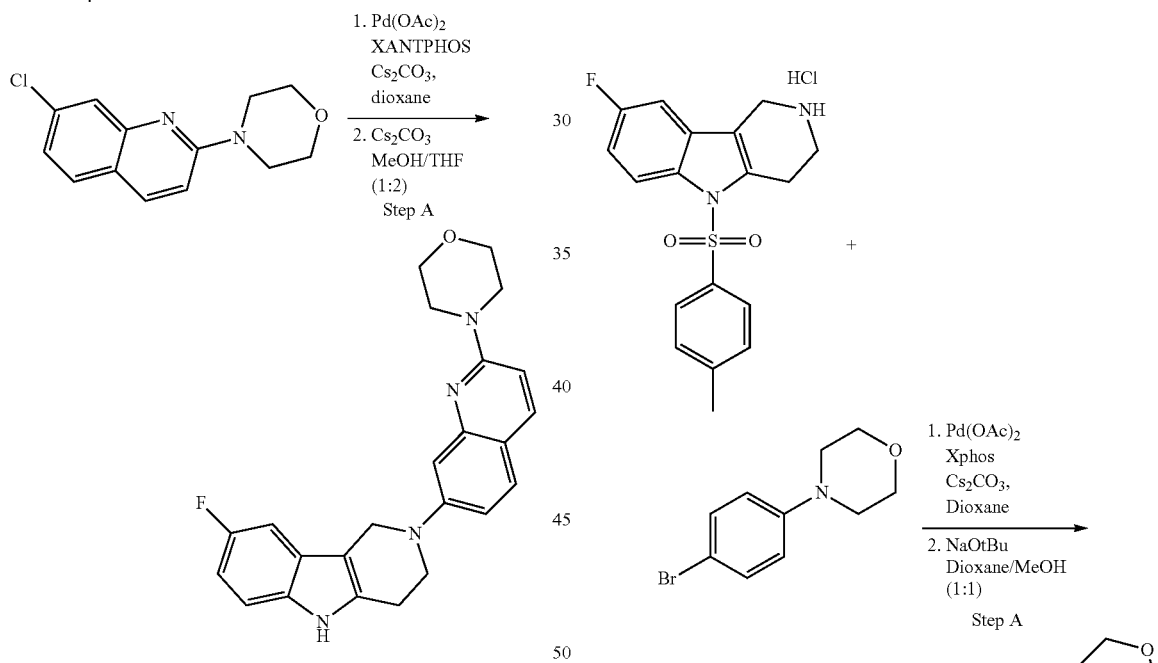

Step A

Palladium (II) acetate (0.013 g, 0.058 mmol) and 4,5-bis(diphenylphosphino)-9,9-dimethylxanthene (XANTPHOS) (0.101 g, 0.174 mmol) were placed in a reaction vial and degassed. 1,4-Dioxane (6 mL) was added. The resulting solution was degassed briefly. The suspension was heated at 100° C. (on a pre-heated heating block) for less than 1 minute until the color of the solution turned from orange to dark pink. Then, the vial was removed from the heating block and the title compound from Preparative Example 51 (144 mg, 0.581 mmol), the title compound from Preparative Example 1 (0.200 g, 0.581 mmol) and cesium carbonate (0.662 g, 2.033 mmol) were added. The reaction vial was filled with argon before closing it. The reaction mixture was heated at 100° C. for 18 h. The reaction mixture was diluted with ethyl acetate and water. The organic layer was separated and the aqueous layer was extracted with ethyl acetate two more times. The combined organic layers were dried over Na₂SO₄, filtered and the solvents were evaporated under reduced pressure. The crude product was purified on a silica gel column using a Biotage Isolera One purification system employing an n-heptane/ethyl acetate gradient (100/00→50/50). The obtained crude reaction mixture (0.122 g, 0.219 mmol) and cesium carbonate (0.214 g, 0.658 mmol) were placed into a microwave tube, followed by MeOH (4 mL) and THF (8 mL). The reaction mixture was irradiated in a microwave to 110° C. for 30 minutes and then allowed to cool down to room temperature. The solvents were removed under reduced pressure and the residue was purified on a silica gel column using a Biotage Isolera One purification system with a gradient of dichloromethane/methanol (100/00→95/05) to afford the title compound as a yellow solid (0.081 g, 35%).

¹H NMR (400 MHz, DMSO-d₆) δ 10.97 (s, 1H), 7.88 (d, 1H), 7.56 (d, 1H), 7.40-7.13 (m, 3H), 7.02 (d, 1H), 6.97-6.79 (m, 2H), 4.49 (s, 2H), 3.80 (t, 2H), 3.72 (t, 4H), 3.60 (t, 4H), 2.93 (d, 2H).

MS: 403.20 (M+H)⁺.

Example 115

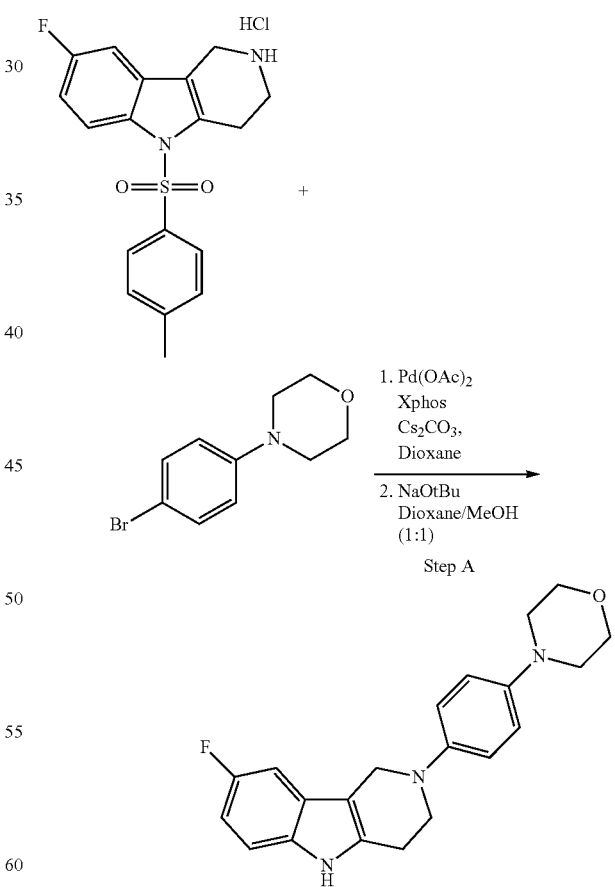

Step A

Pd(OAc)₂ (16 mg, 0.072 mmol) and 2-Dicyclohexylphosphino-2',4',6'-triisopropylbiphenyl (XPhos; 103 mg, 0.2177 mmol) were added to a reaction vial and degazed dioxane (5 ml) was added. The vial was filled with Argon gas and sealed. The suspension was heated at 100° C. for 1 minute then 8-fluoro-5-tosyl-2,3,4,5-tetrahydro-1H-pyrido[4,3-b]indole (Preparative Example 1) (250 mg, 0.725 mmol), 4-(4-bromophenyl)morpholine (210 mg, 0.87 mmol) and $Cs_2CO_3$ (707 mg, 2.177 mmol) were added and the solution was heated at 100° C. for 18 hours. The reaction mixture was diluted with ethyl acetate (30 mL) and water (30 mL). The organic phase was separated and the aqueous phase was extracted with ethyl acetate two more times. The combined organic phase was dried over $Na_2SO_4$, filtered and the solvents were evaporated under reduced pressure. The crude purified on HP-Sil column (Biotage), by employing a DCM/MeOH gradient (100/0→95/05) to afford 4-(4-(8-fluoro-5-tosyl-1,3,4,5-tetrahydro-2H-pyrido[4,3-b]indol-2-yl)phenyl)morpholine (235 mg, 64%) as yellow solid.

To a solution of 4-(4-(8-fluoro-5-tosyl-1,3,4,5-tetrahydro-2H-pyrido[4,3-b]indol-2-yl)phenyl)morpholine (0.235 mg, 0.465 mmol) in Dioxane:MeOH (1:1, 5 vol), NaOtBu (133 mg, 1.39 mmol) was added and heated to 70° C. for 6 hours. The reaction mixture was concentrated under vacuum and the crude product was column purified on HP-Sil column (Biotage), by employing a DCM/MeOH gradient (100/0→95/05) to afford the title compound as off white solid (57 mg, 35%) MS: 352.0 (M+H)$^+$.

$^1$H-NMR (400 MHz, DMSO-d$_6$) δ 10.93 (bs, 1H), 7.21-7.24 (m, 2H), 6.99-7.01 (m, 2H), 6.85-6.86 (m, 3H), 4.24 (s, 2H), 3.73 (bs, 4H), 3.52-3.53 (m, 2H), 2.98 (bs, 4H), 2.86 (bs, 2H).

Example 116

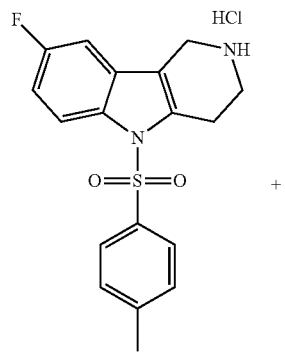

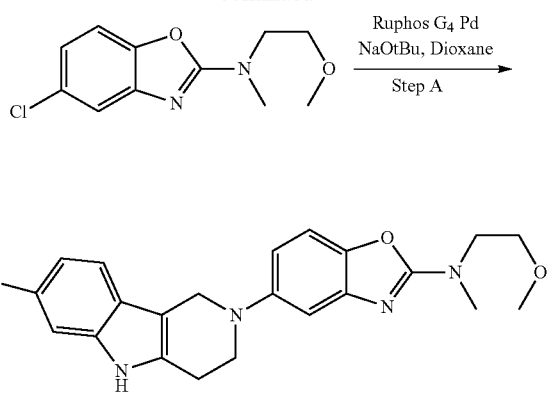

To a stirred solution of 7-fluoro-5-tosyl-2,3,4,5-tetrahydro-1H-pyrido[4,3-b]indole (Preparative Example 7) (250 mg, 0.7267 mmol) in dry dioxane (5 mL), 5-chloro-N-(2-methoxyethyl)-N-methylbenzo[d]oxazol-2-amine (Preparative Example 60) (190 mg, 0.7994 mmol), sodium tert-butoxide (202 mg, 2.180 mmol) were added and degassed for 10 min under $N_2$ Atmosphere. To this reaction mixture was added Ruphos G4 Pd (60 mg, 0.0726 mmol) and heated to 100° C. until the completion of the reaction. After the completion of the reaction, the reaction mixture was filtered through a Celite bed, washed with EtOAc. The filtrate was concentrated and the crude was purified by column chromatography on HP-Sil column (Biotage), by employing a DCM/MeOH gradient (100/0→95/05) to afford the title compound (37 mg, 13%) MS: 395.0 (M+H)$^+$.

1H-NMR (400 MHz, DMSO-d$_6$) δ 10.94 (bs, 1H), 7.43-7.44 (m, 1H), 7.23 (d, J=8.80 Hz, 1H), 7.06-7.06 (m, 1H), 6.99 (d, J=2.40 Hz, 1H), 6.80-6.81 (m, 1H), 6.71-6.72 (m, 1H), 4.32 (s, 2H), 3.64-3.65 (m, 2H), 3.56-3.58 (m, 4H), 3.27 (s, 3H), 3.13 (s, 3H), 2.86 (t, J=5.20 Hz, 2H).

Examples 117 to 145

Following the procedures reported in Example 115 and Example 116, the following compounds were prepared.

TABLE 5

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 117 | 6-fluoro-2,3,4,9-tetrahydro-1H-β-carboline N-Ts, NH·HCl | 4-(4-bromophenyl)morpholine | morpholine-phenyl-tetrahydro-β-carboline (F-substituted) | 1. 55%<br>2. ¹H-NMR (400 MHz, DMSO-d₆): δ 10.93 (bs, 1H), 7.40-7.41 (m, 1H), 6.98-7.00 (m, 3H), 6.81-6.83 (m, 3H), 4.24 (s, 2H), 3.70-3.72 (m, 4H), 3.50-3.51 (m, 2H), 2.95-2.97 (m, 4H), 2.84 (bs, 2H).<br>3. 352.3<br>4. Example 115 |
| 118 | 6-fluoro-2,3,4,9-tetrahydro-1H-β-carboline N-Ts, NH·HCl | 6-chloro-N-(2-methoxyethyl)benzo[d]oxazol-2-amine | benzoxazol-2-amine-tetrahydro-β-carboline (F-substituted) | 1. 10%<br>2. ¹H-NMR (400 MHz, DMSO-d₆): δ 10.94 (bs, 1H), 7.87 (t, J = 5.56 Hz, 1H), 7.43-7.44 (m, 1H), 7.17-7.19 (m, 1H), 7.06-7.07 (m, 1H), 6.98-6.99 (m, 1H), 6.80-6.81 (m, 1H), 6.64-6.66 (m, 1H), 4.31 (s, 2H), 3.59 (t, J = 5.60 Hz, 2H), 3.50 (t, J = 5.32 Hz, 2H), 3.44 (t, J = 5.52 Hz, 2H), 3.28 (s, 3H), 2.86 (bs, 2H).<br>3. 381.1<br>4. Example 116 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 119 | | | | 1. 22%<br>2. ¹H-NMR (400 MHz, DMSO-d₆): δ 8.01 (d, J = 2.92 Hz, 1H), 7.45-7.46 (m, 2H), 7.39 (d, J = 8.12 Hz, 1H), 7.10 (t, J = 7.92 Hz, 1H), 7.01 (t, J = 7.36 Hz, 1H), 6.80 (d, J = 9.08 Hz, 1H), 4.30 (s, 2H), 3.69-3.70 (m, 4H), 3.64 (s, 3H), 3.56-3.58 (m, 2H), 3.27-3.29 (m, 4H), 2.88-2.89 (m, 2H).<br>3. 349.2<br>4. Example 115 |
| 120 | | | | 1. 28%<br>2. ¹H-NMR (400 MHz, DMSO-d₆): δ 7.31 (d, J = 7.60 Hz, 1H), 7.25 (d, J = 8.80 Hz, 1H), 7.04 (d, J = 2.00 Hz, 1H), 6.86-6.88 (m, 2H), 6.77-6.78 (m, 1H), 4.33 (s, 2H), 3.80 (s, 3H), 3.64-3.65 (m, 6H), 3.54-3.56 (m, 4H), 2.88 (bs, 2H).<br>3. 407.2<br>4. Example 115 |
| 121 | | | | 1. 6%<br>2. ¹H-NMR (400 MHz, DMSO-d₆): δ 11.05 (bs, 1H), 8.54 (s, 1H), 7.90 (d, J = 8.00 Hz, 1H), 7.46 (s, 1H), 7.09 (d, J = 8.08 Hz, 2H), 6.85 (t, J = 6.88 Hz, 1H), 4.82 (s, 2H), 4.12 |

TABLE 5-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 122 | 6-fluoro-tetrahydro-β-carboline N-Ts, NH·HCl | 3-morpholino-7-chloroisoquinoline | 6-fluoro-tetrahydro-β-carboline with 3-morpholinoisoquinolin-7-yl | (bs, 2H), 2.88 (bs, 2H). 3. 292.9 4. Example 115 1. 23% 2. ¹H-NMR (400 MHz, DMSO-d₆): δ 10.99 (bs, 1H), 8.85 (s, 1H), 7.63 (s, 2H), 7.46-7.47 (m, 1H), 7.32 (s, 1H), 7.07-7.08 (m, 1H), 6.82-6.83 (m, 2H), 4.44 (s, 2H), 3.70-3.71 (m, 6H), 3.39-3.40 (m, 4H), 2.91-2.93 (m, 2H). 3. 403.2 4. Example 115 |
| 123 | 6-fluoro-tetrahydro-β-carboline N-Ts, NH·HCl | 5-bromo-2-cyanopyridine | 6-fluoro-tetrahydro-β-carboline with 6-cyanopyridin-3-yl | 1. 10% 2. ¹H-NMR (400 MHz, DMSO-d₆): δ 11.05 (bs, 1H), 8.57 (d, J = 2.80 Hz, 1H), 7.78 (d, J = 9.20 Hz, 1H), 7.46-7.47 (m, 2H), 7.09 (dd, J = 2.40, 10.20 Hz, 1H), 6.85-6.86 (m, 1H), 4.62 (s, 2H), 3.90 (t, J = 5.60 Hz, 2H), 2.91 (t, J = 5.20 Hz, 2H). 3. 293.1 4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 124 | | | | 1. 39%<br>2. ¹H-NMR (400 MHz, DMSO-d₆): δ 10.96 (bs, 1H), 7.23-7.26 (m, 1H), 7.20-7.20 (m, 1H), 6.92-6.94 (m, 2H), 6.83-6.84 (m, 2H), 6.73-6.74 (m, 1H), 4.51 (s, 2H), 3.98 (t, J = 5.44 Hz, 2H), 3.73-3.74 (m, 4H), 3.58-3.59 (m, 4H), 2.89 (bs, 2H).<br>3. 393.1<br>4. Example 115 |
| 125 | | | | 1. 32%<br>2. ¹H-NMR (400 MHz, DMSO-d₆): δ 10.95 (bs, 1H), 7.43-7.44 (m, 1H), 7.03-7.03 (m, 1H), 7.02-7.03 (m, 1H), 6.77-6.79 (m, 2H), 4.33 (s, 2H), 3.50-3.51 (m, 9H), 2.86 (bs, 2H), 1.97-1.99 (m, 4H), 1.68-1.71 (m, 2H).<br>3. 433.1<br>4. Example 115 |
| 126 | | | | 1. 47%<br>2. ¹H-NMR (400 MHz, DMSO-d₆): δ 10.95 (bs, 1H), 7.43-7.44 (m, 1H), 7.26 (d, J = 8.68 Hz, 1H), 7.03-7.04 (m, 2H), 6.78-6.79 (m, 2H), 4.32 (s, 2H), 4.04-4.14 (m, 1H), 3.90-3.90 (m, 1H), |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 127 | (8-methoxy tetrahydro-β-carboline) | 6-chloro-2-morpholinobenzoxazole | | 3.59-3.61 (m, 6H), 3.50-3.53 (m, 1H), 2.86 (bs, 2H), 1.28 (d, J = 6.72 Hz, 3H).<br>3. 406.9<br>4. Example 115 |
| | | | | 1. 5%<br>2. ¹H-NMR (400 MHz, DMSO-d₆): δ 10.90 (bs, 1H), 7.26 (d, J = 8.80 Hz, 1H), 7.05 (d, J = 2.40 Hz, 2H), 6.90 (t, J = 7.60 Hz, 1H), 6.76-6.77 (m, 1H), 6.63 (d, J = 7.60 Hz, 1H), 4.31 (s, 2H), 3.90 (s, 3H), 3.60-3.62 (m, 4H), 3.54-3.56 (m, 6H), 2.83-2.85 (m, 2H).<br>3. 405.1<br>4. Example 116 |
| 128 | (7-fluoro tetrahydro-β-carboline, TsN, HCl) | 6-chloro-2-((S)-3-methylmorpholino)benzoxazole | | 1. 33%<br>2. ¹H-NMR (400 MHz, DMSO-d₆): δ 10.95 (bs, 1H), 7.43-7.44 (m, 1H), 7.26 (d, J = 8.76 Hz, 1H), 7.02-7.03 (m, 2H), 6.81-6.83 (m, 2H), 4.32 (s, 2H), 3.87-3.89 (m, 3H), 3.58-3.59 (m, 4H), 3.13-3.14 (m, 1H), 2.82-2.85 (m, 3H), 1.15 (d, J = 6.20 Hz, 3H).<br>3. 407.3<br>4. Example 115 |

TABLE 5-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 129 | | | | 1. 28% 2. ¹H-NMR (400 MHz, DMSO-d₆): δ 10.95 (bs, 1H), 7.43-7.44 (m, 1H), 7.26 (d, J = 8.68 Hz, 1H), 7.03-7.04 (m, 2H), 6.80-6.81 (m, 2H), 4.33 (s, 2H), 4.14-4.16 (m, 1H), 3.89-3.90 (m, 1H), 3.66-3.68 (m, 6H), 3.50-3.52 (m, 1H), 2.86 (sb, 2H), 1.28 (d, J = 6.72 Hz, 3H). 3. 407.1 4. Example 115 |
| 130 | | | | 1. 42% 2. ¹H-NMR (400 MHz, DMSO-d₆): δ 10.94 (bs, 1H), 7.42-7.43 (m, 1H), 7.24 (d, J = 8.80 Hz, 1H), 7.01-7.02 (m, 2H), 6.77-6.78 (m, 2H), 4.31 (s, 2H), 3.86-3.88 (m, 3H), 3.55-3.58 (m, 4H), 3.15-3.18 (m, 1H), 2.80-2.84 (m, 3H), 1.13-1.14 (m, 3H). 3. 407.1 4. Example 115 |
| 131 | | | | 1. 48% 2. ¹H-NMR (400 MHz, DMSO-d₆) δ 10.67 (bs, 1H), 7.25-7.27 (m, 2H), 7.17 (d, J = 8.16 Hz, 1H), 7.02 (s, 1H), 6.85 (d, J = 8.16 Hz, 1H), 6.77 (d, J = 8.24 Hz, 1H), 4.31 (s, 2H), |

TABLE 5-continued

| Example | Tricyclic amino derivative | Bromo or Chloro derivative | Product | 1. Yield 2. ¹H-NMR 3. MH⁺ (ESI) 4. Synthesis procedure |
|---|---|---|---|---|
| 132 | (tricyclic amino derivative with F and N-Ts, NH·HCl) | 2-methoxy-4-bromopyridine | (product with 2-methoxypyridine attached to tetrahydro-β-carboline with F) | 3.70-3.71 (m, 4H), 3.60-3.62 (m, 2H), 3.56-3.57 (m, 4H), 2.85 (bs, 2H), 2.37 (s, 3H). 3. 389.2 4. Example 115 |
| 133 | (tricyclic amino derivative with OMe and N-Ts, NH·HCl) | 2-morpholino-6-chlorobenzoxazole | (product with morpholino-benzoxazole attached to tetrahydro-γ-carboline with OMe) | 1. 19% 2. ¹H-NMR (400 MHz, DMSO-d₆) δ 11.01 (bs, 1H), 7.82 (d, J = 6.12 Hz, 1H), 7.46-7.47 (m, 1H), 7.06-7.07 (m, 1H), 6.81-6.82 (m, 1H), 6.70-6.70 (m, 1H), 6.27 (d, J = 2.20 Hz, 1H), 4.49 (s, 2H), 3.75-3.77 (m, 5H), 2.84-2.86 (m, 2H). 3. 298.2 4. Example 115 1. 23% 2. ¹H-NMR (400 MHz, DMSO-d₆) δ 10.63 (bs, 1H), 7.32 (d, J = 8.40 Hz, 1H), 7.25 (d, J = 8.40 Hz, 1H), 7.01 (d, J = 2.40 Hz, 1H), 6.75-6.76 (m, 2H), 6.62 (dd, J = 2.40, 8.60 Hz, 1H), 4.28 (s, 2H), 3.69-3.70 (m, 7H), 3.53-3.54 (m, 6H), 2.82-2.83 (m, 2H). 3. 405.1 4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 134 | | | | 1. 6%<br>2. ¹H-NMR (400 MHz, DMSO-d₆) δ 11.06 (s, 1H), 7.54 (s, 1H), 7.25-7.27 (m, 2H), 7.01-7.03 (m, 2H), 6.78 (d, J = 8.56 Hz, 1H), 4.33 (s, 2H), 3.70-3.71 (m, 4H), 3.61-3.62 (m, 2H), 3.55-3.56 (m, 4H), 2.88 (s, 2H).<br>3. 409.1<br>4. Example 115 |
| 135 | | | | 1. 6%<br>2. ¹H-NMR (400 MHz, DMSO-d₆) δ 10.96 (bs, 1H), 8.15 (s, 1H), 7.21-7.22 (m, 1H), 7.13 (s, 1H), 6.82-6.83 (m, 1H), 4.60 (s, 2H), 3.98 (bs, 2H), 3.71-3.72 (m, 4H), 3.54-3.55 (m, 4H), 2.87 (bs, 2H).<br>3. 394.1<br>4. Example 116 |
| 136 | | | | 1. 41%<br>2. ¹H-NMR (400 MHz, DMSO-d₆) δ 10.63 (bs, 1H), 7.26 (d, J = 8.72 Hz, 1H), 7.15 (d, J = 8.68 Hz, 1H), 6.98-6.99 (m, 2H), 6.76-6.77 (m, 1H), 6.64-6.65 (m, 1H), 4.30 (s, 2H), 4.02 (q, J = 6.92 Hz, 2H), 3.70-3.71 (m, 4H), 3.56-3.57 (m, 6H), 2.85 (bs, 2H), 1.34 (t, J = 6.92 Hz, 3H). |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 137 | | | | 3. 419.2<br>4. Example 115 |
| 137 | | | | 1. 6%<br>2. ¹H-NMR (400 MHz, DMSO-d₆) δ 10.74 (bs, 1H), 7.25-7.27 (m, 2H), 7.03 (d, J = 2.28 Hz, 1H), 6.77-6.78 (m, 3H), 4.33 (s, 2H), 3.70-3.71 (m, 4H), 3.63 (t, J = 5.52 Hz, 2H), 3.54-3.55 (m, 4H), 2.90-2.91 (m, 2H), 2.43 (s, 3H).<br>3. 389.1<br>4. Example 116 |
| 138 | | | | 1. 44%<br>2. ¹H-NMR (400 MHz, DMSO-d₆) δ 10.99 (bs, 1H), 7.43-7.45 (m, 2H), 7.08 (dd, J = 2.20, 10.18 Hz, 1H), 6.81-6.82 (m, 1H), 6.46 (d, J = 8.08 Hz, 1H), 6.03 (d, J = 7.76 Hz, 1H), 4.63 (s, 2H), 4.00 (t, J = 5.56 Hz, 2H), 3.82 (s, 3H), 2.86 (t, J = 5.24 Hz, 2H).<br>3. 298.2<br>4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 139 | [F-substituted tricyclic amine with TsN and NH·HCl] | [2-isopropoxy-4-bromopyridine] | [7-fluoro tricyclic product with 2-isopropoxypyridin-4-yl group] | 1. 12%<br>2. ¹H-NMR (400 MHz, DMSO-d₆) δ 10.99 (bs, 1H), 7.79 (d, J = 6.00 Hz, 1H), 7.47-7.48 (m, 1H), 7.08 (dd, J = 2.40, 10.20 Hz, 1H), 6.84 (t, J = 2.40 Hz, 1H), 6.65-6.65 (m, 1H), 6.20 (d, J = 2.40 Hz, 1H), 5.20 (t, J = 6.00 Hz, 1H), 4.48 (s, 2H), 3.76 (t, J = 5.60 Hz, 2H), 2.85 (t, J = 5.60 Hz, 2H), 1.24 (d, J = 6.40 Hz, 6H).<br>3. 326.1<br>4. Example 115 |
| 140 | [F-substituted tricyclic amine with TsN and NH·HCl] | [4-methoxy-2-bromopyridine] | [7-fluoro tricyclic product with 4-methoxypyridin-2-yl group] | 1. 38%<br>2. ¹H-NMR (400 MHz, DMSO-d₆) δ 10.98 (s, 1H), 7.96 (d, J = 5.68 Hz, 1H), 7.45-7.46 (m, 1H), 7.08 (d, J = 10.32 Hz, 1H), 6.84 (t, J = 8.48 Hz, 1H), 6.43 (s, 1H), 6.29 (d, J = 5.08 Hz, 1H), 4.65 (s, 2H), 3.99 (t, J = 5.16 Hz, 2H), 3.81 (s, 3H), 2.84 (bs, 2H).<br>3. 298.1<br>4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 141 | [F-substituted tricyclic amine with TsN and NH·HCl] | 5-methoxy-2-bromopyridine | [Product: F-tricyclic-pyrrolidine linked to 5-methoxypyridine, NH] | 1. 33%<br>2. ¹H-NMR (400 MHz, DMSO-d₆) δ 10.96 (bs, 1H), 7.91 (d, J = 2.92 Hz, 1H), 7.42-7.43 (m, 1H), 7.28-7.29 (m, 1H), 7.07 (dd, J = 2.32, 10.20 Hz, 1H), 6.95-6.97 (m, 1H), 6.84-6.85 (m, 1H), 6.79-6.80 (m, 1H), 4.56 (s, 2H), 3.87-3.88 (m, 2H), 3.73 (s, 3H), 2.84 (bs, 2H).<br>3. 298.1<br>4. Example 115 |
| 142 | [F-substituted tricyclic amine with TsN and NH·HCl] | 2-(cis-2,6-dimethylmorpholino)-5-chlorobenzoxazole | [Product: F-tricyclic linked to benzoxazole with dimethylmorpholine, NH] | 1. 22%<br>2. ¹H-NMR (400 MHz, DMSO-d₆) δ 10.95 (bs, 1H), 7.43-7.44 (m, 1H), 7.25 (d, J = 8.80 Hz, 1H), 7.06-7.06 (m, 1H), 7.01-7.02 (m, 1H), 6.81-6.83 (m, 1H), 4.32 (s, 2H), 3.95 (d, J = 12.80 Hz, 2H), 3.64-3.65 (m, 4H), 2.86 (bs, 2H), 2.68-2.73 (m, 2H), 1.15 (d, J = 6.00 Hz, 6H).<br>3. 421.1<br>4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 143 | | | | 1. 5%<br>2. ¹H-NMR (400 MHz, DMSO-d₆): δ 10.93 (bs, 1H), 7.56 (s, 1H), 7.42-7.44 (m, 1H), 7.15 (d, J = 8.80 Hz, 1H), 7.01-7.02 (m, 2H), 6.81-6.82 (m, 1H), 6.69-6.70 (m, 1H), 4.30 (s, 2H), 3.58 (t, J = 5.60 Hz, 2H), 2.85 (t, J = 4.80 Hz, 2H), 1.39 (s, 9H).<br>3. 379.0<br>4. Example 115 |
| 144 | | | | 1. 38%<br>2. ¹H-NMR (400 MHz, DMSO-d₆): δ 7.50 (d, J = 7.60 Hz, 1H), 7.39 (d, J = 8.40 Hz, 1H), 7.26 (d, J = 8.80 Hz, 1H), 7.08-7.10 (m, 1H), 7.01-7.03 (m, 2H), 6.79 (dd, J = 2.40, 8.80 Hz, 1H), 4.35 (s, 2H), 3.64-3.65 (m, 9H), 3.54-3.55 (m, 4H), 2.90 (t, J = 5.20 Hz, 2H).<br>3. 389.0<br>4. Example 115 |

TABLE 5-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| 145 | (structure: fluoro-tetrahydro-β-carboline with N-Tos and NH) | (structure: 5-chloro-2-(4-methylpiperazin-1-yl)benzoxazole) | (structure: coupled product) | 1. 62%<br>2. 1H-NMR (400 MHz, DMSO-d₆): δ 10.95 (bs, 1H), 7.43-7.44 (m, 1H), 7.24 (d, J = 8.68 Hz, 1H), 7.06-7.07 (m, 1H), 7.01-7.02 (m, 1H), 6.81-6.83 (m, 2H), 4.32 (s, 2H), 3.56-3.57 (m, 6H), 2.86 (bs, 2H), 2.40-2.41 (m, 4H), 2.22 (s, 3H).<br>3. 406.1<br>4. Example 115 |

Example 146

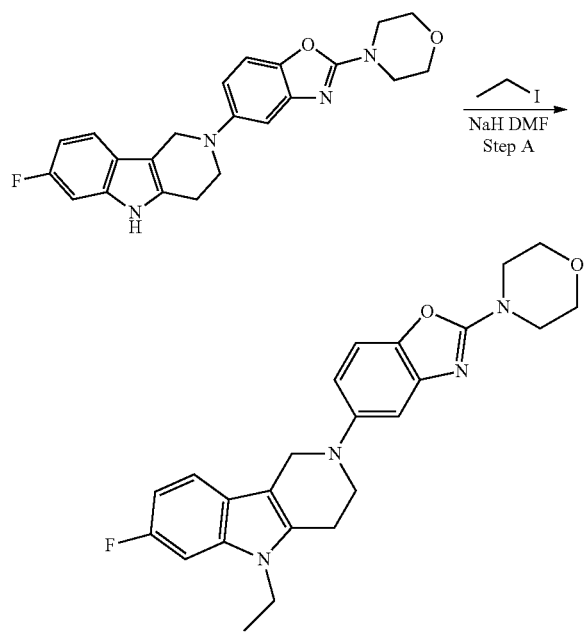

Step A

To a suspension of sodium hydride (0.0293 g, 0.764 mmol) in DMF (3 mL) 5-(7-fluoro-1,3,4,5-tetrahydropyrido[4,3-b]indol-2-yl)-2-morpholino-1,3-benzoxazole (Example 45) (0.100 g, 0.255 mmol) was added drop wise (dissolved in DMF 3 mL) at 0° C., then stirred at room temperature for 60 min. After that iodoethane (0.0596 g, 0.382 mmol) was added at 0° C. dropwise (dissolved in DMF 2 mL) and then stirred at room temperature for 3 h. After completion of the reaction by TLC, the reaction mixture was quenched with ice water followed by extraction using ethyl acetate (20 mL). The organic layer was separated, dried over sodium sulphate, filtered and then concentrated to get crude and then purified by silica gel column (Biotage) using 40-50% of ethyl acetate in pet ether to 5-(5-ethyl-7-fluoro-3,4-dihydro-1H-pyrido[4,3-b]indol-2-yl)-2-morpholino-1,3-benzoxazole as an off-white solid. (15 mg, 14%)

MS: 421.2 (M+H)$^+$.

$^1$H-NMR (400 MHz, DMSO-d$_6$) δ 7.47-7.48 (m, 1H), 7.26-7.28 (m, 2H), 7.06 (d, J=2.40 Hz, 1H), 6.84-6.85 (m, 1H), 6.78-6.79 (m, 1H), 4.33 (s, 2H), 4.10 (q, J=7.20 Hz, 2H), 3.55-3.57 (m, 10H), 2.90 (t, J=4.80 Hz, 2H), 1.22 (t, J=7.20 Hz, 3H).

Examples 147 to 153

Following the palladium coupling procedures as described in Examples 1, 2 and 115, except using the tricyclic amino- and bromo/chloro-derivatives indicated in the table below, the following compounds were prepared.

TABLE 5a

| Example | Tricyclic amino derivative | Bromo or Chloro derivative | Product | 1. Yield<br>2. $^1$H-NMR<br>3. MH$^+$ (ESI)<br>4. Synthesis procedure |
|---|---|---|---|---|
| 147 | | | | 2. 1H NMR (400 MHz, DMSO-d6) δ 7.52-7.43 (m, 1H), 7.30 (d, J = 9.8 Hz, 1H), 7.22 (d, J = 5.8 Hz, 1H), 7.08 (s, 1H), 7.06-6.93 (m, 2H), 4.66 (s, 2H), 3.94 (s, 2H), 3.68 (d, J = 2.3 Hz, 3H), 3.20 (t, J = 5.7 Hz, 2H), 2.12 (s, 3H).<br>4. Example 1 |
| 148 | | | | 1. 91%<br>2. 1H NMR (400 MHz, DMSO-d6) δ 7.68 (d, J = 8.4 Hz, 2H), 7.51-7.40 (m, 1H), 7.30 (d, J = 9.7 Hz, 1H), 7.11 (d, J = 8.4 Hz, 2H), 7.01 (t, J = 9.2 Hz, 1H), 4.71 (s, 2H), 4.13-3.87 (m, 2H), 3.79 (d, J = 2.3 Hz, 3H), 3.69 (s, 3H), 3.25 (t, J = 5.5 Hz, 2H)<br>4. Example 1 |
| 149 | | | | 1. 48.9%<br>2. 1H NMR (400 MHz, DMSO-d6) δ 7.48-7.42 (m, 1H), 7.32-7.23 (m, 1H), 7.20-7.15 (m, 1H), 7.12-7.06 (m, 1H), 7.02-6.94 (m, 2H), 4.62 (s, 2H), 4.25 (s, 3H), 3.94-3.87 (m, 2H), 3.66 (s, 3H), 3.54 (s, 3H), 3.22- |

TABLE 5a-continued

| Example | Tricyclic amino derivative | Bromo or Chloro derivative | Product | 1. Yield<br>2. ¹H-NMR<br>3. MH⁺ (ESI)<br>4. Synthesis procedure |
|---|---|---|---|---|
| | | | | 3.11 (m, 2H).<br>4. Example 1 |
| 150 | | | | 1. 76%<br>2. 1H NMR (400 MHz, DMSO-d6) δ 8.51-8.36 (m, 1H), 8.15-8.05 (m, 1H), 7.80-7.64 (m, 1H), 7.55-7.42 (m, 1H), 7.40-7.33 (m, 1H), 7.32-7.21 (m, 2H), 7.06-6.94 (m, 1H), 5.08 (s, 2H), 4.33 (t, J = 5.8 Hz, 2H), 3.70 (s, 3H), 3.13 (t, J = 5.8 Hz, 2H).<br>4. Example 1 |
| 151 | | | | 1. 99%<br>2. 1H NMR (400 MHz, DMSO-d6) δ 7.47 (dd, J = 8.9, 4.4 Hz, 1H), 7.30 (dd, J = 9.8, 2.6 Hz, 1H), 6.99 (td, J = 9.3, 2.6 Hz, 2H), 6.86 (s, 1H), 4.72-4.46 (m, 2H), 3.80 (s, 3H), 3.69 (s, 3H), 3.45-3.35 (m, 5H).<br>4. Example 1 |
| 152 | | | | 1. 33%<br>2. ¹H-NMR (400 MHz, DMSO-d₆): δ 10.95 (bs, 1H), 7.43 (t, J = 6.00 Hz, 1H), 6.97-7.00 (m, 3H), 6.80 (d, J = 9.20 Hz, 2H), 4.28 (s, 2H), 3.75 (s, 3H), 3.55-3.56 (m, 2H), 2.84 (bs, 2H).<br>3. 315.1<br>4. Example 115 |
| 153 | | | | 3. 315.1<br>4. Example 2 |

HCl Salt of Compounds of the Present Invention

Example 89 HCl

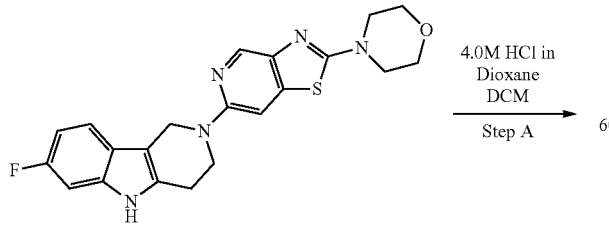

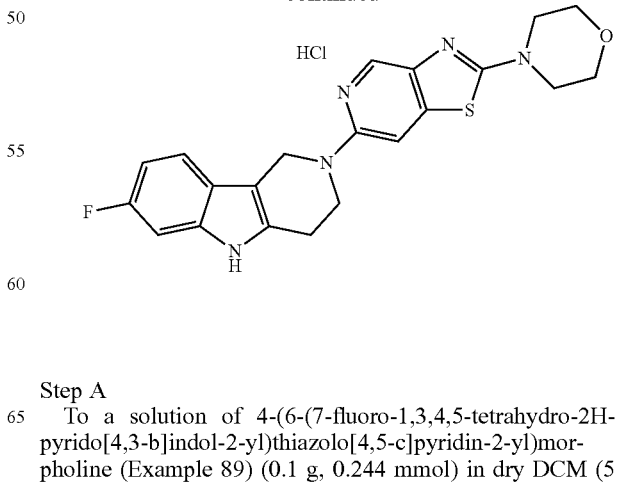

Step A

To a solution of 4-(6-(7-fluoro-1,3,4,5-tetrahydro-2H-pyrido[4,3-b]indol-2-yl)thiazolo[4,5-c]pyridin-2-yl)morpholine (Example 89) (0.1 g, 0.244 mmol) in dry DCM (5 mL), cooled to 0° C., 4M HCl in dioxane (0.2 mL) was added and stirred for 1 hour. The reaction mixture was concentrated under vacuo and triturated with diethylether to the title compound (0.09 g, 83%) as brown solid.

MS: 410.2 (M+H)+.

1H-NMR (400 MHz, DMSO-d6) δ 11.14 (bs, 1H), 8.28 (s, 1H), 7.98 (s, 1H), 7.38-7.40 (m, 1H), 7.11-7.12 (m, 1H), 6.85-6.86 (m, 1H), 4.75 (s, 2H), 4.02 (t, J=5.64 Hz, 2H), 3.73-3.75 (m, 8H), 2.97 (s, 2H).

EXAMPLES

Following the hydrochloride salt procedure as described in Example 89 HCl the following compounds were prepared.

Radioligand Synthesis of Compounds of the Present Invention

Example 3H-12

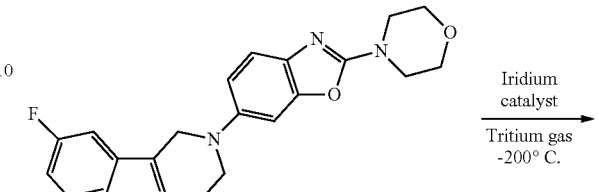

TABLE 6

| Example | Starting Free Base | Product | 1. 1H-NMR<br>2. MH+ (ESI) |
|---|---|---|---|
| 110 HCl | | | 1. 1H-NMR (400 MHz, DMSO-d6) δ 11.04 (bs, 1H), 9.03 (s, 1H), 8.20 (d, J = 9.80 Hz, 1H), 7.67 (d, J = 9.76 Hz, 1H), 7.43-7.45 (m, 1H), 7.34 (s, 1H), 7.08-7.09 (m, 1H), 6.83-6.84 (m, 1H), 4.72 (s, 2H), 4.07 (t, J = 5.52 Hz, 2H), 3.79-3.80 (m, 8H), 2.92 (s, 2H).<br>2. 404.2 |
| 87 HCl | | | 1. 1H-NMR (400 MHz, DMSO-d6) δ 8.16-8.17 (m, 1H), 7.65 (bs, 1H), 7.49-7.50 (m, 1H), 7.30-7.31 (m, 2H), 6.86-6.87 (m, 1H), 4.44 (s, 2H), 3.73-3.74 (m, 6H), 3.73-3.74 (m, 7H), 2.96 (bs, 2H).<br>2. 367.2 |
| 76 HCl | | | 1. 1H-NMR (400 MHz, DMSO-d6) δ δ 11.18 (bs, 1H), 8.07 (d, J = 7.48 Hz, 1H), 7.54 (d, J = 9.84 Hz, 1H), 7.41 (s, 1H), 7.30-7.32 (m, 1H), 7.16-7.17 (m, 1H), 6.89-6.90 (m, 1H), 4.80 (s, 2H), 4.07-4.08 (m, 2H), 3.76-3.77 (m, 4H), 3.10 (bs, 4H), 2.99-3.00 (m, 2H), .<br>2. 353.3 |

-continued

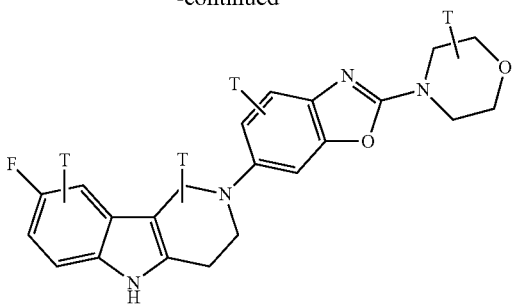

The catalyst was added to a tritium reaction vessel, followed by a solution of the Example 12 starting material (1.0 mg, 0.003 mmol) in dichloromethane. The vessel was attached to the tritium line and pressurized to the tritium gas at −200° C. The solution was stirred for 8 hours, cooled to −200° C. and excess gas removed. The reaction flask was rinsed with 4×1 mL methanol transferring each to 100 mL recovery flask. The combined organic phase was evaporated under vacuum (crude yield: 124 mCi). The crude material was purified by HPLC, the mobile phase was evaporated under vacuum and the product was re-dissolved in absolute ethanol (yield: 17 mCi, purity, >97%). The specific activity was determined to be 80.6 Ci/mmol by mass spectrometry.

Example $^3$H-45

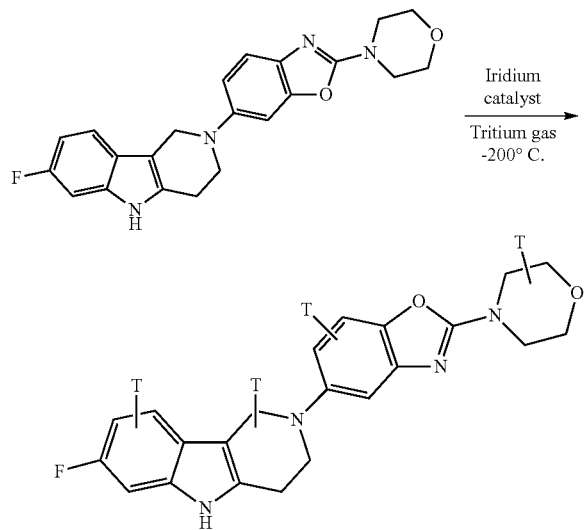

The catalyst was added to a tritium reaction vessel, followed by a solution of the Example 45 starting material (1.0 mg, 0.003 mmol) in dichloromethane. The vessel was attached to the tritium line and pressurized to the tritium gas at −200° C. The solution was stirred for 8 hours, cooled to −200° C. and excess gas removed. The reaction flask was rinsed with 4×1 mL methanol transferring each to 100 mL recovery flask. The combined organic phase was evaporated under vacuum (crude yield: 124 mCi). The crude material was purified by HPLC, the mobile phase was evaporated under vacuum and the product was re-dissolved in absolute ethanol (yield: 17 mCi, purity, >99%). The specific activity was determined to be 96.8 Ci/mmol by mass spectrometry.

Biological Assay Description
Full-Length Tau (flTau) Disaggregation Assay by Thioflavin T (ThT)

The longest isoform of human Tau (2N4R; 441 amino acids) was expressed in bacteria and purified. For the Tau disaggregation assay by ThT, 35 µM of recombinant full-length (fl)Tau in PBS were aggregated for 24 hours at 37° C. in presence of 50 µM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM. flTau aggregates and serial dilutions of compounds were mixed together in PBS (volume 50 µL) to a final concentration of 2 µM of flTau aggregates and from 160 to 0.04 µM of compounds. The mixture was incubated for 30 minutes at room temperature (RT), then 40 µL of this mixture were transferred into a black 384-well plate assay (Perkin-Elmer) and mixed with 10 µL of 100 µM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of flTau disaggregation was then calculated and the half maximal effective concentration ($EC_{50}$) was determined using GraphPad Prism version 5 (GraphPad Software) assuming a one-binding site fitting model.

Tau K18 Disaggregation Assay by ThT

The Tau K18 fragment, encompassing amino acids 244 to 372 of the longest isoform (2N4R) of human Tau441, was expressed in bacteria and purified or bought from Signal-Chem. For the K18 disaggregation assay by ThT, 35 µM of recombinant K18 in PBS were aggregated for 24 hours at 37° C. in presence of 50 µM of heparin (Sigma-Aldrich) and 10 mM of DTT (Sigma-Aldrich) under shaking at 750 RPM. Compounds were dissolved in anhydrous dimethyl sulfoxide (DMSO, Sigma-Aldrich) to reach a concentration of 10 mM. K18 aggregates and serial dilutions of compounds were mixed together in PBS (volume 50 µL) to a final concentration of 2 µM of K18 aggregates and from 160 to 0.04 µM of compounds. The mixture was incubated for 30 minutes at room temperature (RT), then 40 µL of this mixture were transferred into a black 384-well plate assay (Perkin-Elmer) and mixed with 10 µL of 100 µM ThT in 250 mM glycine (both from Sigma-Aldrich) in PBS. Fluorescence (relative fluorescence units; RFU) was measured in monoplicate or duplicate on a Tecan reader (excitation: 440 nm; emission: 485 nm). Percentage of K18 disaggregation was then calculated and half maximal effective concentration ($EC_{50}$) was determined using GraphPad Prism version 5 (GraphPad Software) assuming a one-binding site fitting model.

The following example compounds were measured:

TABLE 7

| Example | Tau K18 disaggregation $EC_{50}$ (µM) | flTau disaggregation $EC_{50}$ (µM) |
|---|---|---|
| 1 | +++ | |
| 3 | +++ | ++ |
| 6 | +++ | |
| 7 | +++ | |
| 9 | +++ | +++ |
| 10 | +++ | |
| 11 | +++ | |
| 12 | +++ | |
| 13 | +++ | ++ |
| 14 | +++ | +++ |
| 15 | + | |

TABLE 7-continued

| Example | Tau K18 disaggregation EC$_{50}$ (μM) | flTau disaggregation EC$_{50}$ (μM) |
|---|---|---|
| 16 |  | +++ |
| 17 |  | +++ |
| 18 |  | ++ |
| 19 |  | +++ |
| 21 |  | ++ |
| 22 |  | + |
| 23 |  | + |
| 24 | +++ | + |
| 25 |  | +++ |
| 28 |  | +++ |
| 29 |  | +++ |
| 30 |  | +++ |
| 31 |  | +++ |
| 32 |  | + |
| 33 |  | +++ |
| 34 |  | +++ |
| 36 |  | +++ |
| 38 | +++ |  |
| 39 |  | + |
| 40 |  | ++ |
| 41 | +++ |  |
| 42 |  | ++ |
| 43 |  | +++ |
| 44 |  | ++ |
| 45 | +++ | +++ |
| 49 |  | +++ |
| 52 |  | +++ |
| 53 | +++ |  |
| 54 |  | +++ |
| 55 |  | +++ |
| 56 |  | +++ |
| 60 |  | +++ |
| 61 |  | +++ |
| 62 |  | +++ |
| 63 |  | +++ |
| 64 |  | +++ |
| 65 |  | +++ |
| 67 |  | +++ |
| 69 |  | +++ |
| 70 | +++ |  |
| 71 | +++ |  |
| 72 | +++ |  |
| 73 | +++ |  |
| 74 |  | + |
| 75 |  | ++ |
| 76 | +++ |  |
| 77 | +++ |  |
| 78 | +++ |  |
| 79 | +++ |  |
| 80 | +++ |  |
| 81 | ++ |  |
| 82 | ++ |  |
| 83 | +++ |  |
| 84 | +++ |  |
| 85 | +++ |  |
| 86 | ++ |  |
| 87 | +++ |  |
| 88 | +++ |  |
| 89 | +++ |  |
| 90 | +++ |  |
| 91 | ++ |  |
| 92 | +++ |  |
| 93 | +++ |  |
| 94 | +++ |  |
| 95 | +++ |  |
| 96 | +++ |  |
| 97 | +++ |  |
| 98 | +++ |  |
| 99 | + |  |
| 100 | + |  |
| 101 | +++ |  |
| 102 | + |  |
| 103 | +++ |  |
| 104 | +++ |  |
| 105 | +++ |  |
| 106 |  | +++ |
| 107 |  | +++ |
| 108 |  | +++ |
| 109 |  | +++ |
| 110 |  | +++ |
| 111 |  | +++ |
| 112 |  | +++ |
| 113 |  | +++ |
| 114 |  | ++ |
| 115 |  | +++ |
| 117 |  | +++ |
| 116 |  | +++ |
| 118 |  | ++ |
| 119 |  | +++ |
| 120 |  | +++ |
| 121 |  | +++ |
| 122 |  | +++ |
| 123 |  | +++ |
| 124 |  | +++ |
| 125 |  | +++ |
| 126 |  | +++ |
| 127 |  | +++ |
| 128 |  | +++ |
| 96a |  | ++ |
| 129 |  | +++ |
| 130 |  | +++ |
| 131 |  | +++ |
| 132 |  | +++ |
| 133 |  | +++ |
| 134 |  | +++ |
| 135 |  | +++ |
| 136 |  | ++ |
| 137 |  | +++ |
| 138 |  | +++ |
| 139 |  | ++ |
| 140 |  | +++ |
| 96b |  | +++ |
| 141 |  | ++ |
| 142 |  | +++ |
| 143 |  | +++ |
| 145 |  | +++ |
| 146 |  | +++ |
| 144 |  | +++ |
| 96e |  | + |
| 96d |  | +++ |
| 105a |  | +++ |
| 105b |  | +++ |
| 105f |  | +++ |
| 147 |  | +++ |
| 148 |  | +++ |
| 149 |  | +++ |
| 150 |  | +++ |
| 151 |  | +++ |
| 152 |  | +++ |
| 153 |  | +++ |

Legend: +++EC$_{50}$ < 10 uM; ++EC$_{50}$ < 10 uM; ++EC$_{50}$ 10 < x < 25 uM; +EC$_{50}$ 25 < x < 50 uM.

Reduction of Intracellular Tau Aggregation

A human neuroblastoma cell line overexpressing the full-length form of human Tau carrying the P301L mutation was cultured in complete medium [DMEM-F12 4.5 g/L Glutamax (Invitrogen), 15% FBS (Biochrom), 1% Peni/Strep (Invitrogen) supplemented with 2.5 μg/ml of G418 (Sigma-Aldrich) selection antibiotic]. The day before the experiment 5×10$^5$ cells/well were plated in a 6 well plate in 3 mL of complete medium. The next day, cells were incubated with DMSO or a compound of the present invention at a 5 μM for additional 24 h at 37° C. After incubation, cells were trypsinized, resuspended in 100 μl of homogenization buffer [25 mM Tris-HCl pH 7.4, 150 mM NaCl, 1 mM EDTA, 1 mM EGTA containing phosphatase inhibitors (30 mM NaF, 0.2 mM Na₃VO₄, 1 nM Okadaic acid, 1 mM PMSF, 5 mM Na₄P₂O₇) and protease inhibitor cocktail (Complete™, Roche)], and then physically lysed with three rapid cycles of freezing and thawing. Samples were then directly tested in the AlphaLISA assay. Phosphorylated, aggregated, and total Tau were quantified by AlphaLisa using the following antibody pairs:

HT7-Acceptor beads+biotin (BT)-Tau13-Donor beads: Total Tau

HT7-Acceptor beads+biotin (BT)-HT7-Donor beads: Aggregated human Tau

The Tau13 (Abcam) was biotinylated using EZ-Link® NHS-PEO Solid Phase biotinylation kit (Thermo Scientific), while the HT7-biotin was from a commercial source (Thermo Scientific).

For each antibody pairs the concentration of acceptor beads and biotinylated antibodies was optimized. All samples were first tested in a dilution series in PBS in order to identify the linear range and optimal dilution for each sample and assay. For the final protocol, the following reagents were added in a 384-well white OptiPlate (PerkinElmer):

5 μL of test diluted sample
20 μL of the mixture biotin-mAb acceptor beads at the following final concentrations:
HT7-BT at 1.25 nM in combination with HT7-Acc beads at 10 μg/ml
Tau13-BT at 5 nM in combination with HT7-Acc beads at 2.5 μg/ml After incubation of this mixture at room temperature for 1 h, 25 μL of Streptavidin Donor beads (Perkin Elmer) at 25 μg/mL were added in the dark. Plates were analyzed after 30 min incubation using the EnSpire Alpha instrument and EnSpire Workstation version 3.00. Data for aggregated Tau were normalized to total Tau and then expressed as percentage of the DMSO-treated cells.

The following example compounds were measured:

TABLE 8

| Example | % Reduction of intracellular Tau aggregation |
|---------|---------------------------------------------|
| 6 | ++ |
| 12 | ++ |
| 14 | ++ |
| 19 | ++ |
| 45 | +++ |
| 52 | + |
| 55 | + |
| 64 | + |
| 69 | +++ |
| 70 | ++ |

Legend: +++ % > 50; ++ % 50 < x < 25; + % 25 < x < 10.

In Vivo Efficacy of the Compounds of the Present Invention
In Vivo Study Design for the Testing of Example 12 and Example 45

Double transgenic rTg4510 mice express the full-length human Tau carrying the P301L mutation (Tau4R0N-P301L) under the control of the tet-inducible CaMKII promoter (Ramsden et al., J. Neurosci., 2005•25(46):10637-10647). Single transgenic mice expressing only the tetracycline-controlled transactivator (tTA) were used as genotype controls. The study comprised 4 treatment groups (n=15 female for tTa group and n=11 female mice/group for the treatment) with the following group distribution (see Table 9). Compounds or vehicle control were administered once daily or bi-daily by gavage for 1 month starting at the age of 5 months. All mice received 200 ppm doxycycline in chow for 3 weeks plus a loading dose in drinking water for the first two days at 1.5 mg/mL in 4% sucrose. Doxycycline administration on dosing started on week 2 and last throughout the dosing period.

Cerebral spinal fluid (CSF) analysis was performed on all animals while histology for misfolded Tau (MC1), total microglia (Iba1) and phagocytic microglia (CD68) were performed on 10 animals/group.

TABLE 9

In vivo study design for the testing of Example 12 and Example 45

| Genotype | Number of mice | Treatment/dose |
|----------|---------------|----------------|
| tTA | 15 | Vehicle[a] |
| rTg4510 | 11 | Vehicle[a] |
| rTg4510 | 11 | Example 12 (30 mg/kg bi-daily) |
| rTg4510 | 11 | Example 45 (30 mg/kg bi-daily) |

[a]vehicle: 0.5% w/v Hydroxypropylmethylcellulose 4000 cps; 0.5% w/v Tween 80

Cerebral Spinal Fluid (CSF) Collection and Analysis

Mice were deeply anesthetized by standard injectable anesthesia and transcardially perfused with cold PBS. Fur and skin from the neck were removed with surgical scissors (the mouse was not decapitated). The tissue surrounding the base of the skull and brain stem was carefully removed via blunt dissection with minimal bleeding. Once the meninges were exposed at the base of the skull, in the area of the foramen magnum, a 27 ga butterfly needle was held perpendicular to the skull and inserted laterally into the cerebrospinal fluid (CSF) space. Samples were rapidly immersed in liquid nitrogen and stored at −80° C. until biochemical analysis was performed by AlphaLISA. Total human Tau in CSF Tau was quantified using the following antibody pairs: HT7-Acceptor beads+biotin (BT)-Tau13-donor beads. The Tau13 (Abcam) antibody was biotinylated using EZ-Link® NHS-PEO Solid Phase biotinylation kit (Thermo Scientific). For the final protocol, the following reagents were added in a 384-well white OptiPlate (PerkinElmer):

5 μL of test diluted sample
20 μL of the mixture biotin-mAb acceptor beads at the final concentrations: Tau13-BT at 0.6 nM in combination with HT7-Acc beads at 2.5 μg/ml After incubation of this mixture at room temperature for 1 hour, 25 μL of Streptavidin Donor beads (Perkin Elmer) at 25 μg/mL were added in the dark. Plates were analyzed after 30 minute incubation using the EnSpire Alpha instrument and EnSpire Workstation version 3.00. Data were analyzed by 1-way ANOVA followed by post-hoc comparisons and shown statistics refers to differences compared to vehicle treated rTg4510 mice.

As shown in FIG. 1, both Example 12 and Example 45 decreased Tau levels in CSF.

Histological Evaluation of rTg4510 Mice Treated with Example 12 and Example 45

After perfusion, brains were then removed and hemisagitally hemisected. The right hemispheres were fixed in 4% paraformaldehyde in PBS for three hours at room temperature, cryopreserved by immersion in 15% sucrose at 4° C. for three days, and prepared for cryosectioning. Fixed hemispheres were then frozen in dry ice on OCT medium in cryo molds and sagittally cryosectioned (10 m thickness) with Leica CM3050 cryotome. Sections from 10 mice per group were collected from around 12 mediolateral levels. A systematic random set of sections from seven sagittal levels per animal was used to quantify the Iba1 and CD68 immunoreactivity while 1 section/animal from the medio-lateral level 4 were used to assess Tau misfolding (MC1 monoclonal antibody). Cryosections were removed from −20° C. and air-dried for 25 minutes at room temperature. Brain tissue was encircled with pap pen liquid blocker and washed one time 5 minutes and one time 10 minutes in PBS at room temperature. Blocking and permeabilization were performed for 2 hours at room temperature with 10% normal goat serum (NGS) and 0.25% Triton X-100 in PBS. Sections were then paper blotted and incubated with mouse monoclonal MC1 antibody diluted 1:1000 in PBS containing 5% NGS and 0.25% Triton X-100 overnight at 4° C. in a humid chamber. Sections were washed three times 10 minutes in PBS at room temperature and incubated with a Cy3-labeled goat anti-mouse IgG (H+L) secondary antibody (Jackson) diluted 1:1000 in PBS for 30 minutes at room temperature protected from light. Following three washes for 10 minutes in PBS, sections were incubated with a solution of 0.1% Sudan Black (Sigma) in 70% ethanol for 30 seconds at room temperature in order to reduce autofluorescence of the tissue. Sections were washed three times for 10 minutes in PBS, mounted using ProLong Gold Antifade reagent with DAPI (Molecular Probes) and coverslipped. Sections were imaged using a digital slide scanner (Panoramic 250 Flash, 3D Histech Ltd.) and quantified using the image visualization software Visiopharm.

MC1 staining was analyzed in the frontal cortex in the upper cortical layers. One region of interest (ROI) corresponding to a field of view at 20× magnification was drawn around the frontal cortex. This ROI was analyzed in Visiopharm using a predetermined threshold for MC1 staining with a pixel intensity threshold above 30 (8 bits pictures) and excluding all detected objects smaller than 20 µm². Data were analyzed by 1-way ANOVA followed by post-hoc test.

Figure 2:
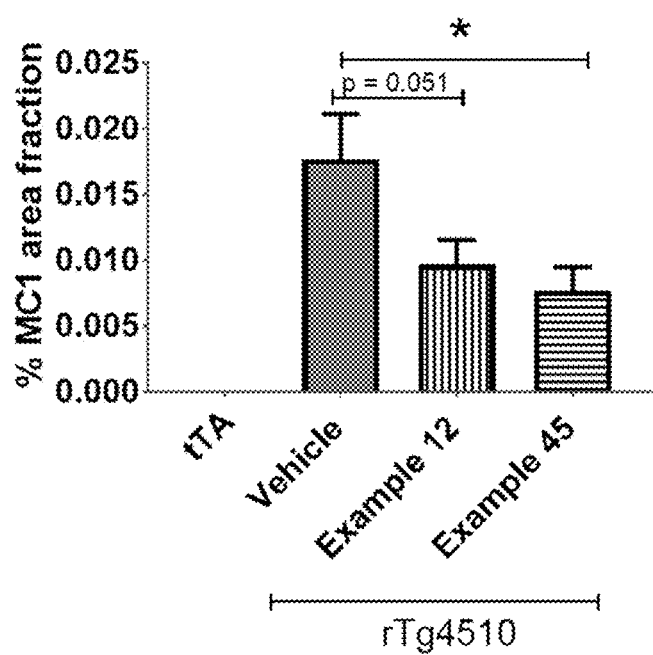
FIG. 2: Tau misfolding quantification in rTg4510 mice treated with Example 12 and Example 45.

As shown in FIG. 2, both Example 12 and Example 45 decreased the MC1 positive area. These data indicate that treatment with both Example 12 and Example 45 in rTg4510 decreases the levels of misfolded Tau in this aggressive Tau transgenic model.

To assess whether the above described effect of tested compounds on Tau had also an effect on neuroinflammation markers, sections were labeled for rat anti mouse CD68 clone FA-11 (BD Biosciences), goat polyclonal anti Iba1 antibody (Abcam) and counterstained with DAPI. Antibody binding was visualized using highly cross-absorbed fluorescently labeled secondary antibodies (Thermo Fisher). The antibody was diluted in antibody diluent (Dako), unspecific endogenous IgG binding was blocked with M.O.M. serum (Vector) before primary incubation. Mounted sections were imaged as a whole on an Axio Scan Z1 slide scanner driven by ZEN software at 20× magnification (plan apochromatic objective), using LED (Colibri2) illumination and a sensitive Orca Flash 4.0 monochromatic camera. Data were analyzed by 1-way ANOVA followed by post-hoc comparisons and shown statistics refers to differences compared to vehicle treated rTg4510 mice.

Figure 3:
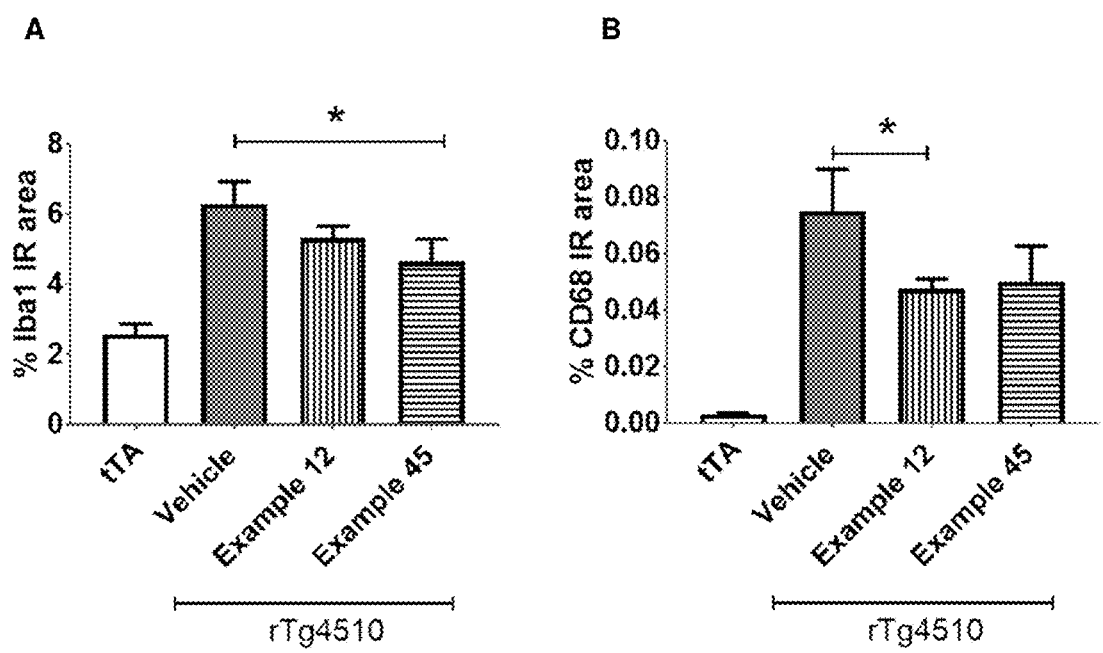
FIG. 3: Iba1 (A) and CD68 (B) quantification in rTg4510 mice treated with Example 12 and Example 45.

As shown in FIG. 3A, both Example 12 and Example 45 decreased microgliosis measured as Iba1 immunoreactive area. Moreover, both Example 12 and 45 decreased highy activated phagocytic migroglial cells that are positive for CD68 (FIG. 3B). Taken together these data indicate that treatment with both Example 12 and Example 45 in rTg4510 decreases the levels of neuroinflammation in this aggressive Tau transgenic model.

Figure 4:
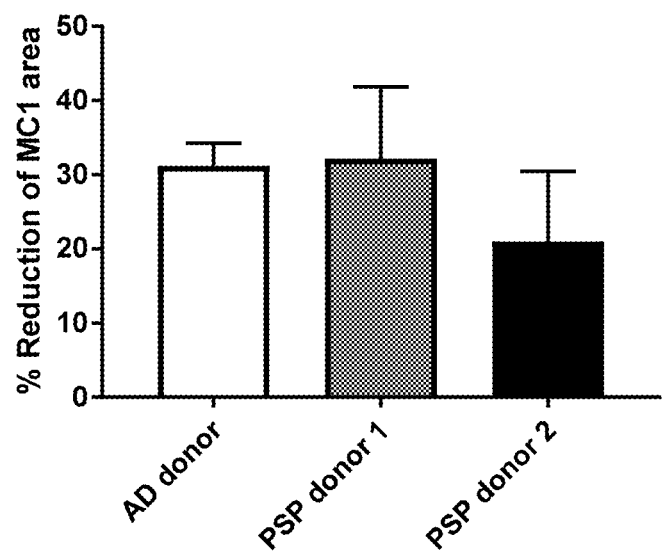
FIG. 4 Reduction of Tau misfolding in NFTs in human AD and PSP brain sections with Example 45.

Reduction of Tau Misfolding in Neurofibrillary Tangles (NFTs) from Human AD and PSP Brain Sections Fresh frozen tissue sections from one AD case and two PSP cases were obtained from a commercial distributor (Tissue Solutions, UK). Tissue sections were incubated with Example 45 at 100 µM or DMSO at room temperature for around 60 hours in a humid chamber. After incubation sections were washed three times in PBS, fixed for 10 min at 4° C. with paraformaldehyde (PFA; Sigma), and then washed again three times in PBS. Sections were then permeabilized in blocking buffer (PBS, 10% Neat Goat Serum (NGS), 0.25% Triton X) for 1 hour at room temperature. After blocking, sections were incubated overnight at 4° C. with a Tau conformational antibody (MC1 monoclonal antibody). in blocking buffer (5% NGS, 0.25% Triton X). The next day, sections were washed three times for five min in PBS and incubated with a Cy3-Conjugated AffiniPure Goat Anti-Mouse antibody (Jackson laboratories) for 1 h at room temperature. Excess antibody was washed away three times for five min in PBS. In order to decrease autofluorescence, the sections were incubated with 0.1% Black Sudan dissolved in 70% ethanol (Sigma) for eight min at room temperature. Finally, the sections were washed five times for five min in PBS and mounted under coverslips using Pro-Long Gold Antifade reagent with DAPI (Invitrogen). Sections were then dried at room temperature for 24 hours before being imaged using a digital slide scanner (Panoramic P250 Flash III, 3D Histech Ltd.) and Tau misolfing in NFTs quantified using the Visiopharm software. As shown in FIG. 4, Example 45 reduces Tau misfolding in NFTs of around 30% with a similar potency on AD and PSP human brain samples.

Ex-Vivo High Resolution Autoradiography with $^3$H-Example 45 in Human AD Brain Sections Fresh frozen tissue sections from one AD case were obtained from a commercial distributor (Tissue Solutions, UK). For autoradiography, brain sections were fixed for 15 minutes at 4° C. with 4% PFA (Sigma). The sections were the incubated with [$^3$H]-Example 45 at 20 nM either alone or together with 5 µM of non-radioactive Example 45) for 1 hour at room temperature. Sections were then washed as follows: first, in ice-cold buffer for 1 minute, then, in ice-cold 70% ethanol twice for 1 minute, in ice-cold buffer for 1 minute and finally, rinsed shortly in ice-cold distilled water. The sections were subsequently dried for 1 hour under a stream of air and then exposed to Ilford Nuclear Emulsion Type K5 (Agar Scientific) for 5 days at 4° C. in a light-proof slide storage box. Exposure to the emulsion was always performed in a darkroom illuminated with a safelight and the emulsion shreds were melted in equal volume of 40° C. preheated water, according to manufacturer's instructions. After 5 days, the sections were developed according to manufacturer's instructions. The sections were mounted using ProLong Gold Antifade reagent (Invitrogen) and imaged a digital slide scanner (Pannoramic P250 Flash III, 3D Histech Ltd.)

Figure 5:
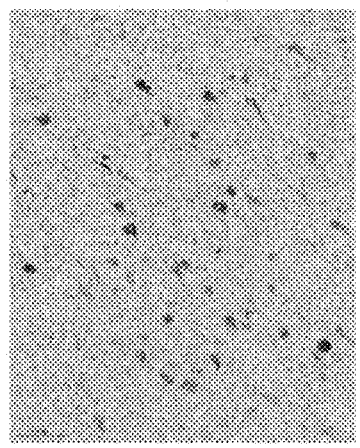
FIG. 5 High resolution autoradiography on human AD brain sections using $^3$H-Example 45 (A) and $^3$H-Example 45 and cold Example 45 (B).
Figure 5:
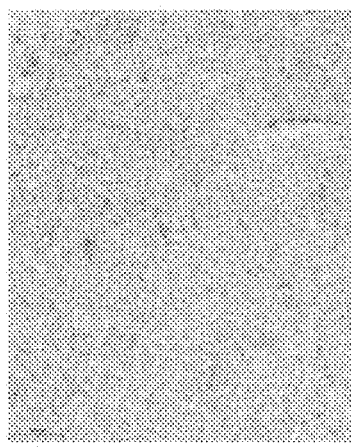

As shown in FIG. 5, Example 45 shows a specific target engagement on Tau NFTs in human AD brain samples.

The invention claimed is:
1. A compound of the formula:

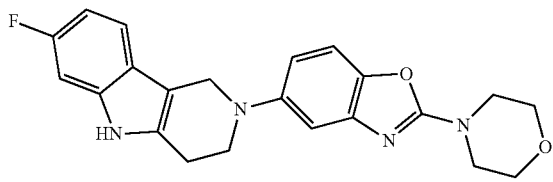 [SMILES: Fc1ccc2c3c([nH]c2c1)CCN(c1ccc2oc(N4CCOCC4)nc2c1)C3]

or a pharmaceutically acceptable salt thereof.

2. A method of treating or alleviating a disorder or abnormality associated with Tau protein aggregates, the method comprising administering an effective amount of a compound or a pharmaceutically acceptable salt thereof as defined in claim 1 to a subject in need thereof.

3. The method according to claim 2, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam,non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease.

4. The method according to claim 2, wherein the disorder is Alzheimer's disease.

5. The method according to claim 2, wherein the disorder is progressive supranuclear palsy (PSP).

6. The method according to claim 2, wherein the method comprises administering at least one additional biologically active compound selected from the group consisting of tacrine, rivastigmine, donepezil, galantamine, niacin and memantine.

7. A method of decreasing Tau aggregation, the method comprising administering an effective amount of a compound or a pharmaceutically acceptable salt thereof as defined in claim 1 to a subject suffering from a disorder associated with Tau protein aggregates.

8. A method of inhibiting Tau aggregation, the method comprising administering an effective amount of a compound or a pharmaceutically acceptable salt thereof as defined in claim 1 to a subject suffering from a disorder associated with Tau protein aggregates.

9. A method of interfering intracellularly with Tau aggregates, the method comprising administering an effective amount of a compound or a pharmaceutically acceptable salt thereof as defined in claim 1 to a subject suffering from a disorder associated with Tau protein aggregates.

10. A method of reducing Tau misfolding and hyperphosphorylation in vivo, the method comprising administering an effective amount of a compound or a pharmaceutically acceptable salt thereof as defined in claim 1 to a subject suffering from a disorder associated with Tau protein aggregates.

11. A method of reducing neuroinflammatory markers, the method comprising administering an effective amount of a compound or a pharmaceutically acceptable salt thereof as defined in claim 1 to a subject suffering from a disorder associated with Tau protein aggregates.

12. The method of according to claim 2, wherein the subject is an animal or human.

13. A compound of the formula:

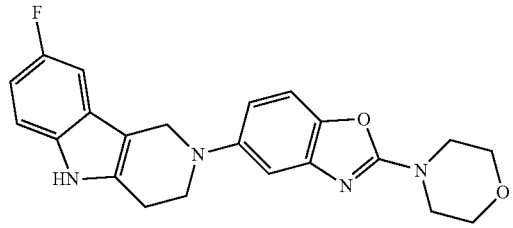 [SMILES: Fc1ccc2[nH]c3c(c2c1)CN(c1ccc2oc(N4CCOCC4)nc2c1)CC3]

or a pharmaceutically acceptable salt thereof.

14. A method of treating or alleviating a disorder or abnormality associated with Tau protein aggregates, the method comprising administering an effective amount of a compound or a pharmaceutically acceptable salt thereof as defined in claim 13 to a subject in need thereof.

15. The method according to claim 14, wherein the disorder is selected from Alzheimer's disease (AD), familial AD, Primary Age-Related Tauopathy (PART), Creutzfeldt-Jacob disease, dementia pugilistica, Down's Syndrome, Gerstmann-Sträussler-Scheinker disease (GSS), inclusion-body myositis, prion protein cerebral amyloid angiopathy, traumatic brain injury (TBI), amyotrophic lateral sclerosis (ALS), Parkinsonism-dementia complex of Guam,non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17 (FTDP-17), Hallervorden-Spatz disease, multiple system atrophy (MSA), Niemann-Pick disease type C, pallido-ponto-nigral degeneration, Pick's disease (PiD), progressive subcortical gliosis, progressive supranuclear palsy (PSP), subacute sclerosing panencephalitis, tangle predominant dementia, postencephalitic Parkinsonism, myotonic dystrophy, subacute sclerosis panencephalopathy, mutations in LRRK2, chronic traumatic encephalopathy (CTE), familial British dementia, familial Danish dementia, other frontotemporal lobar degenerations, Guadeloupean Parkinsonism, neurodegeneration with brain iron accumulation, SLC9A6-related mental retardation, white matter tauopathy with globular glial inclusions, epilepsy, Lewy body dementia (LBD), mild cognitive impairment (MCI), multiple sclerosis, Parkinson's disease, HIV-related dementia, adult onset diabetes, senile cardiac amyloidosis, glaucoma, ischemic stroke, psychosis in AD and Huntington's disease.

16. The method according to claim 14, wherein the disorder is Alzheimer's disease.

17. The method according to claim 14, wherein the disorder is progressive supranuclear palsy (PSP).

18. The method according to claim 14, wherein the method comprises administering at least one additional biologically active compound selected from the group consisting of tacrine, rivastigmine, donepezil, galantamine, niacin and memantine.

19. A method of decreasing Tau aggregation, the method comprising administering an effective amount of a compound or a pharmaceutically acceptable salt thereof as defined in claim 13 to a subject suffering from a disorder associated with Tau protein aggregates.

20. A method of inhibiting Tau aggregation, the method comprising administering an effective amount of a compound or a pharmaceutically acceptable salt thereof as defined in claim 13 to a subject suffering from a disorder associated with Tau protein aggregates.

21. A method of interfering intracellularly with Tau aggregates, the method comprising administering an effective amount of a compound or a pharmaceutically acceptable salt thereof as defined in claim 13 to a subject suffering from a disorder associated with Tau protein aggregates.

22. A method of reducing Tau misfolding and hyperphosphorylation in vivo, the method comprising administering an effective amount of a compound or a pharmaceutically acceptable salt thereof as defined in claim 13 to a subject suffering from a disorder associated with Tau protein aggregates.

23. A method of reducing neuroinflammatory markers, the method comprising administering an effective amount of a compound or a pharmaceutically acceptable salt thereof as defined in claim 13 to a subject suffering from a disorder associated with Tau protein aggregates.

24. The method of according to claim 14, wherein the subject is an animal or human.

\* \* \* \* \*

UNITED STATES PATENT AND TRADEMARK OFFICE
CERTIFICATE OF CORRECTION

PATENT NO. : 10,633,383 B2
APPLICATION NO. : 16/351848
DATED : April 28, 2020
INVENTOR(S) : Sreenivasachary Nampally, Emanuele Gabellieri and Jerome Molette Page 1 of 1

It is certified that error appears in the above-identified patent and that said Letters Patent is hereby corrected as shown below:

In the Claims

Column 282, Line 20, cancel the text beginning with "13. A compound of the formula:" to and ending "or a pharmaceutically acceptable salt thereof." in Column 282, Line 33, and insert the following claim:
--13. A compound of the formula:

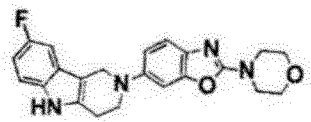

or a pharmaceutically acceptable salt thereof.--

Signed and Sealed this
Second Day of June, 2020

Andrei Iancu
*Director of the United States Patent and Trademark Office*